United States Patent
Lodish et al.

(10) Patent No.: US 10,471,099 B2
(45) Date of Patent: Nov. 12, 2019

(54) IN VITRO PRODUCTION OF RED BLOOD CELLS WITH PROTEINS COMPRISING SORTASE RECOGNITION MOTIFS

(71) Applicant: Whitehead Institute for Biomedical Research, Cambridge, MA (US)

(72) Inventors: Harvey Lodish, Brookline, MA (US); Hidde L. Ploegh, Brookline, MA (US); Hsiang-Ying Lee, Cambridge, MA (US); Jiahai Shi, Kowloon (HK); Lenka Hoffman, Malden, MA (US); Novalia Pishesha, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 14/890,241

(22) PCT Filed: May 9, 2014

(86) PCT No.: PCT/US2014/037554
§ 371 (c)(1),
(2) Date: Nov. 10, 2015

(87) PCT Pub. No.: WO2014/183071
PCT Pub. Date: Nov. 13, 2014

(65) Prior Publication Data
US 2016/0082046 A1     Mar. 24, 2016

Related U.S. Application Data

(60) Provisional application No. 61/822,071, filed on May 10, 2013.

(51) Int. Cl.
| | | |
|---|---|---|
| A61K 39/00 | (2006.01) | |
| C07K 16/28 | (2006.01) | |
| C07K 16/10 | (2006.01) | |
| C07K 1/13 | (2006.01) | |
| A61K 35/18 | (2015.01) | |
| C12N 5/078 | (2010.01) | |
| A01K 67/027 | (2006.01) | |
| C07K 14/47 | (2006.01) | |
| C07K 14/705 | (2006.01) | |

(52) U.S. Cl.
CPC .......... *A61K 35/18* (2013.01); *A01K 67/0275* (2013.01); *C07K 14/47* (2013.01); *C07K 14/705* (2013.01); *C07K 14/70582* (2013.01); *C12N 5/0641* (2013.01); *A01K 2217/072* (2013.01); *A01K 2227/105* (2013.01); *A01K 2267/03* (2013.01); *C12N 2501/125* (2013.01); *C12N 2501/14* (2013.01); *C12N 2501/2303* (2013.01); *C12N 2501/2306* (2013.01); *C12N 2501/26* (2013.01); *C12N 2501/999* (2013.01); *C12N 2506/11* (2013.01); *C12N 2510/02* (2013.01)

(58) Field of Classification Search
None
See application file for complete search history.

(56) References Cited

U.S. PATENT DOCUMENTS

| | | |
|---|---|---|
| 5,728,369 A | 3/1998 | Griffiths et al. |
| 8,211,656 B2 | 7/2012 | Hyde et al. |
| 8,940,501 B2 | 1/2015 | Ploegh et al. |
| 9,751,945 B2 | 9/2017 | Ploegh et al. |
| 10,081,684 B2 | 9/2018 | Ploegh et al. |
| 2003/0022178 A1 | 1/2003 | Schneewind et al. |
| 2004/0213795 A1 | 10/2004 | Collins et al. |
| 2011/0195068 A1 | 8/2011 | Langermann et al. |
| 2011/0321183 A1 | 12/2011 | Ploegh et al. |
| 2012/0039906 A1 | 2/2012 | Olive |
| 2012/0114649 A1 | 5/2012 | Langermann et al. |
| 2013/0095098 A1 | 4/2013 | Tyson |
| 2013/0108651 A1 | 5/2013 | Carven et al. |
| 2013/0109843 A1 | 5/2013 | Carven et al. |
| 2013/0237580 A1 | 9/2013 | Sasikumar et al. |
| 2014/0030697 A1 | 1/2014 | Ploegh et al. |
| 2014/0057317 A1 | 2/2014 | Liu et al. |
| 2014/0249296 A1* | 9/2014 | Ploegh .................. C07K 1/107 530/387.3 |
| 2015/0086576 A1 | 3/2015 | Ploegh et al. |

(Continued)

FOREIGN PATENT DOCUMENTS

| | | |
|---|---|---|
| JP | 2010115136 A | 5/2010 |
| WO | WO 2000/62804 A2 | 10/2000 |

(Continued)

OTHER PUBLICATIONS

Sankaran et al., Cyclin D3 coordinates the cell cycle during differentiation to regulate erythrocyte size and No. Genes & Development 26:2075-2087.*
Pishesha et al Engineered erythrocytes covalently linked to antigenic peptides can protect against autoimmune disease PNAS | Mar. 21, 2017 | vol. 114 | No. 12 | 3157-3162.*
Fusion protein—Wikipedia pp. 1-7 downloaded Feb. 8, 2019.*
Extended European Search Report, dated Nov. 30, 2012, in connection with EP 10736161.0.
Invitation to Pay Additional Fees, dated Nov. 8, 2010, in connection with PCT/US2010/000274.

(Continued)

*Primary Examiner* — Maria G Leavitt
(74) *Attorney, Agent, or Firm* — Wolf, Greenfield & Sacks, P.C.

(57) ABSTRACT

Methods for the in vitro production of enucleated red blood cells and the enucleated red blood cells thus prepared are provided. Such enucleated red blood cells may express a sortaggable surface protein, which allows for surface modification in the presence of a sortase. Also described herein are surface modified enucleated red blood cells, e.g., conjugated with an agent of interest such as a peptide, a detectable label, or a chemotherapeutic agent, and uses thereof in delivering the agent to a subject.

21 Claims, 36 Drawing Sheets
Specification includes a Sequence Listing.

(56) References Cited

U.S. PATENT DOCUMENTS

| | | |
|---|---|---|
| 2016/0097773 A1 | 4/2016 | Pasqual et al. |
| 2016/0122707 A1 | 5/2016 | Ploegh et al. |
| 2016/0287734 A1 | 10/2016 | Rashidian et al. |
| 2018/0280440 A1 | 10/2018 | Lodish et al. |

FOREIGN PATENT DOCUMENTS

| | | |
|---|---|---|
| WO | WO 2005/051976 A2 | 6/2005 |
| WO | WO 2005/086654 A2 | 9/2005 |
| WO | WO 2010/087994 A2 | 8/2010 |
| WO | WO 2011/133704 A2 | 10/2011 |
| WO | WO 2012/142659 A1 | 10/2012 |
| WO | WO 2013/003555 A1 | 1/2013 |
| WO | WO 2014/183006 A2 | 11/2014 |
| WO | WO 2015/073746 A2 | 5/2015 |

OTHER PUBLICATIONS

International Search Report and Written Opinion, dated Dec. 22, 2010, in connection with PCT/US2010/000274.
International Preliminary Report on Patentability, dated Aug. 11, 2011, in connection with PCT/US2010/000274.
Extended European Search Report, dated Nov. 26, 2014, in connection with EP 12804570.5.
International Search Report and Written Opinion, dated Nov. 15, 2012, in connection with PCT/US2012/044584.
International Preliminary Report on Patentability, dated Jan. 16, 2014, in connection with PCT/US2012/044584.
Invitation to Pay Additional Fees, dated Sep. 5, 2014, in connection with PCT/U52014/037554.
International Search Report and Written Opinion, dated Nov. 6, 2014, in connection with PCT/US2014/037554.
International Preliminary Report on Patentability, dated Nov. 19, 2015, in connection with PCT/US2014/037554.
International Search Report and Written Opinion, dated Oct. 27, 2014, in connection with PCT/U52014/037545.
International Preliminary Report on Patentability, dated Nov. 19, 2015, in connection with PCT/U52014/037545.
Invitation to Pay Additional Fees, dated Mar. 20, 2015, in connection with PCT/US14/65574.
International Search Report and Written Opinion, dated Jun. 4, 2015, in connection with PCT/US14/65574.
Antos et al., Lipid modification of proteins through sortase-catalyzed transpeptidation. J Am Chem Soc. Dec. 3, 2008;130(48):16338-43.
Antos et al., Site-specific N- and C-terminal labeling of a single polypeptide using sortases of different specificity. J Am Chem Soc. Aug. 12, 2009;131(31):10800-1. doi: 10.1021/ja902681k.
Arnau et al., Current strategies for the use of affinity tags and tag removal for the purification of recombinant proteins. Protein Expr Purif. Jul. 2006;48(1):1-13. Epub Dec. 28, 2005.
Bader et al., Bioorganic synthesis of lipid-modified proteins for the study of signal transduction. Nature. Jan. 13, 2000;403(6766):223-6. doi: 10.1158/0008-5472.CAN-09-0547. Epub Jun. 9, 2009.
Barnett et al., Differential recognition of surface proteins in *Streptococcus pyogenes* by two sortase gene homologs. J Bacteriol. Apr. 2002;184(8):2181-91.
Baskin et al., Bioorthogonal click chemistry: Covalent labeling in living systems. QSAR Comb Sci. Dec. 2007;26(11-12):1211-9.
Biagiotti et al., Drug delivery by red blood cells. IUBMB Life. Aug. 2011;63(8):621-31. doi: 10.1002/iub.478. Epub Jul. 15, 2011.
Binder et al., 'Click' Chemistry in Polymer and Materials Science. Macromol Rapid Commun. Jan. 5, 2007;28(1):15-54.
Boonyarattanakalin et al., Synthesis of an artificial cell surface receptor that enables oligohistidine affinity tags to func-tion as metal-dependent cell-penetrating peptides. J Am Chem Soc. Mar. 18, 2006;128(14):4917.

Chan et al., Covalent attachment of proteins to solid supports and surfaces via Sortase-mediated ligation. PLoS One. Nov. 14, 2007;2(11):e1164. 5 pages.
Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.
Clow et al., Immobilization of proteins to biacore sensor chips using *Staphylococcus aureus* sortase A. Biotechnol Lett. Sep. 2008;30(9):1603-7. Epub Apr. 15, 2008.
Giarratana et al., Proof of principle for transfusion of in vitro-generated red blood cells. Blood. Nov. 10, 2011;118(19):5071-9. doi:10.1182/blood-2011-06-362038. Epub Sep. 1, 2011.
Godfrin et al., International seminar on the red blood cells as vehicles for drugs. Expert Opin Biol Ther. Jan. 2012;12(1):127-33. doi: 10.1517/14712598.2012.631909. Epub Oct. 25, 2011.
Guimaraes et al., Site-specific C-terminal and internal loop labeling of proteins using sortase-mediated reactions. Nat Protoc. Sep. 2013;8(9):1787-99. doi:10.1038/nprot.2013.101. Epub Aug. 29, 2013.
Heal et al., Site-specific N-terminal labelling of proteins in vitro and in vivo using N-myristoyl transferase and bioorthogonal ligation chemistry. Chem Commun (Camb). Jan. 28, 2008;(4):480-2. Epub Nov. 13, 2007.
Kruger et al., Analysis of the substrate specificity of the *Staphylococcus aureus* sortase transpeptidase SrtA. Biochemistry. Feb. 17, 2004;43(6):1541-51.
Levary et al., Protein-protein fusion catalyzed by sortase A. PLoS One. Apr. 6, 2011;6(4):e18342. doi: 10.1371/journal.pone.0018342. 6 pages.
Mao et al., Sortase-Mediated Protein Ligation: A New Method for Portein Engineering. J Am Chem Soc. Feb. 10, 2004;126:2670-1.
Mao, A self-cleavable sortase fusion for one-step purification of free recombinant proteins. Protein Expr Purif. Sep. 2004;37(1):253-63.
Maresso et al., Surface protein IsdC and Sortase B are required for heme-iron scavenging of *Bacillus anthracis*. J Bacteriol. Dec. 2006;188(23):8145-52. Epub Sep. 29, 2006.
Mariscotti et al., The Listeria monocytogenes sortase-B recognizes varied amino acids at position 2 of the sorting motif. J Biol Chem. Mar. 6, 2009;284(10):6140-6. Epub Jan. 7, 2009.
Marraffini et al., Sortase C-mediated anchoring of BasI to the cell wall envelope of *Bacillus anthracis*. J Bacteriol. Sep. 2007;189(17):6425-36. Epub Jun. 22, 2007.
Matsumoto et al., Site-specific tetrameric streptavidin-protein conjugation using sortase A. J Biotechnol. Mar. 10, 2011;152(1-2):37-42. doi: 10.1016/j.jbiotec.2011.01.008. Epub Jan. 22, 2011.
Mazmanian et al., An iron-regulated sortase anchors a class of surface protein during *Staphylococcus aureus* pathogenesis. Proc Natl Acad Sci U S A. Feb. 19, 2002;99(4):2293-8. Epub 2002 Feb. 5, 2002.
Mazmanian et al., Sortase-catalysed anchoring of surface proteins to the cell wall of *Staphylococcus aureus*. Mol Microbiol. Jun. 2001;40(5):1049-57. Review.
Murciano et al., Prophylactic fibrinolysis through selective dissolution of nascent clots by tPA-carrying erythrocytes. Nat Biotechnol. Aug. 2003;21(8):891-6. Epub Jul. 6, 2003.
Muzykantov, Drug delivery by red blood cells: vascular carriers designed by mother nature. Expert Opin Drug Deliv. Apr. 2010;7(4):403-27. doi:10.1517/17425241003610633.
Ning et al., Visualizing metabolically labeled glycoconjugates of living cells by copper-free and fast huisgen cycloadditions. Angew Chem Int Ed Engl. 2008;47(12):2253-5.
Pallen et al., An embarrassment of sortases—a richness of substrates? Trends Microbiol. Mar. 2001;9(3):97-101.
Parthasarathy et al., Sortase A as a novel molecular "stapler" for sequence-specific protein conjugation. Bioconjug Chem. Mar.-Apr. 2007;18(2):469-76. Epub Feb. 16, 2007.
Piotukh et al., D. Directed evolution of sortase A mutants with altered substrate selectivity profiles. J Am Chem Soc. Nov. 9, 2011;133(44):17536-9. doi: 10.1021/ja205630g. Epub Oct. 13, 2011.
Popp et al., Making and breaking peptide bonds: protein engineering using sortase. Angew Chem Int Ed Engl. May 23, 2011;50(22):5024-32. doi:10.1002/anie.201008267. Epub Apr. 27, 2011.

(56) References Cited

OTHER PUBLICATIONS

Popp et al., Site-specific protein labeling via sortase-mediated transpeptidation. Curr Protoc Protein Sci. Apr. 2009;Chapter 15:Unit 15.3. doi: 10.1002/0471140864.ps1503s56.
Popp et al., Sortagging: a versatile method for protein labeling. Nat Chem Biol. Nov. 2007;3(11):707-8. Epub Sep. 23, 2007.
Sletten et al., Bioorthogonal chemistry: fishing for selectivity in a sea of functionality. Angew Chem Int Ed Engl. 2009;48(38):6974-98. doi: 10.1002/anie.200900942.
Strijbis et al., Protein ligation in living cells using sortase. Traffic. Jun. 2012;13(6):780-9. doi: 10.1111/j.1600-0854.2012.01345.x. Epub Mar. 23, 2012.
Tanaka et al., Site-specific protein modification on living cells catalyzed by Sortase. Chembiochem. Mar. 25, 2008;9(5):802-7.
Theile et al., Site-specific N-terminal labeling of proteins using sortase-mediated reactions. Nat Protoc. Sep. 2013;8(9):1800-7. doi: 10.1038/nprot.2013.102. Epub Aug. 29, 2013.
Ton-That et al., Anchoring of surface proteins to the cell wall of *Staphylococcus aureus*. Sortase catalyzed in vitro transpeptidation reaction using LPXTG peptide and NH(2)-Gly(3) substrates. J Biol Chem. Mar. 31, 2000;275(13):9876-81.
Ton-That et al., Protein sorting to the cell wall envelope of Gram-positive bacteria. Biochim Biophys Acta. Nov. 11, 2004;1694(1-3):269-78.
Ton-That et al., Purification and characterization of sortase, the transpeptidase that cleaves surface proteins of *Staphylococcus aureus* at the LPXTG motif. Proc Natl Acad Sci U S A. Oct. 26, 1999;96(22):12424-9.
Witte et al., Preparation of unnatural N-to-N and C-to-C protein fusions. Proc Natl Acad Sci U S A. Jul. 24, 2012;109(30):11993-8. doi: 10.1073/pnas.1205427109. Epub Jul. 9, 2012.
Witte et al., Production of unnaturally linked chimeric proteins using a combination of sortase-catalyzed transpeptidation and click chemistry. Nat Protoc. Sep. 2013;8(9):1808-19. doi: 10.1038/nprot.2013.103. Epub Apr. 4, 2014. 16 pages.
Wu et al., Sortase A-catalyzed transpeptidation of glycosylphosphatidylinositol derivatives for chemoenzymatic synthesis of GPI-anchored proteins. J Am Chem Soc. Feb. 10, 2010;132(5):156771. doi: 10.1021/ja906611x.
Yamamoto et al., Expansion of the sortase-mediated labeling method for site-specific N-terminal labeling of cell surface proteins on living cells. Chem Commun (Camb). Mar. 7, 2009;(9):1022-4. doi: 10.1039/b818792d. Epub Jan. 7, 2009.
Yoo et al., Bio-inspired, bioengineered and biomimetic drug delivery carriers. Nat Rev Drug Discov. Jul. 1, 2011;10(7):521-35. doi: 10.1038/nrd3499.
Zaitsev et al., Sustained thromboprophylaxis mediated by an RBC-targeted pro-urokinase zymogen activated at the site of clot formation. Blood. Jun. 24, 2010;115(25):5241-8. doi: 10.1182/blood-2010-01-261610. Epub Apr. 21, 2010.
Zaslavskaia et al., Trophic conversion of an obligate photoautotrophic organism through metabolic engineering. Science. Jun. 15, 2001;292(5524):2073-5.
U.S. Appl. No. 14/890,296, filed Nov. 10, 2015, Ploegh et al.
U.S. Appl. No. 14/875,140, filed Nov. 5, 2015, Pasqual et al.
EP 10736161.0, Nov. 30, 2012, Extended European Search Report.
PCT/US2010/000274, Nov. 8, 2010, Invitation to Pay Additional Fees.
PCT/US2010/000274, Dec. 22, 2010, International Search Report and Written Opinion.
PCT/US2010/000274, Aug. 11, 2011, International Preliminary Report on Patentability.
EP 12804570.5, Nov. 26, 2014, Extended European Search Report.
PCT/US2012/044584, Nov. 15, 2012, International Search Report and Written Opinion.
PCT/US2012/044584, Jan. 16, 2014, International Preliminary Report on Patentability.
PCT/US2014/037554, Nov. 6, 2014, International Search Report and Written Opinion.
PCT/US2014/037554, Sep. 5, 2014, Invitation to Pay Additional Fees.
PCT/US2014/037554, Nov. 19, 2015, International Preliminary Report on Patentability.
PCT/US2014/037545, Oct. 27, 2014, International Search Report and Written Opinion.
PCT/US2014/037545, Nov. 19, 2015, International Preliminary Report on Patentability.
PCT/US14/65574, Mar. 20, 2015, Invitation to Pay Additional Fees.
PCT/US14/65574, Jun. 4, 2015, International Search Report and Written Opinion.
Extended European Search Report, dated Nov. 9, 2016, in connection with EP 14795167.7.
GenPept Accession No. YP 187332.1. Gill et al. Dec. 17, 2014.
Ahlgren et al., Targeting of HER2-expressing tumors with a site-specifically 99mTc-labeled recombinant affibody molecule, ZHER2:2395, with C-terminally engineered cysteine. J Nucl Med. May 2009;50(5):781-9. doi: 10.2967/jnumed.108.056929. Epub Apr. 16, 2009.
Chang et al., Development and characterization of 89Zr-labeled panitumumab for immuno-positron emission tomographic imaging of the epidermal growth factor receptor. Mol Imaging. Jan.-Feb. 2013;12(1):17-27.
De Meyer et al., Nanobody-based products as research and diagnostic tools. Trends Biotechnol. May 2014;32(5):263-70. doi:10.1016/j.tibtech.2014.03.001. Epub Apr. 1, 2014.
Delgado, et al. Stabilities of divalent and trivalent metal ion complexes of macrocyclic triazatriacetic acids. Inorg. Chem. 1999; 32, 3320-3326.
Dijkers et al., Biodistribution of 89Zr-trastuzumab and PET imaging of HER2-positive lesions in patients with metastatic breast cancer. Clin Pharmacol Ther. May 2010;87(5):586-92. doi:10.1038/clpt.2010.12. Epub Mar. 31, 2010.
Dorr et al., Reprogramming the specificity of sortase enzymes. Proc Natl Acad Sci U S A. Sep. 16, 2014;111(37):13343-8. doi:10.1073/pnas.1411179111. Epub Sep. 3, 2014.
Engfeldt et al., Chemical synthesis of triple-labelled three-helix bundle binding proteins for specific fluorescent detection of unlabelled protein. Chembiochem. Jun. 2005;6(6):1043-50.
Goldenberg et al., Novel radiolabeled antibody conjugates. Oncogene. May 28, 2007;26(25):3734-44.
Groheux et al., Correlation of high 18F-FDG uptake to clinical, pathological and biological prognostic factors in breast cancer. Eur J Nucl Med Mol Imaging. Mar. 2011;38(3):426-35. doi:10.1007/s00259-010-1640-9. Epub Nov. 6, 2010.
Hackenberger et al., Chemoselective ligation and modification strategies for peptides and proteins. Angew Chem Int Ed Engl. 2008;47(52):10030-74. doi: 10.1002/anie.200801313.
Hochuli et al., Genetic Approach to Facilitate Purification of Recombinant Proteins with a Novel Metal Chelate Adsorbent. Nature Biotechnology. 1988, 6, 1321-1325.
Holm et al., Electrophilic affibodies forming covalent bonds to protein targets. J Biol Chem. Nov. 20, 2009;284(47):32906-13. doi:10.1074/jbc.M109.034322. Epub Sep. 15, 2009.
Keliher et al., High-yielding, two-step 18F labeling strategy for 18F-PARP1 inhibitors. ChemMedChem. Mar. 7, 2011;6(3):424-7. doi: 10.1002/cmdc.201000426. Epub Jan. 4, 2011.
Knowles et al., Advances in immuno-positron emission tomography: antibodies for molecular imaging in oncology. J Clin Oncol. Nov. 1, 2012;30(31):3884-92. doi: 10.1200/JCO.2012.42.4887. Epub Sep. 17, 2012.
Langenhan et al., Recent Carbohydrate-Based Chemoselective Ligation Applications. Current Organic Synthesis. 2005; 2, 59-81.
Lu et al., Biologic properties and enucleation of red blood cells from human embryonic stem cells. Blood. Dec. 1, 2008;112(12):4475-84. doi:10.1182/blood-2008-05-157198.
Lundberg et al., Site-specifically conjugated anti-HER2 Affibody molecules as one-step reagents for target expression analyses on cells and xenograft samples. J Immunol Methods. Jan. 30, 2007;319(1-2):53-63. Epub Nov. 21, 2006.
Nair-Gill et al., Non-invasive imaging of adaptive immunity using positron emission tomography. Immunol Rev. Feb. 2008;221:214-28. doi: 10.1111/j.1600-065X.2008.00585.x.

(56) References Cited

OTHER PUBLICATIONS

Nayak et al., PET and MRI of metastatic peritoneal and pulmonary colorectal cancer in mice with human epidermal growth factor receptor 1-targeted 89Zr-labeled panitumumab. J Nucl Med. Jan. 2012;53(1):113-20. doi: 10.2967/jnumed.111.094169.
Orlova et al., Evaluation of [(111/114m)In]CHX-A"-DTPA-ZHER2:342, an affibody ligand coniugate for targeting of HER2-expressing malignant tumros. Q J Nucl Med Mol Imaging. 2007.
Orlova et al., Tumor imaging using a picomolar affinity HER2 binding affibody molecule. Cancer Res. Apr. 15, 2006;66(8):4339-48.
Poli et al., Radretumab radioimmunotherapy in patients with brain metastasis: a 124I-L19SIP dosimetric PET study. Cancer Immunol Res. Aug. 2013;1(2):134-43. doi: 10.1158/2326-6066.CIR-13-0007. Epub May 20, 2013.
Rashidian et al., A highly efficient catalyst for oxime ligation and hydrazone-oxime exchange suitable for bioconjugation. Bioconjug Chem. Mar. 20, 2013;24(3):333-42. doi: 10.1021/bc3004167.Epub Mar. 6, 2013.
Rashidian et al., Enzymatic labeling of proteins: techniques and approaches. Bioconjug Chem. Aug. 21, 2013;24(8):1277-94.
Salsano et al., "PET imaging using radiolabeled antibodies: future direction in tumor diagnosis and correlate applications." Research and Reports in Nuclear Medicine. 2013: 3; 9-17.
Shi et al., Engineered red blood cells as carriers for systemic delivery of a wide array of functional probes. Proc Natl Acad Sci U S A. Jul. 15, 2014;111(28):10131-6. doi: 10.1073/pnas.1409861111.
Siontorou, Nanobodies as novel agents for disease diagnosis and therapy. Int J Nanomedicine. 2013;8:4215-27. doi: 10.2147/IJN.S39428. Epub Jan. 11, 2013.
Spicer et al., Selective chemical protein modification. Nat Commun. Sep. 5, 2014;5:4740. doi: 10.1038/ncomms5740.
Swee et al., One-step enzymatic modification of the cell surface redirects cellular cytotoxicity and parasite tropism. ACS Chem Biol. Feb. 20, 2015;10(2):460-5. doi: 10.1021/cb500462t.
Ta et al., Enzymatic single-chain antibody tagging: a universal approach to targeted molecular imaging and cell homing in cardiovascular disease. Circ Res. Aug. 5, 2011;109(4):365-73. doi: 10.1161/CIRCRESAHA.111.249375.
Tanaka et al., PET (positron emission tomography) imaging of biomolecules using metal-DOTA complexes: a new collaborative challenge by chemists, biologists, and physicians for future diagnostics and exploration of in vivo dynamics. Org Biomol Chem. Mar. 7, 2008;6(5):815-28. doi: 10.1039/b718157b. Epub Feb. 1, 2008.
Tolmachev et al., Radionuclide therapy of HER2-positive microxenografts using a 177Lu-labeled HER2-specific Affibody molecule. Cancer Res. Mar. 15, 2007;67(6):2773-82.
Tran et al., (99m)Tc-maEEE-Z(HER2:342), an Affibody molecule-based tracer for the detection of HER2 expression in malignant tumors. Bioconjug Chem. Nov.-Dec. 2007;18(6):1956-64. Epub Oct. 19, 2007.
Truong et al., Copper-catalyzed, directing group-assisted fluorination of arene and heteroarene C-H bonds. J Am Chem Soc. Jun. 26, 2013;135(25):9342-5. doi: 10.1021/ja4047125. Epub Jun. 12, 2013.
Vaidyanathan et al., Synthesis of N-succinimidyl 4-[18F]fluorobenzoate, an agent for labeling proteins and peptides with 18F. Nat Protoc. 2006;1(4):1655-61.
Vosjan et al., Conjugation and radiolabeling of monoclonal antibodies with zirconium-89 for PET imaging using the bifunctional chelate p-isothiocyanatobenzyl-desferrioxamine. Nat Protoc. Apr. 2010;5(4):739-43. doi: 10.1038/nprot.2010.13. Epub Mar. 25, 2010.
Waldherr et al., Monitoring antiproliferative responses to kinase inhibitor therapy in mice with 3'-deoxy-3'-18F-fluorothymidine PET. J Nucl Med. Jan. 2005;46(1):114-20.
Wu et al., The use of sortase-mediated ligation for the immobilisation of bacterial adhesins onto fluorescence-labelled microspheres: a novel approach to analyse bacterial adhesion to host cells. Biotechnol Lett. Nov. 2010;32(11):1713-8. doi: 10.1007/s10529-010-0349-y.
Youssef et al., The use of 18F-FDG PET in the diagnosis of cardiac sarcoidosis: a systematic review and metaanalysis including the Ontario experience. J Nucl Med. Feb. 2012;53(2):241-8. doi:10.2967/jnumed.111.090662. Epub 2012 Jan. 6, 2012.
Zhang et al., Positron emission tomography imaging of CD105 expression with a 64Cu-labeled monoclonal antibody: NOTA is superior to DOTA. PLoS One. 2011;6(12):e28005. doi:10.1371/journal.pone.0028005. Epub Dec. 9, 2011.
Zong et al., Crystal structures of *Staphylococcus aureus* sortase A and its substrate complex. J Biol Chem. Jul. 23, 2004;279(30):31383-9. Epub Apr. 26, 2004.
U.S. Appl. No. 15/934,177, filed Mar. 23, 2018, Lodish et al.
U.S. Appl. No. 15/764,087, filed Mar. 28, 2018, Rashidian et al.
PCT/US2016/055074, Apr. 12, 2018, International Preliminary Report on Patentability.
PCT/US2016/055074, Dec. 1, 2016, Invitation to Pay Additional Fees.
PCT/US2016/055074, Feb. 6, 2017, International Search Report and Written Opinion.
Denk et al., Development of a (18) F-labeled tetrazine with favorable pharmacokinetics for bioorthogonal PET imaging. Angew Chem Int Ed Engl. Sep. 1, 2014;53(36):9655-9. doi:10.1002/anie.201404277. Epub Jul. 2, 2014.
Matsumura et al., Emerging principles for the recognition of peptide antigens by MHC class 1 molecules, Sci. 1992;257:927-934.
Tsukiji et al., Sortase-mediated ligation: A Gift from Gram-Positive Bacteria to Protein Engineering, ChemBioChem 2009;10:787-798.
Wriggers et al., Control of Protein Functional Dynamics by Peptide Linkers, Prat. Function. Dynam. 2005;80:736-746.
Xiao et al., Protein N-terminal processing: substrate specificity of *Escherichia coli* and human methionine aminopeptidases. Biochemistry. Jul. 6, 2010;49(26):5588-99. doi: 10.1021/bi1005464.
Extended European Search Report, dated Oct. 13, 2016, in connection with EP 14795120.6.
Lu et al. Biologic properties and enucleation of red blood cells from human embryonic stem cells. Blood. Dec. 1, 2008;112(12):4475-84. doi:10.1182/blood-2008-05-157198. Epub Aug. 19, 2008.
Park et al., Anchoring foreign substances on live cell surfaces using Sortase A specific binding peptide. Chem Commun (Camb). Oct. 25, 2013;49(83):9585-7. doi: 10.1039/c3cc44753g.
Shi et al. Engineered red blood cells as carriers for systemic delivery of a wide array of functional probes. Proc Natl Acad Sci U S A. Jul. 15, 2014;111(28):10131-6. doi: 10.1073/pnas.1409861111. Epub Jun. 30, 2014.

* cited by examiner

Figure 1

| <Expansion> (4 days) | <Differentiation I> (5 days) | <Differentiation II> (4 days) | <Differentiation III> (9 days) |
|---|---|---|---|
| • StemSpan SFEM medium<br>• 1X CC100 cytokine mix (Flt-3 ligand, SCF, IL-3, IL-6)<br>• 2% Pen/Strep | • IMDM<br>• 15% FBS<br>• 2mM glutamine<br>• 1% BSA<br>• 2% Pen/Strep<br>• holo human transferrin: 500 µg/mL<br>• rh insulin: 10 µg/mL<br>• Dexamethasone: 2 µM<br>• β-estradiol: 1 µM<br>• IL-3: 5 ng/mL<br>• SCF 100 ng/mL<br>• Epo 6U | • IMDM<br>• 15% FBS<br>• 2mM glutamine<br>• 1% BSA<br>• 2% Pen/Strep<br>• holo human transferrin: 500 µg/mL<br>• rh insulin: 10 µg/mL<br>• SCF 50 ng/mL<br>• Epo 6U | • IMDM<br>• 15% FBS<br>• 2mM glutamine<br>• 1% BSA<br>• 2% Pen/Strep<br>• holo human transferrin: 500 µg/mL<br>• rh insulin: 10 µg/mL<br>• Epo 2U<br>* Fibronectin plates |

Figure 16 (cont'd)
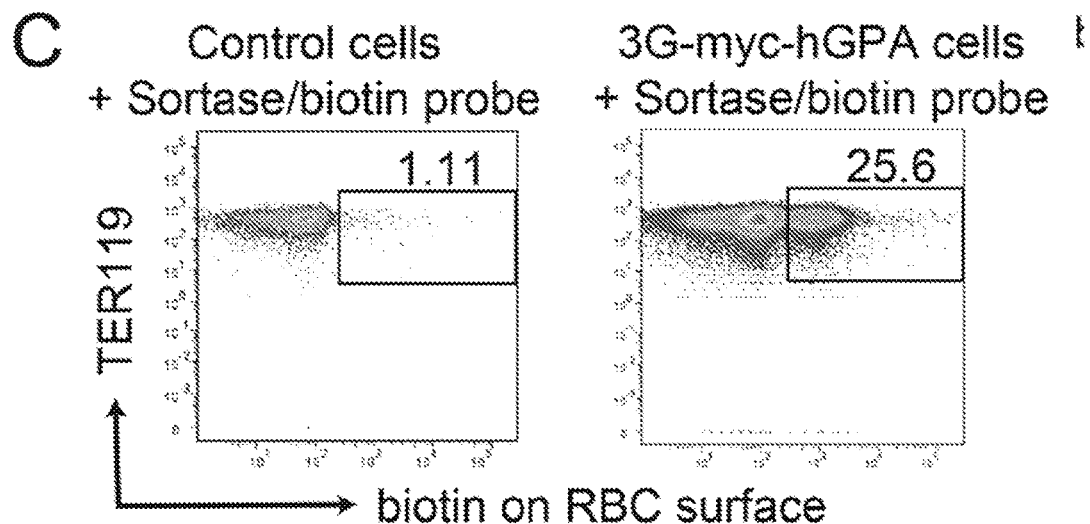
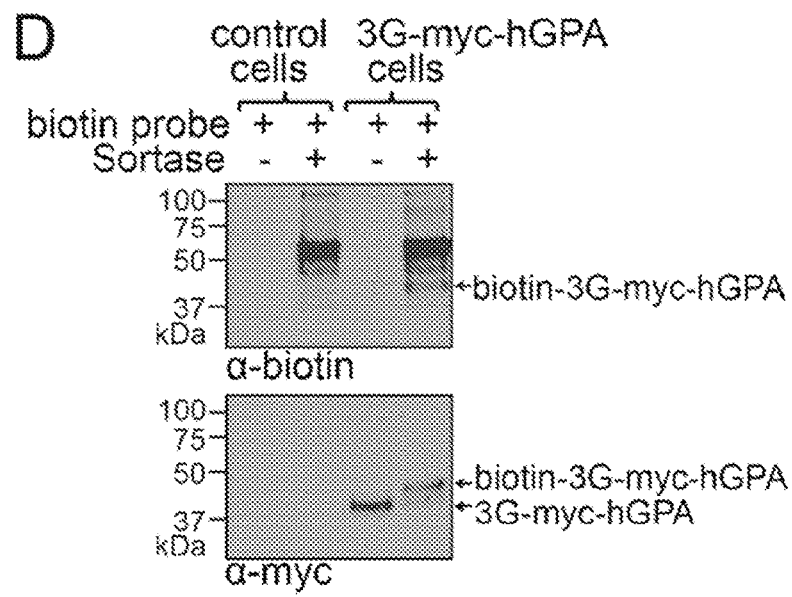

Figure 16 (cont'd)
E
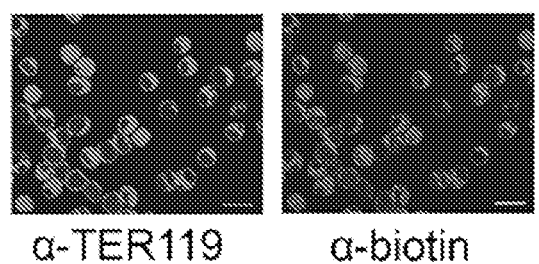
α-TER119    α-biotin
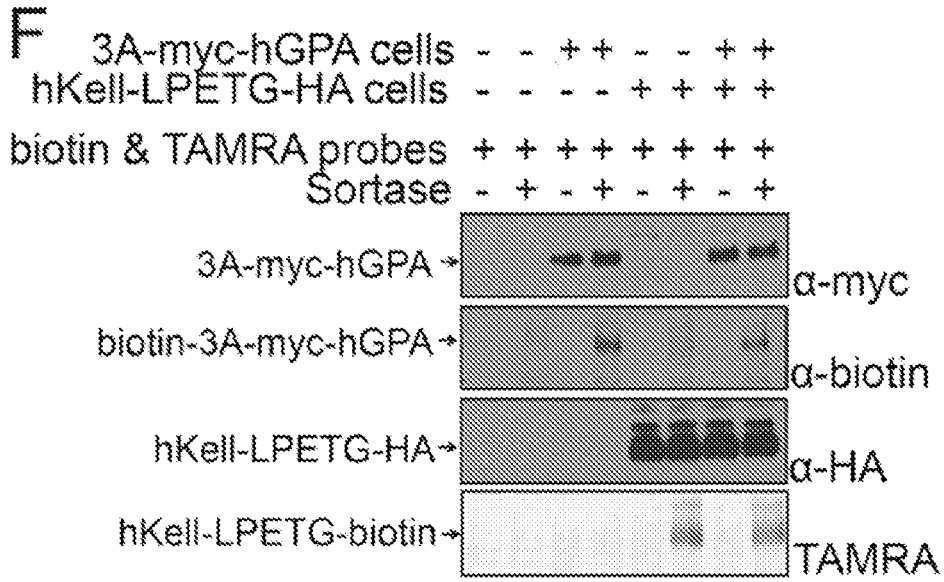

Figure 21 (cont'd)
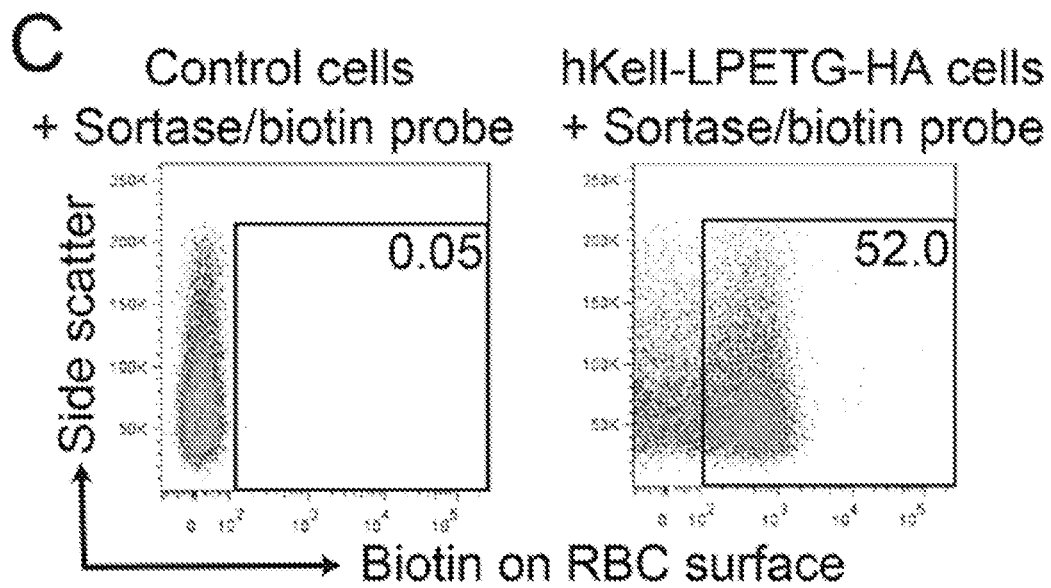
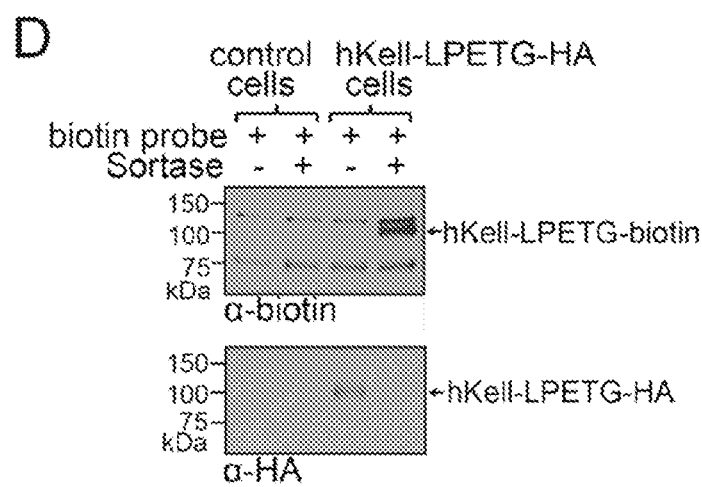
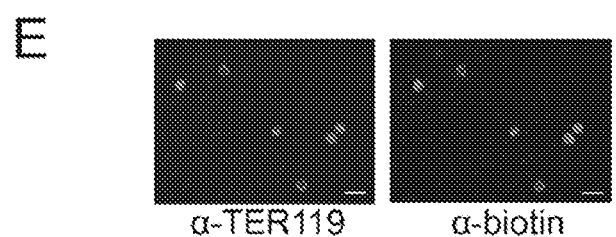

SEQUENCE LISTING

```
<160> NUMBER OF SEQ ID NOS: 126

<210> SEQ ID NO 1
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1

Leu Pro Xaa Thr Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

Leu Pro Xaa Thr Ala
1               5

<210> SEQ ID NO 3
<211> LENGTH: 5
<212> TYPE: PRT
```

<213> ORGANISM: Artificial Sequence
<220> FEATURE:
<223> OTHER INFORMATION: Synthetic Polypeptide

<400> SEQUENCE: 3

```
Gly Gly Gly Gly Gly
1               5
```

<210> SEQ ID NO 4
<211> LENGTH: 303
<212> TYPE: PRT
<213> ORGANISM: Homo sapiens

<400> SEQUENCE: 4

```
Ile Lys Gly Gly Leu Phe Ala Asp Ile Ala Ser His Pro Trp Gln Ala
1               5                   10                  15

Ala Ile Phe Ala Lys His His Arg Arg Gly Gly Glu Arg Phe Leu Cys
                20                  25                  30

Gly Gly Ile Leu Ile Ser Ser Cys Trp Ile Leu Ser Ala Ala His Cys
            35                  40                  45

Phe Gln Gln Gln Gln Gln Glu Glu Glu Glu Arg Arg Arg Arg
    50                  55                  60

Phe Phe Phe Phe Phe Pro Pro Pro Pro His His Leu Thr Val
65                  70                  75                  80

Ile Leu Gly Arg Thr Tyr Arg Val Val Pro Gly Glu Glu Gln Lys
                85                  90                  95

Phe Glu Val Glu Lys Tyr Ile Val His Lys Glu Phe Asp Asp Thr
                100                 105                 110

Tyr Asp Asn Asp Ile Ala Leu Leu Gln Leu Lys Ser Ser Ser Ser Ser
                115                 120                 125

Asp Asp Asp Asp Ser Ser Ser Ser Ser Ser Ser Ser Arg
    130                 135                 140

Arg Arg Arg Arg Cys Ala Gln Glu Ser Ser Val Val Arg Thr Val Cys
145                 150                 155                 160

Leu Pro Pro Ala Asp Leu Gln Leu Pro Asp Trp Thr Glu Cys Glu Leu
                165                 170                 175

Ser Gly Tyr Gly Lys His Glu Ala Leu Ser Pro Phe Tyr Ser Glu Arg
                180                 185                 190

Leu Lys Glu Ala His Val Arg Leu Tyr Pro Ser Ser Arg Cys Thr Thr
                195                 200                 205

Thr Ser Ser Ser Gln Gln Gln His Leu Leu Asn Arg Thr Val Thr Asp
    210                 215                 220

Asn Met Leu Cys Ala Gly Asp Thr Thr Thr Arg Arg Arg Ser Ser Ser
225                 230                 235                 240

Asn Asn Asn Leu His Asp Ala Cys Gln Gly Asp Ser Gly Gly Pro Leu
                245                 250                 255

Val Cys Leu Asn Asp Gly Arg Met Thr Leu Val Gly Ile Ile Ser Trp
                260                 265                 270

Gly Leu Gly Cys Gly Gly Gln Gln Lys Asp Val Pro Gly Val Tyr Thr
                275                 280                 285

Lys Val Thr Asn Tyr Leu Asp Trp Ile Arg Asp Asn Met Arg Pro
                290                 295                 300
```

<210> SEQ ID NO 5
<211> LENGTH: 9
<212> TYPE: PRT
<213> ORGANISM: Homo sapiens

```
<400> SEQUENCE: 5

Thr Thr Cys Cys Gly Leu Arg Gln Tyr
1               5

<210> SEQ ID NO 6
<211> LENGTH: 255
<212> TYPE: PRT
<213> ORGANISM: Homo sapiens

<400> SEQUENCE: 6

Val Val Gly Gly Glu Asp Ala Lys Pro Gly Gln Phe Pro Trp Gln Val
1               5                   10                  15

Val Leu Asn Gly Lys Val Asp Ala Phe Cys Gly Gly Ser Ile Val Asn
                20                  25                  30

Glu Lys Trp Ile Val Thr Ala Ala His Cys Val Glu Thr Thr Gly
            35                  40                  45

Val Lys Ile Thr Val Val Ala Gly Glu His Asn Ile Glu Glu Thr Glu
    50                  55                  60

His Thr Glu Gln Lys Arg Asn Val Ile Arg Ile Pro His His Asn
65                  70                  75                  80

Tyr Asn Asn Asn Ala Ala Ala Ala Ile Asn Lys Tyr Asn His
                85                  90                  95

Asp Ile Ala Leu Leu Glu Leu Asp Glu Pro Leu Val Leu Asn Ser Tyr
                100                 105                 110

Val Thr Pro Ile Cys Ile Ala Asp Lys Glu Tyr Thr Thr Asn Asn
            115                 120                 125

Asn Ile Ile Ile Phe Leu Lys Phe Gly Ser Gly Tyr Val Ser Gly Trp
    130                 135                 140

Gly Arg Val Phe His Lys Gly Arg Ser Ala Leu Val Leu Gln Tyr Leu
145                 150                 155                 160

Arg Val Pro Leu Val Asp Arg Ala Thr Cys Leu Arg Ser Thr Lys Phe
                165                 170                 175

Thr Ile Tyr Asn Asn Met Phe Cys Ala Gly Gly Phe His Glu Gly
                180                 185                 190

Gly Gly Arg Arg Asp Ser Cys Gln Gly Asp Ser Gly Gly Pro His Val
            195                 200                 205

Thr Glu Val Glu Gly Thr Ser Phe Leu Thr Gly Ile Ile Ser Trp Gly
    210                 215                 220

Glu Glu Cys Ala Ala Met Met Lys Gly Lys Tyr Gly Ile Tyr Thr Lys
225                 230                 235                 240

Val Ser Arg Tyr Val Asn Trp Ile Lys Glu Lys Thr Lys Leu Thr
                245                 250                 255

<210> SEQ ID NO 7
<211> LENGTH: 57
<212> TYPE: PRT
<213> ORGANISM: Homo sapiens

<400> SEQUENCE: 7

Met Thr Cys Asn Ile Lys Asn Gly Arg Cys Glu Gln Phe Cys Lys Asn
1               5                   10                  15

Ser Ala Asp Asn Lys Val Val Cys Ser Cys Thr Glu Gly Tyr Arg Leu
                20                  25                  30

Ala Glu Asn Gln Lys Ser Cys Glu Pro Ala Val Pro Phe Pro Cys Gly
            35                  40                  45
```

```
Arg Val Ser Val Ser Gln Thr Ser Lys
    50                  55
```

<210> SEQ ID NO 8
<211> LENGTH: 496
<212> TYPE: PRT
<213> ORGANISM: Homo sapiens

<400> SEQUENCE: 8

```
Glu Phe Ala Arg Pro Cys Ile Pro Lys Ser Phe Gly Tyr Ser Ser Val
1               5                   10                  15

Val Cys Val Cys Asn Ala Thr Tyr Cys Asp Ser Phe Asp Pro Pro Ala
                20                  25                  30

Leu Gly Thr Phe Ser Arg Tyr Glu Ser Thr Arg Ser Gly Arg Arg Met
            35                  40                  45

Glu Leu Ser Met Gly Pro Ile Gln Ala Asn His Thr Gly Thr Gly Leu
    50                  55                  60

Leu Leu Thr Leu Gln Pro Glu Gln Lys Phe Gln Lys Val Lys Gly Phe
65                  70                  75                  80

Gly Gly Ala Met Thr Asp Ala Ala Ala Leu Asn Ile Leu Ala Leu Ser
                85                  90                  95

Pro Pro Ala Gln Asn Leu Leu Leu Lys Ser Tyr Phe Ser Glu Glu Gly
            100                 105                 110

Ile Gly Tyr Asn Ile Ile Arg Val Pro Met Ala Ser Cys Asp Phe Ser
            115                 120                 125

Ile Arg Thr Tyr Thr Tyr Ala Asp Thr Pro Asp Asp Phe Gln Leu His
    130                 135                 140

Asn Phe Ser Leu Pro Glu Glu Asp Thr Lys Leu Lys Ile Pro Leu Ile
145                 150                 155                 160

His Arg Ala Leu Gln Leu Ala Gln Arg Pro Val Ser Leu Leu Ala Ser
                165                 170                 175

Pro Trp Thr Ser Pro Thr Trp Leu Lys Thr Asn Gly Ala Val Asn Gly
            180                 185                 190

Lys Gly Ser Leu Lys Gly Gln Pro Gly Asp Ile Tyr His Gln Thr Trp
            195                 200                 205

Ala Arg Tyr Phe Val Lys Phe Leu Asp Ala Tyr Ala Glu His Lys Leu
    210                 215                 220

Gln Phe Trp Ala Val Thr Ala Glu Asn Glu Pro Ser Ala Gly Leu Leu
225                 230                 235                 240

Ser Gly Tyr Pro Phe Gln Cys Leu Gly Phe Thr Pro Glu His Gln Arg
                245                 250                 255

Asp Phe Ile Ala Arg Asp Leu Gly Pro Thr Leu Ala Asn Ser Thr His
            260                 265                 270

His Asn Val Arg Leu Leu Met Leu Asp Asp Gln Arg Leu Leu Leu Pro
            275                 280                 285

His Trp Ala Lys Val Val Leu Thr Asp Pro Glu Ala Ala Lys Tyr Val
    290                 295                 300

His Gly Ile Ala Val His Trp Tyr Leu Asp Phe Leu Ala Pro Ala Lys
305                 310                 315                 320

Ala Thr Leu Gly Glu Thr His Arg Leu Phe Pro Asn Thr Met Leu Phe
                325                 330                 335

Ala Ser Glu Ala Cys Val Gly Ser Lys Phe Trp Glu Gln Ser Val Arg
            340                 345                 350

Leu Gly Ser Trp Asp Arg Gly Met Gln Tyr Ser His Ser Ile Ile Thr
            355                 360                 365
```

-continued

Asn Leu Leu Tyr His Val Val Gly Trp Thr Asp Trp Asn Leu Ala Leu
            370                 375                 380

Asn Pro Glu Gly Gly Pro Asn Trp Val Arg Asn Phe Val Asp Ser Pro
385                 390                 395                 400

Ile Ile Val Asp Ile Thr Lys Asp Thr Phe Tyr Lys Gln Pro Met Phe
            405                 410                 415

Tyr His Leu Gly His Phe Ser Lys Phe Ile Pro Glu Gly Ser Gln Arg
            420                 425                 430

Val Gly Leu Val Ala Ser Gln Lys Asn Asp Leu Asp Ala Val Ala Leu
            435                 440                 445

Met His Pro Asp Gly Ser Ala Val Val Val Leu Asn Arg Ser Ser
            450                 455                 460

Lys Asp Val Pro Leu Thr Ile Lys Asp Pro Ala Val Gly Phe Leu Glu
465                 470                 475                 480

Thr Ile Ser Pro Gly Tyr Ser Ile His Thr Tyr Leu Trp His Arg Gln
            485                 490                 495

<210> SEQ ID NO 9
<211> LENGTH: 390
<212> TYPE: PRT
<213> ORGANISM: Homo sapiens

<400> SEQUENCE: 9

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
            35                  40                  45

Gly Trp Lys Asp Ala Gly Tyr Glu Tyr Leu Cys Ile Asp Asp Cys Trp
        50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
            85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
            130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
            165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
            195                 200                 205

Lys Ser Ile Leu Asp Trp Thr Ser Phe Asn Gln Glu Arg Ile Val Asp
            210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp

```
            245                 250                 255
Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
            275                 280                 285

Asn Gln Asp Pro Leu Gly Lys Gln Gly Tyr Gln Leu Arg Gln Gly Asp
            290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
            325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
            370                 375                 380

Gln Leu Glu Asn Thr Met
385                 390

<210> SEQ ID NO 10
<211> LENGTH: 479
<212> TYPE: PRT
<213> ORGANISM: Homo sapiens

<400> SEQUENCE: 10

Arg Pro Pro Asn Ile Val Leu Ile Phe Ala Asp Asp Leu Gly Tyr Gly
1               5                   10                  15

Asp Leu Gly Cys Tyr Gly His Pro Ser Ser Thr Thr Pro Asn Leu Asp
            20                  25                  30

Gln Leu Ala Ala Gly Gly Leu Arg Phe Thr Asp Phe Tyr Val Pro Val
            35                  40                  45

Ser Leu Pro Ser Arg Ala Ala Leu Leu Thr Gly Arg Leu Pro Val Arg
        50                  55                  60

Met Gly Met Tyr Pro Gly Val Leu Val Pro Ser Ser Arg Gly Gly Leu
65                  70                  75                  80

Pro Leu Glu Glu Val Thr Val Ala Glu Val Leu Ala Ala Arg Gly Tyr
                85                  90                  95

Leu Thr Gly Met Ala Gly Lys Trp His Leu Gly Val Gly Pro Glu Gly
            100                 105                 110

Ala Phe Leu Pro Pro His Gln Gly Phe His Arg Phe Leu Gly Ile Pro
        115                 120                 125

Tyr Ser His Asp Gln Gly Pro Cys Gln Asn Leu Thr Cys Phe Pro Pro
    130                 135                 140

Ala Thr Pro Cys Asp Gly Gly Cys Asp Gln Gly Leu Val Pro Ile Pro
145                 150                 155                 160

Leu Leu Ala Asn Leu Ser Val Glu Ala Gln Pro Pro Trp Leu Pro Gly
                165                 170                 175

Leu Glu Ala Arg Tyr Met Ala Phe Ala His Asp Leu Met Ala Asp Ala
            180                 185                 190

Gln Arg Gln Asp Arg Pro Phe Phe Leu Tyr Tyr Ala Ser His His Thr
        195                 200                 205

His Tyr Pro Gln Phe Ser Gly Gln Ser Phe Ala Glu Arg Ser Gly Arg
    210                 215                 220
```

Gly Pro Phe Gly Asp Ser Leu Met Glu Leu Asp Ala Ala Val Gly Thr
225                 230                 235                 240

Leu Met Thr Ala Ile Gly Asp Leu Gly Leu Leu Glu Glu Thr Leu Val
            245                 250                 255

Ile Phe Thr Ala Asp Asn Gly Pro Glu Thr Met Arg Met Ser Arg Gly
            260                 265                 270

Gly Cys Ser Gly Leu Leu Arg Cys Gly Lys Gly Thr Thr Tyr Glu Gly
        275                 280                 285

Gly Val Arg Glu Pro Ala Leu Ala Phe Trp Pro Gly His Ile Ala Pro
    290                 295                 300

Gly Val Thr His Glu Leu Ala Ser Ser Leu Asp Leu Leu Pro Thr Leu
305                 310                 315                 320

Ala Ala Leu Ala Gly Ala Pro Leu Pro Asn Val Thr Leu Asp Gly Phe
            325                 330                 335

Asp Leu Ser Pro Leu Leu Gly Thr Gly Lys Ser Pro Arg Gln Ser
            340                 345                 350

Leu Phe Phe Tyr Pro Ser Tyr Pro Asp Glu Val Arg Gly Val Phe Ala
        355                 360                 365

Val Arg Thr Gly Lys Tyr Lys Ala His Phe Phe Thr Gln Gly Ser Ala
    370                 375                 380

His Ser Asp Thr Thr Ala Asp Pro Ala Cys His Ala Ser Ser Ser Leu
385                 390                 395                 400

Thr Ala His Glu Pro Pro Leu Leu Tyr Asp Leu Ser Lys Asp Pro Gly
            405                 410                 415

Glu Asn Tyr Asn Leu Leu Gly Ala Thr Pro Glu Val Leu Gln Ala Leu
        420                 425                 430

Lys Gln Leu Gln Leu Leu Lys Ala Gln Leu Asp Ala Ala Val Thr Phe
    435                 440                 445

Gly Pro Ser Gln Val Ala Arg Gly Glu Asp Pro Ala Leu Gln Ile Cys
450                 455                 460

Cys His Pro Gly Cys Thr Pro Arg Pro Ala Cys Cys His Cys Pro
465                 470                 475

<210> SEQ ID NO 11
<211> LENGTH: 474
<212> TYPE: PRT
<213> ORGANISM: Homo sapiens

<400> SEQUENCE: 11

Ser Arg Pro Pro His Leu Val Phe Leu Leu Ala Asp Asp Leu Gly Trp
1               5                   10                  15

Asn Asp Val Gly Phe His Gly Ser Arg Ile Arg Thr Pro His Leu Asp
            20                  25                  30

Ala Leu Ala Ala Gly Gly Val Leu Leu Asp Asn Tyr Tyr Thr Gln Pro
        35                  40                  45

Leu Thr Pro Ser Arg Ser Gln Leu Leu Thr Gly Arg Tyr Gln Ile Arg
    50                  55                  60

Thr Gly Leu Gln His Gln Ile Ile Trp Pro Cys Gln Pro Ser Cys Val
65                  70                  75                  80

Pro Leu Asp Glu Lys Leu Leu Pro Gln Leu Leu Lys Glu Ala Gly Tyr
                85                  90                  95

Thr Thr His Met Val Gly Lys Trp His Leu Gly Met Tyr Arg Lys Glu
            100                 105                 110

Cys Leu Pro Thr Arg Arg Gly Phe Asp Thr Tyr Phe Gly Tyr Leu Leu
        115                 120                 125

Gly Ser Glu Asp Tyr Tyr Ser His Glu Arg Cys Thr Leu Ile Asp Ala
            130                 135                 140

Leu Asn Val Thr Arg Cys Ala Leu Asp Phe Arg Asp Gly Glu Glu Val
145                 150                 155                 160

Ala Thr Gly Tyr Lys Asn Met Tyr Ser Thr Asn Ile Phe Thr Lys Arg
                165                 170                 175

Ala Ile Ala Leu Ile Thr Asn His Pro Pro Glu Lys Pro Leu Phe Leu
            180                 185                 190

Tyr Leu Ala Leu Gln Ser Val His Glu Pro Leu Gln Val Pro Glu Glu
        195                 200                 205

Tyr Leu Lys Pro Tyr Asp Phe Ile Gln Asp Lys Asn Arg His His Tyr
210                 215                 220

Ala Gly Met Val Ser Leu Met Asp Glu Ala Val Gly Asn Val Thr Ala
225                 230                 235                 240

Ala Leu Lys Ser Ser Gly Leu Trp Asn Asn Thr Val Phe Ile Phe Ser
                245                 250                 255

Thr Asp Asn Gly Gly Gln Thr Leu Ala Gly Gly Asn Asn Trp Pro Leu
            260                 265                 270

Arg Gly Arg Lys Trp Ser Leu Trp Glu Gly Gly Val Arg Gly Val Gly
        275                 280                 285

Phe Val Ala Ser Pro Leu Leu Lys Gln Lys Gly Val Lys Asn Arg Glu
290                 295                 300

Leu Ile His Ile Ser Asp Trp Leu Pro Thr Leu Val Lys Leu Ala Arg
305                 310                 315                 320

Gly His Thr Asn Gly Thr Lys Pro Leu Asp Gly Phe Asp Val Trp Lys
                325                 330                 335

Thr Ile Ser Glu Gly Ser Pro Ser Pro Arg Ile Glu Leu Leu His Asn
            340                 345                 350

Ile Asp Pro Asn Phe Val Asp Ser Ser Pro Cys Ser Ala Phe Asn Thr
        355                 360                 365

Ser Val His Ala Ala Ile Arg His Gly Asn Trp Lys Leu Leu Thr Gly
370                 375                 380

Tyr Pro Gly Cys Gly Tyr Trp Phe Pro Pro Ser Gln Tyr Asn Val
385                 390                 395                 400

Ser Glu Ile Pro Ser Ser Asp Pro Pro Thr Lys Thr Leu Trp Leu Phe
                405                 410                 415

Asp Ile Asp Arg Asp Pro Glu Glu Arg His Asp Leu Ser Arg Glu Tyr
            420                 425                 430

Pro His Ile Val Thr Lys Leu Leu Ser Arg Leu Gln Phe Tyr His Lys
        435                 440                 445

His Ser Val Pro Val Tyr Phe Pro Ala Gln Asp Pro Arg Cys Asp Pro
450                 455                 460

Lys Ala Thr Gly Val Trp Gly Pro Trp Met
465                 470

<210> SEQ ID NO 12
<211> LENGTH: 492
<212> TYPE: PRT
<213> ORGANISM: Homo sapiens

<400> SEQUENCE: 12

Leu Trp Pro Trp Pro Gln Asn Phe Gln Thr Ser Asp Gln Arg Tyr Val
1               5                   10                  15

Leu Tyr Pro Asn Asn Phe Gln Phe Gln Tyr Asp Val Ser Ser Ala Ala

```
            20                  25                  30
Gln Pro Gly Cys Ser Val Leu Asp Glu Ala Phe Gln Arg Tyr Arg Asp
            35                  40                  45
Leu Leu Phe Gly Thr Leu Glu Lys Asn Val Leu Val Ser Val Val
50                      55                  60
Thr Pro Gly Cys Asn Gln Leu Pro Thr Leu Glu Ser Val Glu Asn Tyr
65                  70                  75                  80
Thr Leu Thr Ile Asn Asp Asp Gln Cys Leu Leu Ser Glu Thr Val
                85                  90                  95
Trp Gly Ala Leu Arg Gly Leu Glu Thr Phe Ser Gln Leu Val Trp Lys
                100                 105                 110
Ser Ala Glu Gly Thr Phe Phe Ile Asn Lys Thr Glu Ile Glu Asp Phe
            115                 120                 125
Pro Arg Phe Pro His Arg Gly Leu Leu Leu Asp Thr Ser Arg His Tyr
            130                 135                 140
Leu Pro Leu Ser Ser Ile Leu Asp Thr Leu Asp Val Met Ala Tyr Asn
145                 150                 155                 160
Lys Leu Asn Val Phe His Trp His Leu Val Asp Asp Pro Ser Phe Pro
                165                 170                 175
Tyr Glu Ser Phe Thr Phe Pro Glu Leu Met Arg Lys Gly Ser Tyr Asn
            180                 185                 190
Pro Val Thr His Ile Tyr Thr Ala Gln Asp Val Lys Glu Val Ile Glu
            195                 200                 205
Tyr Ala Arg Leu Arg Gly Ile Arg Val Leu Ala Glu Phe Asp Thr Pro
210                 215                 220
Gly His Thr Leu Ser Trp Gly Pro Gly Ile Pro Gly Leu Leu Thr Pro
225                 230                 235                 240
Cys Tyr Ser Gly Ser Glu Pro Ser Gly Thr Phe Gly Pro Val Asn Pro
                245                 250                 255
Ser Leu Asn Asn Thr Tyr Glu Phe Met Ser Thr Phe Phe Leu Glu Val
                260                 265                 270
Ser Ser Val Phe Pro Asp Phe Tyr Leu His Leu Gly Gly Asp Glu Val
            275                 280                 285
Asp Phe Thr Cys Trp Lys Ser Asn Pro Glu Ile Gln Asp Phe Met Arg
            290                 295                 300
Lys Lys Gly Phe Gly Glu Asp Phe Lys Gln Leu Glu Ser Phe Tyr Ile
305                 310                 315                 320
Gln Thr Leu Leu Asp Ile Val Ser Ser Tyr Gly Lys Gly Tyr Val Val
                325                 330                 335
Trp Gln Glu Val Phe Asp Asn Lys Val Lys Ile Gln Pro Asp Thr Ile
                340                 345                 350
Ile Gln Val Trp Arg Glu Asp Ile Pro Val Asn Tyr Met Lys Glu Leu
            355                 360                 365
Glu Leu Val Thr Lys Ala Gly Phe Arg Ala Leu Leu Ser Ala Pro Trp
            370                 375                 380
Tyr Leu Asn Arg Ile Ser Tyr Gly Pro Asp Trp Lys Asp Phe Tyr Val
385                 390                 395                 400
Val Glu Pro Leu Ala Phe Glu Gly Thr Pro Glu Gln Lys Ala Leu Val
                405                 410                 415
Ile Gly Gly Glu Ala Cys Met Trp Gly Glu Tyr Val Asp Asn Thr Asn
                420                 425                 430
Leu Val Pro Arg Leu Trp Pro Arg Ala Gly Ala Val Ala Glu Arg Leu
            435                 440                 445
```

```
Trp Ser Asn Lys Leu Thr Ser Asp Leu Thr Phe Ala Tyr Glu Arg Leu
450                 455                 460

Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
                485                 490

<210> SEQ ID NO 13
<211> LENGTH: 492
<212> TYPE: PRT
<213> ORGANISM: Homo sapiens

<400> SEQUENCE: 13

Leu Trp Pro Trp Pro Gln Asn Phe Gln Thr Ser Asp Gln Arg Tyr Val
1               5                   10                  15

Leu Tyr Pro Asn Asn Phe Gln Phe Gln Tyr Asp Val Ser Ser Ala Ala
                20                  25                  30

Gln Pro Gly Cys Ser Val Leu Asp Glu Ala Phe Gln Arg Tyr Arg Asp
            35                  40                  45

Leu Leu Phe Gly Thr Leu Glu Lys Asn Val Leu Val Ser Val Val
50                  55                  60

Thr Pro Gly Cys Asn Gln Leu Pro Thr Leu Glu Ser Val Glu Asn Tyr
65                  70                  75                  80

Thr Leu Thr Ile Asn Asp Asp Gln Cys Leu Leu Ser Glu Thr Val
                85                  90                  95

Trp Gly Ala Leu Arg Gly Leu Glu Thr Phe Ser Gln Leu Val Trp Lys
                100                 105                 110

Ser Ala Glu Gly Thr Phe Phe Ile Asn Lys Thr Glu Ile Glu Asp Phe
            115                 120                 125

Pro Arg Phe Pro His Arg Gly Leu Leu Leu Asp Thr Ser Arg His Tyr
130                 135                 140

Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                165                 170                 175

Tyr Glu Ser Phe Thr Phe Pro Glu Leu Met Arg Lys Gly Ser Tyr Asn
            180                 185                 190

Pro Val Thr His Ile Tyr Thr Ala Gln Asp Val Lys Glu Val Ile Glu
            195                 200                 205

Tyr Ala Arg Leu Arg Gly Ile Arg Val Leu Ala Glu Phe Asp Thr Pro
210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                245                 250                 255

Ser Leu Asn Asn Thr Tyr Glu Phe Met Ser Thr Phe Phe Leu Glu Val
            260                 265                 270

Ser Ser Val Phe Pro Asp Phe Tyr Leu His Leu Gly Gly Asp Glu Val
            275                 280                 285

Asp Phe Thr Cys Trp Lys Ser Asn Pro Glu Ile Gln Asp Phe Met Arg
            290                 295                 300

Lys Lys Gly Phe Gly Glu Asp Phe Lys Gln Leu Glu Ser Phe Tyr Ile
305                 310                 315                 320

Gln Thr Leu Leu Asp Ile Val Ser Ser Tyr Gly Lys Gly Tyr Val Val
```

```
                    325                 330                 335
Trp Gln Glu Val Phe Asp Asn Lys Val Lys Ile Gln Pro Asp Thr Ile
                340                 345                 350
Ile Gln Val Trp Arg Glu Asp Ile Pro Val Asn Tyr Met Lys Glu Leu
                355                 360                 365
Glu Leu Val Thr Lys Ala Gly Phe Arg Ala Leu Leu Ser Ala Pro Trp
            370                 375                 380
Tyr Leu Asn Arg Ile Ser Tyr Gly Pro Asp Trp Lys Asp Phe Tyr Val
385                 390                 395                 400
Val Glu Pro Leu Ala Phe Glu Gly Thr Pro Glu Gln Lys Ala Leu Val
                405                 410                 415
Ile Gly Gly Glu Ala Cys Met Trp Gly Glu Tyr Val Asp Asn Thr Asn
                420                 425                 430
Leu Val Pro Arg Leu Trp Pro Arg Ala Gly Ala Val Ala Glu Arg Leu
            435                 440                 445
Trp Ser Asn Lys Leu Thr Ser Asp Leu Thr Phe Ala Tyr Glu Arg Leu
            450                 455                 460
Ser His Phe Arg Cys Glu Leu Leu Arg Arg Gly Val Gln Ala Gln Pro
465                 470                 475                 480
Leu Asn Val Gly Phe Cys Glu Gln Glu Phe Glu Gln
                485                 490

<210> SEQ ID NO 14
<211> LENGTH: 480
<212> TYPE: PRT
<213> ORGANISM: Homo sapiens

<400> SEQUENCE: 14

Pro Ala Leu Trp Pro Leu Pro Leu Ser Val Lys Met Thr Pro Asn Leu
1               5                   10                  15
Leu His Leu Ala Pro Glu Asn Phe Tyr Ile Ser His Ser Pro Asn Ser
                20                  25                  30
Thr Ala Gly Pro Ser Cys Thr Leu Leu Glu Glu Ala Phe Arg Arg Tyr
            35                  40                  45
His Gly Tyr Ile Phe Gly Thr Gln Val Gln Gln Leu Leu Val Ser Ile
        50                  55                  60
Thr Leu Gln Ser Glu Cys Asp Ala Phe Pro Asn Ile Ser Ser Asp Glu
65                  70                  75                  80
Ser Tyr Thr Leu Leu Val Lys Glu Pro Val Ala Val Leu Lys Ala Asn
                85                  90                  95
Arg Val Trp Gly Ala Leu Arg Gly Leu Glu Thr Phe Ser Gln Leu Val
                100                 105                 110
Tyr Gln Asp Ser Tyr Gly Thr Phe Thr Ile Asn Glu Ser Thr Ile Ile
            115                 120                 125
Asp Ser Pro Arg Phe Ser His Arg Gly Ile Leu Ile Asp Thr Ser Arg
        130                 135                 140
His Tyr Leu Pro Val Lys Ile Ile Leu Lys Thr Leu Asp Ala Met Ala
145                 150                 155                 160
Phe Asn Lys Phe Asn Val Leu His Trp His Ile Val Asp Asp Gln Ser
                165                 170                 175
Phe Pro Tyr Gln Ser Ile Thr Phe Pro Glu Leu Ser Asn Lys Gly Ser
                180                 185                 190
Tyr Ser Leu Ser His Val Tyr Thr Pro Asn Asp Val Arg Met Val Ile
            195                 200                 205
```

```
Glu Tyr Ala Arg Leu Arg Gly Ile Arg Val Leu Pro Glu Phe Asp Thr
    210                 215                 220
Pro Gly His Thr Leu Ser Trp Gly Lys Gly Gln Lys Asp Leu Leu Thr
225                 230                 235                 240
Pro Cys Tyr Ser Asp Ser Phe Gly Pro Ile Asn Pro Thr Leu Asn Thr
                245                 250                 255
Thr Tyr Ser Phe Leu Thr Thr Phe Phe Lys Glu Ile Ser Glu Val Phe
            260                 265                 270
Pro Asp Gln Phe Ile His Leu Gly Gly Asp Glu Val Glu Phe Lys Cys
        275                 280                 285
Trp Glu Ser Asn Pro Lys Ile Gln Asp Phe Met Arg Gln Lys Gly Phe
290                 295                 300
Gly Thr Asp Phe Lys Lys Leu Glu Ser Phe Tyr Ile Gln Lys Val Leu
305                 310                 315                 320
Asp Ile Ile Ala Thr Ile Asn Lys Gly Ser Ile Val Trp Gln Glu Val
                325                 330                 335
Phe Asp Asp Lys Ala Lys Leu Ala Pro Gly Thr Ile Val Glu Val Trp
            340                 345                 350
Lys Asp Ser Ala Tyr Pro Glu Glu Leu Ser Arg Val Thr Ala Ser Gly
        355                 360                 365
Phe Pro Val Ile Leu Ser Ala Pro Trp Tyr Leu Asp Leu Ile Ser Tyr
370                 375                 380
Gly Gln Asp Trp Arg Lys Tyr Tyr Lys Val Glu Pro Leu Asp Phe Gly
385                 390                 395                 400
Gly Thr Gln Lys Gln Lys Gln Leu Phe Ile Gly Gly Glu Ala Cys Leu
                405                 410                 415
Trp Gly Glu Tyr Val Asp Ala Thr Asn Leu Thr Pro Arg Leu Trp Pro
            420                 425                 430
Arg Ala Ser Ala Val Gly Glu Arg Leu Trp Ser Ser Lys Asp Val Arg
        435                 440                 445
Asp Met Asp Asp Ala Tyr Asp Arg Leu Thr Arg His Arg Cys Arg Met
450                 455                 460
Val Glu Arg Gly Ile Ala Ala Gln Pro Leu Tyr Ala Gly Tyr Cys Asn
465                 470                 475                 480

<210> SEQ ID NO 15
<211> LENGTH: 481
<212> TYPE: PRT
<213> ORGANISM: Homo sapiens

<400> SEQUENCE: 15

Pro Ala Leu Trp Pro Leu Pro Leu Ser Val Lys Met Thr Pro Asn Leu
1               5                   10                  15
Leu His Leu Ala Pro Glu Asn Phe Tyr Ile Ser His Ser Pro Asn Ser
            20                  25                  30
Thr Ala Gly Pro Ser Cys Thr Leu Leu Glu Glu Ala Phe Arg Arg Tyr
        35                  40                  45
His Gly Tyr Ile Phe Gly Thr Gln Val Gln Gln Leu Leu Val Ser Ile
    50                  55                  60
Thr Leu Gln Ser Glu Cys Asp Ala Phe Pro Asn Ile Ser Ser Asp Glu
65                  70                  75                  80
Ser Tyr Thr Leu Leu Val Lys Glu Pro Val Ala Val Leu Lys Ala Asn
            85                  90                  95
Arg Val Trp Gly Ala Leu Arg Gly Leu Glu Thr Phe Ser Gln Leu Val
        100                 105                 110
```

Tyr Gln Asp Ser Tyr Gly Thr Phe Thr Ile Asn Glu Ser Thr Ile Ile
            115                 120                 125

Asp Ser Pro Arg Phe Ser His Arg Gly Ile Leu Ile Asp Thr Ser Arg
        130                 135                 140

His Tyr Leu Pro Val Lys Ile Ile Leu Lys Thr Leu Asp Ala Met Ala
145                 150                 155                 160

Phe Asn Lys Phe Asn Val Leu His Trp His Ile Val Asp Asp Gln Ser
                165                 170                 175

Phe Pro Tyr Gln Ser Ile Thr Phe Pro Glu Leu Ser Asn Lys Gly Ser
            180                 185                 190

Tyr Ser Leu Ser His Val Tyr Thr Pro Asn Asp Val Arg Met Val Ile
        195                 200                 205

Glu Tyr Ala Arg Leu Arg Gly Ile Arg Val Leu Pro Glu Phe Asp Thr
    210                 215                 220

Pro Gly His Thr Leu Ser Trp Gly Lys Gly Gln Lys Asp Leu Leu Thr
225                 230                 235                 240

Pro Cys Tyr Ser Leu Asp Ser Phe Gly Pro Ile Asn Pro Thr Leu Asn
                245                 250                 255

Thr Thr Tyr Ser Phe Leu Thr Thr Phe Phe Lys Glu Ile Ser Glu Val
            260                 265                 270

Phe Pro Asp Gln Phe Ile His Leu Gly Gly Asp Glu Val Glu Phe Lys
        275                 280                 285

Cys Trp Glu Ser Asn Pro Lys Ile Gln Asp Phe Met Arg Gln Lys Gly
    290                 295                 300

Phe Gly Thr Asp Phe Lys Lys Leu Glu Ser Phe Tyr Ile Gln Lys Val
305                 310                 315                 320

Leu Asp Ile Ile Ala Thr Ile Asn Lys Gly Ser Ile Val Trp Gln Glu
                325                 330                 335

Val Phe Asp Asp Lys Ala Lys Leu Ala Pro Gly Thr Ile Val Glu Val
            340                 345                 350

Trp Lys Asp Ser Ala Tyr Pro Glu Glu Leu Ser Arg Val Thr Ala Ser
        355                 360                 365

Gly Phe Pro Val Ile Leu Ser Ala Pro Trp Tyr Leu Asp Leu Ile Ser
    370                 375                 380

Tyr Gly Gln Asp Trp Arg Lys Tyr Tyr Lys Val Glu Pro Leu Asp Phe
385                 390                 395                 400

Gly Gly Thr Gln Lys Gln Lys Gln Leu Phe Ile Gly Gly Glu Ala Cys
                405                 410                 415

Leu Trp Gly Glu Tyr Val Asp Ala Thr Asn Leu Thr Pro Arg Leu Trp
            420                 425                 430

Pro Arg Ala Ser Ala Val Gly Glu Arg Leu Trp Ser Ser Lys Asp Val
        435                 440                 445

Arg Asp Met Asp Asp Ala Tyr Asp Arg Leu Thr Arg His Arg Cys Arg
    450                 455                 460

Met Val Glu Arg Gly Ile Ala Ala Gln Pro Leu Tyr Ala Gly Tyr Cys
465                 470                 475                 480

Asn

<210> SEQ ID NO 16
<211> LENGTH: 492
<212> TYPE: PRT
<213> ORGANISM: Homo sapiens

<400> SEQUENCE: 16

```
Leu Trp Pro Trp Pro Gln Asn Phe Gln Thr Ser Asp Gln Arg Tyr Val
 1               5                  10                  15

Leu Tyr Pro Asn Asn Phe Gln Phe Gln Tyr Asp Val Ser Ser Ala Ala
                20                  25                  30

Gln Pro Gly Cys Ser Val Leu Asp Glu Ala Phe Gln Arg Tyr Arg Asp
                35                  40                  45

Leu Leu Phe Gly Thr Leu Glu Lys Asn Val Leu Val Val Ser Val Val
            50                  55                  60

Thr Pro Gly Cys Asn Gln Leu Pro Thr Leu Glu Ser Val Glu Asn Tyr
65                  70                  75                  80

Thr Leu Thr Ile Asn Asp Asp Gln Cys Leu Leu Leu Ser Glu Thr Val
                    85                  90                  95

Trp Gly Ala Leu Arg Gly Leu Glu Thr Phe Ser Gln Leu Val Trp Lys
                100                 105                 110

Ser Ala Glu Gly Thr Phe Phe Ile Asn Lys Thr Glu Ile Glu Asp Phe
            115                 120                 125

Pro Arg Phe Pro His Arg Gly Leu Leu Leu Asp Thr Ser Arg His Tyr
            130                 135                 140

Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                    165                 170                 175

Tyr Glu Ser Phe Thr Phe Pro Glu Leu Met Arg Lys Gly Ser Tyr Asn
                180                 185                 190

Pro Val Thr His Ile Tyr Thr Ala Gln Asp Val Lys Glu Val Ile Glu
                    195                 200                 205

Tyr Ala Arg Leu Arg Gly Ile Arg Val Leu Ala Glu Phe Asp Thr Pro
210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                245                 250                 255

Ser Leu Asn Asn Thr Tyr Glu Phe Met Ser Thr Phe Phe Leu Glu Val
                260                 265                 270

Ser Ser Val Phe Pro Asp Phe Tyr Leu His Leu Gly Gly Asp Glu Val
                275                 280                 285

Asp Phe Thr Cys Trp Lys Ser Asn Pro Glu Ile Gln Asp Phe Met Arg
                290                 295                 300

Lys Lys Gly Phe Gly Glu Asp Phe Lys Gln Leu Glu Ser Phe Tyr Ile
305                 310                 315                 320

Gln Thr Leu Leu Asp Ile Val Ser Ser Tyr Gly Lys Gly Tyr Val Val
                    325                 330                 335

Trp Gln Glu Val Phe Asp Asn Lys Val Lys Ile Gln Pro Asp Thr Ile
                340                 345                 350

Ile Gln Val Trp Arg Glu Asp Ile Pro Val Asn Tyr Met Lys Glu Leu
                355                 360                 365

Glu Leu Val Thr Lys Ala Gly Phe Arg Ala Leu Leu Ser Ala Pro Trp
370                 375                 380

Tyr Leu Asn Arg Ile Ser Tyr Gly Pro Asp Trp Lys Asp Phe Tyr Val
385                 390                 395                 400

Val Glu Pro Leu Ala Phe Glu Gly Thr Pro Glu Gln Lys Ala Leu Val
                    405                 410                 415
```

```
Ile Gly Gly Glu Ala Cys Met Trp Gly Glu Tyr Val Asp Asn Thr Asn
                420                 425                 430

Leu Val Pro Arg Leu Trp Pro Arg Ala Gly Ala Val Ala Glu Arg Leu
            435                 440                 445

Trp Ser Asn Lys Leu Thr Ser Asp Leu Thr Phe Ala Tyr Glu Arg Leu
450                 455                 460

Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
                485                 490

<210> SEQ ID NO 17
<211> LENGTH: 307
<212> TYPE: PRT
<213> ORGANISM: Homo sapiens

<400> SEQUENCE: 17

Val Pro Trp Phe Pro Arg Thr Ile Gln Glu Leu Asp Arg Phe Ala Asn
1               5                   10                  15

Gln Ile Leu Ser Tyr Gly Ala Glu Leu Asp Ala Asp His Pro Gly Phe
            20                  25                  30

Lys Asp Pro Val Tyr Arg Ala Arg Arg Lys Gln Phe Ala Asp Ile Ala
        35                  40                  45

Tyr Asn Tyr Arg His Gly Gln Pro Ile Pro Arg Val Glu Tyr Met Glu
    50                  55                  60

Glu Glu Lys Lys Thr Trp Gly Thr Val Phe Lys Thr Leu Lys Ser Leu
65                  70                  75                  80

Tyr Lys Thr His Ala Cys Tyr Glu Tyr Asn His Ile Phe Pro Leu Leu
                85                  90                  95

Glu Lys Tyr Cys Gly Phe His Glu Asp Asn Ile Pro Gln Leu Glu Asp
            100                 105                 110

Val Ser Gln Phe Leu Gln Thr Cys Thr Gly Phe Arg Leu Arg Pro Val
        115                 120                 125

Ala Gly Leu Leu Ser Ser Arg Asp Phe Leu Gly Gly Leu Ala Phe Arg
    130                 135                 140

Val Phe His Cys Thr Gln Tyr Ile Arg His Gly Ser Lys Pro Met Tyr
145                 150                 155                 160

Thr Pro Glu Pro Asp Ile Cys His Glu Leu Leu Gly His Val Pro Leu
                165                 170                 175

Phe Ser Asp Arg Ser Phe Ala Gln Phe Ser Gln Glu Ile Gly Leu Ala
            180                 185                 190

Ser Leu Gly Ala Pro Asp Glu Tyr Ile Glu Lys Leu Ala Thr Ile Tyr
        195                 200                 205

Trp Phe Thr Val Glu Phe Gly Leu Cys Lys Gln Gly Asp Ser Ile Lys
    210                 215                 220

Ala Tyr Gly Ala Gly Leu Leu Ser Ser Phe Gly Glu Leu Gln Tyr Cys
225                 230                 235                 240

Leu Ser Glu Lys Pro Lys Leu Leu Pro Leu Glu Leu Glu Lys Thr Ala
                245                 250                 255

Ile Gln Asn Tyr Thr Val Thr Glu Phe Gln Pro Leu Tyr Tyr Val Ala
            260                 265                 270

Glu Ser Phe Asn Asp Ala Lys Glu Lys Val Arg Asn Phe Ala Ala Thr
        275                 280                 285

Ile Pro Arg Pro Phe Ser Val Arg Tyr Asp Pro Tyr Thr Gln Arg Ile
    290                 295                 300
```

Glu Val Leu
305

<210> SEQ ID NO 18
<211> LENGTH: 452
<212> TYPE: PRT
<213> ORGANISM: Homo sapiens

<400> SEQUENCE: 18

```
Ala Pro Asp Gln Asp Glu Ile Gln Arg Leu Pro Gly Leu Ala Lys Gln
  1               5                  10                  15

Pro Ser Phe Arg Gln Tyr Ser Gly Tyr Leu Lys Ser Ser Gly Ser Lys
             20                  25                  30

His Leu His Tyr Trp Phe Val Glu Ser Gln Lys Asp Pro Glu Asn Ser
         35                  40                  45

Pro Val Val Leu Trp Leu Asn Gly Gly Pro Gly Cys Ser Ser Leu Asp
     50                  55                  60

Gly Leu Leu Thr Glu His Gly Pro Phe Leu Val Gln Pro Asp Gly Val
 65                  70                  75                  80

Thr Leu Glu Tyr Asn Pro Tyr Ser Trp Asn Leu Ile Ala Asn Val Leu
                 85                  90                  95

Tyr Leu Glu Ser Pro Ala Gly Val Gly Phe Ser Tyr Ser Asp Asp Lys
            100                 105                 110

Phe Tyr Ala Thr Asn Asp Thr Glu Val Ala Gln Ser Asn Phe Glu Ala
        115                 120                 125

Leu Gln Asp Phe Phe Arg Leu Phe Pro Glu Tyr Lys Asn Asn Lys Leu
    130                 135                 140

Phe Leu Thr Gly Glu Ser Tyr Ala Gly Ile Tyr Ile Pro Thr Leu Ala
145                 150                 155                 160

Val Leu Val Met Gln Asp Pro Ser Met Asn Leu Gln Gly Leu Ala Val
                165                 170                 175

Gly Asn Gly Leu Ser Ser Tyr Glu Gln Asn Asp Asn Ser Leu Val Tyr
            180                 185                 190

Phe Ala Tyr Tyr His Gly Leu Leu Gly Asn Arg Leu Trp Ser Ser Leu
        195                 200                 205

Gln Thr His Cys Cys Ser Gln Asn Lys Cys Asn Phe Tyr Asp Asn Lys
    210                 215                 220

Asp Leu Glu Cys Val Thr Asn Leu Gln Glu Val Ala Arg Ile Val Gly
225                 230                 235                 240

Asn Ser Gly Leu Asn Ile Tyr Asn Leu Tyr Ala Pro Cys Ala Gly Gly
                245                 250                 255

Val Pro Ser His Phe Arg Tyr Glu Lys Asp Thr Val Val Val Gln Asp
            260                 265                 270

Leu Gly Asn Ile Phe Thr Arg Leu Pro Leu Lys Arg Met Trp His Gln
        275                 280                 285

Ala Leu Leu Arg Ser Gly Asp Lys Val Arg Met Asp Pro Pro Cys Thr
    290                 295                 300

Asn Thr Thr Ala Ala Ser Thr Tyr Leu Asn Asn Pro Tyr Val Arg Lys
305                 310                 315                 320

Ala Leu Asn Ile Pro Glu Gln Leu Pro Gln Trp Asp Met Cys Asn Phe
                325                 330                 335

Leu Val Asn Leu Gln Tyr Arg Arg Leu Tyr Arg Ser Met Asn Ser Gln
            340                 345                 350

Tyr Leu Lys Leu Leu Ser Ser Gln Lys Tyr Gln Ile Leu Leu Tyr Asn
```

```
                355                 360                 365
Gly Asp Val Asp Met Ala Cys Asn Phe Met Gly Asp Glu Trp Phe Val
370                 375                 380

Asp Ser Leu Asn Gln Lys Met Glu Val Gln Arg Arg Pro Trp Leu Val
385                 390                 395                 400

Lys Tyr Gly Asp Ser Gly Glu Gln Ile Ala Gly Phe Val Lys Glu Phe
                405                 410                 415

Ser His Ile Ala Phe Leu Thr Ile Lys Gly Ala Gly His Met Val Pro
                420                 425                 430

Thr Asp Lys Pro Leu Ala Ala Phe Thr Met Phe Ser Arg Phe Leu Asn
                435                 440                 445

Lys Gln Pro Tyr
450

<210> SEQ ID NO 19
<211> LENGTH: 145
<212> TYPE: PRT
<213> ORGANISM: Homo sapiens

<400> SEQUENCE: 19

Leu Pro Gln Ser Phe Leu Leu Lys Cys Leu Glu Gln Val Arg Lys Ile
1               5                   10                  15

Gln Gly Asp Gly Ala Ala Leu Gln Glu Lys Leu Cys Ala Thr Tyr Lys
                20                  25                  30

Leu Cys His Pro Glu Glu Leu Val Leu Leu Gly His Ser Leu Gly Ile
                35                  40                  45

Pro Trp Ala Pro Leu Leu Ala Gly Cys Leu Ser Gln Leu His Ser Gly
            50                  55                  60

Leu Phe Leu Tyr Gln Gly Leu Leu Gln Ala Leu Glu Gly Ile Ser Pro
65                  70                  75                  80

Glu Leu Gly Pro Thr Leu Asp Thr Leu Gln Leu Asp Val Ala Asp Phe
                85                  90                  95

Ala Thr Thr Ile Trp Gln Gln Met Glu Glu Leu Gly Met Met Pro Ala
                100                 105                 110

Phe Ala Ser Ala Phe Gln Arg Arg Ala Gly Gly Val Leu Val Ala Ser
                115                 120                 125

His Leu Gln Ser Phe Leu Glu Val Ser Tyr Arg Val Leu Arg His Leu
                130                 135                 140

Ala
145

<210> SEQ ID NO 20
<211> LENGTH: 105
<212> TYPE: PRT
<213> ORGANISM: Homo sapiens

<400> SEQUENCE: 20

Glu His Val Asn Ala Ile Gln Glu Ala Arg Arg Leu Leu Asn Leu Ser
1               5                   10                  15

Arg Asp Thr Ala Ala Glu Met Asn Glu Thr Val Glu Val Ile Ser Glu
                20                  25                  30

Met Phe Asp Leu Gln Glu Pro Thr Cys Leu Gln Thr Arg Leu Glu Leu
                35                  40                  45

Tyr Lys Gln Gly Leu Arg Gly Ser Leu Thr Lys Leu Lys Gly Pro Leu
            50                  55                  60

Thr Met Met Ala Ser His Tyr Lys Gln His Cys Pro Pro Thr Pro Glu
```

```
            65                  70                  75                  80
Thr Ser Cys Ala Thr Gln Ile Ile Thr Phe Glu Ser Phe Lys Glu Asn
                85                  90                  95

Leu Lys Asp Phe Leu Leu Val Ile Pro
            100                 105

<210> SEQ ID NO 21
<211> LENGTH: 165
<212> TYPE: PRT
<213> ORGANISM: Homo sapiens

<400> SEQUENCE: 21

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
        50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 22
<211> LENGTH: 166
<212> TYPE: PRT
<213> ORGANISM: Homo sapiens

<400> SEQUENCE: 22

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
```

```
                115                 120                 125
Ile Leu His Tyr Leu Lys Ala Lys Glu Tyr Ser His Cys Ala Trp Thr
            130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 23
<211> LENGTH: 242
<212> TYPE: PRT
<213> ORGANISM: Homo sapiens

<400> SEQUENCE: 23

Met Gln Asp Pro Tyr Val Lys Glu Ala Glu Asn Leu Lys Lys Tyr Phe
1               5                   10                  15

Asn Ala Gly His Ser Asp Val Ala Asp Asn Gly Thr Leu Phe Leu Gly
            20                  25                  30

Ile Leu Lys Asn Trp Lys Glu Glu Ser Asp Arg Lys Ile Met Gln Ser
        35                  40                  45

Gln Ile Val Ser Phe Tyr Phe Lys Leu Phe Lys Asn Phe Lys Asp Asp
    50                  55                  60

Gln Ser Ile Gln Lys Ser Val Glu Thr Ile Lys Glu Asp Met Asn Val
65                  70                  75                  80

Lys Phe Phe Asn Ser Asn Lys Lys Arg Asp Asp Phe Glu Lys Leu
                85                  90                  95

Thr Asn Tyr Ser Val Thr Asp Leu Asn Val Gln Arg Lys Ala Ile Asp
                100                 105                 110

Glu Leu Ile Gln Val Met Ala Glu Leu Gly Ala Asn Val Ser Gly Glu
            115                 120                 125

Phe Val Lys Glu Ala Glu Asn Leu Lys Lys Tyr Phe Asn Asp Asn Gly
        130                 135                 140

Thr Leu Phe Leu Gly Ile Leu Lys Asn Trp Lys Glu Glu Ser Asp Arg
145                 150                 155                 160

Lys Ile Met Gln Ser Gln Ile Val Ser Phe Tyr Phe Lys Leu Phe Lys
                165                 170                 175

Asn Phe Lys Asp Asp Gln Ser Ile Gln Lys Ser Val Glu Thr Ile Lys
                180                 185                 190

Glu Asp Met Asn Val Lys Phe Phe Asn Ser Asn Lys Lys Arg Asp Asp
            195                 200                 205

Asp Phe Glu Lys Leu Thr Asn Tyr Ser Val Thr Asp Leu Asn Val Gln
        210                 215                 220

Arg Lys Ala Ile His Glu Leu Ile Gln Val Met Ala Glu Leu Ser Pro
225                 230                 235                 240

Ala Ala

<210> SEQ ID NO 24
<211> LENGTH: 122
<212> TYPE: PRT
<213> ORGANISM: Homo sapiens

<400> SEQUENCE: 24

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30
```

Arg Met Leu Thr Phe Lys Phe Tyr Met Pro Lys Lys Ala Thr Glu Leu
            35                  40                  45

Lys His Leu Gln Cys Leu Glu Glu Leu Lys Pro Leu Glu Glu Val
         50                  55                  60

Leu Asn Leu Ala Gln Asn Phe His Leu Arg Pro Arg Asp Leu Ile Ser
65                  70                  75                  80

Asn Ile Asn Val Ile Val Leu Glu Leu Lys Gly Phe Met Cys Glu Tyr
                    85                  90                  95

Ala Asp Glu Thr Ala Thr Ile Val Glu Phe Leu Asn Arg Trp Ile Thr
                100                 105                 110

Phe Cys Gln Ser Ile Ile Ser Thr Leu Thr
            115                 120

<210> SEQ ID NO 25
<211> LENGTH: 152
<212> TYPE: PRT
<213> ORGANISM: Homo sapiens

<400> SEQUENCE: 25

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
                100                 105                 110

Glu Ser Ala Gln Phe Pro Asn Trp Tyr Ile Ser Thr Ser Gln Ala Glu
            115                 120                 125

Asn Met Pro Val Phe Leu Gly Gly Thr Lys Gly Gly Gln Asp Ile Thr
        130                 135                 140

Asp Phe Thr Met Gln Phe Val Ser
145                 150

<210> SEQ ID NO 26
<211> LENGTH: 148
<212> TYPE: PRT
<213> ORGANISM: Homo sapiens

<400> SEQUENCE: 26

Asp Lys Pro Val Ala His Val Val Ala Asn Pro Gln Ala Glu Gly Gln
1               5                   10                  15

Leu Gln Trp Ser Asn Arg Arg Ala Asn Ala Leu Leu Ala Asn Gly Val
            20                  25                  30

Glu Leu Arg Asp Asn Gln Leu Val Val Pro Ile Glu Gly Leu Phe Leu
        35                  40                  45

Ile Tyr Ser Gln Val Leu Phe Lys Gly Gln Gly Cys Pro Ser Thr His
    50                  55                  60

Val Leu Leu Thr His Thr Ile Ser Arg Ile Ala Val Ser Tyr Gln Thr
65                  70                  75                  80

```
Lys Val Asn Leu Leu Ser Ala Ile Lys Ser Pro Cys Gln Arg Glu Thr
                 85                  90                  95

Pro Glu Gly Ala Glu Ala Lys Pro Trp Tyr Glu Pro Ile Tyr Leu Gly
            100                 105                 110

Gly Val Phe Gln Leu Glu Lys Gly Asp Arg Leu Ser Ala Glu Ile Asn
        115                 120                 125

Arg Pro Asp Tyr Leu Asp Phe Ala Glu Ser Gly Gln Val Tyr Phe Gly
    130                 135                 140

Ile Ile Ala Leu
145

<210> SEQ ID NO 27
<211> LENGTH: 144
<212> TYPE: PRT
<213> ORGANISM: Homo sapiens

<400> SEQUENCE: 27

Lys Pro Ala Ala His Leu Ile Gly Asp Pro Ser Lys Gln Asn Ser Leu
1               5                   10                  15

Leu Trp Arg Ala Asn Thr Asp Arg Ala Phe Leu Gln Asp Gly Phe Ser
            20                  25                  30

Leu Ser Asn Asn Ser Leu Leu Val Pro Thr Ser Gly Ile Tyr Phe Val
        35                  40                  45

Tyr Ser Gln Val Val Phe Ser Gly Lys Ala Tyr Ser Pro Lys Ala Thr
    50                  55                  60

Ser Ser Pro Leu Tyr Leu Ala His Glu Val Gln Leu Phe Ser Ser Gln
65                  70                  75                  80

Tyr Pro Phe His Val Pro Leu Leu Ser Ser Gln Lys Met Val Tyr Pro
                85                  90                  95

Gly Leu Gln Glu Pro Trp Leu His Ser Met Tyr His Gly Ala Ala Phe
            100                 105                 110

Gln Leu Thr Gln Gly Asp Gln Leu Ser Thr His Thr Asp Gly Ile Pro
        115                 120                 125

His Leu Val Leu Ser Pro Ser Thr Val Phe Phe Gly Ala Phe Ala Leu
    130                 135                 140

<210> SEQ ID NO 28
<211> LENGTH: 166
<212> TYPE: PRT
<213> ORGANISM: Homo sapiens

<400> SEQUENCE: 28

Ala Pro Pro Arg Leu Ile Cys Asp Ser Arg Val Leu Glu Arg Tyr Leu
1               5                   10                  15

Leu Glu Ala Lys Glu Ala Glu Lys Ile Thr Thr Gly Cys Ala Glu His
            20                  25                  30

Cys Ser Leu Asn Glu Lys Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Lys Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110
```

```
Gly Ala Gln Lys Glu Ala Ile Ser Asn Ser Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 29
<211> LENGTH: 21
<212> TYPE: PRT
<213> ORGANISM: Homo sapiens

<400> SEQUENCE: 29

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 30
<211> LENGTH: 29
<212> TYPE: PRT
<213> ORGANISM: Homo sapiens

<400> SEQUENCE: 30

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 31
<211> LENGTH: 166
<212> TYPE: PRT
<213> ORGANISM: Homo sapiens

<400> SEQUENCE: 31

Phe Pro Thr Ile Pro Leu Ser Arg Leu Ala Asp Asn Ala Trp Leu Arg
1               5                   10                  15

Ala Asp Arg Leu Asn Gln Leu Ala Phe Asp Thr Tyr Gln Glu Phe Glu
            20                  25                  30

Glu Ala Tyr Ile Pro Lys Glu Gln Ile His Ser Phe Trp Trp Asn Pro
        35                  40                  45

Gln Thr Ser Leu Cys Pro Ser Glu Ser Ile Pro Thr Pro Ser Asn Lys
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Ala Leu Leu Lys Asn Tyr Gly Leu Leu Tyr Cys Phe Asn Lys Asp
    130                 135                 140

Met Ser Lys Val Ser Thr Tyr Leu Arg Thr Val Gln Cys Arg Ser Val
145                 150                 155                 160
```

```
Glu Gly Ser Cys Gly Phe
                165

<210> SEQ ID NO 32
<211> LENGTH: 242
<212> TYPE: PRT
<213> ORGANISM: Homo sapiens

<400> SEQUENCE: 32

Cys His His Arg Ile Cys His Cys Ser Asn Arg Val Phe Leu Cys Gln
1               5                   10                  15

Glu Ser Lys Val Thr Glu Ile Pro Ser Asp Leu Pro Arg Asn Ala Ile
            20                  25                  30

Glu Leu Arg Phe Val Leu Thr Lys Leu Arg Val Ile Gln Lys Gly Ala
        35                  40                  45

Phe Ser Gly Phe Gly Asp Leu Glu Lys Ile Glu Ile Ser Gln Asn Asp
    50                  55                  60

Val Leu Glu Val Ile Glu Ala Asp Val Phe Ser Asn Leu Pro Lys Leu
65                  70                  75                  80

His Glu Ile Arg Ile Glu Lys Ala Asn Asn Leu Leu Tyr Ile Asn Pro
                85                  90                  95

Glu Ala Phe Gln Asn Leu Pro Asn Leu Gln Tyr Leu Leu Ile Ser Asn
            100                 105                 110

Thr Gly Ile Lys His Leu Pro Asp Val His Lys Ile His Ser Leu Gln
        115                 120                 125

Lys Val Leu Leu Asp Ile Gln Asp Asn Ile Asn Ile His Thr Ile Glu
    130                 135                 140

Arg Asn Ser Phe Val Gly Leu Ser Phe Glu Ser Val Ile Leu Trp Leu
145                 150                 155                 160

Asn Lys Asn Gly Ile Gln Glu Ile His Asn Cys Ala Phe Asn Gly Thr
                165                 170                 175

Gln Leu Asp Glu Leu Asn Leu Ser Asp Asn Asn Asn Leu Glu Glu Leu
            180                 185                 190

Pro Asn Asp Val Phe His Gly Ala Ser Gly Pro Val Ile Leu Asp Ile
        195                 200                 205

Ser Arg Thr Arg Ile His Ser Leu Pro Ser Tyr Gly Leu Glu Asn Leu
    210                 215                 220

Lys Lys Leu Arg Ala Arg Ser Thr Tyr Asn Leu Lys Lys Leu Pro Thr
225                 230                 235                 240

Leu Glu

<210> SEQ ID NO 33
<211> LENGTH: 130
<212> TYPE: PRT
<213> ORGANISM: Homo sapiens

<400> SEQUENCE: 33

Ile Gln Lys Val Gln Asp Asp Thr Lys Thr Leu Ile Lys Thr Ile Val
1               5                   10                  15

Thr Arg Ile Asn Asp Ile Leu Asp Phe Ile Pro Gly Leu His Pro Ile
            20                  25                  30

Leu Thr Leu Ser Lys Met Asp Gln Thr Leu Ala Val Tyr Gln Gln Ile
        35                  40                  45

Leu Thr Ser Met Pro Ser Arg Asn Val Ile Gln Ile Ser Asn Asp Leu
    50                  55                  60

Glu Asn Leu Arg Asp Leu Leu His Val Leu Ala Phe Ser Lys Ser Cys
```

```
                 65                  70                  75                  80
His Leu Pro Glu Ala Ser Gly Leu Glu Thr Leu Asp Ser Leu Gly Gly
                    85                  90                  95

Val Leu Glu Ala Ser Gly Tyr Ser Thr Glu Val Val Ala Leu Ser Arg
                    100                 105                 110

Leu Gln Gly Ser Leu Gln Asp Met Leu Trp Gln Leu Asp Leu Ser Pro
                    115                 120                 125

Gly Cys
    130

<210> SEQ ID NO 34
<211> LENGTH: 62
<212> TYPE: PRT
<213> ORGANISM: Homo sapiens

<400> SEQUENCE: 34

Pro Glu Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
                20                  25                  30

Ser Ser Arg Arg Ala Pro Gln Thr Gly Ile Val Asp Glu Cys Cys Phe
            35                  40                  45

Arg Ser Cys Asp Leu Arg Arg Leu Glu Met Tyr Cys Ala Pro
        50                  55                  60

<210> SEQ ID NO 35
<211> LENGTH: 125
<212> TYPE: PRT
<213> ORGANISM: Homo sapiens

<400> SEQUENCE: 35

Met Tyr Arg Ser Ala Phe Ser Val Gly Leu Glu Thr Arg Val Thr Val
1               5                   10                  15

Pro Asn Val Pro Ile Arg Phe Thr Lys Ile Phe Tyr Asn Gln Gln Asn
                20                  25                  30

His Tyr Asp Gly Ser Thr Gly Lys Phe Tyr Cys Asn Ile Pro Gly Leu
            35                  40                  45

Tyr Tyr Phe Ser Tyr His Ile Thr Val Tyr Met Lys Asp Val Lys Val
        50                  55                  60

Ser Leu Phe Lys Lys Asp Lys Ala Val Leu Phe Thr Tyr Asp Gln Tyr
65                  70                  75                  80

Gln Glu Asn Val Asp Gln Ala Ser Gly Ser Val Leu Leu His Leu Glu
                    85                  90                  95

Val Gly Asp Gln Val Trp Leu Gln Val Tyr Tyr Ala Asp Asn Val Asn
                    100                 105                 110

Asp Ser Thr Phe Thr Gly Phe Leu Leu Tyr His Asp Thr
                115                 120                 125

<210> SEQ ID NO 36
<211> LENGTH: 111
<212> TYPE: PRT
<213> ORGANISM: Homo sapiens

<400> SEQUENCE: 36

Met Tyr Arg Ser Ala Phe Ser Val Gly Leu Pro Asn Val Pro Ile Arg
1               5                   10                  15

Phe Thr Lys Ile Phe Tyr Asn Gln Gln Asn His Tyr Asp Gly Ser Thr
                20                  25                  30
```

```
Gly Lys Phe Tyr Cys Asn Ile Pro Gly Leu Tyr Tyr Phe Ser Tyr His
            35                  40                  45

Ile Thr Val Tyr Met Lys Asp Val Lys Val Ser Leu Phe Lys Lys Asp
 50                  55                  60

Lys Val Leu Phe Thr Tyr Asp Gln Tyr Gln Glu Lys Val Asp Gln Ala
65                  70                  75                  80

Ser Gly Ser Val Leu Leu His Leu Glu Val Gly Asp Gln Val Trp Leu
                85                  90                  95

Gln Val Tyr Asp Ser Thr Phe Thr Gly Phe Leu Leu Tyr His Asp
                100                 105                 110

<210> SEQ ID NO 37
<211> LENGTH: 102
<212> TYPE: PRT
<213> ORGANISM: Homo sapiens

<400> SEQUENCE: 37

Met Tyr Arg Ser Ala Phe Ser Val Gly Leu Glu Thr Arg Val Thr Val
1               5                   10                  15

Pro Ile Arg Phe Thr Lys Ile Phe Tyr Asn Gln Gln Asn His Tyr Asp
                20                  25                  30

Gly Ser Thr Gly Lys Phe Tyr Cys Asn Ile Pro Gly Leu Tyr Tyr Phe
            35                  40                  45

Ser Tyr His Ile Thr Val Asp Val Lys Val Ser Leu Phe Lys Lys Asp
 50                  55                  60

Lys Ala Val Leu Phe Thr Gln Ala Ser Gly Ser Val Leu Leu His Leu
65                  70                  75                  80

Glu Val Gly Asp Gln Val Trp Leu Gln Asn Asp Ser Thr Phe Thr Gly
                85                  90                  95

Phe Leu Leu Tyr His Asp
                100

<210> SEQ ID NO 38
<211> LENGTH: 693
<212> TYPE: PRT
<213> ORGANISM: Homo sapiens

<400> SEQUENCE: 38

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
 50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
        130                 135                 140
```

-continued

```
Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ala Ala Ser Ala Arg Ala Trp Pro Lys Met
    210                 215                 220

His Thr Val Asn Gly Tyr Val Asn Arg Ser Leu Pro Gly Leu Ile Gly
225                 230                 235                 240

Cys His Arg Lys Ser Val Tyr Trp His Val Ile Gly Met Gly Thr Thr
                245                 250                 255

Pro Glu Val His Ser Ile Phe Leu Glu Gly His Thr Phe Leu Val Arg
                260                 265                 270

Asn His Arg Gln Ala Ser Leu Glu Ile Ser Pro Ile Thr Phe Leu Thr
            275                 280                 285

Ala Gln Thr Leu Leu Met Asp Leu Gly Gln Phe Leu Leu Phe Cys His
        290                 295                 300

Ile Ser Ser His Gln His Asp Gly Met Glu Ala Tyr Val Lys Val Asp
305                 310                 315                 320

Ser Cys Pro Glu Glu Pro Gln Phe Asp Asp Asn Ser Pro Ser Phe
                325                 330                 335

Ile Gln Ile Arg Ser Val Ala Lys Lys His Pro Lys Thr Trp Val His
            340                 345                 350

Tyr Ile Ala Ala Glu Glu Glu Asp Trp Asp Tyr Ala Pro Leu Val Leu
        355                 360                 365

Ala Pro Asp Asp Arg Ser Tyr Lys Ser Gln Tyr Leu Asn Asn Gly Pro
    370                 375                 380

Gln Arg Ile Gly Arg Lys Tyr Lys Lys Val Arg Phe Met Ala Tyr Thr
385                 390                 395                 400

Asp Glu Thr Phe Lys Thr Arg Glu Ala Ile Gln His Glu Ser Gly Ile
                405                 410                 415

Leu Gly Pro Leu Leu Tyr Gly Glu Val Gly Asp Thr Leu Leu Ile Ile
                420                 425                 430

Phe Lys Asn Gln Ala Ser Arg Pro Tyr Asn Ile Tyr Pro His Gly Ile
        435                 440                 445

Thr Asp Val Arg Pro Leu Tyr Ser Arg Arg Leu Pro Lys Gly Val Lys
    450                 455                 460

His Leu Lys Asp Phe Pro Ile Leu Pro Gly Glu Ile Phe Lys Tyr Lys
465                 470                 475                 480

Trp Thr Val Thr Val Glu Asp Gly Pro Thr Lys Ser Asp Pro Arg Cys
                485                 490                 495

Leu Thr Arg Tyr Tyr Ser Ser Phe Val Asn Met Glu Arg Asp Leu Ala
            500                 505                 510

Ser Gly Leu Ile Gly Pro Leu Leu Ile Cys Tyr Lys Glu Ser Val Asp
        515                 520                 525

Gln Arg Gly Asn Gln Ile Met Ser Asp Lys Arg Asn Val Ile Leu Phe
    530                 535                 540

Ser Val Phe Asp Glu Asn Arg Ser Trp Tyr Leu Thr Glu Asn Ile Gln
545                 550                 555                 560
```

```
Arg Phe Leu Pro Asn Pro Ala Gly Val Gln Leu Glu Asp Pro Glu Phe
                565                 570                 575

Gln Ala Ser Asn Ile Met His Ser Ile Asn Gly Tyr Val Phe Asp Ser
            580                 585                 590

Leu Gln Leu Ser Val Cys Leu His Glu Val Ala Tyr Trp Tyr Ile Leu
        595                 600                 605

Ser Ile Gly Ala Gln Thr Asp Phe Leu Ser Val Phe Phe Ser Gly Tyr
    610                 615                 620

Thr Phe Lys His Lys Met Val Tyr Glu Asp Thr Leu Thr Leu Phe Pro
625                 630                 635                 640

Phe Ser Gly Glu Thr Val Phe Met Ser Met Glu Asn Pro Gly Leu Trp
                645                 650                 655

Ile Leu Gly Cys His Asn Ser Asp Phe Arg Asn Arg Gly Met Thr Ala
            660                 665                 670

Leu Leu Lys Val Ser Ser Cys Asp Lys Asn Thr Gly Asp Tyr Tyr Glu
        675                 680                 685

Asp Ser Tyr Glu Asp
    690

<210> SEQ ID NO 39
<211> LENGTH: 644
<212> TYPE: PRT
<213> ORGANISM: Homo sapiens

<400> SEQUENCE: 39

Arg Ser Phe Gln Lys Lys Thr Arg His Tyr Phe Ile Ala Ala Val Glu
1               5                   10                  15

Arg Leu Trp Asp Tyr Gly Met Ser Ser Ser Pro His Val Leu Arg Asn
                20                  25                  30

Arg Ala Gln Ser Gly Ser Val Pro Gln Phe Lys Lys Val Val Phe Gln
            35                  40                  45

Glu Phe Thr Asp Gly Ser Phe Thr Gln Pro Leu Tyr Arg Gly Glu Leu
        50                  55                  60

Asn Glu His Leu Gly Leu Leu Gly Pro Tyr Ile Arg Ala Glu Val Glu
65                  70                  75                  80

Asp Asn Ile Met Val Thr Phe Arg Asn Gln Ala Ser Arg Pro Tyr Ser
                85                  90                  95

Phe Tyr Ser Ser Leu Ile Ser Tyr Glu Glu Asp Gln Arg Gln Gly Ala
            100                 105                 110

Glu Pro Arg Lys Asn Phe Val Lys Pro Asn Glu Thr Lys Thr Tyr Phe
        115                 120                 125

Trp Lys Val Gln His His Met Ala Pro Thr Lys Asp Glu Phe Asp Cys
    130                 135                 140

Lys Ala Trp Ala Tyr Ser Ser Asp Val Asp Leu Glu Lys Asp Val His
145                 150                 155                 160

Ser Gly Leu Ile Gly Pro Leu Leu Val Cys His Thr Asn Thr Leu Asn
                165                 170                 175

Pro Ala His Gly Arg Gln Val Thr Val Gln Glu Phe Ala Leu Phe Phe
            180                 185                 190

Thr Ile Phe Asp Glu Thr Lys Ser Trp Tyr Phe Thr Glu Asn Met Glu
        195                 200                 205

Arg Asn Cys Arg Ala Pro Cys Asn Ile Gln Met Glu Asp Pro Thr Phe
    210                 215                 220

Lys Glu Asn Tyr Arg Phe His Ala Ile Asn Gly Tyr Ile Met Asp Thr
225                 230                 235                 240
```

-continued

Leu Pro Gly Leu Val Met Ala Gln Asp Gln Arg Ile Arg Trp Tyr Leu
            245                 250                 255

Leu Ser Met Gly Ser Asn Glu Asn Ile His Ser Ile His Phe Ser Gly
            260                 265                 270

His Val Phe Thr Val Arg Lys Lys Glu Glu Tyr Lys Met Ala Leu Tyr
            275                 280                 285

Asn Leu Tyr Pro Gly Val Phe Glu Thr Val Glu Met Leu Pro Ser Lys
            290                 295                 300

Ala Gly Ile Trp Arg Val Glu Cys Leu Ile Gly Glu His Leu His Ala
305                 310                 315                 320

Gly Met Ser Thr Leu Phe Leu Val Tyr Ser Asn Lys Cys Gln Thr Pro
                325                 330                 335

Leu Gly Met Ala Ser Gly His Ile Arg Asp Phe Gln Ile Thr Ala Ser
                340                 345                 350

Gly Gln Tyr Gly Gln Trp Ala Pro Lys Leu Ala Arg Leu His Tyr Ser
            355                 360                 365

Gly Ser Ile Asn Ala Trp Ser Thr Lys Glu Pro Phe Ser Trp Ile Lys
            370                 375                 380

Val Asp Leu Leu Ala Pro Met Ile Ile His Gly Ile Lys Thr Gln Gly
385                 390                 395                 400

Ala Arg Gln Lys Phe Ser Ser Leu Tyr Ile Ser Gln Phe Ile Ile Met
                405                 410                 415

Tyr Ser Leu Asp Gly Lys Lys Trp Gln Thr Tyr Arg Gly Asn Ser Thr
                420                 425                 430

Gly Thr Leu Met Val Phe Phe Gly Asn Val Asp Ser Ser Gly Ile Lys
            435                 440                 445

His Asn Ile Phe Asn Pro Pro Ile Ile Ala Arg Tyr Ile Arg Leu His
            450                 455                 460

Pro Thr His Tyr Ser Ile Arg Ser Thr Leu Arg Met Glu Leu Met Gly
465                 470                 475                 480

Cys Asp Leu Asn Ser Cys Ser Met Pro Leu Gly Met Glu Ser Lys Ala
                485                 490                 495

Ile Ser Asp Ala Gln Ile Thr Ala Ser Ser Tyr Phe Thr Asn Met Phe
            500                 505                 510

Ala Thr Trp Ser Pro Ser Lys Ala Arg Leu His Leu Gln Gly Arg Ser
            515                 520                 525

Asn Ala Trp Arg Pro Gln Val Asn Asn Pro Lys Glu Trp Leu Gln Val
            530                 535                 540

Asp Phe Gln Lys Thr Met Lys Val Thr Gly Val Thr Thr Gln Gly Val
545                 550                 555                 560

Lys Ser Leu Leu Thr Ser Met Tyr Val Lys Glu Phe Leu Ile Ser Ser
                565                 570                 575

Ser Gln Asp Gly His Gln Trp Thr Leu Phe Phe Gln Asn Gly Lys Val
            580                 585                 590

Lys Val Phe Gln Gly Asn Gln Asp Ser Phe Thr Pro Val Val Asn Ser
            595                 600                 605

Leu Asp Pro Pro Leu Leu Thr Arg Tyr Leu Arg Ile His Pro Gln Ser
            610                 615                 620

Trp Val His Gln Ile Ala Leu Arg Met Glu Val Leu Gly Cys Glu Ala
625                 630                 635                 640

Gln Asp Leu Tyr

<210> SEQ ID NO 40
<211> LENGTH: 578
<212> TYPE: PRT
<213> ORGANISM: Homo sapiens

<400> SEQUENCE: 40

```
Ser Glu Val Ala His Arg Phe Lys Asp Leu Gly Glu Glu Asn Phe Lys
1               5                   10                  15

Ala Leu Val Leu Ile Ala Phe Ala Gln Tyr Leu Gln Gln Cys Pro Phe
            20                  25                  30

Glu Asp His Val Lys Leu Val Asn Glu Val Thr Glu Phe Ala Lys Thr
        35                  40                  45

Cys Val Ala Asp Glu Ser Ala Glu Asn Cys Asp Lys Ser Leu His Thr
50                  55                  60

Leu Phe Gly Asp Lys Leu Cys Thr Val Ala Thr Leu Arg Glu Thr Tyr
65                  70                  75                  80

Gly Glu Met Ala Asp Cys Cys Ala Lys Gln Glu Pro Glu Arg Asn Glu
                85                  90                  95

Cys Phe Leu Gln His Lys Asp Asp Asn Pro Asn Leu Pro Arg Leu Val
            100                 105                 110

Arg Pro Glu Val Asp Val Met Cys Thr Ala Phe His Asp Asn Glu Glu
        115                 120                 125

Thr Phe Leu Lys Lys Tyr Leu Tyr Glu Ile Ala Arg Arg His Pro Tyr
    130                 135                 140

Phe Tyr Ala Pro Glu Leu Leu Phe Phe Ala Lys Arg Tyr Lys Ala Ala
145                 150                 155                 160

Phe Thr Glu Cys Cys Gln Ala Ala Asp Lys Ala Ala Cys Leu Leu Pro
                165                 170                 175

Lys Leu Asp Glu Leu Arg Asp Glu Gly Lys Ala Ser Ser Ala Lys Gln
            180                 185                 190

Arg Leu Lys Cys Ala Ser Leu Gln Lys Phe Gly Glu Arg Ala Phe Lys
        195                 200                 205

Ala Trp Ala Val Ala Arg Leu Ser Gln Arg Phe Pro Lys Ala Glu Phe
    210                 215                 220

Ala Glu Val Ser Lys Leu Val Thr Asp Leu Thr Lys Val His Thr Glu
225                 230                 235                 240

Cys Cys His Gly Asp Leu Leu Glu Cys Ala Asp Asp Arg Ala Asp Leu
                245                 250                 255

Ala Lys Tyr Ile Cys Glu Asn Gln Asp Ser Ile Ser Ser Lys Leu Lys
            260                 265                 270

Glu Cys Cys Glu Lys Pro Leu Leu Glu Lys Ser His Cys Ile Ala Glu
        275                 280                 285

Val Glu Asn Asp Glu Met Pro Ala Asp Leu Pro Ser Leu Ala Ala Asp
    290                 295                 300

Phe Val Glu Ser Lys Asp Val Cys Lys Asn Tyr Ala Glu Ala Lys Asp
305                 310                 315                 320

Val Phe Leu Gly Met Phe Leu Tyr Glu Tyr Ala Arg Arg His Pro Asp
                325                 330                 335

Tyr Ser Val Val Leu Leu Leu Arg Leu Ala Lys Thr Tyr Glu Thr Thr
            340                 345                 350

Leu Glu Lys Cys Cys Ala Ala Ala Asp Pro His Glu Cys Tyr Ala Lys
        355                 360                 365

Val Phe Asp Glu Phe Lys Pro Leu Val Glu Glu Pro Gln Asn Leu Ile
    370                 375                 380
```

-continued

```
Lys Gln Asn Cys Glu Leu Phe Glu Gln Leu Gly Glu Tyr Lys Phe Gln
385                 390                 395                 400

Asn Ala Leu Leu Val Arg Tyr Thr Lys Lys Val Pro Gln Val Ser Thr
            405                 410                 415

Pro Thr Leu Val Glu Val Ser Arg Asn Leu Gly Lys Val Gly Ser Lys
            420                 425                 430

Cys Cys Lys His Pro Glu Ala Lys Arg Met Pro Cys Ala Glu Asp Tyr
            435                 440                 445

Leu Ser Val Val Leu Asn Gln Leu Cys Val Leu His Glu Lys Thr Pro
            450                 455                 460

Val Ser Asp Arg Val Thr Lys Cys Cys Thr Glu Ser Leu Val Asn Arg
465                 470                 475                 480

Arg Pro Cys Phe Ser Ala Leu Glu Val Asp Glu Thr Tyr Val Pro Lys
            485                 490                 495

Glu Phe Asn Ala Glu Thr Phe Thr Phe His Ala Asp Ile Cys Thr Leu
            500                 505                 510

Ser Glu Lys Glu Arg Gln Ile Lys Lys Gln Thr Ala Leu Val Glu Leu
            515                 520                 525

Val Lys His Lys Pro Lys Ala Thr Lys Glu Gln Leu Lys Ala Val Met
            530                 535                 540

Asp Asp Phe Ala Ala Phe Val Glu Lys Cys Cys Lys Ala Asp Asp Lys
545                 550                 555                 560

Glu Thr Cys Phe Ala Glu Gly Lys Lys Leu Val Ala Ala Ser Gln
            565                 570                 575

Ala Ala

<210> SEQ ID NO 41
<211> LENGTH: 578
<212> TYPE: PRT
<213> ORGANISM: Homo sapiens

<400> SEQUENCE: 41

Ser Glu Val Ala His Arg Phe Lys Asp Leu Gly Glu Glu Asn Phe Lys
1               5                   10                  15

Ala Leu Val Leu Ile Ala Phe Ala Gln Tyr Leu Gln Gln Cys Pro Phe
            20                  25                  30

Glu Asp His Val Lys Leu Val Asn Glu Val Thr Glu Phe Ala Lys Thr
        35                  40                  45

Cys Val Ala Asp Glu Ser Ala Glu Asn Cys Asp Lys Ser Leu His Thr
    50                  55                  60

Leu Phe Gly Asp Lys Leu Cys Thr Val Ala Thr Leu Arg Glu Thr Tyr
65                  70                  75                  80

Gly Glu Met Ala Asp Cys Cys Ala Lys Gln Glu Pro Glu Arg Asn Glu
                85                  90                  95

Cys Phe Leu Gln His Lys Asp Asp Asn Pro Asn Leu Pro Arg Leu Val
            100                 105                 110

Arg Pro Glu Val Asp Val Met Cys Thr Ala Phe His Asp Asn Glu Glu
        115                 120                 125

Thr Phe Leu Lys Lys Tyr Leu Tyr Glu Ile Ala Arg Arg His Pro Tyr
    130                 135                 140

Phe Tyr Ala Pro Glu Leu Leu Phe Phe Ala Lys Arg Tyr Lys Ala Ala
145                 150                 155                 160

Phe Thr Glu Cys Cys Gln Ala Ala Asp Lys Ala Ala Cys Leu Leu Pro
                165                 170                 175
```

```
Lys Leu Asp Glu Leu Arg Asp Glu Gly Lys Ala Ser Ser Ala Lys Gln
            180                 185                 190

Arg Leu Lys Cys Ala Ser Leu Gln Lys Phe Gly Glu Arg Ala Phe Lys
        195                 200                 205

Ala Trp Ala Val Ala Arg Leu Ser Gln Arg Phe Pro Lys Ala Glu Phe
    210                 215                 220

Ala Glu Val Ser Lys Leu Val Thr Asp Leu Thr Lys Val His Thr Glu
225                 230                 235                 240

Cys Cys His Gly Asp Leu Leu Glu Cys Ala Asp Asp Arg Ala Asp Leu
                245                 250                 255

Ala Lys Tyr Ile Cys Glu Asn Gln Asp Ser Ile Ser Ser Lys Leu Lys
            260                 265                 270

Glu Cys Cys Glu Lys Pro Leu Leu Glu Lys Ser His Cys Ile Ala Glu
        275                 280                 285

Val Glu Asn Asp Glu Met Pro Ala Asp Leu Pro Ser Leu Ala Ala Asp
    290                 295                 300

Phe Val Glu Ser Lys Asp Val Cys Lys Asn Tyr Ala Glu Ala Lys Asp
305                 310                 315                 320

Val Phe Leu Gly Met Phe Leu Tyr Glu Tyr Ala Arg Arg His Pro Asp
                325                 330                 335

Tyr Ser Val Val Leu Leu Leu Arg Leu Ala Lys Thr Tyr Glu Thr Thr
            340                 345                 350

Leu Glu Lys Cys Cys Ala Ala Ala Asp Pro His Glu Cys Tyr Ala Lys
        355                 360                 365

Val Phe Asp Glu Phe Lys Pro Leu Val Glu Glu Pro Gln Asn Leu Ile
    370                 375                 380

Lys Gln Asn Cys Glu Leu Phe Glu Gln Leu Gly Glu Tyr Lys Phe Gln
385                 390                 395                 400

Asn Ala Leu Leu Val Arg Tyr Thr Lys Lys Val Pro Gln Val Ser Thr
                405                 410                 415

Pro Thr Leu Val Glu Val Ser Arg Asn Leu Gly Lys Val Gly Ser Lys
            420                 425                 430

Cys Cys Lys His Pro Glu Ala Lys Arg Met Pro Cys Ala Glu Asp Tyr
        435                 440                 445

Leu Ser Val Val Leu Asn Gln Leu Cys Val Leu His Glu Lys Thr Pro
    450                 455                 460

Val Ser Asp Arg Val Thr Lys Cys Cys Thr Glu Ser Leu Val Asn Arg
465                 470                 475                 480

Arg Pro Cys Phe Ser Ala Leu Glu Val Asp Glu Thr Tyr Val Pro Lys
                485                 490                 495

Glu Phe Asn Ala Glu Thr Phe Thr Phe His Ala Asp Ile Cys Thr Leu
            500                 505                 510

Ser Glu Lys Glu Arg Gln Ile Lys Lys Gln Thr Ala Leu Val Glu Leu
        515                 520                 525

Val Lys His Lys Pro Lys Ala Thr Lys Glu Gln Leu Lys Ala Val Met
    530                 535                 540

Asp Asp Phe Ala Ala Phe Val Glu Lys Cys Cys Lys Ala Asp Asp Lys
545                 550                 555                 560

Glu Thr Cys Phe Ala Glu Glu Gly Lys Lys Leu Val Ala Ala Ser Gln
                565                 570                 575

Ala Ala

<210> SEQ ID NO 42
```

```
<211> LENGTH: 141
<212> TYPE: PRT
<213> ORGANISM: Homo sapiens

<400> SEQUENCE: 42

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 43
<211> LENGTH: 146
<212> TYPE: PRT
<213> ORGANISM: Homo sapiens

<400> SEQUENCE: 43

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 44
<211> LENGTH: 5
<212> TYPE: PRT
<213> ORGANISM: Artificial Sequence
<220> FEATURE:
<223> OTHER INFORMATION: Synthetic Polypeptide
```

```
<400> SEQUENCE: 44

Leu Pro Glu Thr Gly
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Biotinylated

<400> SEQUENCE: 45

Lys Leu Pro Glu Thr Ala Ala
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 46

Leu Pro Xaa Thr Gly Gly
1               5

<210> SEQ ID NO 47
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Biotinylated

<400> SEQUENCE: 47

Gly Gly Gly Lys
1

<210> SEQ ID NO 48
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 48

Gly Gly Gly Cys
1

<210> SEQ ID NO 49
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 49
```

```
Leu Pro Glu Thr
1

<210> SEQ ID NO 50
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be D, E, A, N, Q, K, L, S, or R

<400> SEQUENCE: 50

Leu Pro Xaa Thr
1

<210> SEQ ID NO 51
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 51

Leu Pro Lys Thr Gly
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 52

Leu Pro Ile Thr Gly
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 53

Leu Pro Asp Thr Ala
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 54

Ser Pro Lys Thr Gly
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic Polypeptide
```

<400> SEQUENCE: 55

Leu Ala Glu Thr Gly
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 56

Leu Ala Ala Thr Gly
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 57

Leu Ala His Thr Gly
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 58

Leu Ala Ser Thr Gly
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 59

Leu Pro Leu Thr Gly
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 60

Leu Ser Arg Thr Gly
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic Polypeptide

```
<400> SEQUENCE: 61

Val Pro Asp Thr Gly
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 62

Ile Pro Gln Thr Gly
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 63

Tyr Pro Arg Arg Gly
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 64

Leu Pro Met Thr Gly
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 65

Leu Ala Phe Thr Gly
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 66

Leu Pro Gln Thr Ser
1               5

<210> SEQ ID NO 67
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
```

```
<222> LOCATION: (3)..(3)
<223> OTHER INFORMATION: Xaa can be any naturally occurring amino acid

<400> SEQUENCE: 67

Leu Ala Xaa Thr
1

<210> SEQ ID NO 68
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 68

Leu Pro Xaa Ala
1

<210> SEQ ID NO 69
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 69

Leu Gly Xaa Thr
1

<210> SEQ ID NO 70
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 70

Ile Pro Xaa Thr
1

<210> SEQ ID NO 71
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 71

Asn Pro Xaa Thr
1

<210> SEQ ID NO 72
<211> LENGTH: 4
```

```
<212> TYPE: PRT
<213> ORGANISM: Artificial Sequence
<220> FEATURE:
<223> OTHER INFORMATION: Synthetic Polypeptide

<400> SEQUENCE: 72

Asn Pro Gln Ser
1

<210> SEQ ID NO 73
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 73

Leu Pro Ser Thr
1

<210> SEQ ID NO 74
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 74

Asn Ser Lys Thr
1

<210> SEQ ID NO 75
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 75

Asn Pro Gln Thr
1

<210> SEQ ID NO 76
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 76

Asn Ala Lys Thr
1

<210> SEQ ID NO 77
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 77

Leu Pro Ile Thr
1

<210> SEQ ID NO 78
<211> LENGTH: 4
<212> TYPE: PRT
```

```
<213> ORGANISM: Artificial Sequence
<220> FEATURE:
<223> OTHER INFORMATION: Synthetic Polypeptide

<400> SEQUENCE: 78

Leu Ala Glu Thr
1

<210> SEQ ID NO 79
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 79

Ala Ala Ala Ala Ala
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 80

Leu Pro Xaa Thr Xaa
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 81

Leu Pro Lys Thr Gly
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 82

Leu Pro Ala Thr Gly
1               5

<210> SEQ ID NO 83
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 83
```

Leu Pro Asn Thr Gly
1               5

<210> SEQ ID NO 84
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 84

Leu Pro Xaa Ala Gly
1               5

<210> SEQ ID NO 85
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 85

Leu Pro Asn Ala Gly
1               5

<210> SEQ ID NO 86
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 86

Leu Pro Asn Thr Ala
1               5

<210> SEQ ID NO 87
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 87

Leu Gly Xaa Thr Gly
1               5

<210> SEQ ID NO 88
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 88

Leu Gly Ala Thr Gly
1               5

<210> SEQ ID NO 89
<211> LENGTH: 5

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 89

Ile Pro Xaa Thr Gly
1               5

<210> SEQ ID NO 90
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 90

Ile Pro Asn Thr Gly
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 91

Ile Pro Glu Thr Gly
1               5

<210> SEQ ID NO 92
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 92

Asn Pro Xaa Thr Xaa
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be Q or K
<220> FEATURE:
<221> NAME/KEY: misc_feature
<222> LOCATION: (4)..(4)
<223> OTHER INFORMATION: Xaa can be T or S
<220> FEATURE:
<221> NAME/KEY: misc_feature
<222> LOCATION: (5)..(5)
```

<223> OTHER INFORMATION: Xaa can be N, G, or S

<400> SEQUENCE: 93

Asn Pro Xaa Xaa Xaa
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 94

Asn Pro Gln Thr Asn
1               5

<210> SEQ ID NO 95
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 95

Asn Pro Lys Thr Gly
1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 96

Asn Ser Lys Thr Ala
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 97

Asn Pro Gln Thr Gly
1               5

<210> SEQ ID NO 98
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 98

Asn Ala Lys Thr Asn
1               5

<210> SEQ ID NO 99
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 99

Asn Pro Gln Ser Ser
1               5

<210> SEQ ID NO 100
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be E, A, S, or H

<400> SEQUENCE: 100

Asn Ala Xaa Thr Gly
1               5

<210> SEQ ID NO 101
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 101

Leu Ala Xaa Thr Gly
1               5

<210> SEQ ID NO 102
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 102

Leu Pro Asn Thr Ala
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 103

Gln Val Pro Thr Gly Val
1               5

<210> SEQ ID NO 104
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can Q or K
<220> FEATURE:
<221> NAME/KEY: misc_feature

```
<222> LOCATION: (5)..(5)
<223> OTHER INFORMATION: Xaa can be A or S

<400> SEQUENCE: 104

Leu Pro Xaa Thr Xaa Thr
1               5

<210> SEQ ID NO 105
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be A or S

<400> SEQUENCE: 105

Leu Pro Xaa Thr Xaa
1               5

<210> SEQ ID NO 106
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 106

Leu Pro Ser Thr Ser
1               5

<210> SEQ ID NO 107
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 107

Leu Pro Glu Thr Gly Gly
1               5

<210> SEQ ID NO 108
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 108

Leu Pro Glu Thr Ala Ala
1               5

<210> SEQ ID NO 109
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 109
gagcagaaac tcatctcaga agaggatctg                                      30
```

<210> SEQ ID NO 110
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 110
ggtggcggag gtgga                                                     15

<210> SEQ ID NO 111

<400> SEQUENCE: 111

000

<210> SEQ ID NO 112
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 112
gaacaaaaac ttatttctga agaagatct                                      29

<210> SEQ ID NO 113
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 113
ctgccagaaa ctggtgga                                                  18

<210> SEQ ID NO 114
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 114
tacccatacg acgtcccaga ctacgct                                        27

<210> SEQ ID NO 115
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 115

Leu Pro Glu Thr Gly Gly His His His His His His
1               5                   10

<210> SEQ ID NO 116
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)

<223> OTHER INFORMATION: Biotinylated

<400> SEQUENCE: 116

Lys Leu Pro Arg Thr Gly Gly
1               5

<210> SEQ ID NO 117
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 117

Gly Gly Gly Lys
1

<210> SEQ ID NO 118
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 118

Leu Pro Arg Thr Gly Gly
1               5

<210> SEQ ID NO 119
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 119

Leu Pro Glu Thr Ala
1               5

<210> SEQ ID NO 120
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 120
ctctgcccgc tgcaagctct gg                                              22

<210> SEQ ID NO 121
<211> LENGTH: 196
<212> TYPE: DNA
<213> ORGANISM: Artificial Sequence
<220> FEATURE:
<223> OTHER INFORMATION: Synthetic Oligonucleotide

<400> SEQUENCE: 121
tgagcaatac tccagatttt gccaaacatt tcattgtcc acgtgggacc cttctgaatc      60
cctctgcccg ctgcaagctc ggaggatcag gaggatcatt accagagaca ggaggatggt    120
aaaacttggc taccaaagag actgatgtaa atgcatgggc tgcttgtgag tcatccttg     180 aagtcaaaat aaatct                                                    196

<210> SEQ ID NO 122
<211> LENGTH: 60

```
<212> TYPE: DNA
<213> ORGANISM: Artificial Sequence
<220> FEATURE:
<223> OTHER INFORMATION: Synthetic Oligonucleotide

<400> SEQUENCE: 122
taatacgact cactatagct ctgcccgctg caagctcgtt ttagagctag aaatagcaag    60

<210> SEQ ID NO 123
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 123
taagttatgt aacgggtac                                                 19

<210> SEQ ID NO 124
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 124
atctaaccca tccctatcac cctatgg                                        27

<210> SEQ ID NO 125
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 125
atggagatgt agctgatgag cagc                                           24

<210> SEQ ID NO 126
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 126

Leu Pro Glu Thr Gly His His His His His His
1               5                   10
```

IN VITRO PRODUCTION OF RED BLOOD CELLS WITH PROTEINS COMPRISING SORTASE RECOGNITION MOTIFS

RELATED APPLICATIONS

This application is a national stage filing under 35 U.S.C. § 371 of international PCT application, PCT/US2014/037554, filed May 9, 2014, which claims priority under 35 U.S.C. § 119(e) to U.S. Provisional Application, U.S. Ser. No. 61/822,071, filed on May 10, 2013, the content of each of which is hereby incorporated by reference in its entirety.

GOVERNMENT SUPPORT

This invention was made with government support under Grant No. HR0011-12-2-0015, awarded by the Defense Advanced Research Projects Agency (DARPA). The Government has certain rights in this invention.

BACKGROUND OF THE INVENTION

Cell surfaces can be modified in order to modulate surface function or to confer new functions to such surfaces. Surface functionalization may, for example, include an addition of a detectable label, a binding moiety, or a therapeutic agent to a surface protein, allowing for the detection or isolation of the surface-modified cells, for the generation of new cell-cell interactions that do not naturally occur, or for the conjugation of a therapeutic or diagnostic agent to the cell surface.

Cell surface modification can be achieved by genetic engineering or by chemical modifications of cell surface proteins. Both approaches are, however, limited in their capabilities, for example, in that many surface proteins do not tolerate insertions above a certain size without suffering impairments in their function or expression, and in that many chemical modifications require non-physiological reaction conditions.

SUMMARY OF THE INVENTION

The present disclosure is based on the development of an in vitro multi-phase culturing process for differentiating human CD34$^+$ peripheral blood cells into enucleated red blood cells. This in vitro culturing process unexpectedly synchronized erythroid expansion, terminal differentiation, and enucleation of mobilized human CD34$^+$ peripheral blood cells. The present disclosure is also based on the development of a sortagging system for surface modification of red blood cells, in which an agent of interest is conjugated to the surface of the enucleated red blood cells. The enucleated red blood cells can be produced by the in vitro multi-phase culturing system described herein. Such surface modified enucleated red blood cells can be used for diagnostic and therapeutic purposes.

Accordingly, one aspect of the present disclosure features a method for producing human enucleated red blood cells, the method comprising: (i) providing a population of human CD34$^+$ progenitor cells (e.g., human CD34$^+$ peripheral blood cells); (ii) expanding the population of human CD34$^+$ progenitor cells in a first medium for 0~6 days (e.g., 4 days), wherein the first medium comprises Flt-3 ligand, stem cell factor (SCF), interleukin 3 (IL-3), and interleukin 6 (IL-6); (iii) differentiating the expanded human CD34$^+$ progenitor cells obtained from step (ii) in a second medium for 4~7 days (e.g., 5 days), wherein the second medium comprises dexamethasone, β-estradiol, IL-3, SCF, and erythropoietin (EPO); (iv) differentiating the cells obtained from step (iii) in a third medium for 3~5 days (e.g., 4 days), wherein the third medium comprises SCF and EPO; (v) differentiating the cells obtained from step (iv) in a fourth medium for 4~12 days (e.g., 9 days) to produce human enucleated red blood cells, wherein the fourth medium comprises EPO; and (vi) collecting the human enucleated red blood cells obtained from step (v). In some embodiments, the total time period for steps (ii)-(v) of the method described above ranges from 11-25 days (e.g., 21 days). Step (v) may be performed in a culturing container coated with a component from the extracellular matrix, such as fibronectin.

In some embodiments, one or more of the second, third, and fourth media can further comprise holo human transferrin and insulin. When necessary, all of the second, third, and fourth media further comprise these two cytokines. In other embodiments, the second, third, and/or fourth media may be free of certain cytokines, for example, thrombopoietin (TPO), granulocyte macrophage colony-stimulating factor (GM-CSF), or both.

In one example, the second medium used in any of the in vitro production methods described herein can comprise 250~1500 µg/ml (e.g., 500 µg/ml) holo human transferrin, 5~20 µg/ml insulin (e.g., 10 µg/ml), 100 nM-5 µM (e.g., 2 µM) dexamethasone, 0.5~5 µM (e.g., 1 µM) β-estradiol, 1~10 ng/ml (e.g., 5 ng) IL-3, 10~500 ng/ml (e.g., 100 ng/ml) SCF, and/or 2~10 U (e.g., 6 U) EPO. The second medium can be free of certain cytokines, for example, Flt-3, IL-6, or both.

In another example, the third medium used in any of the in vitro production methods described herein can comprise 250~1500 µg/ml (e.g., 500 µg/ml) holo human transferrin, 5~20 µg/ml (e.g., 10 µg/ml) insulin, 10~100 ng/ml (e.g., 50 ng/ml) SCF, and/or 2~10 U (e.g., 6 U) EPO. The third medium may be may be free of certain cytokines, for example, Flt-3, IL-6, dexamethasone, β-estradiol, or any combination thereof.

In yet another example, the fourth medium used in any of the in vitro production methods described herein can comprise 250~1500 µg/ml (e.g., 500 µg/ml) holo human transferrin, 5~20 µg/ml (e.g., 10 µg/ml) insulin, and/or 0.5~3 U (e.g., 2 U) EPO. The fourth medium may be free of certain cytokines, for example, Flt-3, IL-6, dexamethasone, β-estradiol, SCF, or any combination thereof.

In any of the in vitro production methods described herein, the human CD34$^+$ progenitor cells can be any of the genetically engineered enucleated blood cells (which are not naturally occurring) as described herein, for example, a human CD34$^+$ expressing a fusion protein comprising a red blood cell membrane protein and a peptide of interest. In some embodiments, the fusion protein comprises a type I red blood cell transmembrane protein (e.g., glycophorin A) fused to an acceptor peptide at the N-terminus of the type I red blood cell transmembrane protein. The acceptor peptide may include an oligoglycine moiety, e.g., a 1-5 glycine fragment, or an oligoalanine (e.g., a 1-5 alanine fragment) moiety. In other embodiments, the fusion protein comprises a type II red blood cell transmembrane protein (e.g., Kell or CD71) fused to a peptide comprising a sequence recognized by a sortase (e.g., a sortase A) at the C-terminus of the type II red blood cell transmembrane protein. The sequence recognizable by the sortase can be LPXTG (SEQ ID NO:1), in which X is any amino acid residue. In still other embodiments, the membrane protein is a type III red blood cell transmembrane protein, such as glucose transporter 1 (GLUT1).

In another aspect, the present disclosure provides a genetically engineered enucleated blood cell which expresses on the surface a first fusion protein comprising a first peptide of interest and a first red blood cell membrane protein. In some embodiments, the first red blood cell membrane protein is a type I red blood cell transmembrane protein (e.g., glycophorin A such as human glycophorin A), and the first peptide of interest is fused to the N-terminus of the type I red blood cell transmembrane protein. In other embodiments, the first red blood cell membrane protein is a type II transmembrane protein (e.g., Kell or CD71), and the first peptide of interest is fused to the C-terminus of the type II transmembrane protein. The first peptide of interest may comprise a sequence recognizable by a sortase, such as sortase A. In one example, the sequence recognizable by the sortase is LPXTG (SEQ ID NO: 1), in which X is any amino acid residue. In still other embodiments, the first red blood cell membrane protein is a type III red blood cell transmembrane protein, such as GLUT1.

In some embodiments, the first fusion protein further comprises a protein of interest (e.g., a cytoplasmic protein, which can be a diagnostic agent or a therapeutic agent). The protein of interest is fused to the terminus of the first red blood cell membrane protein that is exposed to a cytoplasmic space and the first peptide of interest is fused to the terminus of the first red blood cell membrane protein that is exposed to an extracellular or luminal space.

In some examples, the first red blood cell membrane protein can be a type I membrane protein (e.g., a GPA). The protein of interest is fused to the C-terminus of the type I membrane protein and the first peptide of interest is fused to the N-terminus of the type I membrane protein.

In other examples, the first red blood cell membrane protein is a type II membrane protein. The protein of interest is fused to the N-terminus of the type II membrane protein, and the first peptide of interest is fused to the C-terminus of the type I membrane protein.

In yet other embodiments, the genetically engineered enucleated blood cell as described herein can further express on the surface a second fusion protein comprising a second peptide of interest and a second red blood cell membrane protein.

In some examples, the first peptide of interest in the first fusion protein comprises a recognizable site or an acceptable peptide of a first sortase and the second peptide of interest in the second fusion protein comprises a recognizable site or an acceptable peptide of a second sortase. The first sortase and the second sortase use different recognizable sites and different acceptable peptides. In one example, the first peptide of interest comprises the motif of LPXTA (SEQ ID NO:2), in which X is any amino acid residue, or an oligoalanine; and the second peptide of interest comprises the motif LPXTG (SEQ ID NO:1), or an oligoglycine (e.g., consisting of 1-5 glycine residues). In another example, the first fusion protein comprises Kell, the C-terminus of which is fused to a first peptide of interest comprising the motif LPXTG (SEQ ID NO:1), and the second fusion protein comprises GPA, the C-terminus of which is fused to a second peptide of interest comprising an oligoalanine (e.g., consisting of 1-5 alanine residues).

In any of the genetically engineered enucleated blood cells described herein that express two fusion proteins on the surface, either one or both of the fusion proteins can be conjugated to two different functional moieties.

The above described enucleated blood cell may be prepared by any of the in vitro culturing methods described herein.

In some instances, the first peptide of interest, the second peptide of interest, or both, that are fused to the red blood cell membrane protein(s) described herein may comprise a protein drug (e.g., an antibody or an antigen-binding fragment thereof, which can be a single domain antibody), a vaccine antigen, a fluorescent protein, streptavidin, biotin, an enzyme, or a peptide capable of targeting a cell (e.g., a disease cell). In other instances, the peptide of interest is conjugated to a detectable label or a chemotherapeutic agent. For example, the peptide of interest may be conjugated to a lipid, a carbohydrate, a nucleic acid, a binding agent, a click-chemistry handle, a polymer, a peptide, a protein, a metal, a chelator, a radiolabel, or a small molecule.

In yet another aspect, the present disclosure provides methods for delivering an agent to a subject, the method comprising administering any of the enucleated blood cells described herein to the subject. In some examples, the enucleated blood cell being delivered is derived from the same subject the cell is being delivered to.

Also within the scope of the present disclosure are methods for conjugating any of the peptides of interest described herein to the surface of red blood cells. This method comprises: (i) providing a red blood cell expressing a fusion protein comprising a membrane protein and a first peptide, and (ii) contacting the red blood cell with a peptide of interest in the presence of a sortase (e.g., sortase A) under conditions suitable for the sortase to conjugate the peptide of interest to the first peptide in the fusion protein. Either the first peptide in the fusion protein or the peptide of interest comprises a sequence recognized by the sortase. In one example, the sequence recognizable by the sortase is LPXTG (SEQ ID NO:1), in which X is any amino acid residue.

In some embodiments, the membrane protein is a type I red blood cell transmembrane protein (e.g., glycophorin A) and the first peptide is an acceptor peptide (e.g., including an oligoglycine fragment such as a 1-5 glycine fragment) fused to the N-terminus of the type I red blood cell transmembrane protein, wherein the peptide of interest comprises the sequence recognized by the sortase. In other embodiments, the membrane protein is a type II red blood cell transmembrane protein (e.g., Kell or CD71) and the first peptide is fused to the C-terminus of the type II red blood cell transmembrane protein, wherein the first peptide comprises the sequence recognizable by the sortase. In still other embodiments, the membrane protein is a type III red blood cell transmembrane protein such as GLUT1.

In some embodiments, the first fusion protein in any of the methods described herein may further comprise a protein of interest (e.g., a cytoplasmic protein, which can be a diagnostic agent or a therapeutic agent), which is fused to the terminus of the first red blood cell membrane protein that is exposed to a cytoplasmic space. The first peptide of interest in the fusion protein is fused to the terminus of the first red blood cell membrane protein that is exposed to an extracellular or luminal space.

In some examples, the first red blood cell membrane protein is a type I membrane protein. The first protein of interest is fused to the C-terminus of the type I membrane protein, and the first peptide is fused to the N-terminus of the type I membrane protein. In other examples, the first red blood cell membrane protein is a type II membrane protein. The protein of interest is fused to the N-terminus of the type II membrane protein, and the first peptide is fused to the C-terminus of the type I membrane protein.

In yet other embodiments, any of the methods described herein can further comprise contacting the red blood cell in the presence of a second sortase under conditions suitable for the second sortase to conjugate a second peptide of interest to a second fusion protein expressed on the surface of the red blood cell. The second fusion protein comprises a second red blood cell membrane protein and a second peptide to which the second peptide of interest conjugates. In some examples, either the second peptide in the fusion protein or the second peptide of interest comprises a sequence recognizable by the second sortase. The sequence recognizable by the first sortase differ from the sequence recognizable by the second sortase.

In some examples, the first peptide in the first fusion protein comprises a sequence recognizable by the first sortase or an acceptable peptide of the first sortase; and/or the second peptide in the second fusion protein comprises a sequence recognizable by the second sortase or an acceptable peptide of the second sortase. The acceptable peptide of the first sortase is different from the acceptable peptide of the second sortase. The first sortase may be Sortase A from *Staphylococcus arreus*. One of the first peptide in the first fusion protein and the first peptide of interest comprises the motif LPXTG (SEQ ID NO:1), in which X is any amino acid residue, and the other comprises an acceptable peptide, which is an oligoglycin. The first fusion protein may comprise Kell, the C-terminus of which is fused to the first peptide which comprises the motif LPXTG (SEQ ID NO:1), and the first peptide of interest comprises an oligoglycine (e.g., consisting of 1-5 glycine residues).

In some examples, the second sortase is Sortase A from *Streptococcus pyogenes*. One of the second peptide in the second fusion protein and the second peptide of interest may comprise the motif LPXTA (SEQ ID NO:2), in which X is any amino acid residue, and the other may comprise an acceptable peptide, which can be an oligoalanine (e.g., consisting of 1-5 alanine residues). The second fusion protein may comprise GPA, the N-terminus of which is fused to the second peptide which comprises an oligoglycine. The second peptide of interest may comprise the motif LPXTG (SEQ ID NO:1), in which X is any amino acid residue.

In some embodiments, the first and second peptides of interest comprises or are conjugated to two different functional moieties. Alternatively or in addition, the first peptide of interest, the second peptide of interest, or both, may be a protein drug, a vaccine antigen, a fluorescent protein, streptavidin, biotin, an enzyme, or a peptide capable of targeting a cell. In one example, one of the first and second peptide of interest is a peptide capable of targeting a disease cell.

Further, the present disclosure provides (a) pharmaceutical compositions for diagnostic or therapeutic uses, the pharmaceutical composition comprising any of the enucleated red blood cells described herein, which carry any of the peptide of interest as described herein, and a pharmaceutically acceptable carrier, and (b) uses of the pharmaceutical compositions for manufacturing medicaments for diagnostic or therapeutic purposes.

The details of one or more embodiments of the invention are set forth in the description below. Other features or advantages of the present invention will be apparent from the following Drawings and Detailed Description of Certain Embodiments, and also from the Claims.

BRIEF DESCRIPTION OF THE DRAWINGS

FIG. 1 illustrates an exemplary in vitro culturing process for producing enucleated red blood cells from human CD34+ progenitor cells.

DETAILED DESCRIPTION CERTAIN EMBODIMENTS OF THE INVENTION

Figure 2:
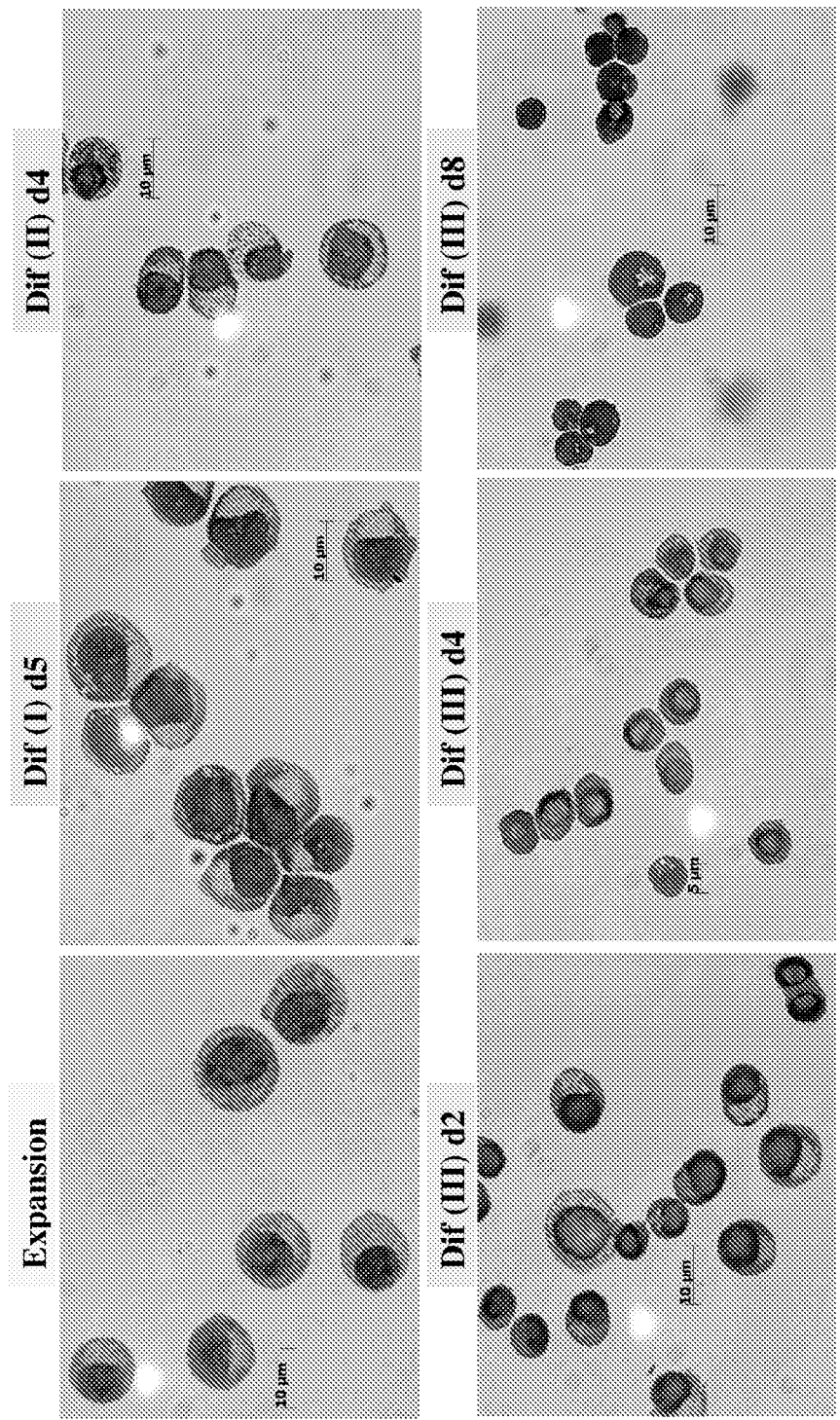
FIG. 2 includes photographs showing morphology of cells at expansion and different differentiation stages in the in vitro culturing process described herein.
Figure 3:
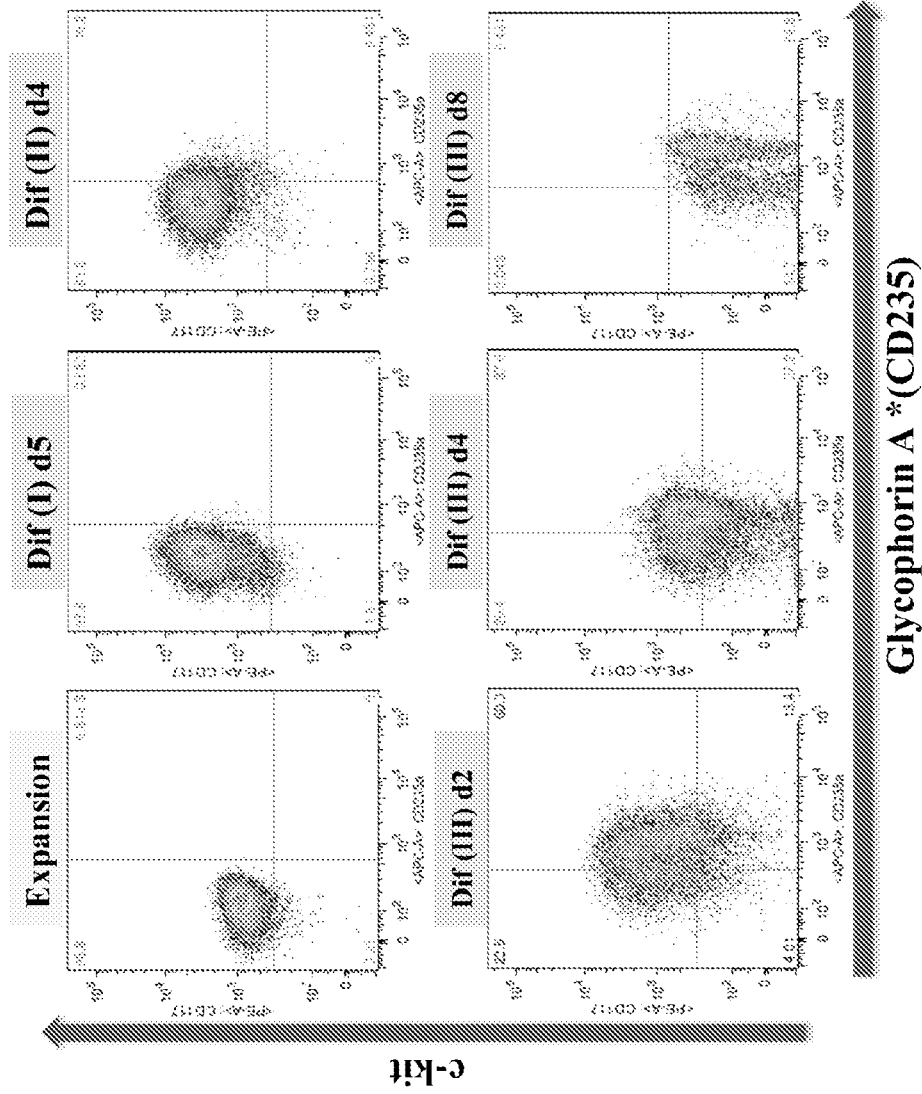
FIG. 3 is a diagram showing the expression of cell surface markers glycophorin A (CD235) and c-kit in cells at expansion and different differentiation stages in the in vitro culturing process described herein, as determined by FACS analysis.

Red blood cells are the most numerous cell type in blood and account for a quarter of the total number of cells in the human body. RBCs possesses many unique characteristics that make them an attractive tool in therapeutics and diagnostics for various purposes, e.g., for in vivo delivery of natural or synthetic payloads. Yoo et al., 2011, *Nature Reviews. Drug Delivery* 10(7):521-535. For example, mature red blood cells do not have nuclei (i.e., enucleated) and thus there will be no risk of delivering remnants of foreign genes into a host. Thus, the possibility of tumorigenicity a key risk of stem cell-based therapies (Gruen et al., 2006 *Stem cells* 24(10):2162-2169) is thereby eliminated. Further, red blood cells have a long lifespan in vivo, e.g., about 120 days in the human blood stream, and about 50 days in mice, and presence throughout the macro- and micro-circulation. Modification of red cells with bioavailable therapeutics might thus lead to prolonged efficacy and coverage of all areas perfused by the circulation in vivo. Moreover, RBCs have large cell surface areas of about 140 $\mu m^2$ with a favorable surface to volume ratio. Also, red blood cells have good biocompability when used as carriers for delivery of therapeutic or diagnostic agents. Finally, old or damaged RBCs can be removed by cells of the reticuloendothelial system. Thus, any modification made to the DNA of RBC precursors is eliminated upon their enucleation and cannot lead to abnormal growth or tumorigenicity after their transfusion into a recipient.

Accordingly, it is of great interest to develop methods for producing enucleated red blood cells that carry an agent of interest, such as diagnostic or therapeutic agents. Such enucleated red blood cells can be used for, e.g., delivering the agent of interest into a subject.

Engineered RBCs have been generated using encapsulation (Biagiotti et al., 2011, *IUBMB life* 63(8):621-631; Godfrin et al., 2012, *Expert Opinion on Biological Therapy* 12(1):127-133; and Muzykantov, 2010, *Expert Opinion on Drug Delivery* 7(4):403-427), by non-covalent attachment of foreign peptides, or through installation of proteins by fusion to a monoclonal antibody specific for a RBC surface protein (Murciano, 2003, *Nature Biotechnology* 21(8):891-896; and Zaitsev et al., 2010, *Blood* 115(25):5241-5248). Modified RBCs face limitations if intended for application in vivo. Encapsulation allows entrapment of sizable quantities of material, but at the expense of disrupting plasma membrane integrity, with a concomitant reduction in circulatory half-life of the modified red blood cells. Osmosis driven entrapment limits the chemical nature of materials that can be successfully encapsulated, the site of release is difficult to control, and encapsulated enzymes are functional only at the final destination, compromising reusability at other sites. Murciano et al., 2003 and Zaitsev et al., 2010. Targeting of cargo to RBCs by fusion to an RBC-specific antibody, (e.g., antiglycophorin antibody), has its limitations because this mode of attachment to the RBC is non-covalent and readily dissociates, thus reducing circulatory half life and mass of cargo available for delivery. Murciano et al., 2003 and Zaitsev et al., 2010. Other developments that exploit RBCs for targeted delivery include nanoparticles enveloped by an RBC-mimicking membrane as well as RBC-shaped polymers. Yoo et al., 2011 *Nature Reviews. Drug Discovery* 10(7):521-535. The short in vivo survival rate of these RBC-inspired carriers 7 days maximum) may limit their therapeutic utility.

Another technical difficulty associated with engineering RBCs is lack of a suitable in vitro system for culturing and differentiation of RBCs. Human $CD34^+$ cell culture systems have been disclosed in Miharada et al., *Nat. Biotechnol.*, 24(10):1255-1256, 2006; Sankaran et al., *Science*, 322 (5909):1839-1842, 2008, and Giarratana et al., *Blood*, 118 (19):5071-5079, 2011. However, the mature enucleated red blood cells obtained from these cell culture systems did not show similar hemoglobin contents and/or cell sizes as compared to normal human reticulocytes or red blood cells, did not show synchronized expression of cell surface differentiation markers during the culture process. Also, the cell culture system taught in Sankaran et al. did not generate terminally-differentiated erythroid cells or enucleated red cells.

In light of the disadvantages associated with the existing technology, there is a need to develop new methodology for engineering RBCs, such that they can carry a wide variety of useful cargoes to specific locations in the body.

In the present studies, modified red blood cells were developed to serve as carriers for systemic delivery of a wide array of payloads. These RBCs contain modified proteins on their plasma membrane, which can be labeled in a sortase-catalyzed reaction under native conditions without inflicting damage on the target membrane or cell. Sortase accommodates a wide range of natural and synthetic payloads that allow modification of RBCs with substituents that cannot be encoded genetically. The present studies demonstrate the successful site-specific conjugation of biotin to in vitro differentiated mouse erythroblasts as well as to mature mouse RBCs. Unexpectedly, these modified red cells remain in the bloodstream for up to 28 days, which is far in excess of red blood cells engineered by methods known in the art. A single domain antibody attached enzymatically to RBCs enables them to bind specifically to target cells that express the antibody target. This study was extended to human red cells and demonstrate unexpected efficient sortase-mediated labeling of in vitro differentiated human reticulocytes.

The engineering and labeling processes described herein do not damage the cells or affect their survival in vivo. Most importantly, the engineered red blood cells can be labeled with a wide array of functional probes, including small molecules, peptides, and proteins and thus have the potential to be carriers of a variety of therapeutic substances into the bloodstream. Thus, the methods described herein offer advantages over the osmosis-driven encapsulation methods known in the art.

Sortase-mediated cell surface labeling has been exploited previously, for example to explore trafficking of flu glycoproteins. Popp et al., 2012 *PLos Pathogens* 8(3):e1002604; and Sanyal et al., 2013 *Cell Host & Microbe* 14(5):510-521. This methodology was modified and applied to primary cells as a platform for diagnostic or therapeutic purposes. A sortase A variant from *S. aureus* active at 0° C. (Chen et al., 2011 *PNAS* 108(28):11399-11404) to reduce the risk of inflicting cellular damage in the course of labeling.

There are many other possible applications for the methods presented here, where the wide variety of possible payloads—ranging from proteins and peptides to synthetic compounds and fluorescent probes may serve as a guide. For example, such methods would enable the targeting of the modified red cells to a specific cell type. Further, the methods described herein can be combined with established protocols of small molecule encapsulation (Godfrin et al., 2012). In this scenario, engineered red cells loaded in the cytosol with a therapeutic agent and modified on the surface with a cell-type specific recognition module could be used to deliver payloads to a precise tissue/location in the body. It has been demonstrated herein attachment of two different functional probes to the surface of red blood cells, exploiting the subtly different recognition specificities of two distinct sortases. It should therefore be possible to attach both a therapeutic moiety as well as a targeting module to the red cell surface, to direct the engineered red cells to tumors or other diseased cells. Conjugation of an imaging probe, i.e., a radioisotope, together with such a targeting moiety could also be used for diagnostic purposes.

The in vitro generation of human RBCs and genetic engineering of their precursors as described herein may provide a robust platform for application of this surface engineering method, e.g., in conjunction with cytosolic modification, to clinical applications (Liu et al., 2010 *Blood* 115(10):2021-2027; Cong et al., 2013 *Science* 339(6121): 819-826; Mali et al., *Science* 339(6121):823-826; Giarratana et al., 2011 *Blood* 118(19):5071-5079; Douay et al., 2009 *Blood* 105(1):85-94; and Griffiths et al., 2012 *Blood* 119 (26):6296-6306.) Moreover, the established safety of blood transfusions inspires confidence that these engineered red blood cells will indeed find use in humans.

Accordingly, described herein is an in vitro multi-phase culturing process for producing enucleated red blood cells from mobilized $CD34^+$ progenitor cells (e.g., human mobilized $CD34^+$ peripheral blood cells). Such enucleated red blood cells can be genetically engineered such that they express proteins of interest, e.g., sortaggable surface proteins. Also described herein are methods for conjugating one or more agents of interest to the surface of the genetically engineered enucleated red blood cells via a sortase-mediated transpeptide reaction, as well as methods for producing cytoplasmically disposed protein of interest in mature RBCs such as human RBCs while retaining the ability to selectively target the RBCs to an intended target via sortagging of a modified membrane protein with a target moiety of interest.

I. In vitro Culturing Systems for Producing Enucleated Red Blood Cells

Described herein is an in vitro culturing process for producing mature enucleated red blood cells from $CD34^+$ progenitor cells (e g from a human subject). This culturing process involves multiple differentiation stages (e.g., 2, 3, or more) and optionally an expansion stage prior to the differentiation phases. The total time period for the in vitro culturing process described herein can range from 11-25 days (e.g., 15-25 days, 15-20 days, or 18-21 days). In one example, the total time period is 21 days.

a. $CD34^+$ Progenitor Cells

CD34 is a cell surface glycoprotein and functions as a cell-cell adhesion factor. Many human progenitor cells express this cell surface marker. Novershtern et al., *Cell* 144:296-309, 2011. A progenitor cell, like a stem cell, has a tendency to differentiate into a specific type of cell. Progenitor cells are usually more specific than stem cells and are often pushed to differentiate into the target cells. Any type of CD34+ progenitor cells that possess the tendency of differentiating into red blood cells can be used in the in vitro culturing process described herein. Such progenitor cells are well known in the art. See, e.g., Novershtern et al., Cell 144:296-309, 2011. In some examples, the in vitro culturing process described herein utilizes mobilized CD34+ peripheral blood cells as the progenitor cells for differentiation into enucleated red blood cells. CD34+ progenitor cells can also be derived from other sources (e.g., bone marrow).

Various techniques can be used to separate or isolate the $CD34^+$ cell population from a suitable source such as peripheral blood cells. For example, antibodies such as monoclonal antibodies binding to CD34 can be used to enrich or isolate $CD34^+$ cells. The anti-CD34 antibodies can be attached to a solid support such that cells expressing these surface markers are immobilized, thereby allowing for the separation of $CD34^+$ cells from cells that do not express this surface marker. The separation techniques used should maximize the retention of viable cells to be collected. Such separation techniques can result in sub-populations of cells where up to 10%, usually not more than about 5%, preferably not more than about 1%, of the selected cells do not express CD34. The particular technique employed will depend upon the efficiency of separation, associated cytotoxicity, ease and speed of performance, and necessity for sophisticated equipment and/or technical skill.

An "isolated" or "purified" population of $CD34^+$ cells for use in the in vitro culturing process described herein is substantially free of cells and materials with which it is associated in nature, in particular, free of cells that lack the desired phenotype, e.g., expressing CD34. Substantially free or substantially purified includes at least 50% $CD34^+$ cells, preferably at least 70%, more preferably at least 80%, and even more preferably at least 90% $CD34^+$ cells.

Procedures for separating the $CD34^+$ population of cells can include, but are not limited to, physical separation, magnetic separation, antibody-coated magnetic beads, affinity chromatography, cytotoxic agents joined to a monoclonal antibody or used in conjunction with a monoclonal antibody, including, but not limited to, complement and cytotoxins, and "palming" with antibody attached to a solid matrix, e.g., plate, elutriation or any other convenient technique.

The use of physical separation techniques also include those based on differences in physical (density gradient centrifugation and counter-flow centrifugal elutriation), cell surface (lectin and antibody affinity), and vital staining properties (mitochondria-binding dye rho123 and DNA-binding dye Hoechst 33342). These procedures are well known to those of skill in this art.

Techniques providing accurate separation of $CD34^+$ cells further include flow cytometry, which can have varying degrees of sophistication, e.g., a plurality of color channels, low angle and obtuse light scattering detecting channels, impedance channels. $CD34^+$ cells also can be selected by flow cytometry based on light scatter characteristics, where the target cells are selected based on low side scatter and low to medium forward scatter profiles.

b. Expansion Stage

Optionally, the in vitro culturing process described herein includes an expansion stage, in which the $CD34^+$ progenitor cells are allowed to proliferate. As used herein, expansion or proliferation includes any increase in cell number. Expansion includes, for example, an increase in the number of CD34+ cells over the number of CD34+ cells present in the cell population used to initiate the culture. Expansion can also include increased survival of existing CD34+ cells. The term survival refers to the ability of a cell to continue to remain alive or function.

A population of $CD34^+$ progenitor cells (e.g., mobilized $CD34^+$ peripheral blood cells) can be placed in a suitable container for expanding the CD34+ cells. For example, suitable containers for culturing the population of cells include flasks, tubes, or plates. In one embodiment, the flask can be T-flask such as a 12.5 cm$^2$, or a 75 cm$^2$ T-flask. The plate can be a 10 cm plate, a 3.5 cm plate, or a multi-welled plate such as a 12, 24, or 96 well plate. The wells can be flat, v-bottom, or u-bottom wells. The containers can be treated with any suitable treatment for tissue culture to promote cell adhesion or to inhibit cell adhesion to the surface of the container. Such containers are commercially available from Falcon, Corning and Costar. As used herein, "expansion container" also is intended to include any chamber or container for expanding cells whether or not free standing or incorporated into an expansion apparatus.

The cell density of the cultured population of CD34$^+$ cells can be at least from about $1\times10^2$ cells to about $1\times10^7$ cells/mL. Preferably, the cell density can be from about $1\times10^5$ to about $1\times10^6$ cells/mL. The cells can be cultured at an oxygen concentration of from about 2 to 20%.

Various media can be used to expand the population of CD34$^+$ progenitor cells, including, but not limited to, Dulbecco's MEM, IMDM, X-Vivo 15 (serum-depleted) and RPMI-1640. Such culture media can be serum free. In one embodiment, the medium is serum free StemSpan (Stem Cell Technologies), which can be supplemented with 10 µg/ml heparin.

The culture medium for use in the expansion stage can contain one or more cytokines. As used herein, cytokines are factors that exert a variety of effects on cells, for example, growth or proliferation. Non-limiting examples of the cytokines that may be used in one or more stages of the in vitro culturing process (e.g., in the expansion stage or any of the differentiation stages described below) include interleukin-2 (IL-2), interleukin 3 (IL-3), interleukin 6 (IL-6) including soluble IL-6 receptor, interleukin 12 (IL12), G-CSF, granulocyte-macrophage colony stimulating factor (GM-CSF), interleukin 1 alpha (IL-1 .alpha.), interleukin 11 (IL-11), MIP-1α, leukemia inhibitory factor (LIF), c-kit ligand, and flt3 ligand. In some examples, the in vitro culturing process described herein, or any stages thereof, can include culture conditions, in which one or more cytokine is specifically excluded from the culture medium. Cytokines are commercially available from several vendors such as, for example, Amgen (Thousand Oaks, Calif.), R & D Systems and Immunex (Seattle, Wash.). Cytokine can also include fibroblast growth factor (FGF) (e.g., FGF-1 or FGF-2), insulin-like growth factor (e.g., IGF-2, or IGF-1), thrombopoietin (TPO), and stem cell factor (SCF), or analogs and equivalents thereof. Equivalents thereof include molecules having similar biological activity to these factors (e.g., FGF, TPO, IGF, and SCF) in wild-type or purified form (e.g., recombinantly produced). Analogs include fragments retaining the desired activity and related molecules. For example, TPO is a ligand of the mpl receptor, thus molecules capable of binding the mpl receptor and initiating one or more biological actions associated with TPO binding to mpl are also within the scope of the invention. An example of a TPO mimetic is found in Cwirla et. al. (1997) Science 276:1696.

In one example, the expansion stage of the in vitro culturing process described herein can be performed as follows. A population of human mobilized CD34$^+$ peripheral blood cells is placed in an expansion container at a cell density of $10\times10^4$-$10\times10^6$ (e.g., $1\times10^5$) cells/mL. The CD34$^+$ cells are cultured in an expansion medium (e.g., StemSpan serum-free medium) supplemented with a cytokine mixture of Flt-3 ligand, SCF, IL-3, and IL-6 and 2% penicillin and streptomycin under suitable conditions (e.g., 37° C.) for 1-6 days (e.g., 2-5 days, 3-4 days, or 4 days). The expanded CD34+ cells can be collected and subjected to further in vitro culturing under conditions allowing for differentiation toward mature enucleated red blood cells.

C. Multiple Differentiation Stages

The in vitro culturing process described herein involves multiple differentiation stages (2, 3, 4, or more), in which CD34+ progenitor cells differentiate into mature enucleated red blood cells. In each differentiation stage, CD34+ progenitor cells (either obtained from the expansion stage or collected from the original source) or cells obtained from the preceding differentiation stage can be cultured in a medium comprising one or more suitable cytokines (e.g., those described herein) under suitable conditions for a suitable period of time. Biological properties of the cells, such as cell size and expression of surface markers, may be monitored during the course or at the end of each differentiation stage to evaluate the status of erythropoiesis. Whenever necessary, cytokines can be timely supplied and/or withdrawn at each differentiation stage to achieve optimal erythroid differentiation and/or synchronizing the cell population in culture.

At each of the differentiation stages, CD34$^+$ progenitor cells, either obtained from the expansion stage described herein or isolated from an original source (e.g., human peripheral blood), or cells obtained from the preceding differentiation stage can be cultured in a suitable medium, such as those described above, supplemented with one or more cytokines under suitable culturing conditions for a suitable period of time. In one example, the culture medium (e.g., IMDM) is supplemented with holo human transferrin and insulin at suitable concentrations. For example, the concentration of hobo human transferrin ranges from 250-1,500 µg/ml (e.g., 250-1,000 µg/ml; 300-800 µg/ml, or 400-600 µg/ml); and the concentration of insulin can range from 5-20 µg/ml (e.g., 5-15 µg/ml, 5-10 µg/ml, or 10-20 µg/ml). The culture medium may also be supplemented with other components commonly used in cell culture, e.g., fetal bovine serum, glutamine, bovine serum albumin, one or more antibiotics (e.g., penicillin and streptomycin), or any combination thereof.

In some embodiments, the in vitro culturing process described herein includes three differentiation stages, Differentiation stage I ('Dif. I), Differentiation stage II ("Dif. II"), and Differentiation stage III ("Dif. III").

In Dif. I, the cells may be cultured in the presence of a mixture of cytokines including a glucocorticoid (e.g., dexamethasone), β-estradiol, IL-3, SCF, and EPO (including human EPO, EPO from other species, or EPO analogs such as Epoetin alfa, Epoetin beta, or Darbepoetin alfa) at suitable concentrations for a suitable period of time (e.g., 4-7 days, 4-6 days, 5-7 days, or 5-6 days). In some examples, the concentration of dexamethasone may range from 100 nM to 5 µM (e.g., 100 nM to 2 µM, 500 nM to 5 µM, 1 µM to 3 µM, 1 µM to 2 µM, or 2 µM to 5 µM). The concentration of β-estradiol may range from 0.5-5 µM (e.g., 0.5-4 µM, 1-5 µM, 0.5-3 µM, 0.5-2 µM, 0.5-1 µM, 1-2 µM, 1-3 µM, or 3-5 µM). The concentration of IL-3 may range from 1-10 ng/ml (e.g., 1-8 ng/ml, 1-5 ng/ml, 3-6 ng/ml, 4-8 ng/ml, or 5-10 ng/ml). The concentration of SCF may range from 10-500 ng/ml (e.g., 10-300 ng/ml, 50-500 ng/ml, 50-200 ng/ml, 50-100 ng/ml, 100-200 ng/ml, or 100-400 ng/ml). Alternatively or in addition, the amount of EPO may range from 2-10 U (e.g., 2-8 U, 2-6 U, 5-10 U, or 6-10 U). As well known in the art, one EPO unit elicits the same erythropoiesis stimulating response in rodents (historically: fasted rats) as five micromoles of cobaltous chloride. See, e.g., Jelkmann, Nephrol Dial. Transplant, 2009. In some examples, the medium used in Dif. I contains holo human transferrin, insulin, dexamethasone, β-estradiol, IL-3, SCF, and EPO. This medium may be substantially free of certain other cytokines, such as Flt-3 ligand or IL-6, or substantially free of other cytokines.

In Dif. II, the cells obtained from Dif. I may be cultured in the presence of a mixture of cytokines including SCF and EPO at suitable concentrations for a suitable period of time (e.g., 3-5 days, 3-4 days, or 4-5 days). In some examples, the concentration of SCF can range from 10-100 ng/ml (e.g., 10-80 ng/ml, 20-80 ng/ml, 20-50 ng/ml, 30-50 ng/ml, 40-50 ng/ml, 50-80 ng/ml, or 50-60 ng/ml). Alternatively or in addition, the amount of EPO can range from 2-10 U (e.g., 2-8 U, 2-6 U, 5-10 U, or 6-10 U). In some examples, the medium used in Dif. II contains holo human transferrin, insulin, SCF, and EPO. This medium may be substantially free of certain cytokines, such as Flt-3, IL-6, dexamethasone, β-estradiol, IL-3, or any combination thereof, or may be substantially free of other cytokines.

In Dif. III, the cells obtained from Dif. II may be cultured in the presence of EPO at a suitable concentration for a suitable period of time (e.g., 4-12 days, 5-10 days, 8-12 days, or 8-10 days). In some examples, the amount of EPO may range from 0.5-3 U (e.g., 1-3 U, 0.5-2 U, 1-2 U, or 2-3 U). In some examples, the medium used in Dif. III contains holo human transferrin, insulin, and EPO. This medium may be substantially free of certain cytokines, for example, Flt-3, IL-6, dexamethasone, β-estradiol, IL-3, SCF, or any combination thereof, or substantially free of other cytokines.

In some embodiments, the in vitro culturing process described herein may include one or any combination of the differentiation stages described herein, for example, Dif. I and Dif. III, Dif. II and Dif. III, or Dif. I and Dif. II.

Prior to the differentiation stages, the CD34+ progenitor cells may be genetically modified such that they express surface proteins of interest, for example, sortaggable surface proteins, which are discussed in detail below.

II. Preparation of Red Blood Cells Expressing Surface Proteins of Interest

Also described herein are methods of preparing genetically engineered red blood cells capable of expressing surface proteins of interest, such as sortaggable surface proteins, fluorescent proteins such as green fluorescent protein (GFP), or protein drugs (e.g., antibodies or antigen-binding fragments thereof).

(a) Genetic Modification of Progenitor Cells

Expression vectors for producing the surface protein of interest may be introduced into CD34+ progenitor cells, which can be isolated from an original source or obtained from the expansion stage described above via routine recombinant technology. In some instances, the expression vectors can be designed such that they can incorporate into the genome of cells by homologous or non-homologous recombination by methods known in the art. Methods for transferring expression vectors into CD34+ progenitor cells include, but are not limited to, viral mediated gene transfer, liposome mediated transfer, transformation, transfection and transduction, e.g., viral mediated gene transfer such as the use of vectors based on DNA viruses such as adenovirus, adeno-associated virus and herpes virus, as well as retroviral based vectors. Examples of modes of gene transfer include e.g., naked DNA, $CaPO_4$ precipitation, DEAE dextran, electroporation, protoplast fusion, lipofection, cell microinjection, and viral vectors, adjuvant-assisted DNA, gene gun, catheters. In one example, a viral vector is used. To enhance delivery of non-viral vectors to a cell, the nucleic acid or protein can be conjugated to antibodies or binding fragments thereof which bind cell surface antigens, e.g., CD34. Liposomes that also include a targeting antibody or fragment thereof can be used in the methods described herein.

A "viral vector" as described herein refers to a recombinantly produced virus or viral particle that comprises a polynucleotide to be delivered into a host cell, either in vivo, ex vivo or in vitro. Examples of viral vectors include retroviral vectors such as lentiviral vectors, adenovirus vectors, adeno-associated virus vectors and the like. In aspects where gene transfer is mediated by a retroviral vector, a vector construct refers to the polynucleotide comprising the retroviral genome or part thereof, and a therapeutic gene.

A gene encoding the surface protein of interest can be inserted into a suitable vector (e.g., a retroviral vector) using methods well known in the art. Sambrook et al., Molecular Cloning, A Laboratory Mannual, $3^{rd}$ Ed., Cold Spring Harbor Laboratory Press. For example, the gene and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Suitable vectors and methods for producing vectors containing transgenes are well known and available in the art. Sambrook et al., Molecular Cloning, A Laboratory Mannual, $3^{rd}$ Ed., Cold Spring Harbor Laboratory Press.

Modification of CD34+ progenitor cells can comprise the use of an expression cassette created for either constitutive or inducible expression of the introduced gene. Such an expression cassette can include regulatory elements such as a promoter, an initiation codon, a stop codon, and a polyadenylation signal. The elements are preferably operable in the progenitor cells or in cells that arise from the progenitor cells (e.g., enucleated red blood cells) after administration (e.g., infusion) into an individual. Moreover, the elements can be operably linked to the gene encoding the surface protein of interest such that the gene is operational (e.g., is expressed) in the progenitor cells or red blood cells derived therefrom.

A variety of promoters can be used for expression of the surface protein of interest. Promoters that can be used to express the protein are well known in the art. Promoters include cytomegalovirus (CMV) intermediate early promoter, a viral LTR such as the Rous sarcoma virus LTR, HIV-LTR, HTLV-1 LTR, the simian virus 40 (SV40) early promoter, E. coli lac UV5 promoter and the herpes simplex tk virus promoter.

Regulatable promoters can also be used. Such regulatable promoters include those using the lac repressor from E. coli as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone or rapamycin. Inducible systems are available from Invitrogen, Clontech and Ariad.

Regulatable promoters that include a repressor with the operon can be used. In one embodiment, the lac repressor from E. coli can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter [F. Yao et al., Human Gene Therapy, supra]. One particular advantage of this tetracycline inducible switch is that it does not require the use of a tetracycline repressor-mammalian cells transactivator or repressor fusion protein, which in some instances can be toxic to cells [M. Gossen et al., Natl. Acad. Sci. USA, 89:5547-5551 (1992); P. Shockett et al., Proc. Natl. Acad. Sci. USA, 92:6522-6526 (1995)], to achieve its regulatable effects.

The effectiveness of some inducible promoters can be increased over time. In such cases one can enhance the effectiveness of such systems by inserting multiple repressors in tandem, e.g., TetR linked to a TetR by an internal ribosome entry site (IRES). Alternatively, one can wait at least 3 days before screening for the desired function. While some silencing may occur, it can be minimized by using a suitable number of cells, preferably at least $1 \times 10^4$, more preferably at least $1 \times 10^5$, still more preferably at least $1 \times 10^6$, and even more preferably at least $1 \times 10^7$. One can enhance expression of desired proteins by known means to enhance the effectiveness of this system. For example, using the Woodchuck Hepatitis Virus Posttranscriptional Regulatory Element (WPRE). See Loeb, V. E., et al., Human Gene Therapy 10:2295-2305 (1999); Zufferey, R., et al., J. of Virol. 73:2886-2892 (1999); Donello, J. E., et al., J. of Virol. 72:5085-5092 (1998).

Examples of polyadenylation signals useful to practice the methods described herein include, but are not limited to, human collagen I polyadenylation signal, human collagen II polyadenylation signal, and SV40 polyadenylation signal.

The exogenous genetic material that includes the surface protein-encoding gene operably linked to the regulatory elements may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA, which can integrate into the chromosome, may be introduced into the cell. When introducing DNA into the cell, reagents, which promote DNA integration into chromosomes, may be added. DNA sequences, which are useful to promote integration, may also be included in the DNA molecule. Alternatively, RNA may be introduced into the cell.

Selectable markers can be used to monitor uptake of the desired transgene into the progenitor cells described herein. These marker genes can be under the control of any promoter or an inducible promoter. These are known in the art and include genes that change the sensitivity of a cell to a stimulus such as a nutrient, an antibiotic, etc. Genes include those for neo, puro, tk, multiple drug resistance (MDR), etc. Other genes express proteins that can readily be screened for such as green fluorescent protein (GFP), blue fluorescent protein (BFP), luciferase, and LacZ.

(b) Genetic Modification for Expressing Sortaggable Surface Proteins

In some embodiments, the CD34$^+$ progenitor cells can be genetically modified using any of the methods described herein or known in the art such that they are capable of expressing a sortaggable surface protein, such as a fusion protein comprising a red blood cell membrane protein and a peptide (e.g., a peptide heterologous to the membrane protein). A sortaggable surface protein can be conjugated to another peptide via a sortase-mediated transpeptidation reaction. Strijbis et al., Traffic 13(6):780-789, 2012. Preferably the transduction of the CD34$^+$ progenitor cells with a gene encoding a sortaggable surface protein is via a viral vector such as a retroviral vector (as described in for example, in WO 94/29438, WO 97/21824 and WO 97/21825).

A sortaggable surface protein can be a fusion protein comprising a membrane protein and at least one heterologous protein. In some embodiments, a membrane protein for use in the methods described herein, which may present on mature RBCs, inhibit neither erythroid differentiation nor be targeted for degradation during the extensive membrane remodeling that occurs during enucleation and at the later reticulocyte stage. Such membrane proteins are known in the art. See, e.g., Liu et al., 2010, Blood, 115(10):2021-2027. For example, red blood cell precursors express high levels of the transferrin receptor (Tfr), a type II membrane protein, but since it is no longer present on mature RBCs, Tfr may not be a suitable target for use in preparing a sortaggable surface protein. Any membrane proteins present in mature RBCs can be used for constructing the sortaggable surface protein as described herein. The membrane protein can be fused to a heterologous peptide at the terminus that is exposed to the extracellular or luminal space. In some examples, the terminus of the membrane protein that is exposed to cytoplasm may also be fused to a second heterologous protein of interest, which can be a cytoplasmic protein.

When the N-terminus of the membrane protein is exposed to the extracellular or luminal space (e.g., a Type I membrane protein), the heterologous protein may comprise an acceptor peptide to which another peptide can conjugate via a sortase-catalyzed transpeptidation reaction. Typically, the acceptor peptide is an oligoglycine or oligoalanine, such as a 1-5 glycine fragment or a 1-5 alanine fragment. In some examples, the oligoglycine consists of 3 or 5 glycine (SEQ ID NO: 3) residues. In other examples, the oligoalanine consists of 3 or 5 alanine residues (SEQ ID NO: 79).

In one example, the sortaggable surface protein is a fusion protein comprising a type I red blood cell transmembrane protein, such as glycophorin A, intercellular adhesion molecule 4 (ICAM-4), Lutheran glycoprotein (CD329), Basigin (CD147), and a peptide that comprises an acceptor peptide (e.g., a peptide that includes an oligoglycine moiety, such as a 1-5 glycine fragment). These membrane proteins can be human proteins. The acceptor peptide is fused to the N-terminus of the type I transmembrane protein. Type I transmembrane proteins are single-pass transmembrane proteins which have their N-termini exposed to the extracellular or luminal space.

In another example, the sortaggable surface protein is a fusion protein comprising a type II red blood cell transmembrane protein, e.g., Kell, or CD71, and a peptide that comprises a sequence recognizable by a sortase (e.g., sortase A). Type II transmembrane proteins are single-pass transmembrane proteins which have their C-termini exposed to the extracellular or luminal space.

Motifs recognizable by a sortase are well known in the art. One exemplary motif recognizable by a sortase, particularly sortase A, is LPXTG (SEQ ID NO: 1), in which X can be any amino acid residue (naturally-occurring or non-naturally occurring), e.g., any of the 20 standard amino acids found most commonly in proteins found in living organisms. In some examples, the recognition motif is LPXTG (SEQ ID NO: 1) or LPXT (SEQ ID NO: 50), in which X is D, E, A, N, Q, K, or R. In other examples, X is selected from K, E, N, Q, A in an LPXTG (SEQ ID NO: 1) or LPXT (SEQ ID NO: 50) motif, which are recognizable by a sortase A. In yet other examples, X is selected from K, S, E, L, A, N in an LPXTG (SEQ ID NO: 1) or LPXT (SEQ ID NO: 50) motif, which are recognizable by a class C sortase. Exemplary sortase recognition motifs include, but are not limited to, LPKTG (SEQ ID NO: 51), LPITG (SEQ ID NO: 52), LPDTA (SEQ ID NO: 53), SPKTG (SEQ ID NO: 54), LAETG (SEQ ID NO: 55), LAATG (SEQ ID NO: 56), LAHTG (SEQ ID NO: 57), LASTG (SEQ ID NO: 58), LPLTG (SEQ ID NO: 59), LSRTG (SEQ ID NO: 60), LPETG (SEQ ID NO: 44), VPDTG (SEQ ID NO: 61), IPQTG (SEQ ID NO: 62), YPRRG (SEQ ID NO: 63), LPMTG (SEQ ID NO: 64), LAFTG (SEQ ID NO: 65), LPQTS (SEQ ID NO: 66), LPXT (SEQ ID NO: 50), LAXT (SEQ ID NO: 67), LPXA (SEQ ID NO: 68), LGXT (SEQ ID NO: 69), IPXT (SEQ ID NO: 70), NPXT (SEQ ID NO: 71), NPQS (SEQ ID NO: 72), LPST (SEQ ID NO: 73), NSKT (SEQ ID NO: 74), NPQT (SEQ ID NO: 75), NAKT (SEQ ID NO: 76), LPIT (SEQ ID NO: 77), or LAET (SEQ ID NO: 78)

The sortaggable surface protein described herein can also be a fusion protein comprising a type III red cell transmembrane protein and a heterologous peptide. Type III membrane proteins are multi-pass structures, which usually have their N-termini exposed to the extracellular or luminal space. Examples of type III red cell transmembrane proteins include GLUT1, Aquaporin 1, and Band 3. In one example, a type III transmembrane protein can be fused with an acceptor peptide at the N-terminus of the transmembrane protein.

In some embodiments, a sortase recognition sequence as described above can further comprises one or more additional amino acids, e.g., at the N or C terminus. For example, one or more amino acids (e.g., up to 5 amino acids) having the identity of amino acids found immediately N-terminal to, or C-terminal to, a five (5) amino acid recognition sequence in a naturally occurring sortase substrate may be incorporated. Such additional amino acids may provide context that improves the recognition of the recognition motif.

In some embodiments, a sortase recognition motif can be masked. In contrast to an unmasked sortase recognition motif, which can be can be recognized by a sortase, a masked sortase recognition motif is a motif that is not recognized by a sortase but that can be readily modified ("unmasked") such that the resulting motif is recognized by the sortase. For example, in some embodiments at least one amino acid of a masked sortase recognition motif comprises a side chain comprising a moiety that inhibits, e.g., prevents, recognition of the sequence by a sortase of interest, e.g., SrtAaureus. Removal of the inhibiting moiety, in turn, allows recognition of the motif by the sortase. Masking may, for example, reduce recognition by at least 80%, 90%, 95%, or more (e.g., to undetectable levels) in certain embodiments. By way of example, in certain embodiments a threonine residue in a sortase recognition motif such as LPXTG (SEQ ID NO: 1) may be phosphorylated, thereby rendering it refractory to recognition and cleavage by SrtA. The masked recognition sequence can be unmasked by treatment with a phosphatase, thus allowing it to be used in a SrtA-catalyzed transamidation reaction.

When necessary, the genetically modified membrane protein of a CD34+ progenitor cell can further include additional suitable tags, which include, but are not limited to, amino acids, nucleic acids, polynucleotides, sugars, carbohydrates, polymers, lipids, fatty acids, and small molecules. Other suitable tags will be apparent to those of skill in the art and the invention is not limited in this aspect.

In some embodiments, such a tag comprises a sequence useful for purifying, expressing, solubilizing, and/or detecting a polypeptide. In some embodiments, a tag can serve multiple functions. In some embodiments, the tag is relatively small, e.g., ranging from a few amino acids up to about 100 amino acids long. In some embodiments, a tag is more than 100 amino acids long, e.g., up to about 500 amino acids long, or more. In some embodiments, a tag comprises an HA, TAP, Myc, 6×His, Flag, streptavidin, biotin, or GST tag, to name a few examples. In some embodiments, a tag comprises a solubility-enhancing tag (e.g., a SUMO tag, NUS A tag, SNUT tag, or a monomeric mutant of the Ocr protein of bacteriophage T7). See, e.g., Esposito D and Chatterjee D K. Curr Opin Biotechnol.; 17(4):353-8 (2006). In some embodiments, a tag is cleavable, so that it can be removed, e.g., by a protease. In some embodiments, this is achieved by including a protease cleavage site in the tag, e.g., adjacent or linked to a functional portion of the tag. Exemplary proteases include, e.g., thrombin, TEV protease, Factor Xa, PreScission protease, etc. In some embodiments, a "self-cleaving" tag is used. See, e.g., Wood et al., International PCT Application PCT/US2005/05763, filed on Feb. 24, 2005, and published as WO/2005/086654 on Sep. 22, 2005.

In some embodiments, the genetically modified red blood cells may express a fusion protein on the surface, the fusion protein comprising a red blood cell membrane protein as described herein, a first heterologous peptide fused to the terminus of the membrane protein that is exposed to the extracellular or luminal space, and a second heterologous protein fused to the terminus of the membrane protein that is exposed to the cytoplasmic space. The first heterologous peptide may comprise an acceptor peptide of a sortase (any acceptor peptides as described herein), if it is fused to the N-terminus of the membrane protein (e.g., a Type I membrane protein). Alternatively, the first heterologous peptide may comprise a sequence recognizable by a sortase (e.g., LPXTG (SEQ ID NO: 1) or LPXT (SEQ ID NO: 50)), if it is fused to the C-terminus of the membrane protein (e.g., a Type II membrane protein).

When the membrane protein is a Type I (e.g., GPA) or Type III membrane protein, the second heterologous protein is fused to the C-terminus of the membrane protein. The expression cassette for producing such a fusion protein may contain two copies of sequences encoding the second heterologous protein, one being fused in-frame with the membrane protein while the other being located 3' downstream to an IRES site located between the two copies. This design would allow for production of the second heterologous protein in free form and in fusion form with the membrane protein. See, e.g., Examples below. Alternatively, when the membrane protein is a Type II membrane protein (e.g., Kell), the second heterologous protein is fused to the N-terminus of the membrane protein. The expression cassette for producing such a fusion protein may contain two copies of the sequence encoding the second heterologous protein, which are separated by an IRES site, so as to produce the second heterologous protein in both free and fusion form.

The second heterologous protein can be a cytoplasmic protein. In some examples, the heterologous protein is a diagnostic protein, e.g., a protein such as a fluorescent protein (e.g., GFP) which can release a detectable signal under suitable conditions. In other examples, the heterologous protein is a therapeutic protein, e.g., a protein drug.

When necessary, a targeting agent may be conjugated to the first heterologous peptide as described above via a sortase reaction. Such a target agent (e.g., an antibody such as a single domain antibody) may specifically bind to a specific type of cells (e.g., disease cells such as cancer cells). The resultant genetically modified red blood cells are useful in delivering the cytoplasmically deposed protein of interest (the second heterologous protein) to intended target cells recognizable by the target agent.

Alternatively or in addition, the present disclosure provides genetically engineered red blood cells that express two sortaggable surface proteins, which can be conjugated to different functional moieties via reactions catalyzed by sortase enzymes having different substrate specificity. See below discussions. In one example, both of the two sortaggable surface proteins comprise a Type I membrane protein (e.g., GPA). In one sortaggable surface protein, the N-terminus of the Type I membrane protein is fused to an oligoglycine (e.g., $G_3$ or $G_5$ (SEQ ID NO: 3)); in the other sortaggable surface protein, the N-terminus of the Type I membrane protein is fused to an oligoalanine (e.g., $A_3$ or $A_5$ (SEQ ID NO: 79)). In another example, both of the two sortaggable surface proteins comprise a Type II membrane protein (e.g., Kell or CD71). In one sortaggable surface protein, the C-terminus of the Type II membrane protein is fused to the motif LPXTG (SEQ ID NO: 1); in the other sortaggable surface protein, the C-terminus of the Type II membrane protein is fused to the motif LPXTA (SEQ ID NO: 2). In yet another example, one of the sortaggable surface protein comprises a Type I membrane protein (e.g., GPA), the N-terminus of which is fused to an acceptor peptide, and the other sortaggable surface protein comprises a Type II membrane protein (e.g., Kell or CD71), the C-terminus of which is fused to a sequence recognizable by a sortase. When the acceptor peptide is an oligoglycine (e.g., $G_3$ or $G_5$ (SEQ ID NO: 3)), the sequence recognizable by a sortase may be the motif of LPXTA (SEQ ID NO: 2). When the acceptor peptide is an oligoalanine (e.g., $A_3$ or $A_5$ (SEQ ID NO: 79)), the sequence recognizable by a sortase may be the motif of LPXTG (SEQ ID NO: 1).

Any of the genetically modified CD34$^+$ progenitor cells described herein can be cultured under suitable conditions allowing for differentiation into mature enucleated red blood cells, e.g., the in vitro culturing process described herein. The resultant enucleated red blood cells are capable of expressing the surface protein of interest, such as a sortaggable surface protein as described herein, which can be evaluated and confirmed by routine methodology (e.g., Western blotting or FACS analysis).

III. Conjugation of Agents to Cells Expression Sortaggable Surface Proteins Via Sortagging Any of the genetically modified cells (e.g., CD34+ progenitor cells or mature enucleated red blood cells) expressing sortagaggle surface protein can be modified in the presence of a sortase to conjugate an agent of interest to the surface of the cells, a process known as sortagging. The term, "sortagging," as used herein, refers to the process of adding a tag, e.g., a moiety or molecule (e.g., a protein, polypeptide, detectable label, binding agent, or click chemistry handle, onto a target molecule, for example, a target protein on the surface of a red blood cell via a sortase-mediated transpeptidation reaction.

(a) Sortase

Sortase is a family of enzymes capable of carrying out a transpeptidation reaction conjugating the C-terminus of a protein to the N-terminus of another protein via transamidation. Sortases are also referred to as transamidases, and typically exhibit both a protease and a transpeptidation activity. Various sortases from prokaryotic organisms have been identified. For example, some sortases from Gram-positive bacteria cleave and translocate proteins to proteoglycan moieties in intact cell walls. Among the sortases that have been isolated from *Staphylococcus aureus*, are sortase A (Srt A) and sortase B (Srt B). Thus, in certain embodiments, a transamidase used in accordance with the conjugation methods described herein is sortase A, e.g., that from *S. aureus*, also referred to herein as SrtA$_{aureus}$. In other embodiments, a transamidase is a sortase B, e.g., from *S. aureus*, also referred to herein as SrtB$_{aureus}$.

Sortases have been classified into four classes, designated A, B, C, and D (i.e., sortase A, sortase B, sortase C, and sortase D, respectively) based on sequence alignment and phylogenetic analysis of 61 sortases from Gram-positive bacterial genomes (Dramsi et al., *Res Microbiol*.156(3):289-97, 2005; the entire contents of which are incorporated herein by reference). These classes correspond to the following subfamilies, into which sortases have also been classified by Comfort and Clubb (Comfort et al., *Infect Immun.*, 72(5):2710-22, 2004; the entire contents of which are incorporated herein by reference): Class A (Subfamily 1), Class B (Subfamily 2), Class C (Subfamily 3), Class D (Subfamilies 4 and 5). The aforementioned references disclose numerous sortases and their recognition motifs. See also Pallen et al., *TRENDS in Microbiology*, 2001, 9(3), 97-101; the entire contents of which are incorporated herein by reference). Those skilled in the art will readily be able to assign a sortase to the correct class based on its sequence and/or other characteristics such as those described in Drami, et al., supra.

The term "sortase A" is used herein to refer to a class A sortase, usually named SrtA in any particular bacterial species, e.g., SrtA from *S. aureus*. Likewise "sortase B" is used herein to refer to a class B sortase, usually named SrtB in any particular bacterial species, e.g., SrtB from *S. aureus*. The present disclosure encompasses embodiments relating to any of the sortase classes known in the art (e.g., a sortase A from any bacterial species or strain, a sortase B from any bacterial species or strain, a class C sortase from any bacterial species or strain, and a class D sortase from any bacterial species or strain).

Amino acid sequences of Srt A and Srt B and the nucleotide sequences that encode them are known to those of skill in the art and are disclosed in a number of references cited herein, the entire contents of all of which are incorporated herein by reference. The amino acid sequences of *S. aureus* SrtA and SrtB are homologous, sharing, for example, 22% sequence identity and 37% sequence similarity. The amino acid sequence of a sortase-transamidase from *Staphylococcus aureus* also has substantial homology with sequences of enzymes from other Gram-positive bacteria, and such transamidases can be utilized in the ligation processes described herein. For example, for SrtA there is about a 31% sequence identity (and about 44% sequence similarity) with best alignment over the entire sequenced region of the *S. pyogenes* open reading frame. There is about a 28% sequence identity with best alignment over the entire sequenced region of the *A. naeslundii* open reading frame. It will be appreciated that different bacterial strains may exhibit differences in sequence of a particular polypeptide, and the sequences herein are exemplary.

In certain embodiments a transamidase bearing 18% or more sequence identity, 20% or more sequence identity, or 30% or more sequence identity with an *S. pyogenes, A. naeslundii, S. mutans, E. faecalis* or *B. subtilis* open reading frame encoding a sortase can be screened, and enzymes having transamidase activity comparable to Srt A or Srt B from *S. aureas* can be utilized (e.g., comparable activity sometimes is 10% of Srt A or Srt B activity or more).

In some embodiments, the conjugation methods described herein use a sortase A (SrtA). SrtA recognizes the motif LPXTX (SEQ ID NO: 80; wherein each occurrence of X represents independently any amino acid residue), with common recognition motifs being, e.g., LPKTG (SEQ ID NO: 81), LPATG (SEQ ID NO: 82), LPNTG (SEQ ID NO: 83). In some embodiments LPETG (SEQ ID NO: 44) is used as the sortase recognition motif. However, motifs falling outside this consensus may also be recognized. For example, in some embodiments the motif comprises an 'A' rather than a 'T' at position 4, e.g., LPXAG (SEQ ID NO: 84), e.g., LPNAG (SEQ ID NO: 85). In some embodiments the motif comprises an 'A' rather than a 'G' at position 5, e.g., LPXTA (SEQ ID NO: 2), e.g., LPNTA (SEQ ID NO: 86). In some embodiments the motif comprises a 'G' rather than 'P' at position 2, e.g., LGXTG (SEQ ID NO: 87), e.g., LGATG (SEQ ID NO: 88). In some embodiments the motif comprises an 'I' rather than 'L' at position 1, e.g., IPXTG (SEQ ID NO: 89), e.g., IPNTG (SEQ ID NO: 90) or IPETG (SEQ ID NO: 91). Additional suitable sortase recognition motifs will be apparent to those of skill in the art, and the invention is not limited in this respect. It will be appreciated that the terms "recognition motif" and "recognition sequence", with respect to sequences recognized by a transamidase or sortase, are used interchangeably. Such sortase recognition motifs can be used for constructing the sortaggable surface proteins described herein.

In some embodiments of the invention the sortase is a sortase B (SrtB), e.g., a sortase B of *S. aureus, B. anthracis*, or *L. monocytogenes*. Motifs recognized by sortases of the B class (SrtB) often fall within the consensus sequences NPXTX (SEQ ID NO: 92), e.g., NP[Q/K]-[T/s]-[N/G/s] (SEQ ID NO: 93), such as NPQTN (SEQ ID NO: 94) or NPKTG (SEQ ID NO: 95). For example, sortase B of *S. aureus* or *B. anthracis* cleaves the NPQTN (SEQ ID NO: 94) or NPKTG (SEQ ID NO: 95) motif of IsdC in the respective bacteria (see, e.g., Marraffini et al., *Journal of Bacteriology*, 189(17): 6425-6436, 2007). Other recognition motifs found in putative substrates of class B sortases are NSKTA (SEQ ID NO: 96), NPQTG (SEQ ID NO: 97), NAKTN (SEQ ID NO: 98), and NPQSS (SEQ ID NO: 99). For example, SrtB from *L. monocytogenes* recognizes certain motifs lacking P at position 2 and/or lacking Q or K at position 3, such as NAKTN (SEQ ID NO: 98) and NPQSS (SEQ ID NO: 99) (Mariscotti et al., *J Biol Chem.* 2009 Jan. 7). Such sortase recognition motifs can also be used for constructing the sortaggable surface proteins described herein.

Using sortases with distinct substrate specificity, it is possible to combine N-terminal and C-terminal labeling strategies (Antos et al., 2009, 1 *Am. Chem. Soc.*, 131(31): 10800-10801) to generate multi-labeled RBCs. For example, unlike Sortase A from *Staphylococcus aureus*, Sortase A derived from *Streptococcus pyogenes* recognizes LPXTA (SEQ ID NO: 2) motifs and accepts oligo-alanine probes as nucleophiles. Therefore, the sortase reactions of both enzymes can be performed as orthogonal reactions. Utilization of such sortase reactions with suitable sortase(s) is also within the scope of the present disclosure.

In some embodiments, the sortase is a sortase C (Srt C). Sortase C may utilize LPXTX (SEQ ID NO: 80) as a recognition motif, with each occurrence of X independently representing any amino acid residue. This recognition motif can be used for constructing the sortaggable surface proteins described herein.

In yet other embodiments, the sortase is a sortase D (Srt D). Sortases in this class are predicted to recognize motifs with a consensus sequence NA-[E/A/S/H]-TG (SEQ ID NO: 100; Comfort D, supra). Sortase D has been found, e.g., in *Streptomyces* spp., *Corynebacterium* spp., *Tropheryma whipplei, Thermobifida fusca*, and *Bifidobacterium longhum*. LPXTA (SEQ ID NO: 2) or LAXTG may serve as a recognition sequence for sortase D, e.g., of subfamilies 4 and 5, respectively subfamily-4 and subfamily-5 enzymes process the motifs LPXTA (SEQ ID NO: 2) and LAXTG (SEQ ID NO: 101), respectively. For example, *B. anthracis* Sortase C has been shown to specifically cleave the LPNTA (SEQ ID NO: 102) motif in *B. anthracis* BasI and BasH (see Marrafini, supra).

Additional sortases, including, but not limited to, sortases recognizing additional sortase recognition motifs are also suitable for use in some embodiments of this invention. For example, sortases described in Chen et al., *Proc Natl Acad Sci USA.* 2011 Jul. 12; 108(28):11399, the entire contents of which are incorporated herein; and a sortase that recognizes QVPTGV (SEQ ID NO: 103) motif as described in Barnett et al., *Journal of Bacteriology*, Vol. 184, No. 8, p. 2181-2191, 2002; the entire contents of which are incorporated herein by reference).

The use of sortases found in any gram-positive organism, such as those mentioned herein and/or in the references (including databases) cited herein is contemplated in the context of some embodiments of this invention. Also contemplated is the use of sortases found in gram negative bacteria, e.g., *Colwellia psychrerythraea, Microbulbifer degradans, Bradyrhizobium japonicum, Shewanella oneidensis*, and *Shewanella putrefaciens*. Such sortases recognize sequence motifs outside the LPXTX (SEQ ID NO: 80) consensus, for example, LP[Q/K]T[A/S]T (SEQ ID NO: 104). In keeping with the variation tolerated at position 3 in sortases from gram-positive organisms, a sequence motif LPXT[A/S] (SEQ ID NO: 105), e.g., LPXTA (SEQ ID NO: 2) or LPSTS (SEQ ID NO: 106) may be used.

(b) Agent for Conjugation to Cell Surface

Agents that can be conjugated to cell surfaces via sortagging (directly or indirectly) can be any molecule, entity, or moiety, including, but are not limited to a protein, an amino acid, a peptide, a polynucleotide, a carbohydrate, a detectable label, a binding agent, a tag, a metal atom, a contrast agent, a catalyst, a non-polypeptide polymer, a synthetic polymer, a recognition element, a lipid, a linker, or chemical compound, such as a small molecule. In some embodiments, the agent is a binding agent, for example, a ligand or a ligand-binding molecule such as streptavidin/biotin, and an antibody or an antibody fragment.

When the agent is a polypeptide, it can be conjugated directly to a cell expressing a sortaggable surface protein in the presence of a sortase. The terms "protein," "peptide" and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

A protein to be conjugated to cell surfaces by the conjugation methods described herein can be any protein having a desired bioactivity, e.g., diagnostic or therapeutic. In some examples, the protein is a protein drug (e.g., an antibody or a fragment thereof), a peptide capable of targeting a specific type of cells (e.g., disease cells such as cancer cells), or an immunogenic peptide capable of eliciting desired immune responses (e.g., B cell responses or T cell responses). Such a protein can also be a protein-based binding agent, e.g., streptavidin.

Without limiting the present disclosure in any way, this section discusses certain target proteins. In general, any protein or polypeptide can be modified to carry a click chemistry handle and/or conjugated to another molecule via click chemistry according to methods provided herein. In some embodiments the target protein comprises or consists of a polypeptide that is at least 80%, or at least 90%, e.g., at least 95%, 86%, 97%, 98%, 99%, 99.5%, or 100% identical to a naturally occurring protein or polypeptide. In some embodiments, the target protein has no more than 1, 2, 3, 4, 5, 6, 7, 8, 9, or 10 amino acid differences relative to a naturally occurring sequence. In some embodiments the naturally occurring protein is a mammalian protein, e.g., of human origin.

The term "antibody," as used herein, refers to a protein belonging to the immunoglobulin superfamily. The terms antibody and immunoglobulin are used interchangeably. With some exceptions, mammalian antibodies are typically made of basic structural units each with two large heavy chains and two small light chains. There are several different types of antibody heavy chains, and several different kinds of antibodies, which are grouped into different isotypes based on which heavy chain they possess. Five different antibody isotypes are known in mammals, IgG, IgA, IgE, IgD, and IgM, which perform different roles, and help direct the appropriate immune response for each different type of foreign object they encounter. In some embodiments, an antibody is an IgG antibody, e.g., an antibody of the IgG1, 2, 3, or 4 human subclass. Antibodies from mammalian species (e.g., human, mouse, rat, goat, pig, horse, cattle, camel) are within the scope of the term, as are antibodies from non-mammalian species (e.g., from birds, reptiles, amphibia) are also within the scope of the term, e.g., IgY antibodies.

Only part of an antibody is involved in the binding of the antigen, and antigen-binding antibody fragments, their preparation and use, are well known to those of skill in the art. As is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). Suitable antibodies and antibody fragments for use in the context of some embodiments of the present invention include, for example, human antibodies, humanized antibodies, domain antibodies, F(ab'), F(ab')2, Fab, Fv, Fc, and Fd fragments, antibodies in which the Fc and/or FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; and antibodies in which the FR and/or CDR1 and/or CDR2 regions have been replaced by homologous human or non-human sequences. In some embodiments, so-called single chain antibodies (e.g., ScFv), (single) domain antibodies, and other intracellular antibodies may be used in the context of the present invention. Domain antibodies (single domain antibodies), camelid and camelized antibodies and fragments thereof, for example, VHH domains, or nanobodies, such as those described in patents and published patent applications of Ablynx N V and Domantis are also encompassed in the term antibody. A single domain antibody may consist of a single monomeric variable antibody domain and is capable of specifically binding to an antigen. Further, chimeric antibodies, e.g., antibodies comprising two antigen-binding domains that bind to different antigens, are also suitable for use in the context of some embodiments of the present invention.

The term "antigen-binding antibody fragment," as used herein, refers to a fragment of an antibody that comprises the paratope, or a fragment of the antibody that binds to the antigen the antibody binds to, with similar specificity and affinity as the intact antibody. Antibodies, e.g., fully human monoclonal antibodies, may be identified using phage display (or other display methods such as yeast display, ribosome display, bacterial display). Display libraries, e.g., phage display libraries, are available (and/or can be generated by one of ordinary skill in the art) that can be screened to identify an antibody that binds to an antigen of interest, e.g., using panning. See, e.g., Sidhu, S. (ed.) Phage Display in Biotechnology and Drug Discovery (Drug Discovery Series; CRC Press; 1st ed., 2005; Aitken, R. (ed.) Antibody Phage Display: Methods and Protocols (Methods in Molecular Biology) Humana Press; 2nd ed., 2009.

Exemplary antibodies include, but are not limited to, Abciximab (glycoprotein IIb/IIIa; cardiovascular disease), Adalimumab (TNF-α, various auto-immune disorders, e.g., rheumatoid arthritis), Alemtuzumab (CD52; chronic lymphocytic leukemia), Basiliximab (IL-2Rα receptor (CD25); transplant rejection), Bevacizumab (vascular endothelial growth factor A; various cancers, e.g., colorectal cancer, non-small cell lung cancer, glioblastoma, kidney cancer; wet age-related macular degeneration), Catumaxomab, Cetuximab (EGF receptor, various cancers, e.g., colorectal cancer, head and neck cancer), Certolizumab (e.g., Certolizumab pegol) (TNF alpha; Crohn's disease, rheumatoid arthritis), Daclizumab (IL-2Rα receptor (CD25); transplant rejection), Eculizumab (complement protein C5; paroxysmal nocturnal hemoglobinuria), Efalizumab (CD11a; psoriasis), Gemtuzumab (CD33; acute myelogenous leukemia (e.g., with calicheamicin)), Ibritumomab tiuxetan (CD20; Non-Hodgkin lymphoma (e.g., with yttrium-90 or indium-111)), Infliximab (TNF alpha; various autoimmune disorders, e.g., rheumatoid arthritis) Muromonab-CD3 (T Cell CD3 receptor; transplant rejection), Natalizumab (alpha-4 (α4) integrin; multiple sclerosis, Crohn's disease), Omalizumab (IgE; allergy-related asthma), Palivizumab (epitope of RSV F protein; Respiratory Syncytial Virus infection), Panitumumab (EGF receptor; cancer, e.g., colorectal cancer), Ranibizumab (vascular endothelial growth factor A; wet age-related macular degeneration) Rituximab (CD20; Non-Hodgkin lymphoma), Tositumomab (CD20; Non-Hodgkin lymphoma), Trastuzumab (ErbB2; breast cancer), and any antigen-binding fragment thereof.

The term "binding agent," as used herein refers to any molecule that binds another molecule with high affinity. In some embodiments, a binding agent binds its binding partner with high specificity. Examples for binding agents include, without limitation, antibodies, antibody fragments, receptors, ligands, aptamers, and adnectins.

In some embodiments, the protein of interest to be conjugated to red blood cells is a cytokine, e.g., a type I cytokine. In some embodiments of particular interest, the target protein is a four-helix bundle protein, e.g., a four-helix bundle cytokine. Exemplary four-helix bundle cytokines include, e.g., certain interferons (e.g., a type I interferon, e.g., IFN-α), interleukins (e.g., IL-2, IL-3, IL-4, IL-5, IL-6, IL-7, IL-12), and colony stimulating factors (e.g., G-CSF, GM-CSF, M-CSF). The IFN can be, e.g., interferon alpha 2a or interferon alpha 2b. See, e.g., Mott H R and Campbell I D. "*Four-helix bundle growth factors and their receptors: protein-protein interactions.*" Curr Opin Struct Biol. 1995 February; 5(1):114-21; Chaiken I M, Williams W V. "*Identifying structure-function relationships in four-helix bundle cytokines: towards de novo mimetics design.*" Trends Biotechnol. 1996 October; 14(10):369-75; Klaus W, et al., "*The three-dimensional high resolution structure of human interferon alpha-2a determined by heteronuclear NMR spectroscopy in solution*". J Mol Biol., 274(4):661-75, 1997, for further discussion of certain of these cytokines.

The protein of interest may also be a cytokine protein that has a similar structure to one or more of the afore-mentioned cytokines. For example, the cytokine can be an IL-6 class cytokine such as leukemia inhibitory factor (LIF) or oncostatin M. In some embodiments, the cytokine is one that in nature binds to a receptor that comprises a GP 130 signal transducing subunit. Other four-helix bundle proteins of interest include growth hormone (GH), prolactin (PRL), and placental lactogen. In some embodiments, the target protein is an erythropoiesis stimulating agent, e.g., (EPO), which is also a four-helix bundle cytokine. In some embodiments, an erythropoiesis stimulating agent is an EPO variant, e.g., darbepoetin alfa, also termed novel erythropoiesis stimulating protein (NESP), which is engineered to contain five N-linked carbohydrate chains (two more than recombinant HuEPO). In some embodiments, the protein comprises five helices. For example, the protein can be an interferon beta, e.g., interferon beta-1a or interferon beta-1b, which (as will be appreciated) is often classified as a four-helix bundle cytokine. In some embodiments, a target protein is IL-9, IL-10, IL-11, IL-13, or IL-15. See, e.g., Hunter, C A, Nature Reviews Immunology 5, 521-531, 2005, for discussion of certain cytokines. See also Paul, W E (ed.), Fundamental immunology, Lippincott Williams & Wilkins; 6th ed., 2008. Any protein described in the references cited herein, all of which are incorporated herein by reference, can be used as a target protein.

In addition, the protein of interest may be a protein that is approved by the US Food & Drug Administration (or an equivalent regulatory authority such as the European Medicines Evaluation Agency) for use in treating a disease or disorder in humans. Such proteins may or may not be one for which a PEGylated version has been tested in clinical trials and/or has been approved for marketing.

The protein of interest may also be a neurotrophic factor, i.e., a factor that promotes survival, development and/or function of neural lineage cells (which term as used herein includes neural progenitor cells, neurons, and glial cells, e.g., astrocytes, oligodendrocytes, microglia). For example, in some embodiments, the target protein is a factor that promotes neurite outgrowth. In some embodiments, the protein is ciliary neurotrophic factor (CNTF; a four-helix bundle protein) or an analog thereof such as Axokine, which is a modified version of human Ciliary neurotrophic factor with a 15 amino acid truncation of the C terminus and two amino acid substitutions, which is three to five times more potent than CNTF in in vitro and in vivo assays and has improved stability properties.

In another example, the protein of interest is a protein that forms homodimers or heterodimers, (or homo- or heterooligomers comprising more than two subunits, such as tetramers). In certain embodiments the homodimer, heterodimer, or oligomer structure is such that a terminus of a first subunit is in close proximity to a terminus of a second subunit. For example, an N-terminus of a first subunit is in close proximity to a C-terminus of a second subunit. In certain embodiments the homodimer, heterodimer, or oligomer structure is such that a terminus of a first subunit and a terminus of a second subunit are not involved in interaction with a receptor, so that the termini can be joined via a non-genetically encoded peptide element without significantly affecting biological activity. In some embodiments, termini of two subunits of a homodimer, heterodimer, or oligomer are conjugated via click chemistry using a method described herein, thereby producing a dimer (or oligomer) in which at least two subunits are covalently joined. For example, the neurotrophins nerve growth factor (NGF); brain-derived neurotrophic factor (BDNF); neurotrophin 3 (NT3); and neurotrophin 4 (NT4) are dimeric molecules which share approximately 50% sequence identity and exist in dimeric forms. See, e.g., Robinson R C, et al., "*Structure of the brain-derived neurotrophic factor/neurotrophin 3 heterodimer.*", Biochemistry. 34(13):4139-46, 1995; Robinson R C, et al., "*The structures of the neurotrophin 4 homodimer and the brain-derived neurotrophic factor/neurotrophin 4 heterodimer reveal a common Trk-binding site.*" Protein Sci. 8(12):2589-97, 1999, and references therein. In some embodiments, the dimeric protein is a cytokine, e.g., an interleukin.

Alternatively, the protein of interest is an enzyme, e.g., an enzyme that is important in metabolism or other physiological processes. As is known in the art, deficiencies of enzymes or other proteins can lead to a variety of disease. Such diseases include diseases associated with defects in carbohydrate metabolism, amino acid metabolism, organic acid metabolism, porphyrin metabolism, purine or pyrimidine metabolism, lysosomal storage disorders, blood clotting, etc. Examples include Fabry disease, Gaucher disease, Pompe disease, adenosine deaminase deficiency, asparaginase deficiency, *porphyria*, hemophilia, and hereditary angioedema. In some embodiments, a protein is a clotting or coagulation factor, (e.g., factor VII, VIIa, VIII or IX). In other embodiments a protein is an enzyme that plays a role in carbohydrate metabolism, amino acid metabolism, organic acid metabolism, porphyrin metabolism, purine or pyrimidine metabolism, and/or lysosomal storage, wherein exogenous administration of the enzyme at least in part alleviates the disease.

Moreover, the protein of interest may be a receptor or receptor fragment (e.g., extracellular domain). In some embodiments the receptor is a TNFα receptor. In certain embodiments, the target protein comprises urate oxidase.

In some embodiments, the protein of interest is an antigenic protein, which may derive from a pathogen (e.g., a virus or bacterium). An antigenic protein may be naturally occurring or synthetic in various embodiments. It may be naturally produced by and/or comprises a polypeptide or peptide that is genetically encoded by a pathogen, an infected cell, or a neoplastic cell (e.g., a cancer cell). In some examples, the antigenic protein is an autoantigen ("self antigen"), that has the capacity to initiate or enhance an autoimmune response. In other examples, the antigenic protein is produced or genetically encoded by a virus, bacteria, fungus, or parasite which, in some embodiments, is a pathogenic agent. In some embodiments, an agent (e.g., virus, bacterium, fungus, parasite) infects and, in some embodiments, causes disease in, at least one mammalian or avian species, e.g., human, non-human primate, bovine, ovine, equine, caprine, and/or porcine species. In some embodiments, a pathogen is intracellular during at least part of its life cycle. In some embodiments, a pathogen is extracellular. It will be appreciated that an antigen that originates from a particular source may, in various embodiments, be isolated from such source, or produced using any appropriate means (e.g., recombinantly, synthetically, etc.), e.g., for purposes of using the antigen, e.g., to identify, generate, test, or use an antibody thereto). An antigen may be modified, e.g., by conjugation to another molecule or entity (e.g., an adjuvant), chemical or physical denaturation, etc. In some embodiments, an antigen is an envelope protein, capsid protein, secreted protein, structural protein, cell wall protein or polysaccharide, capsule protein or polysaccharide, or enzyme. In some embodiments an antigen is a toxin, e.g., a bacterial toxin.

Exemplary viruses include, e.g., Retroviridae (e.g., lentiviruses such as human immunodeficiency viruses, such as HIV-I); Caliciviridae (e.g. strains that cause gastroenteritis); Togaviridae (e.g., equine encephalitis viruses, rubella viruses); Flaviridae (e.g. dengue viruses, encephalitis viruses, yellow fever viruses, hepatitis C virus); Coronaviridae (e.g. coronaviruses); Rhabdoviridae (e.g. vesicular stomatitis viruses, rabies viruses); Filoviridae (e.g. Ebola viruses); Paramyxoviridae (e.g. parainfluenza viruses, mumps virus, measles virus, respiratory syncytial virus); Orthomyxoviridae (e.g. influenza viruses); Bunyaviridae (e.g. Hantaan viruses, bunga viruses, phleboviruses and Nairo viruses); Arenaviridae (hemorrhagic fever viruses); Reoviridae (erg., reoviruses, orbivurses and rotaviruses); Birnaviridae; Hepadnaviridae (Hepatitis B virus); Parvoviridae (parvoviruses); Papovaviridae (papilloma viruses, polyoma viruses); Adenoviridae; Herpesviridae (herpes simplex virus (HSV) 1 and 2, varicella zoster virus, cytomegalovirus (CMV), EBV, KSV); Poxviridae (variola viruses, vaccinia viruses, pox viruses); and Picornaviridae (e.g. polio viruses, hepatitis A virus; enteroviruses, human coxsackie viruses, rhinoviruses, echoviruses).

Exemplary bacteria include, e.g., *Helicobacter pylori, Borellia burgdorferi, Legionella pneumophilia, Mycobacteria* (e.g., *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae, Campylobacter* sp., *Enterococcus* sp., *Chlamydia* sp., *Haemophilus influenzae, Bacillus anthracia, Corynebacterium diphtheriae, Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira, Actinomyces israelii* and *Francisella tularensis*.

Exemplary fungi include, e.g., *Aspergillus*, such as *Aspergillus flavus, Aspergillus fumigatus, Aspergillus niger, Blastomyces*, such as *Blastomyces dermatitidis, Candida*, such as *Candida albicans, Candida glabrata, Candida guilliermondii, Candida krusei, Candida parapsilosis, Candida tropicalis, Coccidioides*, such as *Coccidioides immitis, Cryptococcus*, such as *Cryptococcus neoformans, Epidermophyton, Fusarium, Histoplasma*, such as *Histoplasma capsulatum, Malassezia*, such as *Malassezia furfur, Microsporum, Mucor, Paracoccidioides*, such as *Paracoccidioides brasiliensis, Penicillium*, such as *Penicillium marneffei, Pichia*, such as *Pichia anomala, Pichia guilliermondii, Pneumocystis*, such as *Pneumocystis carinii, Pseudallescheria*, such as *Pseudallescheria boydii, Rhizopus*, such as *Rhizopus oryzae, Rhodotorula*, such as *Rhodotorula rubra, Scedosporium*, such as *Scedosporium apiospermum, Schizophyllum*, such as *Schizophyllum commune, Sporothrix*, such as *Sporothrix schenckii, Trichophyton*, such as *Trichophyton mentagrophytes, Trichophyton rubrum, Trichophyton verrucosum, Trichophyton violaceutn, Trichosporon*, such as *Trichosporon asahii, Trichosporon cutaneum, Trichosporon inkin*, and *Trichosporon mucoides*.

In some embodiments, an antigen is a tumor antigen (TA). In general, a tumor antigen can be any antigenic substance produced by tumor cells (e.g., tumorigenic cells or in some embodiments tumor stromal cells, e.g., tumor-associated cells such as cancer-associated fibroblasts). In many embodiments, a tumor antigen is a molecule (or portion thereof) that is differentially expressed by tumor cells as compared with non-tumor cells. Tumor antigens may include, e.g., proteins that are normally produced in very small quantities and are expressed in larger quantities by tumor cells, proteins that are normally produced only in certain stages of development, proteins whose structure (e.g., sequence or post-translational modification(s)) is modified due to mutation in tumor cells, or normal proteins that are (under normal conditions) sequestered from the immune system. Tumor antigens may be useful in, e.g., identifying or detecting tumor cells (e.g., for purposes of diagnosis and/or for purposes of monitoring subjects who have received treatment for a tumor, e.g., to test for recurrence) and/or for purposes of targeting various agents (e.g., therapeutic agents) to tumor cells. For example, in some embodiments, a chimeric antibody is provided, comprising an antibody of antibody fragment that binds a tumor antigen, and conjugated via click chemistry to a therapeutic agent, for example, a cytotoxic agent. In some embodiments, a TA is an expression product of a mutated gene, e.g., an oncogene or mutated tumor suppressor gene, an overexpressed or aberrantly expressed cellular protein, an antigen encoded by an oncogenic virus (e.g., HBV; HCV; herpesvirus family members such as EBV, KSV; papilloma virus, etc.), or an oncofetal antigen. Oncofetal antigens are normally produced in the early stages of embryonic development and largely or completely disappear by the time the immune system is fully developed. Examples are alphafetoprotein (AFP, found, e.g., in germ cell tumors and hepatocellular carcinoma) and carcinoembryonic antigen (CEA, found, e.g., in bowel cancers and occasionally lung or breast cancer). Tyrosinase is an example of a protein normally produced in very low quantities but whose production is greatly increased in certain tumor cells (e.g., melanoma cells). Other exemplary TAs include, e.g., CA-125 (found, e.g., in ovarian cancer); MUC-1 (found, e.g., in breast cancer); epithelial tumor antigen (found, e.g., in breast cancer); melanoma-associated antigen (MAGE; found, e.g., in malignant melanoma); prostatic acid phosphatase (PAP, found in prostate cancer). In some embodiments, a TA is at least in part exposed at the cell surface of tumor cells. In some embodiments, a tumor antigen comprises an abnormally modified polypeptide or lipid, e.g., an aberrantly modified cell surface glycolipid or glycoprotein. It will be appreciated that a TA may be expressed by a subset of tumors of a particular type and/or by a subset of cells in a tumor.

Table 1 below lists exemplary proteins of interest and their amino acid sequences:

TABLE 1

Sequences of Exemplary Proteins of Interest:

| Protein | Sequence |
|---|---|
| Tissue plasminogen activator (1rtf) | Chain A: TTCCGLRQY (SEQ ID NO: 5)<br>Chain B:<br>IKGGLFADIASHPWQAAIFAKHHRRGGERFLCGGILISSCWILS<br>AAHCFQQQQQEEEEERRRRRFFFFFPPPPPPHHLTVILGRTYR<br>VVPGEEEQKFEVEKYIVHKEFDDDTYDNDIALLQLKSSSSSD<br>DDDDSSSSSSSSSRRRRRCAQESSVVRTVCLPPADLQLPDWT<br>ECELSGYGKHEALSPFYSERLKEAHVRLYPSSRCTTTSSSQQQ<br>HLLNRTVTDNMLCAGDTTTRRRSSSNNNLHDACQGDSGGPL<br>VCLNDGRMTLVGIISWGLGCGGQQKDVPGVYTKVTNYLDW<br>IRDNMRP (SEQ ID NO: 4) |
| Factor IX | Chain A:<br>VVGGEDAKPGQFPWQVVLNGKVDAFCGGSIVNEKWIVTAA<br>HCVEETTGVKITVVAGEHNIEETEHTEQKRNVIRIIPHHNYNN<br>NAAAAAAINKYNHDIALLELDEPLVLNSYVTPICIADKEYTTT<br>NNNIIIFLKFGSGYVSGWGRVFHKGRSALVLQYLRVPLVDRA<br>TCLRSTKFTIYNNMFCAGGFFHEGGGRRDSCQGDSGGPHVTE<br>VEGTSFLTGIISWGEECAAMMKGKYGIYTKVSRYVNWIKEK<br>TKLT (SEQ ID NO: 6)<br>Chain B:<br>MTCNIKNGRCEQFCKNSADNKVVCSCTEGYRLAENQKSCEP<br>AVPFPCGRVSVSQTSK (SEQ ID NO: 7) |
| Glucocerebrosidase | EFARPCIPKSFGYSSVVCVCNATYCDSFDPPALGTFSRYESTR<br>SGRRMELSMGPIQANHTGTGLLLTLQPEQKFQKVKGFGGAM<br>TDAAALNILALSPPAQNLLLKSYFSEEGIGYNIIRVPMASCDFS<br>IRTYTYADTPDDFQLHNFSLPEEDTKLKIPLIHRALQLAQRPV<br>SLLASPWTSPTWLKTNGAVNGKGSLKGQPGDIYHQTWARYF<br>VKFLDAYAEHKLQFWAVTAENEPSAGLLSGYPFQCLGFTPE<br>HQRDFIARDLGPTLANSTHHNVRLLMLDDQRLLLPHWAKVV<br>LTDPEAAKYVHGIAVHWYLDFLAPAKATLGETHRLFPNTML<br>FASEACVGSKFWEQSVRLGSWDRGMQYSHSIITNLLYHVVG<br>WTDWNLALNPEGGPNWVRNFVDSPIIVDITKDTFYKQPMFY<br>HLGHFSKFIPEGSQRVGLVASQKNDLDAVALMHPDGSAVVV<br>VLNRSSKDVPLTIKDPAVGFLETISPGYSIHTYLWHRQ (SEQ ID NO: 8) |
| alpha galactosidase A | LDNGLARTPTMGWLHWERFMCNLDCQEEPDSCISEKLFMEM<br>AELMVSEGWKDAGYEYLCIDDCWMAPQRDSEGRLQADPQR<br>FPHGIRQLANYVHSKGLKLGIYADVGNKTCAGFPGSFGYYDI<br>DAQTFADWGVDLLKFDGCYCDSLENLADGYKHMSLALNRT<br>GRSIVYSCEWPLYMWPFQKPNYTEIRQYCNHWRNFADIDDS<br>WKSIKSILDWTSFNQERIVDVAGPGGWNDPDMLVIGNFGLS<br>WNQQVTQMALWAIMAAPLFMSNDLRHISPQAKALLQDKDV<br>IAINQDPLGKQGYQLRQGDNFEVWERPLSGLAWAVAMINRQ<br>EIGGPRSYTIAVASLGKGVACNPACFITQLLPVKRKLGFYEWT<br>SRLRSHINPTGTVLLQLENTM (SEQ ID NO: 9) |
| arylsulfatase-A (iduronidase, α-L-) | RPPNIVLIFADDLGYGDLGCYGHPSSTTPNLDQLAAGGLRFT<br>DFYVPVSLPSRAALLTGRLPVRMGMYPGVLVPSSRGGLPLEE<br>VTVAEVLAARGYLTGMAGKWHLGVGPEGAFLPPHQGFHRF<br>LGIPYSHDQGPCQNLTCFPPATPCDGGCDQGLVPIPLLANLSV<br>EAQPPWLPGLEARYMAFAHDLMADAQRQDRPFFLYYASHH<br>THYPQFSGQSFAERSGRGPFGDSLMELDAAVGTLMTAIGDLG<br>LLEETLVIFTADNGPETMRMSRGGCSGLLRCGKGTTYEGGVR<br>EPALAFWPGHIAPGVTHELASSLDLLPTLAALAGAPLPNVTL<br>DGFDLSPLLLGTGKSPRQSLFFYPSYPDEVRGVFAVRTGKYK<br>AHFFTQGSAHSDTTADPACHASSSLTAHEPPLLYDLSKDPGE<br>NYNLLGATPEVLQALKQLQLLKAQLDAAVTFGPSQVARGED<br>PALQICCHPGCTPRPACCHCP (SEQ ID NO: 10) |

TABLE 1-continued

Sequences of Exemplary Proteins of Interest:

| | |
|---|---|
| arylsulfatase B (N-acetylgalactos-amine-4-sulfatase) (1fsu) | SRPPHLVFLLADDLGWNDVGFHGSRIRTPHLDALAAGGVLL<br>DNYYTQPLTPSRSQLLTGRYQIRTGLQHQIIWPCQPSCVPLDE<br>KLLPQLLKEAGYTTHMVGKWHLGMYRKECLPTRRGFDTYF<br>GYLLGSEDYYSHERCTLIDALNVTRCALDFRDGEEVATGYK<br>NMYSTNIFTKRAIALITNHPPEKPLFLYLALQSVHEPLQVPEE<br>YLKPYDFIQDKNRHHYAGMVSLMDEAVGNVTAALKSSGLW<br>NNTVFIFSTDNGGQTLAGGNNWPLRGRKWSLWEGGVRGVG<br>FVASPLLKQKGVKNRELIHISDWLPTLVKLARGHTNGTKPLD<br>GFDVWKTISEGSPSPRIELLHNIDPNFVDSSPCSAFNTSVHAAI<br>RHGNWKLLTGYPGCGYWFPPPSQYNVSEIPSSDPPTKTLWLF<br>DIDRDPEERHDLSREYPHIVTKLLSRLQFYHKHSVPVYFPAQD<br>PRCDPKATGVWGPWM (SEQ ID NO: 11) |
| beta-hexosaminidase A (2gjx) | LWPWPQNFQTSDQRYVLYPNNFQFQYDVSSAAQPGCSVLDE<br>AFQRYRDLLFGTLEKNVLVVSVVTPGCNQLPTLESVENYTLT<br>INDDQCLLLSETVWGALRGLETFSQLVWKSAEGTFFINKTEIE<br>DFPRFPHRGLLLDTSRHYLPLSSILDTLDVMAYNKLNVFHWH<br>LVDDPSFPYESFTFPELMRKGSYNPVTHIYTAQDVKEVIEYAR<br>LRGIRVLAEFDTPGHTLSWGPGIPGLLTPCYSGSEPSGTFGPV<br>NPSLNNTYEFMSTFFLEVSSVFPDFYLHLGGDEVDFTCWKSN<br>PEIQDFMRKKGFGEDFKQLESFYIQTLLDIVSSYGKGYVVWQ<br>EVFDNKVKIQPDTIIQVWREDIPVNYMKELELVTKAGFRALL<br>SAPWYLNRISYGPDWKDFYVVEPLAFEGTPEQKALVIGGEAC<br>MWGEYVDNTNLVPRLWPRAGAVAERLWSNKLTSDLTFAYE<br>RLSHFRCELLRRGVQAQPLNVGFCEQEFEQ (SEQ ID NO: 12) |
| Hexosaminidase A and B (2gjx) | CHAIN A:<br>LWPWPQNFQTSDQRYVLYPNNFQFQYDVSSAAQPGCSVLDE<br>AFQRYRDLLFGTLEKNVLVVSVVTPGCNQLPTLESVENYTLT<br>INDDQCLLLSETVWGALRGLETFSQLVWKSAEGTFFINKTEIE<br>DFPRFPHRGLLLDTSRHYLPLSSILDTLDVMAYNKLNVFHWH<br>LVDDPSFPYESFTFPELMRKGSYNPVTHIYTAQDVICEVIEYAR<br>LRGIRVLAEFDTPGHTLSWGPGIPGLLTPCYSGSEPSGTFGPV<br>NPSLNNTYEFMSTFFLEVSSVFPDFYLHLGGDEVDFTCWKSN<br>PEIQDFMRKKGFGEDFKQLESFYIQTLLDIVSSYGKGYVVWQ<br>EVFDNKVKIQPDTIIQVWREDIPVNYMKELELVTKAGFRALL<br>SAPWYLNRISYGPDWKDFYVVEPLAFEGTPEQKALVIGGEAC<br>MWGEYVDNTNLVPRLWPRAGAVAERLWSNKLTSDLTFAYE<br>RLSHFRCELLRRGVQAQPLNVGFCEQEFEQ (SEQ ID NO: 13)<br>Chain B:<br>PALWPLPLSVKMTPNLLHLAPENFYISHSPNSTAGPSCTLLEE<br>AFRRYHGYIFGTQVQQLLVSITLQSECDAFPNISSDESYTLLV<br>KEPVAVLKANRVWGALRGLETFSQLVYQDSYGTFTINESTII<br>DSPRFSHRGILIDTSRHYLPVKIILKTLDAMAFNKFNVLHWHI<br>VDDQSFPYQSITFPELSNKGSYSLSHVYTPNDVRMVIEYARLR<br>GIRVLPEFDTPGHTLSWGKGQKDLLTPCYSDSFGPINPTLNTT<br>YSFLTTFFKEISEVFPDQFIHLGGDEVEFKCWESNPKIQDFMR<br>QKGFGTDFKKLESFYIQKVLDIIATINKGSIVWQEVFDDKAKL<br>APGTIVEVWKDSAYPEELSRVTASGFPVILSAPWYLDLISYGQ<br>DWRKYYKVEPLDFGGTQKQKQLFIGGEACLWGEYVDATNL<br>TPRLWPRASAVGERLWSSKDVRDMDDAYDRLTRHRCRMVE<br>RGIAAQPLYAGYCN (SEQ ID NO: 14)<br>Chain C:<br>PALWPLPLSVKMTPNLLHLAPENFYISHSPNSTAGPSCTLLEE<br>AFRRYHGYIFGTQVQQLLVSITLQSECDAFPNISSDESYTLLV<br>KEPVAVLKANRVWGALRGLETFSQLVYQDSYGTFTINESTII<br>DSPRFSHRGILIDTSRHYLPVKIILKTLDAMAFNKFNVLHWHI<br>VDDQSFPYQSITFPELSNKGSYSLSHVYTPNDVRMVIEYARLR<br>GIRVLPEFDTPGHTLSWGKGQKDLLTPCYSLDSFGPINPTLNT<br>TYSFLTTFFKEISEVFPDQFIHLGGDEVEFKCWESNPKIQDFM<br>RQKGFGTDFKKLESFYIQKVLDIIATINKGSIVWQEVFDDKAK<br>LAPGTIVEVWKDSAYPEELSRVTASGFPVILSAPWYLDLISYG<br>QDWRKYYKVEPLDFGGTQKQKQLFIGGEACLWGEYVDATN<br>LTPRLWPRASAVGERLWSSKDVRDMDDAYDRLTRHRCRMV<br>ERGIAAQPLYAGYCN (SEQ ID NO: 15)<br>Chain D:<br>LWPWPQNFQTSDQRYVLYPNNFQFQYDVSSAAQPGCSVLDE<br>AFQRYRDLLFGTLEKNVLVVSVVTPGCNQLPTLESVENYTLT<br>INDDQCLLLSETVWGALRGLETFSQLVWKSAEGTFFINKTEIE<br>DFPRFPHRGLLLDTSRHYLPLSSILDTLDVMAYNKLNVFHWH<br>LVDDPSFPYESFTFPELMRKGSYNPVTHIYTAQDVKEVIEYAR<br>LRGIRVLAEFDTPGHTLSWGPGIPGLLTPCYSGSEPSGTFGPV<br>NPSLNNTYEFMSTFFLEVSSVFPDFYLHLGGDEVDFTCWKSN<br>PEIQDFMRKKGFGEDFKQLESFYIQTLLDIVSSYGKGYVVWQ<br>EVFDNKVKIQPDTIIQVWREDIPVNYMKELELVTKAGFRALL<br>SAPWYLNRISYGPDWKDFYVVEPLAFEGTPEQKALVIGGEAC |

TABLE 1-continued

Sequences of Exemplary Proteins of Interest:

| | |
|---|---|
| | MWGEYVDNTNLVPRLWPRAGAVAERLWSNKLTSDLTFAYE<br>RLSHFRCELLRRGVQAQPLNVGFCEQEFEQ (SEQ ID NO: 16) |
| phenylalanine hydroxylase (PAH) (1j8u) | VPWFPRTIQELDRFANQILSYGAELDADHPGFKDPVYRARRK<br>QFADIAYNYRHGQPIPRVEYMEEEKKTWGTVFKTLKSLYKT<br>HACYEYNHIFPLLEKYCGFHEDNIPQLEDVSQFLQTCTGFRLR<br>PVAGLLSSRDFLGGLAFRVFHCTQYIRHGSKPMYTPEPDICHE<br>LLGHVPLFSDRSFAQFSQEIGLASLGAPDEYIEKLATIYWFTV<br>EFGLCKQGDSIKAYGAGLLSSFGELQYCLSEKPKLLPLELEKT<br>AIQNYTVTEFQPLYYVAESFNDAKEKVRNFAATIPRPFSVRY<br>DPYTQRIEVL (SEQ ID NO: 17) |
| Cathepsin A | APDQDEIQRLPGLAKQPSFRQYSGYLKSSGSKHLHYWFVESQ<br>KDPENSPVVLWLNGGPGCSSLDGLLTEHGPFLVQPDGVTLEY<br>NPYSWNLIANVLYLESPAGVGFSYSDDKFYATNDTEVAQSNF<br>EALQDFFRLFPEYKNNKLFLTGESYAGIYIPTLAVLVMQDPS<br>MNLQGLAVGNGLSSYEQNDNSLVYFAYYHGLLGNRLWSSL<br>QTHCCSQNKCNFYDNKDLECVTNLQEVARIVGNSGLNIYNL<br>YAPCAGGVPSHFRYEKDTVVVQDLGNIFTRLPLKRMWHQAL<br>LRSGDKVRMDPPCTNTTAASTYLNNPYVRKALNIPEQLPQW<br>DMCNFLVNLQYRRLYRSMNSQYLKLLSSQKYQILLYNGDVD<br>MACNFMGDEWFVDSLNQKMEVQRRPWLVKYGDSGEQIAGF<br>VKEFSHIAFLTIKGAGHMVPTDKPLAAFTMFSRFLNKQPY<br>(SEQ ID NO: 18) |
| G-CSF | LPQSFLLKCLEQVRKIQGDGAALQEKLCATYKLCHPEELVLL<br>GHSLGIPWAPLLAGCLSQLHSGLFLYQGLLQALEGISPELGPT<br>LDTLQLDVADFATTIWQQMEELGMMPAFASAFQRRAGGVL<br>VASHLQSFLEVSYRVLRHLA (SEQ ID NO: 19) |
| GM-CSF | EHVNAIQEARRLLNLSRDTAAEMNETVEVISEMFDLQEPTCL<br>QTRLELYKQGLRGSLTKLKGPLTMMASHYKQHCPPTPETSC<br>ATQIITFESFKENLKDFLLVIP (SEQ ID NO: 20) |
| Interferon alfa-2 | CDLPQTHSLGSRRTLMLLAQMRKISLFSCLKDRHDFGFPQEE<br>FGNQFQKAETIPVLHEMIQQIFNLFSTKDSSAAWDETLIDKFY<br>TELYQQLNDLEACVIQGVGVTETPLMKEDSILAVRKYFQRIT<br>LYLKEKKYSPCAWEVVRAEIMRSFSLSTNLQESLRSKE (SEQ<br>ID NO: 21) |
| Interferon beta-1 | MSYNLLGFLQRSSNFQCQKLLWQLNGRLEYCLKDRMNFDIP<br>EEIKQLQQFQKEDAALTIYEMLQNIFAIFRQDSSSTGWNETIV<br>ENLLANVYHQINHLKTVLEEKLEKEDFTRGKLMSSLHLKRY<br>YGRILHYLKAKEYSFICAWTIVRVEILRNFYFINRLTGYLRN<br>(SEQ ID NO: 22) |
| Interferon gamma-1b | MQDPYVKEAENLKKYFNAGHSDVADNGTLFLGILKNWKEE<br>SDRKIMQSQIVSFYFKLFKNFKDDQSIQKSVETIKEDMNVKFF<br>NSNKKKRDDFEKLTNYSVTDLNVQRKAIDELIQVMAELGAN<br>VSGEFVKEAENLKKYFNDNGTLFLGILKNWKEESDRKIMQS<br>QIVSFYFKLFKNFKDDQSIQKSVETIKEDMNVKFFNSNKKKR<br>DDFEKLTNYSVTDLNVQRKAIHELIQVMAELSPAA (SEQ ID<br>NO: 23) |
| IL-2 (1M47) | STKKTQLQLEHLLLDLQMILNGINNYKNPKLTRMLTFKFYMP<br>KKATELKHLQCLEEELKPLEEVLNLAQNFHLRPRDLISNINVI<br>VLELKGFMCEYADETATIVEFLNRWITFCQSIISTLT (SEQ<br>NO: 24) |
| IL-1 (2nvh) | APVRSLNCTLRDSQQKSLVMSGPYELKALHLQGQDMEQQV<br>VFSMSFVQGEESNDKIPVALGLKEKNLYLSCVLKDDKPTLQL<br>ESVDPKNYPKKKMEKRFVFNKIEINNKLEFESAQFPNWYISTS<br>QAENMPVFLGGTKGGQDITDFTMQFVS (SEQ ID NO: 25) |
| TNF-alpha (4tsv) | DKPVAHVVANPQAEGQLQWSNRRANALLANGVELRDNQLV<br>VPIEGLFLIYSQVLFKGQGCPSTHVLLTHTISRIAVSYQTKVNL<br>LSAIKSPCQRETPEGAEAKPWYEPIYLGGVFQLEKGDRLSAEI<br>NRPDYLDFAESGQVYFGIIAL (SEQ ID NO: 26) |
| TNF-beta (lymphotoxin) (1tnr) | KPAAHLIGDPSKQNSLLWRANTDRAFLQDGFSLSNNSLLVPT<br>SGIYFVYSQVVFSGKAYSPKATSSPLYLAHEVQLFSSQYPFHV<br>PLLSSQKMVYPGLQEPWLHSMYHGAAFQLTQGDQLSTHTDG<br>IPHLVLSPSTVFFGAFAL (SEQ ID NO: 27) |
| Erythropoietin | APPRLICDSRVLERYLLEAKEAEKITTGCAEHCSLNEKITVPD<br>TKVNFYAWKRMEVGQQAVEVWQGLALLSEAVLRGQALLV<br>KSSQPWEPLQLHVDKAVSGLRSLTTLLRALGAQKEAISNSDA<br>ASAAPLRTITADTFRKLFRVYSNFLRGKLKLYTGEACRTGDR |

TABLE 1-continued

Sequences of Exemplary Proteins of Interest:

(SEQ ID NO: 28)

| Protein | Sequence |
|---|---|
| Insulin | Chain A: GIVEQCCTSICSLYQLENYCN (SEQ ID NO: 29)<br>Chain B: FVNQHLCGSHLVEALYLVCGERGFFYTPK (SEQ ID NO: 30) |
| Growth hormone (GH) (Somatotropin) (1huw) | FPTIPLSRLADNAWLRADRLNQLAFDTYQEFEEAYIPKEQIHS<br>FWWNPQTSLCPSESIPTPSNKEETQQKSNLELLRISLLLIQSWL<br>EPVQFLRSVFANSLVYGASDSNVYDLLKDLEEGIQTLMGRLE<br>ALLKNYGLLYCFNKDMSKVSTYLRTVQCRSVEGSCGF (SEQ ID NO: 31) |
| Follicle-stimulating hormone (FSH) | CHHRICHCSNRVFLCQESKVTEIPSDLPRNAIELRFVLTKLRVI<br>QKGAFSGFGDLEKIEISQNDVLEVIEADVFSNLPKLHEIRIEKA<br>NNLLYINPEAFQNLPNLQYLLISNTGIKHLPDVHKIHSLQKVL<br>LDIQDNINIHTIERNSFVGLSFESVILWLNKNGIQEIHNCAFNG<br>TQLDELNLSDNNNLEELPNDVFHGASGPVILDISRTRIHSLPSY<br>GLENLKKLRARSTYNLKKLPTLE (SEQ ID NO: 32) |
| Leptin (1ax8) | IQKVQDDTKTLIKTIVTRINDILDFIPGLHPILTLSKMDQTLAV<br>YQQILTSMPSRNVIQISNDLENLRDLLHVLAFSKSCHLPEASG<br>LETLDSLGGVLEASGYSTEVVALSRLQGSLQDMLWQLDLSP<br>GC (SEQ ID NO: 33) |
| Insulin-like growth factor (or somatomedin) (1wqj) | PETLCGAELVDALQFVCGDRGFYFNKPTGYGSSSRRAPQTGI<br>VDECCFRSCDLRRLEMYCAP (SEQ ID NO: 34) |
| Adiponectin (1c28) | Chain A.<br>MYRSAFSVGLETRVTVPNVPIRFTKIFYNQQNHYDGSTGKFY<br>CNIPGLYYFSYHITVYMKDVKVSLFKKDKAVLFTYDQYQEN<br>VDQASGSVLLHLEVGDQVWLQVYYADNVNDSTFTGFLLYH<br>DT (SEQ ID NO: 35)<br>Chain B.<br>MYRSAFSVGLPNVPIRFTKIFYNQQNHYDGSTGKFYCNIPGL<br>YYFSYHITVYMKDVKVSLFKKDKVLFTYDQYQEKVDQASGS<br>VLLHLEVGDQVWLQVYDSTFTGFLLYHD (SEQ ID NO: 36)<br>Chain C:<br>MYRSAFSVGLETRVTVPIRFTKIFYNQQNHYDGSTGKFYCNIP<br>GLYYFSYHITVDVKVSLFKKDKAVLFTQASGSVLLHLEVGD<br>QVWLQNDSTFTGFLLYHD (SEQ ID NO: 37) |
| Factor VIII (aka antihemophilic factor) (2r7e) | Chain A:<br>ATRRYYLGAVELSWDYMQSDLGELPVDARFPPRVPKSFPFN<br>TSVVYKKTLFVEFTDHLFNIAKPRPPWMGLLGPTIQAEVYDT<br>VVITLKNMASHPVSLHAVGVSYWKASEGAEYDDQTSQREKE<br>DDKVFPGGSHTYVWQVLKENGPMASDPLCLTYSYLSHVDLV<br>KDLNSGLIGALLVCREGSLAKEKTQTLHKFILLFAVFDEGKS<br>WHSETKNAASARAWPKMHTVNGYVNRSLPGLIGCHRKSVY<br>WHVIGMGTTPEVHSIFLEGHTFLVRNHRQASLEISPITFLTAQT<br>LLMDLGQFLLFCHISSHQHDGMEAYVKVDSCPEEPQFDDDN<br>SPSFIQIRSVAKKHPKTWVHYIAAEEEDWDYAPLVLAPDDRS<br>YKSQYLNNGPQRIGRKYKKVRFMAYTDETFKTREAIQHESGI<br>LGPLLYGEVGDTLLIIFKNQASRPYNIYPHGITDVRPLYSRRLP<br>KGVKHLKDFPILPGEIFKYKWTVTVEDGPTKSDPRCLTRYYS<br>SFVNMERDLASGLIGPLLICYKESVDQRGNQIMSDKRNVILFS<br>VFDENRSWYLTENIQRFLPNPAGVQLEDPEFQASNIMHSING<br>YVFDSLQLSVCLHEVAYWYILSIGAQTDFLSVFFSGYTFKHK<br>MVYEDTLTLFPFSGETVFMSMENPGLWILGCHNSDFRNRGM<br>TALLKVSSCDKNTGDYYEDSYED (SEQ ID NO: 38)<br>Chain B:<br>RSFQKKTRHYFIAAVERLWDYGMSSSPHVLRNRAQSGSVPQ<br>FKKVVFQEFTDGSFTQPLYRGELNEHLGLLGPYIRAEVEDNI<br>MVTFRNQASRPYSFYSSLISYEEDQRQGAEPRKNFVKPNETK<br>TYFWKVQHHMAPTKDEFDCKAWAYSSDVDLEKDVHSGLIG<br>PLLVCHTNTLNPAHGRQVTVQEFALFFTIFDETKSWYFTENM<br>ERNCRAPCNIQMEDPTFKENYRFHAINGYIMDTLPGLVMAQ<br>DQRIRWYLLSMGSNENIHSIHFSGHVFTVRKKEEYKMALYNL<br>YPGVFETVEMLPSKAGIWRVECLIGEHLHAGMSTLFLVYSNK<br>CQTPLGMASGHIRDFQITASGQYGQWAPKLARLHYSGSINA<br>WSTKEPFSWIKVDLLAPMIIHGIKTQGARQKFSSLYISQFIIMY<br>SLDGKKWQTYRGNSTGTLMVFFGNVDSSGIKHNIFNPPIIARY<br>IRLHPTHYSIRSTLRMELMGCDLNSCSMPLGMESKAISDAQIT<br>ASSYFTNMFATWSPSKARLHLQGRSNAWRPQVNNPKEWLQ<br>VDFQKTMKVTGVTTQGVKSLLTSMYVKEFLISSSQDGHQWT<br>LFFQNGKVKVFQGNQDSFTPVVNSLDPPLLTRYLRIHPQSWV<br>HQIALRMEVLGCEAQDLY (SEQ ID NO: 39) |

TABLE 1-continued

Sequences of Exemplary Proteins of Interest:

| | |
|---|---|
| Human serum albumin (1ao6) | Chain A:<br>SEVAHRFKDLGEENFKALVLIAFAQYLQQCPFEDHVKLVNEV<br>TEFAKTCVADESAENCDKSLHTLFGDKLCTVATLRETYGEM<br>ADCCAKQEPERNECFLQHKDDNPNLPRLVRPEVDVMCTAFH<br>DNEETFLKKYLYEIARRHPYFYAPELLFFAKRYKAAFTECCQ<br>AADKAACLLPKLDELRDEGKASSAKQRLKCASLQKFGERAF<br>KAWAVARLSQRFPKAEFAEVSKLVTDLTKVHTECCHGDLLE<br>CADDRADLAKYICENQDSISSKLKECCEKPLLEKSHCIAEVEN<br>DEMPADLPSLAADFVESKDVCKNYAEAKDVFLGMFLYEYA<br>RRHPDYSVVLLLRLAKTYETTLEKCCAAADPHECYAKVFDE<br>FKPLVEEPQNLIKQNCELFEQLGEYKFQNALLVRYTKKVPQV<br>STPTLVEVSRNLGKVGSKCCKHPEAKRMPCAEDYLSVVLNQ<br>LCVLHEKTPVSDRVTKCCTESLVNRRPCFSALEVDETYVPKE<br>FNAETFTFHADICTLSEKERQIKKQTALVELVKHKPKATKEQ<br>LKAVMDDFAAFVEKCCKADDKETCFAEEGKKLVAASQAA<br>(SEQ ID NO: 40)<br>Chain B:<br>SEVAHRFKDLGEENFKALVLIAFAQYLQQCPFEDHVKLVNEV<br>TEFAKTCVADESAENCDKSLHTLFGDKLCTVATLRETYGEM<br>ADCCAKQEPERNECFLQHKDDNPNLPRLVRPEVDVMCTAFH<br>DNEETFLKKYLYEIARRHPYFYAPELLFFAKRYKAAFTECCQ<br>AADKAACLLPKLDELRDEGKASSAKQRLKCASLQKFGERAF<br>KAWAVARLSQRFPKAEFAEVSKLVTDLTKVHTECCHGDLLE<br>CADDRADLAKYICENQDSISSKLKECCEKPLLEKSHCIAEVEN<br>DEMPADLPSLAADFVESKDVCKNYAEAKDVFLGMFLYEYA<br>RRHPDYSVVLLLRLAKTYETTLEKCCAAADPHECYAKVFDE<br>FKPLVEEPQNLIKQNCELFEQLGEYKFQNALLVRYTKKVPQV<br>STPTLVEVSRNLGKVGSKCCKHPEAKRMPCAEDYLSVVLNQ<br>LCVLHEKTPVSDRVTKCCTESLVNRRPCFSALEVDETYVPKE<br>FNAETFTFHADICTLSEKERQIKKQTALVELVKHKPKATKEQ<br>LKAVMDDFAAFVEKCCKADDKETCFAEEGKKLVAASQAA<br>(SEQ ID NO: 41) |
| Hemoglobin (1bz0) | Chain A:<br>VLSPADKTNVKAAWGKVGAHAGEYGAEALERMFLSFPTTK<br>TYFPHFDLSHGSAQVKGHGKKVADALTNAVAHVDDMPNAL<br>SALSDLHAHKLRVDPVNFKLLSHCLLVTLAAHLPAEFTPAVH<br>ASLDKFLASVSTVLTSKYR (SEQ ID NO: 42)<br>Chain B:<br>VHLTPEEKSAVTALWGKVNVDEVGGEALGRLLVVYPWTQR<br>FFESFGDLSTPDAVMGNPKVKAHGKKVLGAFSDGLAHLDNL<br>KGTFATLSELHCDKLHVDPENFRLLGNVLVCVLAHHFGKEFT<br>PPVQAAYQKVVAGVANALAHKYH (SEQ ID NO: 43) |

Any of the proteins of interest as described herein may be modified, which may comprise (i) one or more nucleophilic residues such as glycine at the N-terminus (e.g., between 1 and 10 residues) and, optionally, a cleavage recognition sequence, e.g., a protease cleavage recognition sequence that masks the nucleophilic residue(s); or (ii) a sortase recognition motif at or near the C-terminus. In some embodiments, the target protein comprises both (i) and (ii). Such modified proteins can be used in the methods of protein conjugation as described herein.

One of skill in the art will be aware that certain proteins, e.g., secreted eukaryotic (e.g., mammalian) proteins, often undergo intracellular processing (e.g., cleavage of a secretion signal prior to secretion and/or removal of other portion(s) that are not required for biological activity), to generate a mature form. Such mature, biologically active versions of target proteins are used in certain embodiments of the present disclosure.

Other proteins of interest may be found in, e.g., U.S. Ser. Nos. 10/773,530; 11/531,531; 11/707,014; 11/429,276; 11/365,008, all of which are incorporated by reference herein. The invention encompasses application of the inventive methods to any of the proteins described herein and any proteins known to those of skill in the art.

When the agent is not a protein, such an agent can be conjugated to a protein backbone, which can be ligated to a surface sortaggable protein in the presence of a sortase. Non-protein agents include, but are not limited to a lipid, a carbohydrate, a small molecule such as a click chemistry handle or a chemotherapeutic agent, a detectable label (e.g., an imaging agent), or a chemotherapeutic agent. Additional agents suitable for use in embodiments of the present disclosure will be apparent to the skilled artisan.

In some examples, the non-protein agent is antigenic such that it can elicit immune responses. Such antigenic agents may comprise, for example, a polysaccharide, a carbohydrate, a lipid, a nucleic acid, or combination thereof, and may derived from a pathogen, e.g., those described herein.

The term "conjugated" or "conjugation" refers to an association of two molecules, for example, two proteins or a protein and an agent, e.g., a small molecule, with one another in a way that they are linked by a direct or indirect covalent or non-covalent interaction. In certain embodiments, the association is covalent, and the entities are said to be "conjugated" to one another. In some embodiments, a protein is post-translationally conjugated to another molecule, for example, a second protein, a small molecule, a detectable label, a click chemistry handle, or a binding agent, by forming a covalent bond between the protein and the other molecule after the protein has been formed, and, in some embodiments, after the protein has been isolated. In some embodiments, two molecules are conjugated via a linker connecting both molecules. For example, in some embodiments where two proteins are conjugated to each other to form a protein fusion, the two proteins may be conjugated via a polypeptide linker, e.g., an amino acid sequence connecting the C-terminus of one protein to the N-terminus of the other protein. In some embodiments, two proteins are conjugated at their respective C-termini, generating a C—C conjugated chimeric protein. In some embodiments, two proteins are conjugated at their respective N-termini, generating an N-N conjugated chimeric protein. In some embodiments, conjugation of a protein to a peptide is achieved by transpeptidation using a sortase. See, e.g., Ploegh et al., International PCT Patent Application, PCT/US2010/000274, filed Feb. 1, 2010, published as WO/2010/087994 on Aug. 5, 2010, and Ploegh et al., International Patent Application PCT/US2011/033303, filed Apr. 20, 2011, published as WO/2011/133704 on Oct. 27, 2011, the entire contents of each of which are incorporated herein by reference, for exemplary sortases, proteins, recognition motifs, reagents, and methods for sortase-mediated transpeptidation.

Click chemistry is a chemical philosophy introduced by K. Barry Sharpless of The Scripps Research Institute, describing chemistry tailored to generate covalent bonds quickly and reliably by joining small units comprising reactive groups together (see H. C. Kolb, M. G. Finn and K. B. Sharpless (2001). Click Chemistry: Diverse Chemical Function from a Few Good Reactions. *Angewandte Chemie International Edition* 40 (11): 2004-2021. Click chemistry does not refer to a specific reaction, but to a concept including, but not limited to, reactions that mimic reactions found in nature. In some embodiments, click chemistry reactions are modular, wide in scope, give high chemical yields, generate inoffensive byproducts, are stereospecific, exhibit a large thermodynamic driving force >84 kJ/mol to favor a reaction with a single reaction product, and/or can be carried out under physiological conditions. In some embodiments, a click chemistry reaction exhibits high atom economy, can be carried out under simple reaction conditions, use readily available starting materials and reagents, uses no toxic solvents or use a solvent that is benign or easily removed (preferably water), and/or provides simple product isolation by non-chromatographic methods (crystallisation or distillation).

A click chemistry handle can be a reactant, or a reactive group, that can partake in a click chemistry reaction. For example, a strained alkyne, e.g., a cyclooctyne, is a click chemistry handle, since it can partake in a strain-promoted cycloaddition. In general, click chemistry reactions require at least two molecules comprising click chemistry handles that can react with each other. Such click chemistry handle pairs that are reactive with each other are sometimes referred to herein as partner click chemistry handles. For example, an azide is a partner click chemistry handle to a cyclooctyne or any other alkyne. Exemplary click chemistry handles suitable for use according to some aspects of this invention are described herein, for example, in Tables A and B. Other suitable click chemistry handles are known to those of skill in the art. For two molecules to be conjugated via click chemistry, the click chemistry handles of the molecules have to be reactive with each other, for example, in that the reactive moiety of one of the click chemistry handles can react with the reactive moiety of the second click chemistry handle to form a covalent bond. Such reactive pairs of click chemistry handles are well known to those of skill in the art and include, but are not limited to, those described in Table 2:

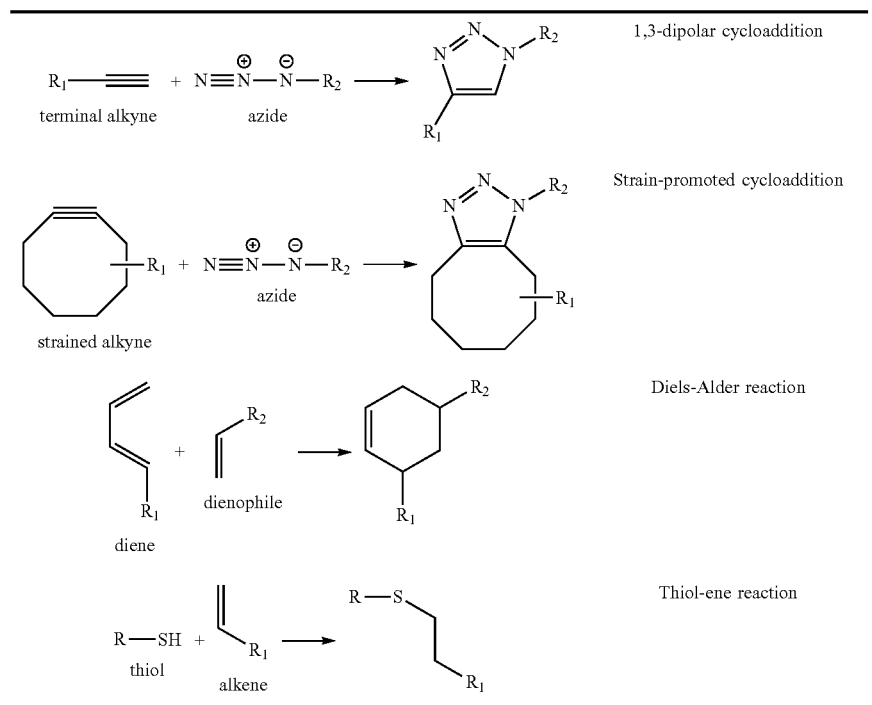

Table 2 provides examples of click chemistry handles and reactions. R, R1, and R2 may represent any molecule comprising a sortase recognition motif. In some embodiments, each occurrence of R, R1, and R2 is independently RR-LPXT (SEQ ID NO: 50)-[X]y-, or -[X]y-LPXT (SEQ ID NO: 50)-RR, wherein each occurrence of X independently represents any amino acid residue, each occurrence of y is an integer between 0 and 10, inclusive, and each occurrence of RR independently represents a protein or an agent (e.g., a protein, peptide, a detectable label, a binding agent, a small molecule, etc.), and, optionally, a linker.

In some embodiments, click chemistry handles are used that can react to form covalent bonds in the absence of a metal catalyst. Such click chemistry handles are well known to those of skill in the art and include the click chemistry handles described in Becer, Hoogenboom, and Schubert, Click Chemistry beyond Metal-Catalyzed Cycloaddition, *Angewandte Chemie International Edition* (2009) 48: 4900-4908. See Table 3 below.

FKBP). In certain embodiments, a label comprises a radioactive isotope, preferably an isotope which emits detectable particles, such as β particles. In certain embodiments, the label comprises a fluorescent moiety. In certain embodiments, the label is the fluorescent label fluorescein-isothiocyanate (FITC). In certain embodiments, the label comprises a ligand moiety with one or more known binding partners. In certain embodiments, the label comprises biotin. In some embodiments, a label is a fluorescent polypeptide (e.g., GFP or a derivative thereof such as enhanced GFP (EGFP)) or a luciferase (e.g., a firefly, *Renilla*, or *Gaussia* luciferase). It

TABLE 3

Exemplary click chemistry handles and reactions.

| | Reagent A | Reagent B | Mechanism | Notes on reaction[a] | Reference |
|---|---|---|---|---|---|
| 0 | azide | alkyne | Cu-catalyzed [3 + 2] azide-alkyne cycloaddition (CuAAC) | 2 h at 60° C. in H$_2$O | [9] |
| 1 | azide | cyclooctyne | strain-promoted [3 + 2] azide-alkyne cycloaddition (SPAAC) | 1 h at RT | [6-8, 10, 11] |
| 2 | azide | activated alkyne | [3 + 2] Huisgen cycloaddition | 4 h at 50° C. | [12] |
| 3 | azide | electron-deficient alkyne | [3 + 2] cycloaddition | 12 h at RT in H$_2$O | [13] |
| 4 | azide | aryne | [3 + 2] cycloaddition | 4 h at RT in THF with crown ether or 24 h at RT in CH$_3$CN | [14, 15] |
| 5 | tetrazine | alkene | Diels-Alder retro-[4 + 2] cycloaddition | 40 min at 25° C. (100% yield) N$_2$ is the only by-product | [36-38] |
| 6 | tetrazole | alkene | 1,3-dipolar cycloaddition (photoclick) | few min UV irradiation and then overnight at 4° C. | [39, 40] |
| 7 | dithioester | diene | hetero-Diels-Alder cycloaddition | 10 min at RT | [43] |
| 8 | anthracene | maleimide | [4 + 2] Diels-Alder reaction | 2 days at reflux in toluene | [41] |
| 9 | thiol | alkene | radical addition (thio click) | 30 min UV (quantitative conv.) or 24 h UV irradiation (>96%) | [19-23] |
| 10 | thiol | enone | Michael addition | 24 h at RT in CH$_3$CN | [27] |
| 11 | thiol | maleimide | Michael addition | 1 h at 40° C. in THF or 16 h at RT in dioxane | [24-26] |
| 12 | thiol | para-fluoro | nucleophilic substitution | overnight at RT in DMF or 60 min at 40° C. in DMF | [32] |
| 13 | amine | para-fluoro | nucleophilic substitution | 20 min MW at 95° C. in NMP as solvent | [30] |

[a]RT = room temperature, DMF = N,N-dimethylformamide, NMP = N-methylpyrolidone, THF = tetrahydrofuran, CH$_3$CN = acetonitrile.

A detectable label is a moiety that has at least one element, isotope, or functional group incorporated into the moiety which enables detection of the molecule, e.g., a protein or peptide, or other entity, to which the label is attached. Labels can be directly attached (i.e., via a bond) or can be attached by a linker (such as, for example, an optionally substituted alkylene; an optionally substituted alkenylene; an optionally substituted alkynylene; an optionally substituted heteroalkylene; an optionally substituted heteroalkenylene; an optionally substituted heteroalkynylene; an optionally substituted arylene; an optionally substituted heteroarylene; or an optionally substituted acylene, or any combination thereof, which can make up a linker). It will be appreciated that the label may be attached to or incorporated into a molecule, for example, a protein, polypeptide, or other entity, at any position. In general, a detectable label can fall into any one (or more) of five classes: a) a label which contains isotopic moieties, which may be radioactive or heavy isotopes, including, but not limited to, 2H, 3H, 13C, 14C, 15N, 18F, 31P, 32P, 35S, 67Ga, 76Br, 99mTc (Tc-99m), 111In, 123I, 125I, 131I, 153Gd, 169Yb, and 186Re; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label fluorescein-isothiocyanate (FITC); d) a label which has one or more photo affinity moieties; and e) a label which is a ligand for one or more known binding partners (e.g., biotin-streptavidin, FK506- will be appreciated that, in certain embodiments, a label may react with a suitable substrate (e.g., a luciferin) to generate a detectable signal. Non-limiting examples of fluorescent proteins include GFP and derivatives thereof, proteins comprising fluorophores that emit light of different colors such as red, yellow, and cyan fluorescent proteins. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See, e.g., Chalfie, M. and Kain, S R (eds.) Green fluorescent protein: properties, applications, and protocols Methods of biochemical analysis, v. 47 Wiley-Interscience, Hoboken, N. J., 2006; and Chudakov, D M, et al., Physiol Rev. 90(3): 1103-63, 2010, for discussion of GFP and numerous other fluorescent or luminescent proteins. In some embodiments, a label comprises a dark quencher, e.g., a substance that absorbs excitation energy from a fluorophore and dissipates the energy as heat.

"Small molecule" refer to molecules, whether naturally-occurring or artificially created (e.g., via chemical synthesis) that have a relatively low molecular weight. Typically, a small molecule is an organic compound (i.e., it contains carbon). A small molecule may contain multiple carbon-carbon bonds, stereocenters, and other functional groups (e.g., amines, hydroxyl, carbonyls, heterocyclic rings, etc.).

In some embodiments, small molecules are monomeric and have a molecular weight of less than about 1500 g/mol. In certain embodiments, the molecular weight of the small molecule is less than about 1000 g/mol or less than about 500 g/mol. In certain embodiments, the small molecule is a drug, for example, a drug that has already been deemed safe and effective for use in humans or animals by the appropriate governmental agency or regulatory body.

Any of the non-protein agent described herein can be conjugated to a protein backbone via methods known to those skilled in the art.

(c) Sortase-Catalyzed Transpeptidation Reaction

Sortase-catalyzed transacylation reactions, and their use in transpeptidation (sometimes also referred to as transacylation) for protein engineering are well known to those of skill in the art (see, e.g., Ploegh et al., WO/2010/087994, and Ploegh et al., WO/2011/133704, the entire contents of which are incorporated herein by reference). In general, the transpeptidation reaction catalyzed by sortase results in the conjugation of a first protein containing a C-terminal sortase recognition motif, e.g., LPXTX (SEQ ID NO: 80; wherein each occurrence of X independently represents any amino acid residue), with a second protein comprising an N-terminal sortase acceptor peptide, e.g., one or more N-terminal glycine residues. In some embodiments, the sortase recognition motif is a sortase recognition motif described herein. In certain embodiments, the sortase recognition motif is LPXT (SEQ ID NO: 50) motif or LPXTG (SEQ ID NO: 1).

The sortase transacylation reaction provides means for efficiently linking an acyl donor with a nucleophilic acyl acceptor. This principle is widely applicable to many acyl donors and a multitude of different acyl acceptors. Previously, the sortase reaction was employed for ligating proteins and/or peptides to one another, ligating synthetic peptides to recombinant proteins, linking a reporting molecule to a protein or peptide, joining a nucleic acid to a protein or peptide, conjugating a protein or peptide to a solid support or polymer, and linking a protein or peptide to a label. Such products and processes save cost and time associated with ligation product synthesis and are useful for conveniently linking an acyl donor to an acyl acceptor. However, the modification and functionalization of proteins on the surface of viral particles via sortagging, as provided herein, has not been described previously.

Sortase-mediated transpeptidation reactions (also sometimes referred to as transacylation reactions) are catalyzed by the transamidase activity of sortase, which forms a peptide linkage (an amide linkage), between an acyl donor compound and a nucleophilic acyl acceptor containing an NH2-CH2-moiety. In some embodiments, the sortase employed to carry out a sortase-mediated transpeptidation reaction is sortase A (SrtA). However, it should be noted that any sortase, or transamidase, catalyzing a transacylation reaction can be used in some embodiments of this invention, as the invention is not limited to the use of sortase A.

Typically, an agent of interest (e.g., a protein or a non-protein agent conjugated to a protein backbone) can be ligated to the surface of a cell expressing sortaggable surface protein by contacting the protein agent or protein backbone to which an agent of interest is conjugated with the cell under suitable conditions allowing for occurrence of the transpeptidation reaction. In some examples, the agent of interest can be incubated with a sortase first under suitable conditions for a suitable period of time allowing for cleavage at the sortase recognition site. The mixture is then in contact with the cells under suitable conditions such that the agent of interest is conjugated to the surface sortaggable protein on the cells.

In some instances, the cell, such as a CD4+ progenitor cell or an enucleated red blood cell, expresses a fusion protein that comprises a sortase recognition motif at the C-terminus (e.g., a type II red cell transmembrane protein fused to a sortase recognition motif at the C-terminus). A protein of interest or a protein backbone conjugated with an agent of interest can be conjugated to the C-terminus of the fusion protein in the presence of a sortase. In other instances, the cell expresses a fusion protein comprising a membrane protein and an acceptor peptide (e.g., a glycine polymer) fused to the N-terminus of the membrane protein (e.g., a type I or type III transmembrane protein). A protein to be conjugated with the cell-surface fusion protein comprises a sortase recognition motif as described above at the C-terminal and can be conjugated to the N-terminus of the surface fusion protein.

The use of a specific sortase in a conjugation method as described herein would depend on the sortase recognition motif included either in the surface sortaggable protein on the cells or in the protein to be conjugated to the surface protein. This is well within the knowledge of those skilled in the art. See, e.g., descriptions above regarding recognition sites for various sortases.

In some embodiments, CD34+ or enucleated red blood cells derived therefrom can express a plurality of different surface sortaggable proteins (e.g., 2, 3, or more). In some embodiments, specific modification of one or more of the plurality of surface sortaggable proteins involves the use of different sortases, each specifically recognizing a different sortase recognition motif included in the one or more sortaggable proteins. For example, a first sortaggable protein can be modified with $SrtA_{aureus}$, recognizing the C-terminal sortase recognition motif LPETGG (SEQ ID NO: 107) and the N-terminal sortase recognition motif $(G)_n$, and a second sortaggable can be modified with $SrtA_{pyogenes}$, recognizing the C-terminal sortase recognition motif LPETAA (SEQ ID NO: 108) and the N-terminal sortase recognition motif $(A)_n$. The sortases in this example recognize their respective recognition motif but do not recognize the other sortase recognition motif to a significant extent, and, thus, "specifically" recognize their respective recognition motif. In some embodiments, a sortase binds a sortase recognition motif specifically if it binds the motif with an affinity that is at least 5-fold, 10-fold, 20-fold, 50-fold, 100-fold, 200-fold, 500-fold, 1000-fold, or more than 1000-fold higher than the affinity that the sortase binds a different motif. Such a pairing of orthogonal sortases and their respective recognition motifs, e.g., of the orthogonal sortase A enzymes $SrtA_{aureus}$ and $SrtA_{pyogenes}$, can be used to site-specifically conjugate two different moieties onto two different surface sortaggable proteins.

In other embodiments, sortagging of a plurality of different proteins is achieved by sequentially contacting a cell comprising the different sortaggable surface proteins with a first sortase recognizing a sortase recognition motif of a first sortaggable protein and a suitable first protein of interest, and then with a second sortase recognizing a sortase recognition motif of a second sortaggable protein and a second protein of interest, and so forth. Alternatively, the cell may be contacted with a plurality of sortases in parallel, for example, with a first sortase recognizing a sortase recognition motif of a first sortaggable protein and a suitable first protein of interest, and with a second sortase recognizing a sortase recognition motif of a second target protein and a second protein of interest, and so forth.

For example, in some embodiments, a first sortaggable protein, e.g., a type I transmembrane protein fused to an oligoglycine, is modified using sortase A from *Staphylococcus aureus* (SrtA$_{aureus}$), and a second sortaggable protein, e.g., a type II transmembrane protein fused to a suitable sortase recognition motif, is modified using sortase A from *Streptococcus pyogenes* (SrtA$_{pyogenes}$). SrtA$_{aureus}$ recognizes the motif LPXTG (SEQ ID NO: 1), in which X is any amino acid residue, and uses oligoglycine as the acceptor peptide. Differently, SrtA$_{pyogenes}$ recognizes the motif LPXTA (SEQ ID NO: 2), in which X is any amino acid residue, and uses oligoalanine as the acceptor peptide.

Any sortases that recognize sufficiently different sortase recognition motifs with sufficient specificity are suitable for sortagging of a plurality of sortaggable proteins expressed on red blood cells. The respective sortase recognition motifs can be inserted into the sortaggable proteins or the proteins to be conjugated to the sortaggable proteins using recombinant technologies known to those of skill in the art. In some embodiments, suitable sortase recognition motifs may be present in a wild type membrane protein. The skilled artisan will understand that the choice of a suitable sortase for the conjugation of a given protein may depend on the sequence of the sortaggable protein, e.g., on whether or not the sortaggable protein comprises a sequence at its C-terminus or its N-terminus that can be recognized as a substrate by any known sortase. In some embodiments, use of a sortase that recognizes a naturally-occurring C-terminal or N-terminal recognition motif is preferred since further engineering of the target protein can be avoided.

IV. Uses of Red Blood Cells as a Carrier for in vivo Delivery of Agents of Interest Any of the genetically modified CD34+ progenitor cells and enucleated red blood cells (including those obtained from the in vitro culturing process described herein), which can also be genetically modified as described, are within the scope of the present disclosure.

Enucleated red blood cells having a surface modification of an agent of interest as, described herein can be administered to a subject in need thereof (e.g., a human patient) for various purposes, e.g., treating a specific disease when the agent of interest is a therapeutic agent, detecting the presence of specific cell types when the agent of interest is capable of recognizing the target cells, and eliciting desired immune responses when the agent of interest is immunogenic. Any suitable delivery route can be used in the methods described herein, e.g., cell infusion.

In some examples, the red blood cells are delivered to the same subject from which the cells are originally obtained. For example, peripheral blood cells can be obtained from a subject such as human patient, expanded in vitro, genetically modified such that they express sortaggable surface proteins, differentiated into enucleated red blood cells, and conjugated with an agent of interest. The modified enucleated red blood cells can then be administered to the same subject.

In other examples, the CD34+ progenitor cells are obtained from a suitable subject and, after being differentiated and genetically modified as described herein, the resultant enucleated red blood cells are administered to a different subject, which preferably is immunocompatible with the donor (e.g., administration of the enucleated blood cells would not elicit undesirable immune responses).

The enucleated red blood cells can be administered to a subject who has or suspected of having a condition associated with red blood cell deficiency, for example, anemia, blood loss due to surgery or trauma. The enucleated red blood cells can also be administered to a subject in need of a treatment or diagnosis that can be achieved by the agent of interest conjugated on the surface of the enucleated red blood cells. For example, the enucleated red blood cells may be conjugated to an cancer antigen or an antigen derived from a pathogen. Such cells can be delivered to a subject in need (e.g., a human subject having or at risk for cancer or infection by the pathogen) for either preventive or therapeutic treatment.

In another example, the nucleated red blood cells can be conjugated to an enzyme effective in treating a disease or disorder associated with deficiency of the enzyme, e.g., Fabry disease, Gaucher disease, Pompe disease, adenosine deaminase deficiency, asparaginase deficiency, *porphyria*, hemophilia, and hereditary angioedema.

In other examples, the enucleated red blood cells carry a clotting or coagulation factor, (e.g., factor VII, VIIa, VIII or IX) and may be delivered to a human subject having or suspected of having conditions associated with abnormal blood clotting or coagulation.

V. Kits

Some aspects of the present disclosure provide kits useful for the genetic modification and surface modification of red blood cells via sortagging. Such a kit can comprise one or more expression vectors encoding one or more fusion protein each comprising a red blood cell membrane protein and a peptide as described herein. If a kit comprises multiple expression vectors as described, they can include sequences encoding different sortase recognition motifs. In some embodiments, the different sortase recognition motifs are recognized by orthogonal sortases, for example, one by SrtA$_{aureus}$ and another by SrtA$_{pyogenes}$.

Alternatively or in addition, the kits described herein can comprise one or more of the medium components for use in the in vitro culturing process for producing enucleated red blood cells, e.g., one or more of the cytokines used therein, and one or more of the media used therein, and/or other components for cell culture.

Further, the kit can comprise one or more suitable sortases. Typically, the sortase comprised in the kit recognizes a sortase recognition motif encoded by a nucleic acid comprised in the kit. In some embodiments, the sortase is provided in a storage solution and under conditions preserving the structural integrity and/or the activity of the sortase. In some embodiments, where two or more orthogonal sortase recognition motifs are encoded by the nucleic acid(s) comprised in the kit, a plurality of sortases is provided, each recognizing a different sortase recognition motif encoded by the nucleic acid(s). In some embodiments, the kit comprises SrtA$_{aureus}$ and/or SrtA$_{pyogenes}$.

In some embodiments, the kit further comprises an agent of interest, e.g., a protein of interest or a protein backbone conjugated with a non-protein agent. In some embodiments, the protein of interest or the protein backbone comprises a sortase recognition motif, which may be compatible with the peptide in the fusion protein encoded by a nucleic acid in the kit in that both motifs can partake in a sortase-mediated transpeptidation reaction catalyzed by the same sortase. For example, if the kit comprises a nucleic acid encoding a fusion membrane protein comprising a SrtA$_{aureus}$ N-terminal recognition sequence, the kit may also comprise SrtA$_{aureus}$ and a protein of interest or a protein backbone, which will comprise the C-terminal sortase recognition motif.

In some embodiments, the kit further comprises a buffer or reagent useful for carrying out a sortase-mediated transpeptidation reaction, for example, a buffer or reagent described in the Examples section.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

In Vitro Production of Human Mature Enucleated Red Blood Cells

Human peripheral blood G-CSF mobilized hematopoietic stem/progenitor cells enriched for CD34+ are purchased from Fred Hutchinson Cancer Research Center (FHCRC), Seattle. Cells are thawed according to the FHCRC protocol. The human $CD^{34+}$ ($hCD^{34+}$) blood cells were differentiated into mature enucleated red blood cells by a method composed of 4 phases in 21 days: (a) Expansion, (b) Differentiation I ("Dif I"), (c) Differentiation II ("Dif II"), and Differentiation III ("Dif III") illustrated in FIG. 1, and described below.

In the Expansion phase, the human $CD^{14+}$ blood cells were cultured in Expansion medium (StemspanSFEM, CC 100 cytokine mix, which includes Flt-3 ligant, SCF, IL-3 and IL-6, and 2% penicillin-streptomycin) at $10^5$ cells/mL from Day 1~4. After expansion, cells are subsequently cultured in IMDM-based erythroid differentiation medium supplemented with different cytokines in Dif I, II and III. The medium base for all three differentiation phases comprises: IMDM, 15% FBS, 2 mM glutamine, 1% BSA, 500 µg/mL holo human transferrin, 10 µg/mL recombinant human insulin and 2% penicillin-streptomycin. Day 5~9, cells are cultured in Dif I medium, which contains erythroid medium base, 2 µM Dexamethasone, 1 µM b-estradiol, 5 ng/mL IL-3, 100 ng/mL SCF and 6 U Epo. Day 10~13, cells are grown in Dif II medium containing erythroid medium base, 50 ng/mL SCF and 6 U Epo. Day 14~21, cells were cultured in fibronectin-coated plates in Dif III medium, which is erythroid medium base supplemented with 2 U Epo. Cell numbers re-seeded in the beginning of Dif I, II and III were $10^5$, $2 \times 10^5$, and $3 \times 10^5$/mL, respectively.

The red blood cells at various time points during the above-noted 4-phrase process were subjected to Benzidine-Giemsa staining and the cell morphology was observed under a microscope. As shown in FIG. 2, decrease of cell sizes was observed upon erythroid maturation and enucleated red blood cells were observed at day 8 of Dif. III. The sizes of the enucleated red blood cells obtained from the 4-phrase method described were found to be similar to those of normal human reticulocytes or red blood cells. Table 4 below.

TABLE 4

Diameters and Areas of Red Cell Clones

| Cell# | Diameter (µm) | Area (µm²) |
|---|---|---|
| 1 | 6.81 | 39.79 |
| 2 | 6.91 | 38.37 |

TABLE 4-continued

Diameters and Areas of Red Cell Clones

| Cell# | Diameter (µm) | Area (µm²) |
|---|---|---|
| 3 | 5.15 | 23.12 |
| 4 | 6.74 | 38.14 |
| 5 | 6.02 | 28.16 |
| 6 | 6.95 | 43.01 |
| 7 | 6.05 | 37.62 |
| 8 | 7 | 38.34 |
| 9 | 7.99 | 56.24 |
| 10 | 7.63 | 46.1 |
| Mean | 6.73 | 38.89 |

Cell Nos. 1-5: Enucleated red blood cells obtained from the differentiation process described above
Cell Nos. 6-10: normal human reticulocytes or red blood cells The hemoglobin contents of the red blood cells at Dif I, Dif II, and Dif III were determined by Drabkin's reagent. The results indicate that the enucleated blood cells obtained at the end of the differentiation process is around 30 pg/cell.

Figure 4:
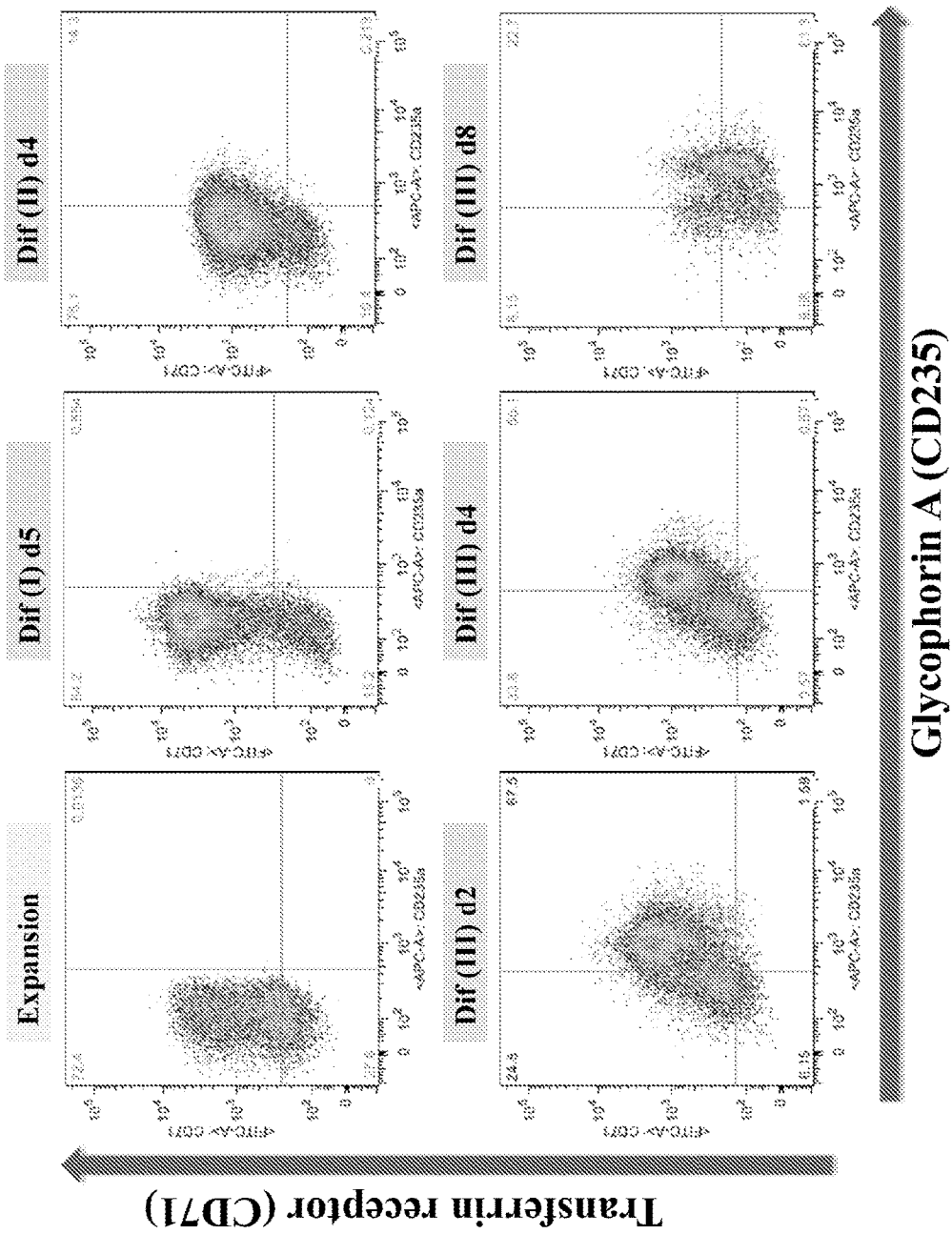
FIG. 4 is a diagram showing the expression of cell surface markers glycophorin A (CD235) and transferrin receptor (CD71) in cells at expansion and different differentiation stages in the in vitro culturing process described herein, as determined by FACS analysis.
Figure 5:
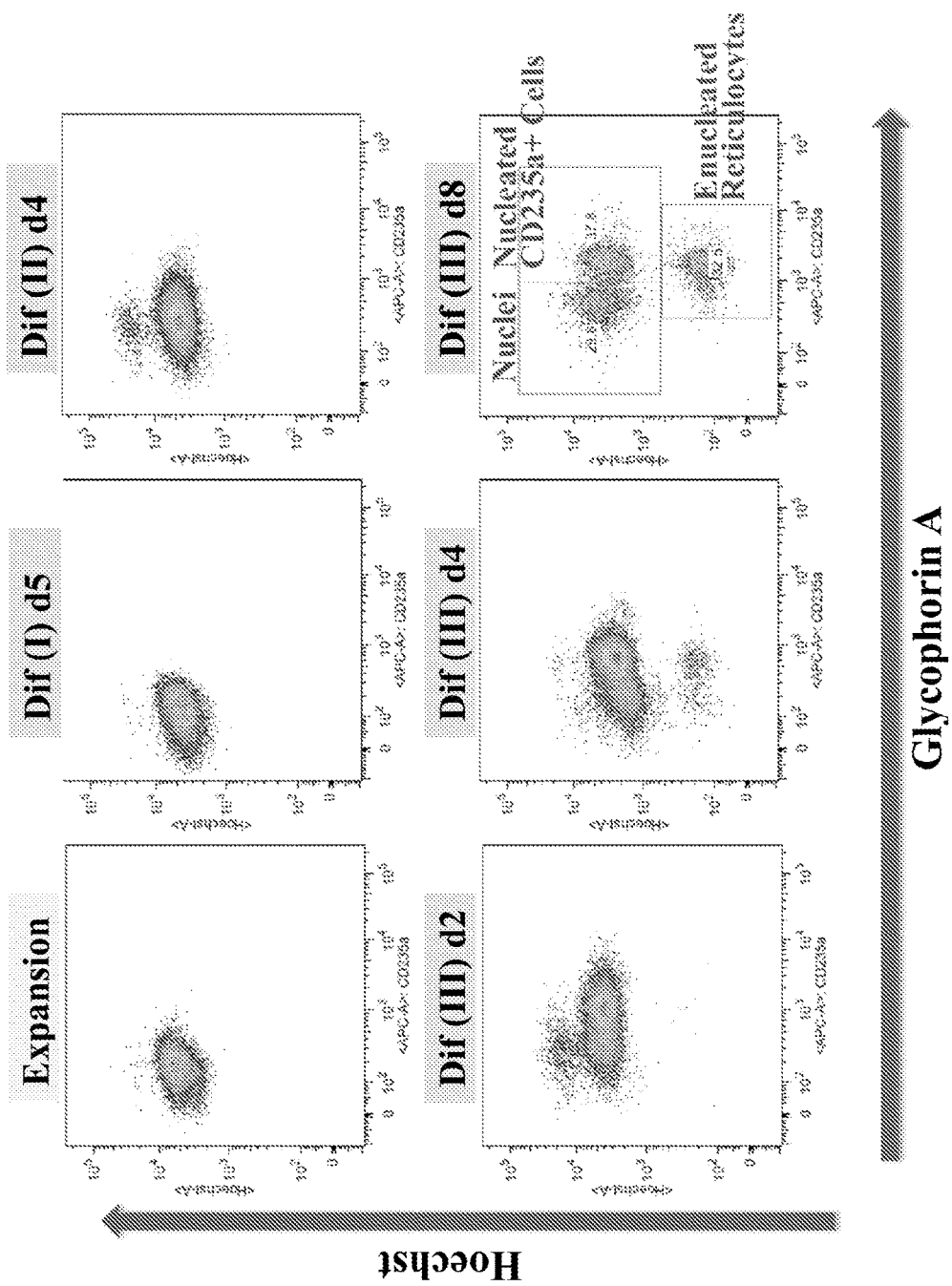
FIG. 5 is a diagram showing the enucleation of cells at expansion and different differentiation stages in the in vitro culturing process described herein.

The expression levels of various red blood cell surface proteins, including CD235a (Glycophorin A), c-Kit, and CD71, were examined. FACS analysis indicated that CD235a expression was elevated during red erythropoiesis (red blood cell differentiation). The expression levels of CD235a versus those of c-kit or CD71 (transferrin) at different stages of the differentiation process are shown in FIGS. 4 and 5. Hoechst and glycophorin A staining indicated that around 40-50% of the red blood cells underwent enucleation at the end of the differentiation process. FIG. 5. Enucleation %=32.5/(37.8+32.5)=46.2%.

Figure 6:
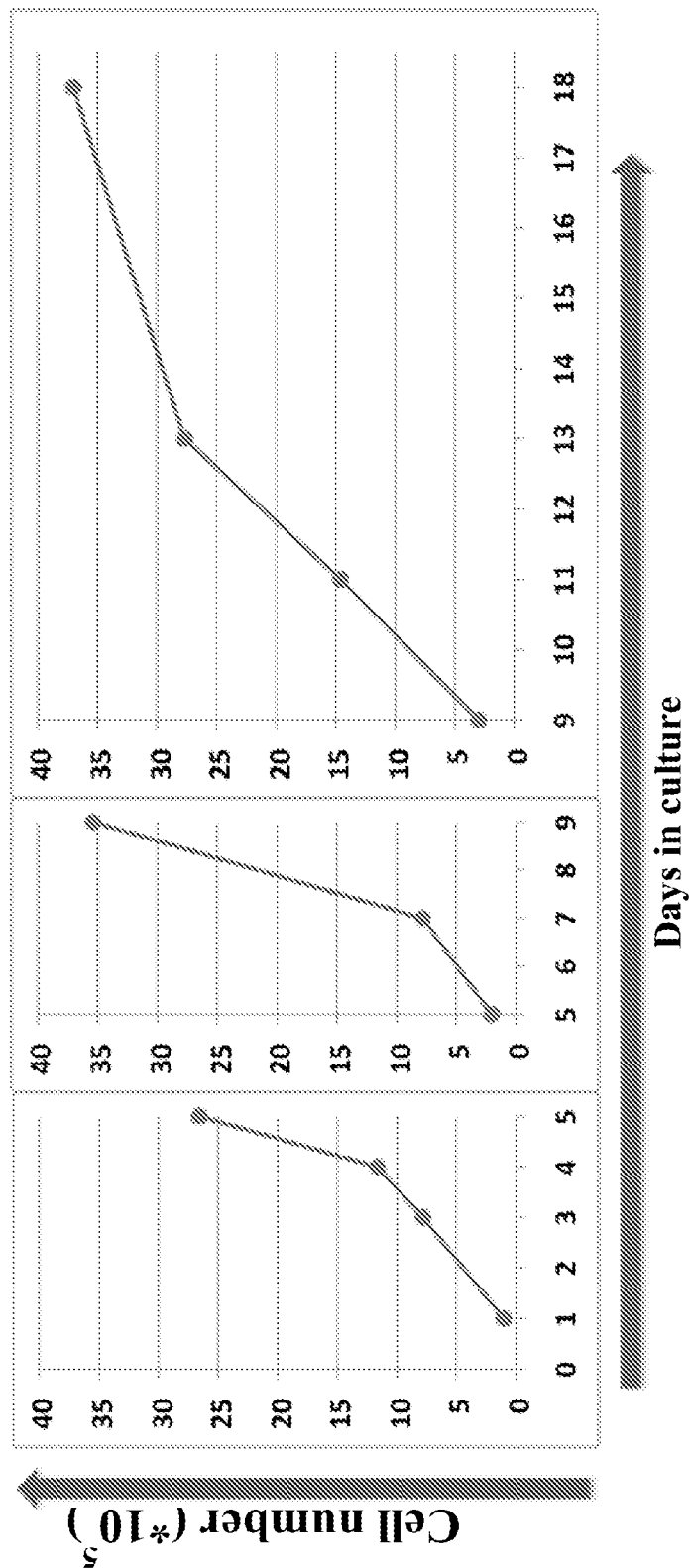
FIG. 6 includes charts showing cell proliferation at different differentiation stages.
Figure 7:
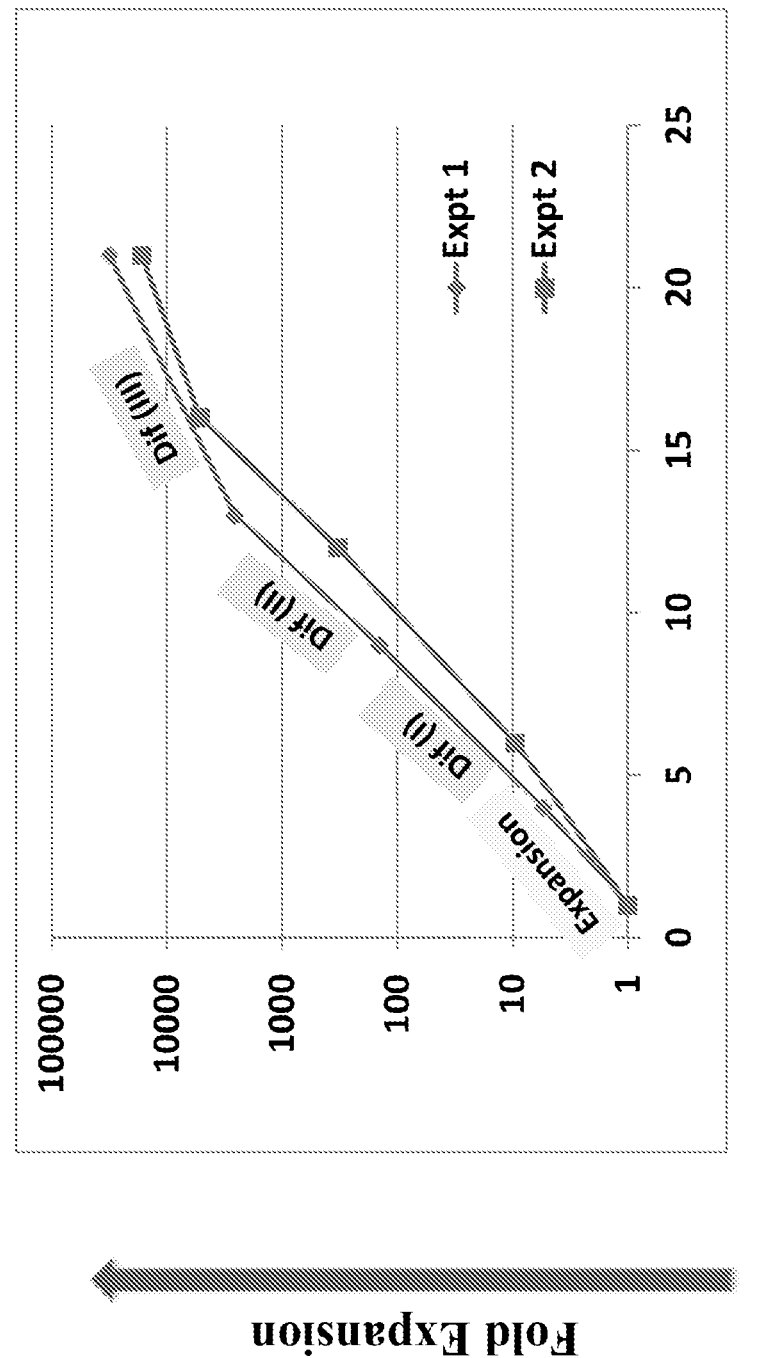
FIG. 7 is a chart showing cell proliferation in a window of around 20 days.
Figure 8:
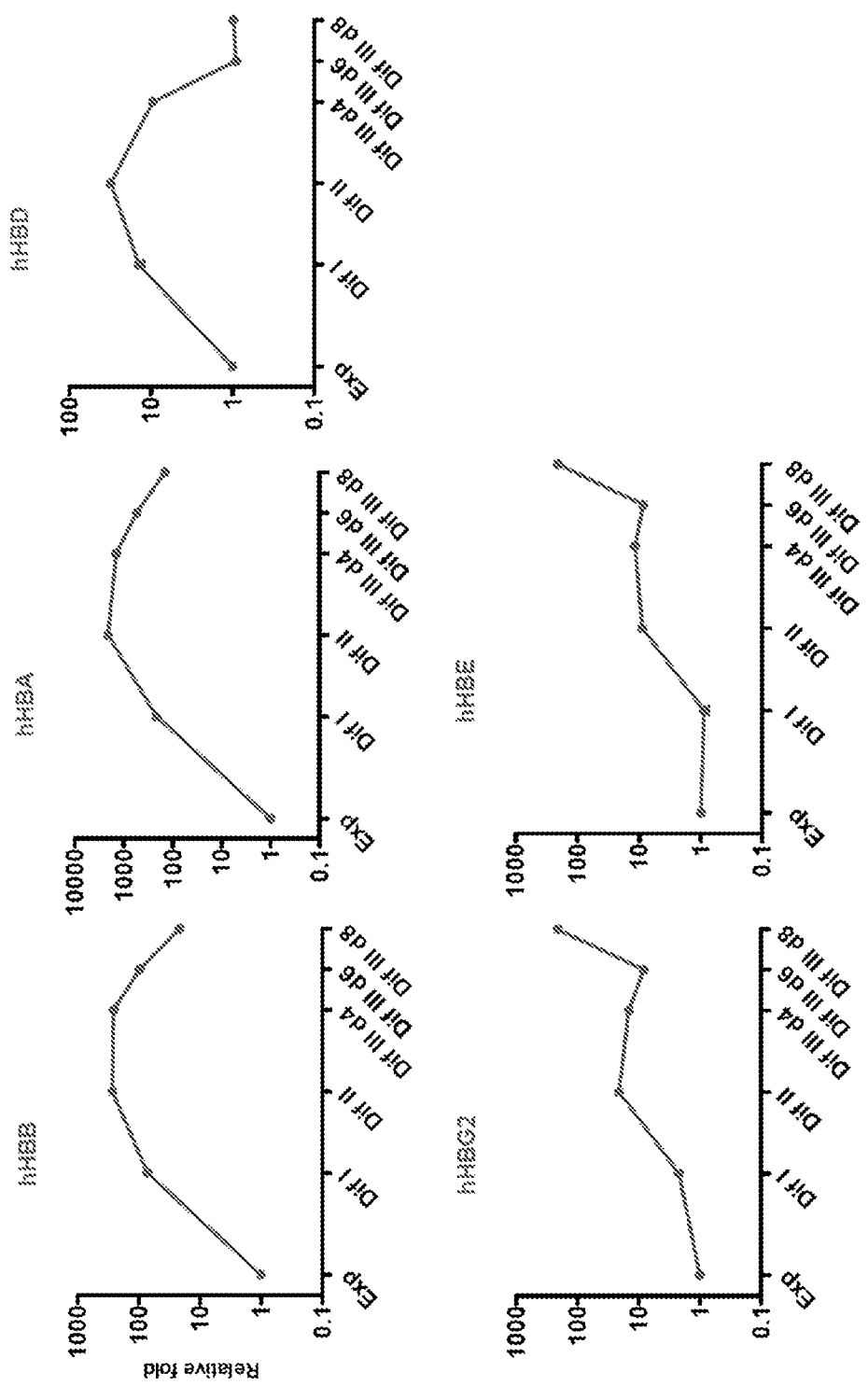
FIG. 8 include charts showing the expression of globin genes as indicated during hCD34+ cell differentiation.
Figure 9:
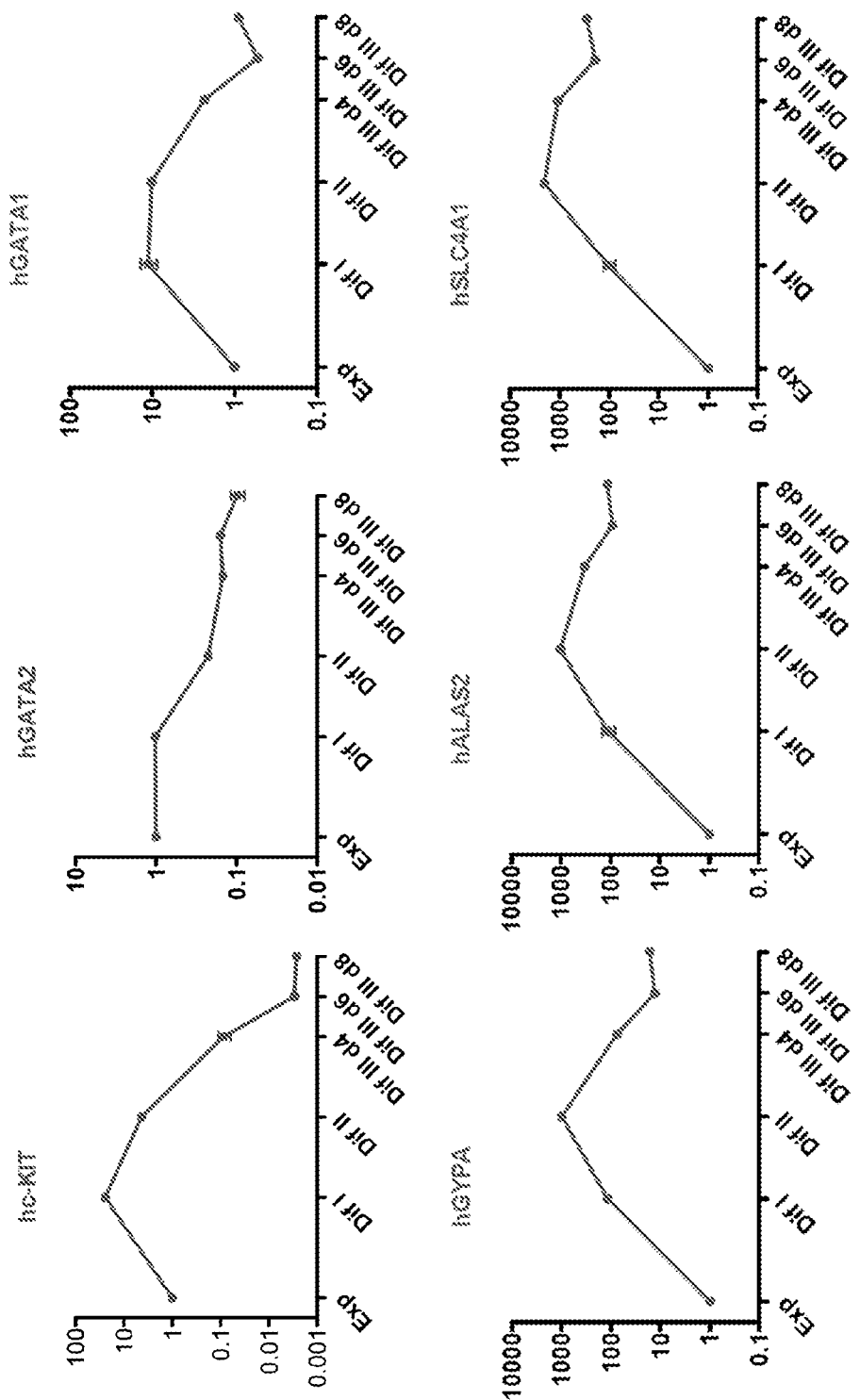
FIG. 9 includes charts showing the expression of various genes as indicated during hCD34+ cell differentiation.

The cell numbers during the differentiation process were counted and the results indicate that the cell number doubled almost every day during Dif I to early Dif. III. FIGS. 6 and 7. The expression levels of globin genes, as well as other genes (hc-kit, hGATA2, hGATA1, hGYPA, hALAS2, and hSLCA1) during $hCD^{34+}$ cell differentiation were also examined by FACS analysis. The results are shown in FIGS. 8 and 9.

In sum, the study described above indicates that a four-phase $hCD^{34+}$ cell culture and differentiation process has been successfully developed. This process yielded about 17,000-32,000-fold cell expansion (14-15 doubling) after a 21-day culture and around 40-50% of the cells were found to undergo enucleation. The enucleated red blood cells obtained from this culturing process are similar to normal human reticulocytes or normal red blood cells in cell size, hemoglobin content (~30 pg/cell), and cell surface marker expression.

Example 2

Conjugation of Functional Probes to Engineered Red Blood Cells Via Sortase Reaction RBCs lack a nucleus and at their mature stage cannot be genetically modified. Therefore erythroid precursors were genetically engineered to express sortase-modifiable proteins that are retained on the plasma membrane of mature RBCs. In this study, two sortase-modifiable membrane proteins were expressed in erythroid progenitors, Kell and Glycophorin A (GPA):

(1) The blood group antigen Kell is a type II membrane protein with an extracellularly exposed C-terminus and was selected as a target for C-terminal labeling.

(2) GPA, a type I membrane protein with its N-terminus extracellularly disposed, is the most abundant protein on the RBC surface and was chosen for N-terminal modification.

Materials and Methods (i) Plasmids

The coding sequences of human, mouse glycophorin A (GPA) and Kell were obtained from NCBI ref sequence NM_002099.6, NM_010369.3, and NM_000420.2, respectively. The Myc-tag coding sequence (GAGCAGAAACT-CATCTCAGAAGAGGATCTG; SEQ ID NO: 109) was inserted between the signal peptide and the mature GPA for detection of cell surface expression. To attach the sortase tag at the N terminus of GPA, five glycine (SEQ ID NO: 3) or three glycine tag coding sequences (GGTGGCGGAG-GTGGA; SEQ ID NO: 110 or GGTGGCGGA) were inserted immediately after the signal peptide. The full length of engineered human and mouse GPAs were synthesized by Genscript, and subsequently cloned into MSCV retroviral vectors. Human Kell was cloned into MSCV retroviral vector extended at its C-terminus with the coding sequence for Myc tag (GAACAAAAACTTATTTCTGAAGAA GATCTG; SEQ ID NO: 112), LPETGG (SEQ ID NO: 107) (CTGCCAGAAACTGGTGGA; SEQ ID NO: 113), followed by HA epitope tag (TACCCATACGACGTCCCA-GACTACGCT; SEQ ID NO: 114).

(ii) Protein Expression and Purification

Both, sortase A from *Staphylococcus aureus* Δ59 mutated for Kcat improvement (1) (P94R, D160N, D165A, K190E, K196T) and $Ca^{2+}$ independent activity (Hirakawa et al., *Biotechnol. Bioeng* 109(12):2955-2961) (E105K, E108Q) in pET30 and sortase A from *Streptococcus pyogenes* were expressed and purified as described previously. Guimaraes et al., (2013) *Nat Protoc* 8(9):1787-1799. VHH7 C-terminally extended with LPETGGHHHHHH (SEQ ID NO: 115) in pHEN was expressed and purified as described previously (4). Design and synthesis of sortase probes are been described previously as well. Guimaraes et al., 2013; and Theile et al., (2013) *Nat. Protoc.* 8(9):1800-1807.

(iii) Sortase Labeling Reaction

For labeling of GPA N-terminus with biotin, 30 µl of 500 µM *S. aureus* sortase, 1 mM K(biotin)LPRTGG (SEQ ID NO: 116) peptide in 83 mM Tris-HCl pH 7.5, 250 mM NaCl buffer was pre-incubated on ice for 15 minutes and added to 70 µl of ~1×10⁶ cultured cells (reticulocytes or HEK293T cells) or up to 5×10⁷ red blood cells (10 µl of whole blood) in DMEM (pre-washed with DMEM). For labeling GPA N-terminus with VHH7, 50 µl of 100 µM *S. aureus* sortase, 100 µM VHH-LPETG-His6 (SEQ ID NO: 126) in 50 mM Tris-HCl pH 7.5, 150 mM NaCl buffer was pre-incubated on ice for 15 minutes and added to 50 µl of up to 5×10⁷ red blood cells in DMEM. For labeling Kell C-terminus with biotin, 30 µl of 500 µM *S. aureus* sortase, 1.4 mM GGGK (biotin) (SEQ ID NO: 47) peptide in 83 mM Tris-HCl pH 7.5, 250 mM NaCl buffer was added to 70 µl of ~1×106 cultured cells (reticulocytes or HEK293T cells) or up to 5×107 red blood cells in DMEM (pre-washed with DMEM). All sortase and cell mixtures were incubated on ice for 30 minutes with occasional gentle mixing. They were spun at 2000 RPM for 2 minutes at 4° C. to remove buffer/DMEM and washed 3 times with 1 ml of ice-cold PBS. For sequential dual labeling of GPA and Kell, 30 µl of 333 µM *S. pyogenes* sortase, 1.33 mM K(biotin)LPETAA (SEQ ID NO: 45) peptide in 83 mM TrisHCl, 250 mM NaCl, 16.7 mM CaCl2 buffer was pre-incubated at 37° C. for 15 minutes, added to 70 µl of 1×10⁶ HEK293T cells in DMEM (pre-washed with DMEM) and incubated at 37° C. for 25 minutes with occasional gentle mixing. Cells were spun down at 2000 RPM for 2 minutes at 4° C., washed 2 times with 1 ml of ice-cold PBS and finally re-suspended into 70 µl of ice-cold DMEM. 30 µl of 333 µM *S. aureus* sortase, 1.67 mM GGGK(Alexa647; SEQ ID NO: 117) peptide in 83 mM Tris-HCl pH 7.5, 250 mM NaCl was added to the cells and incubated for 30 minutes on ice with occasional gentle mixing. Cells were washed 3 times with 1 ml of ice-cold PBS.

(iv) Western Blotting

When sortase-labeling whole blood, red blood were first lysed with 500 µl of ammonium chloride solution (Stemcell Technologies) via a 5 minute incubation on ice and spun down at 14000 RPM for 10 minutes at 4° C. Membranes were washed once with 500 µl of PBS. Cells were solubilized in 25 mM Tris-HCl pH7.5, 0.5% NP40, 5 mM $MgCl_2$, 150 mM NaCl supplemented with a Complete mini protease inhibitor cocktail tablet (Roche), vortexed, incubated on ice for 10 minutes, and spun at 14,000 RPM for 10 minutes at 4° C. Supernatant was incubated with SDS sample buffer and boiled for 8 minutes. After SDS-PAGE, proteins were transferred onto PVDF membrane and immunoblotted for biotin (using streptavidin-HRP (GE Healthcare)), myc tag (Cell Signaling #2040), HA tag (Roche 3F10), hemoglobin, or CD19 (Cell Signaling #3574).

(v) Transfection

Virus production: Six million 293T cells were split and plated on 10 cm plates one day before transfection in antibiotic free Dulbecco's Modified Eagle Medium (DMEM) with added 15% Fetal Bovine Serum (FBS) and 2 mM L-Glutamine (Invitrogen). On day 0, 10 ug plasmids together with 5 ug packaging vector were added to the 293T 10-cm plate with Fugene 6 (Promega). Six-eight hours later, new DMEM with added 15% FBS, 2 mM L-Glutamine, and 1× Pen Strep (Invitrogen) replaced the old medium. On day 1, the supernatant containing fresh virus was collected, filtered through 0.45 µm filter (Millipore), and then immediately used to infect the murine erythroid progenitors. GPA & Kell expression: HEK293T cells were plated on 10 cm dish and transfected with either 15 µg of Gn-myc-h/mGPA constructs in retroviral vectors, or 7.5 µg of hKell-LPETG (SEQ ID NO: 44)-HA and 7.5 µg of 3G-myc-hGPA both in retroviral vectors (for sequential dual sortase labeling) using TransIT transfection reagent according to manufacturer's recommendations (*Mirus*). Cells were analyzed for protein expression and sortase-labeled 24 hours after cellular transfection.

(vi) Isolation of Erythroid Progenitors from Murine E14.5 Fetal Liver Cells

After etherization by carbon dioxide, Day 14.5 pregnant C57BL/6J mice were dissected, and the embryos were isolated. The entire fetal livers were carefully separated and placed in Phosphate Buffered Saline (PBS) with 2% Fetal Bovine Serum (FBS) and 100 uM EDTA. Single fetal liver cell suspensions were obtained after triturating and filtering through a 70 µm filter (BD). Mature red blood cells among fetal liver cell suspension were lysed after incubation with Ammonium Chloride Solution (Stemcell) for ten minutes. Nucleated cells were collected by centrifugation at 1500 RPM for 5 minutes, and resuspended in PBS. Using BD Biotin Mouse Lineage Panel (559971) and BD Streptavidin Particles Plus DM (557812), we purified lineage negative fetal liver cells, which were enriched for erythroid progenitors (more than 90%).

(viii) Viral Infection and Culture of Murine Erythroid Progenitors

After purification, lineage negative fetal liver cells were prepared at a concentration of 10 million cells per ml. Ten microliters of the cells were plated in each well of a 24-well plate, together with 1 ml virus-containing supernatant with 5 ug/ml polybrene. The plate was spun at 2000 RPM for 90 min at 37 degree. Immediately following spin-infection, the virus-containing supernatant was aspirated and replaced with erythroid maintenance medium (StemSpan-SFEM (StemCell Technologies) supplemented with recombinant mouse stem cell factor (100 ng/ml SCF, R&D), recombinant mouse IGF-1 (40 ng/ml, R&D), dexamethasone (100 nM, Sigma), and erythropoietin (2 u/ml, Amgen)). The next morning, the infection rate was examined by flow cytometry by checking for the population of GFP positive cells. It was typically more than 95%. The cells were then cultured in Epo-only erythroid differentiation medium (Iscove modified Dulbecco's medium (IMDM) containing 15% FBS (Stemcell), 1% detoxified bovine serum albumin (BSA) (Stemcell), 500 µg/mL holo-transferrin (Sigma-Aldrich), 0.5 U/mL Epo (Amgen), 10 µg/mL recombinant human insulin (Sigma-Aldrich), 2 mM L-glutamine (Invitrogen), and 1× Pen Strep (Invitrogen)) for 48 hours.

(ix) Flow Cytometry

The desired cells, washed them once by PBS, and resuspended them at a density of 5-10 Mimi in PBS with 1 µg/ml PI for FACS sorting or analysis. During enucleation analysis, the cells were first stained with Anti-Mouse TER-119 antibody (eBioscience, 14-5921) and Hoechst (Sigma) for 15 minutes at room temperature. For detecting the surface expression or labelling of Myc-tag, HA-tag or Biotin-labelling, the cells were stained with anti-Myc antibody (Cell signalling, 3739), anti-HA antibody (Thermo Fisher Scientific, NC9843881) or anti-biotin antibody (eBioscience, 12-9895-82), respectively, for 30 minutes at room temperature.

(x) Viral Infection of Bone Marrow Cells

Bone marrow in femur and tibias from C57BL/6J mice was isolated using 23G needle and cultured at density of 2×106 cells/ml for 18 hours in DMEM supplemented with 15% fetal calf serum, 2 mM L-Glutamine (Invitrogen), 1× Pen/Strep (Invitrogen), 20 ng/ml IL-3 (Peprotech), 50 ng/ml SCF (Peprotech), and 50 ng/ml IL-6 (Peprotech) in 6-well plates. Cells were infected by incubating 4×106 cells in 500 µl of retrovirus-containing media, 500 µl DMEM, and 5 µg/ml polybrene and spinning the cells at 2500 RPM for 1.5 hours at room temperature and further incubating them in a $CO_2$ incubator for 5 hours. Cells were returned to the above IL-3/SCF/IL-6 supplemented media and further incubated for 16 hours.

(xi) Irradiation Procedure and Mouse Fatal Liver Transplantation

B6.SJL-Ptprca Pep3b/BoyJ mice (The Jackson Lab) were subjected to total body irradiation with 1050 cGy in a Gammacell 40 irradiator chamber 1 day before transplantation. Mouse fetal liver cells were harvested and prepared as mentioned above. Following retroviral infection, cells were cultured in erythroid maintenance media for 18 hours. Alternatively, mouse bone marrow cells were harvested and retrovirus transduced as described above. Infected cells were then washed 2 times in sterile PBS and resuspended in sterile PBS at 2-5 million cells/mL. 100 µl of these mouse stem and progenitor cells were then retro-orbitally injected into the lethally irradiated mice. Starting from four weeks, mature red cells were extracted from the irradiated mice for analysis and sortagging.

(xii) Cytospin Preparation and Immunofluorescence

After mature red blood cells and in vitro differentiated reticulocytes were sortagged with biotin, they were washed twice in cold 1×PBS. 50,000 sorted, biotinylated mature red blood cells or unsorted, in vitro differentiated reticulocytes were centrifuged onto Poly-L-Lysine coated slides for 5 minutes at 400 rpm (Cytospin 3, Thermo Shandon). Samples were air dried, fixed in 4% paraformaldehyde for 30 minutes at room temperature and blocked for 1 hour in blocking buffer (2% BSA+2% Donkey Serum in PBS). Cells were then incubated with primary antibodies: PE-conjugated anti-biotin (1:1000, eBioscience, 12-9895-82) and APC-conjugated anti-Ter119 (1:100, eBioscience, 14-5921) in blocking buffer overnight at 4° C., followed with three washes in cold 1×PBS. Finally, cells were mounted with mounting media containing DAPI (Prolong Gold Antifade, Invitrogen) to visualize nuclei in all immunostaining experiments. Visualization was carried out using a Zeiss LSM 700 Laser Scanning Confocal Microscope.

(xiii) Transfusion and Survival of eRBC

After mature RBCs were sortagged, they were washed twice in 1×PBS and resuspended in RPMI medium. These sortagged RBCs were collected by centrifugation at 1500 rpm for 5 minutes and labeled with 5 µM CFSE in Hank's Balanced Salt Solution (HBSS) for 8 minutes (Life Technologies). Equivolumes of 10% FBS in HBSS were then added to quench the reaction. RBCs were washed, counted, and resuspended in sterile HBSS for injection. 2.5 billion CFSElabeled RBCs (±300 µl mouse blood) were then injected intravenously into recipient $CD^{45.1+}$ mice. Normal RBCs served as a control. Since only 20~50% of RBCs expressed engineered hGPA or hKell, the rest of the RBCs were normal and served as an internal control by monitoring the CFSE signal. One hour after transfusion, the first blood sample (20 µl) were collected from retro orbital and labeled as Day 0. The subsequent blood samples with same amount were collected at days 1, 4, 7, and so on, until 28. The blood samples were stained with anti-biotin antibody conjugated with PE (ebioscience), so that eRBCs linked with biotin had strong PE signal during flow cytometry analysis. However, RBCs with hKell-biotin had very low red fluorescent intensity after staining with anti-biotin antibody conjugated with PE. It was difficult to detect it in the presence of strong green fluorescent signal from CFSE. The hKell-RBCs were stortagged with biotin, and transfused into mice without CFSE staining. The hKell-RBCs were monitored by their inherent GFP signal and weak PE signal from anti-biotin antibodies conjugated with PE. The control RBCs and hGPA-RBCs were transfused into a total of six mice in two separate times. The hKell-RBCs were transfused to a total of three mice, with one dying for an unknown reason.

Figure 10:
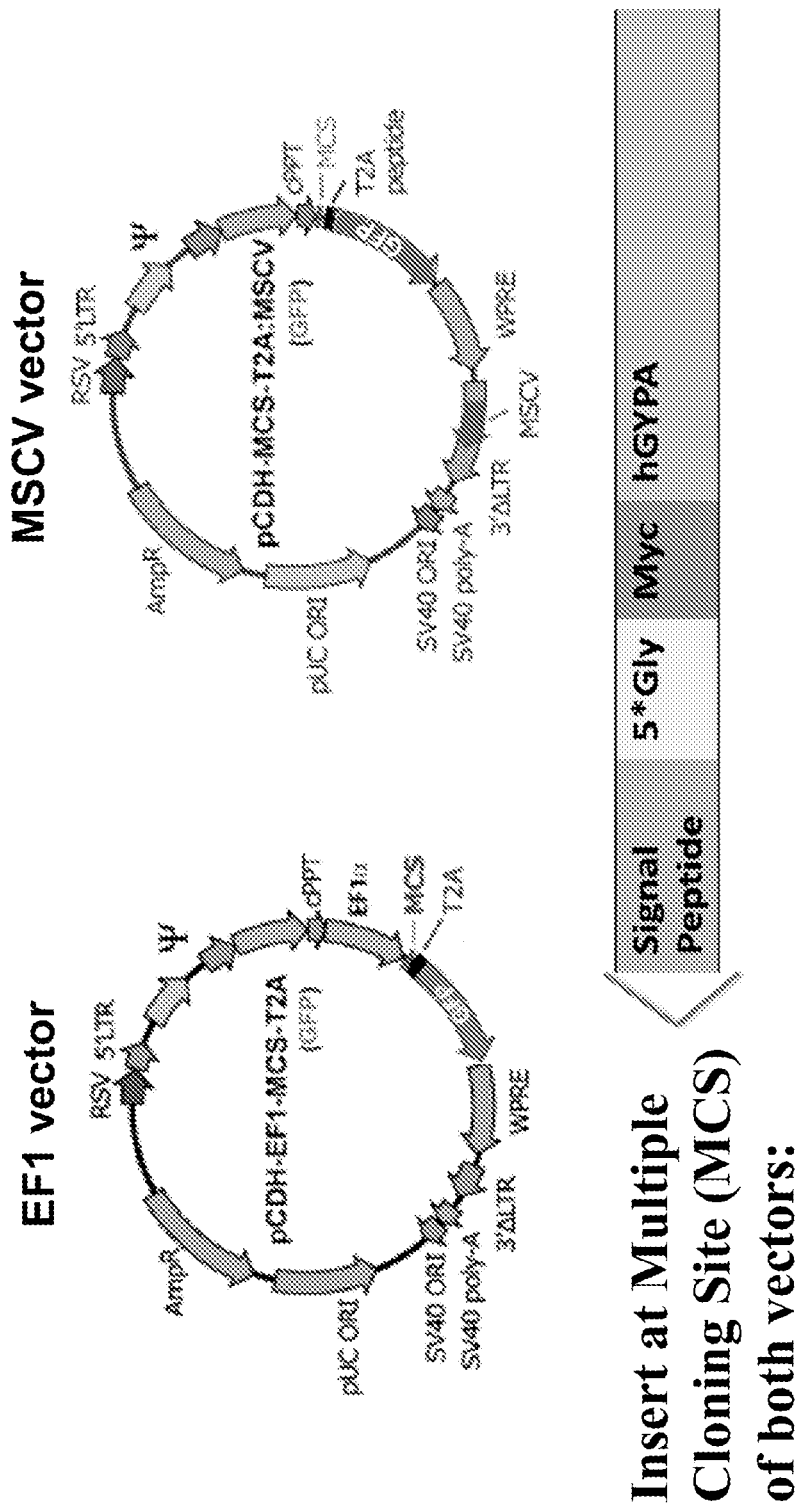
FIG. 10 is a diagram showing construction of EF1 and MSCV expression vectors for producing 5Gly (SEQ ID NO: 3)-myc-human glycophorin A (hGYPA or hGPA) fusion protein.

Results (I) Genetically Modified Type-I Membrane Protein Human Glycophorin a (GPA) was Expressed and Sortase-labeled on the RBC Surface (a) Expression of Sortaggable Human Glycophorin (hGPA) on RBCs The expression cassettes of fusion proteins 5Gly (SEQ ID NO: 3)-myc-hGYPA and 3Gly-myc-hGYPA were inserted into two lentiviral vectors EF1 and MSCV (System Biosciences, Inc.) as shown in FIG. 10. Both vectors carry GFP as a report gene. The resultant lentiviral vectors for expressing the fusion proteins were transduced into human $CD34^+$ cells in the beginning of Dif I.

Figure 11:
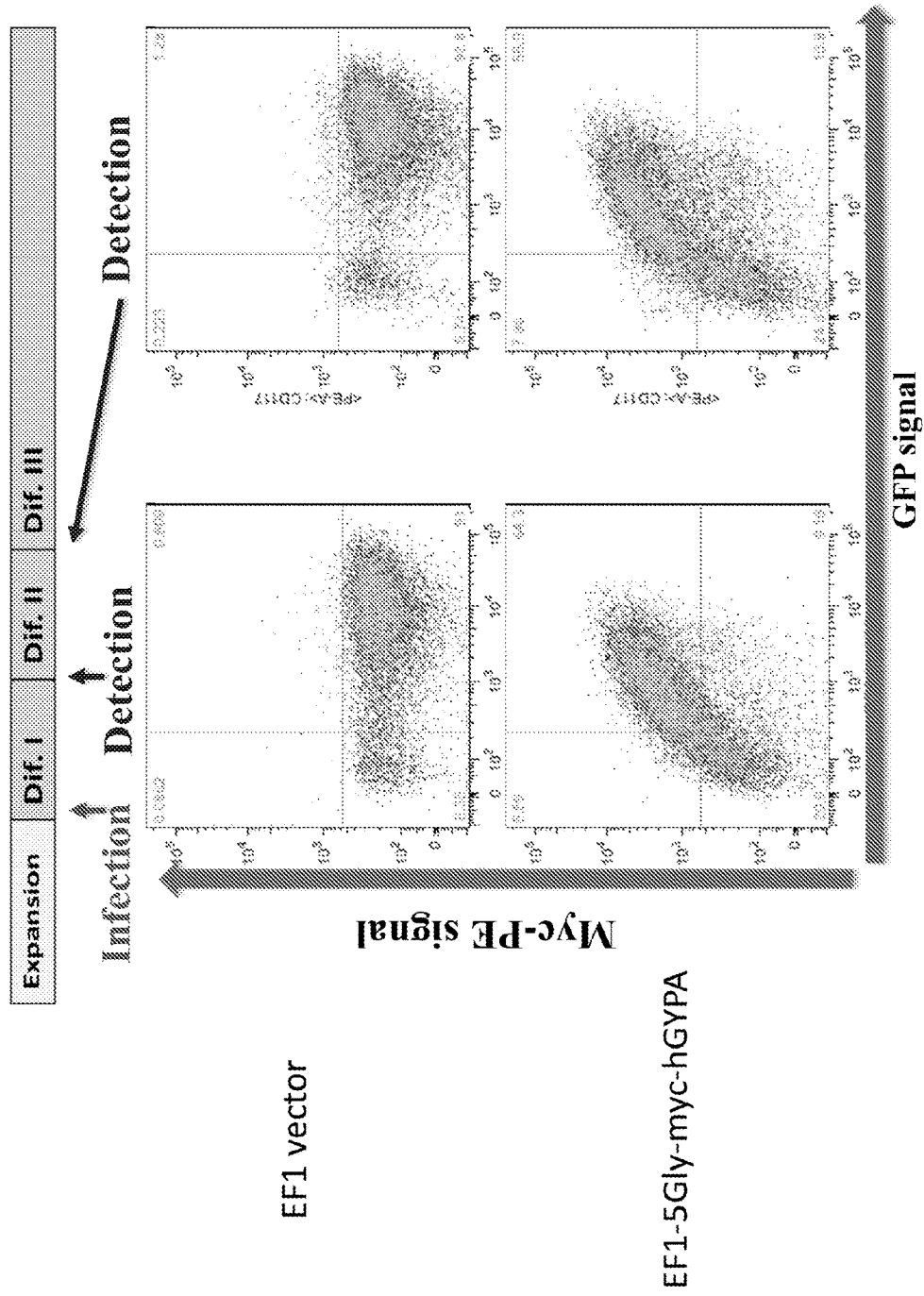
FIG. 11 is a diagram showing surface expression of sortaggable hGYPA on hCD34+ erythroid progenitors (at different differentiation stages) using EF1 expression vectors; 5Gly: (SEQ ID NO:3).

FIG. 11 shows the expression of the fusion proteins in the human $CD34^+$ cells and red blood cells obtained at the end of Dif. I and Dif II as described in Example 1 above. The expression of 5Gly (SEQ ID NO: 3)-myc-hGYPA fusion protein on the surface of red blood cells transduced by the EF1 vectors was observed at least at the end of Dif. II.

Figure 12:
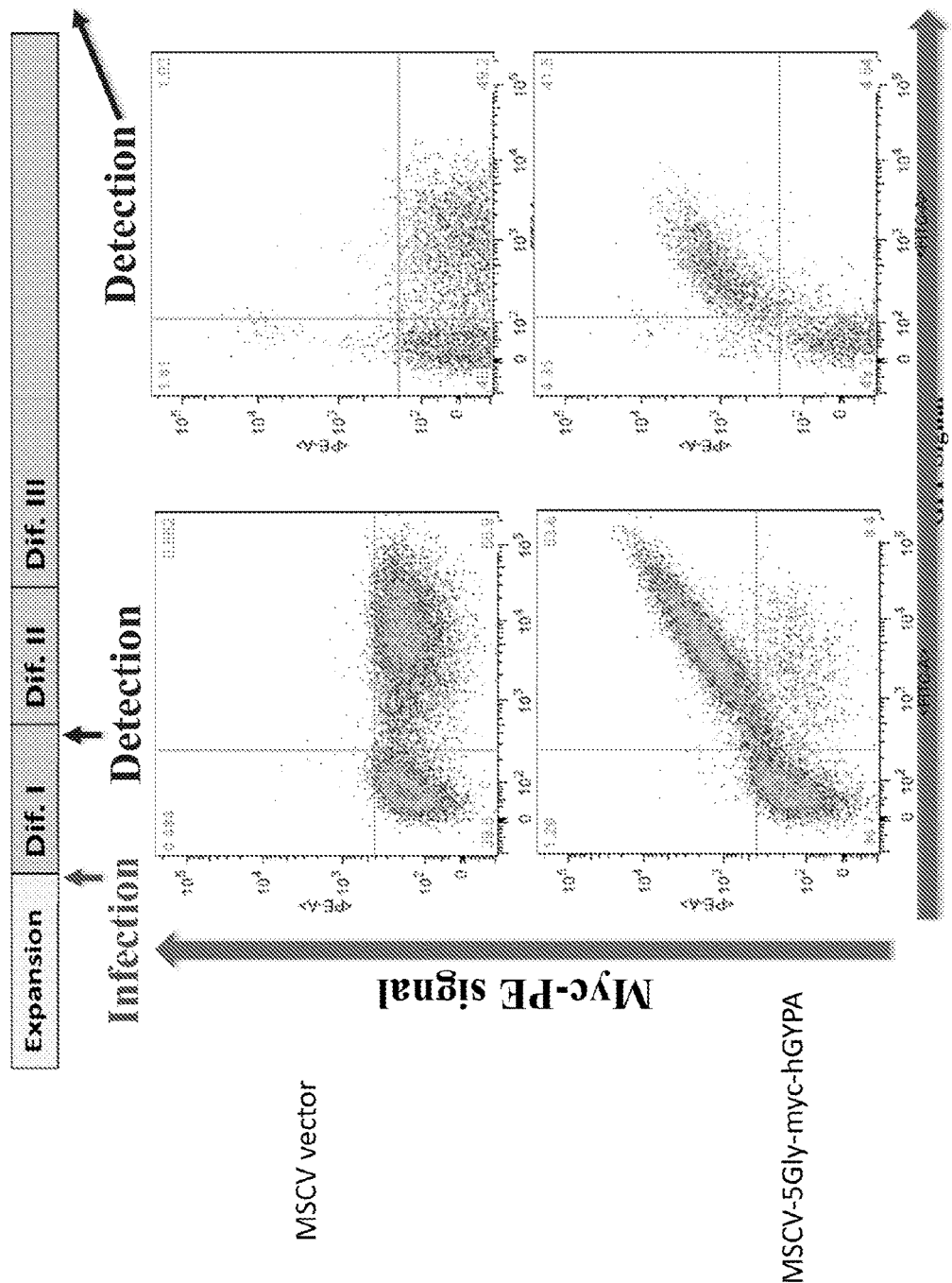
FIG. 12 is a diagram showing surface expression of sortaggable hGYPA on hCD34+ erythroid progenitors (at different differentiation stages) using MSCV expression vectors; 5Gly: (SEQ ID NO:3).

Similar results were observed in red blood cells transduced with the MSCV expression vectors. As shown in FIG. 12, expression of MSCV-5Gly (SEQ ID NO: 3)-myc-hGYPA on the surface of red blood cells was observed at the end of Dif. III.

The lentiviral vectors for expressing the 5Gly (SEQ ID NO: 3)-myc-hGYPA and 3Gly-myc-hGYPA fusion proteins were also transduced into K562 cells and expression of both fusion proteins were observed on the surface of the K562 cells.

In sum, expression of sortaggable hGYPA were detected in 50~70% of the cells at the end of Dif I by flow cytometry and Western blotting. hGYPA expression remained constant and last until the end of Dif III.

(b) Conjugate an Agent of Interest to Red Blood Cell Surface in the Presence of a Sortase To sortag hGYPA, 300 μM sortase A of *Staphylococcus aureus* and 500 μM biotin-LPRTGG (SEQ ID NO: 118) were pre-incubated in a sortase buffer at 37° C. for 30 minutes. One million red blood cells expressing sortaggable hGYPA (5Gly (SEQ ID NO: 3)-myc-hGYPA or 3Gly-myc-hGYPA) were then incubated with the sortase-substrate mix at 37° C. for 1 hour. The cells were washed with PBS for 3~4 times before detection by flow cytometry or Western blotting for biotin conjugation. Labeling efficiency is normally 80~100%.

Figure 13:
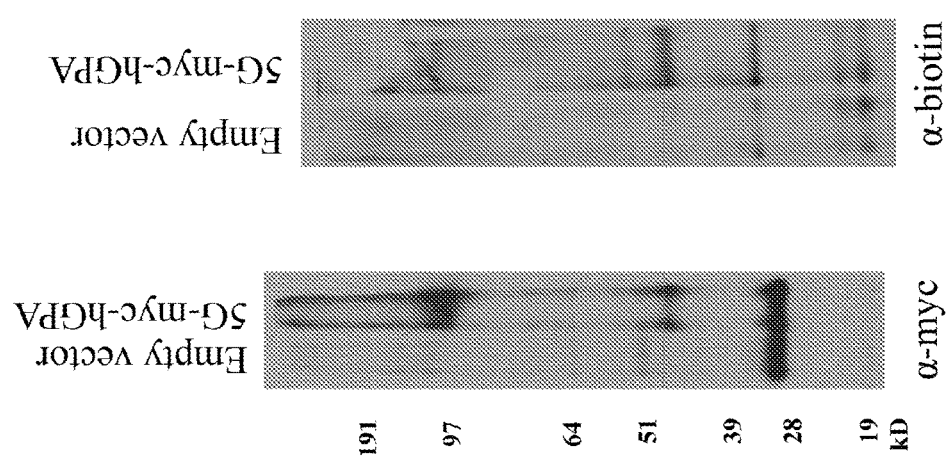
FIG. 13 is a photograph showing conjugation of biotin to hGYPA on hCD34+ erythroid progenitor cells by sortagging as determined by Western blotting; 5G: (SEQ ID NO:3).
Figure 14:
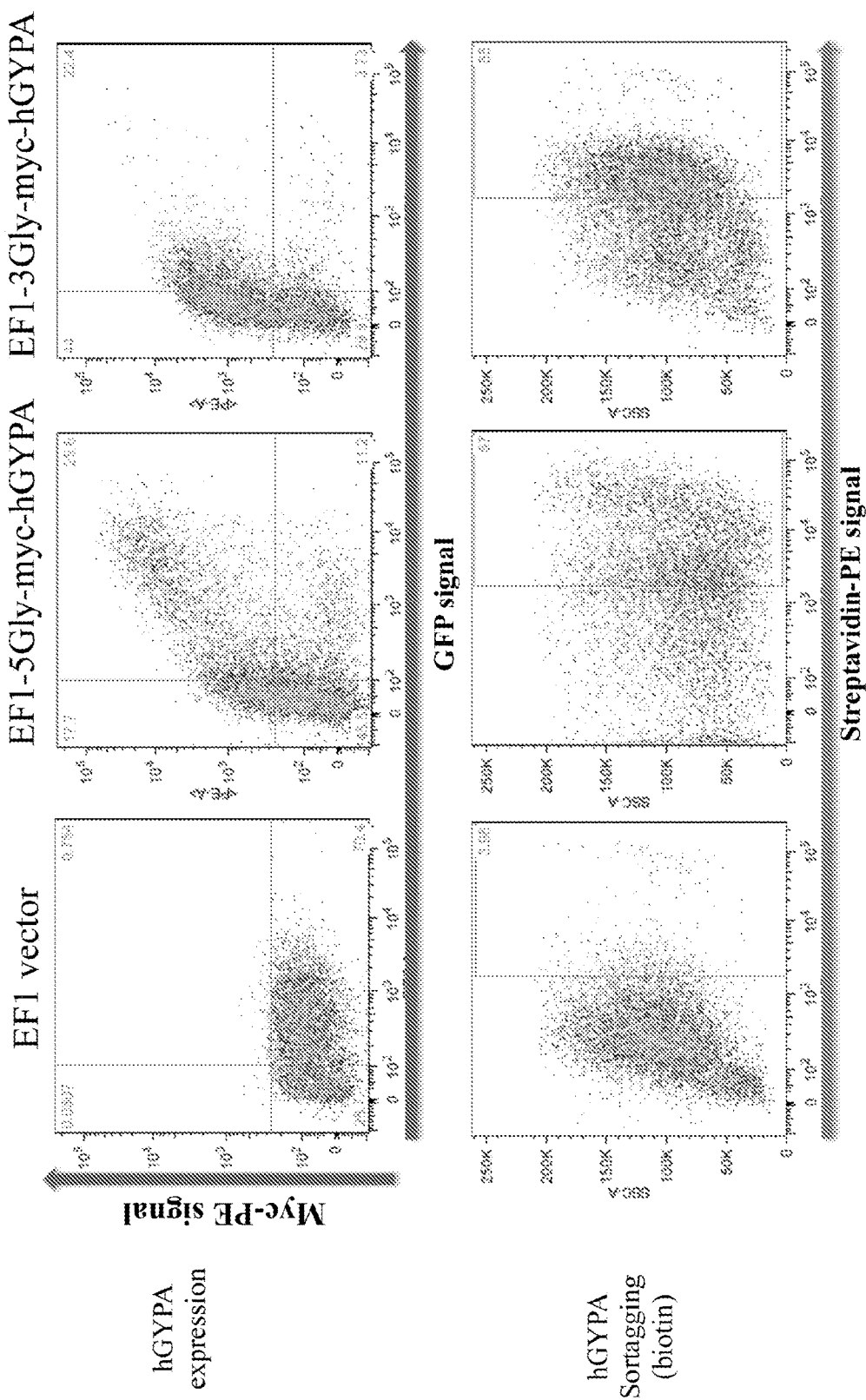
FIG. 14 is a diagram showing conjugation of biotin to the surface of human CD34+ cells at the terminal differentiation stage via sortagging; 5Gly: (SEQ ID NO:3).
Figure 15:
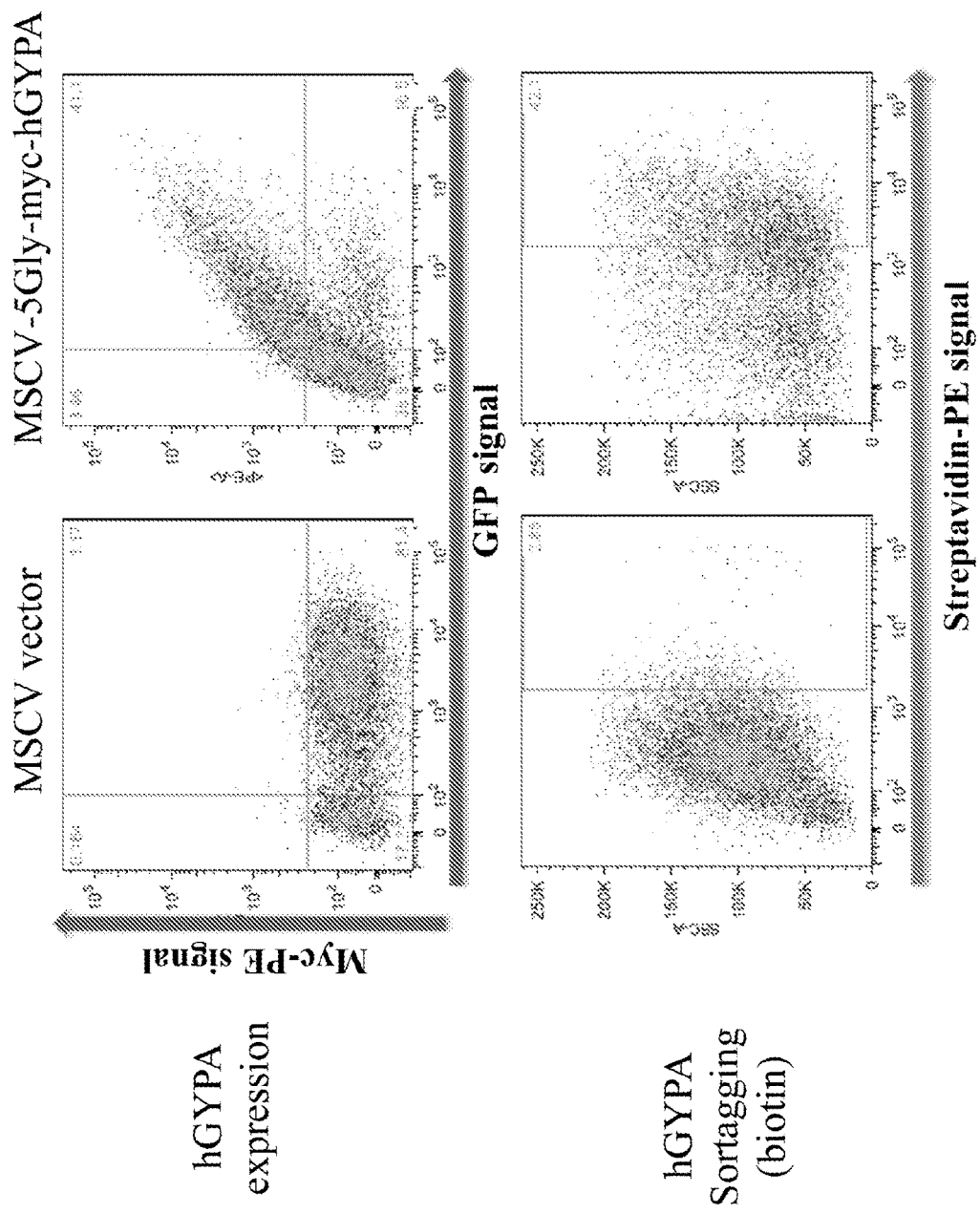
FIG. 15 is a diagram showing conjugation of biotin to the surface of human CD34+ cells at the terminal differentiation stage via sortagging; 5Gly: (SEQ ID NO:3).

As shown in FIG. 13, Western blotting results indicate expression of 5Gly (SEQ ID NO: 3)-myc-hGYPA on red blood cells and the conjugation of biotin to the hGYPA. FACS analysis indicated that biotin was conjugated to the surface of red blood cells at day 8 of Dif. III. FIGS. 14 and 15. This result shows that the surface of mature enucleated red blood cells can be modified via a sortase-catalyzed reaction.

Similarly, sortaggable hGYPA expressed on K562 cells was successfully modified by biotin in the presence of a sortase.

In another experiment, a PE-conjugated peptide comprising the LPXTG (SEQ ID NO: 1) motif was included with sortase A for 45 minutes at 37° C. The mixture was then incubated with erythrocytes expressing 3Gly-GYPA or 5Gly (SEQ ID NO: 3)-GYPA sortaggable surface protein for 30 minutes at 37° C. The cells were then subjected to FACS analysis. Results thus obtained indicate that the PE-conjugated peptide was conjugated to both 3Gly-GYPA and 5Gly (SEQ ID NO: 3)-GYPA on the surface of the erythrocytes.

(c) Genetically Modified hGPA was Expressed as Sortase-labeled on Murine RBCs

Figure 16:
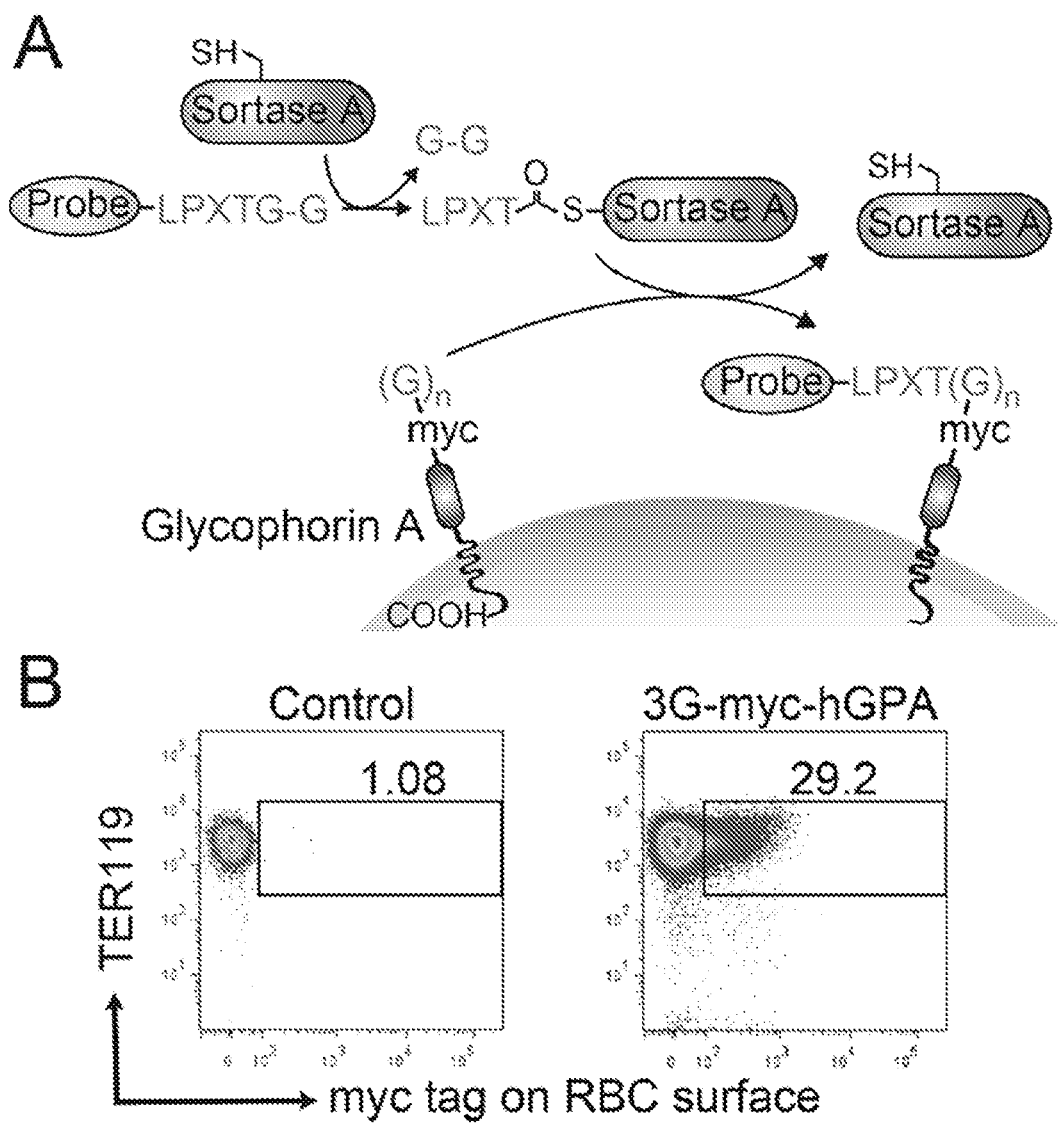
FIG. 16 is a diagram showing the expression and sortase-mediated N-terminal labeling of glycophorin A on the surface of mature mouse red blood cells. (A) Schematic for glycophorin A N-terminal sortase labeling. GPA was extended at the N-terminus to include 3 glycine residues and a myc tag. Pre-incubation of sortase with a probe, which contains a C-terminal sortase recognition motif, LPETG (SEQ ID NO:44). leads to cleavage between T and G and formation of an acyl enzyme intermediate between Cys on sortase and Thr on the probe. Nucleophilic attack of the N-terminal glycine on GPA resolves the intermediate, thus ligating the probe to GPA. The probe can be a peptide, protein, lipid, carbohydrate, small molecule, etc. For conjugation of biotin to GPA, the probe is K(biotin)LPRTGG (SEQ ID NO:45); LPXTGG: (SEQ ID NO:46). (B) Evaluation of mature RBCs for the presence of 3G-myc-hGPA on the cell surface by staining either control blood or blood from mice that have undergone bone marrow transplantation to express 3G-myc-hGPA, with α-TER119 and α-myc tag antibodies and analyzing via flow cytometry. (C) Evaluation of mature RBCs for sortase-labeling by incubating control blood or 3G-myc-hGPA blood with sortase and the biotin containing probe, staining with α-TER119 and α-biotin antibodies, and analyzing via flow cytometry. (D) Evaluation of RBCs for sortase-labeling by immunoblotting. Control or 3G-myc-hGPA blood was incubated with biotin probe with or without sortase, and total cell protein was resolved by SDS-PAGE and immunoblotted for α-myc tag and α-biotin. The shift in molecular weight of GPA upon biotin conjugation in the α-myc tag immunoblot indicates almost complete modification. Biotin conjugated GPA is indicated in the α-biotin immunoblot with an arrow. (E) RBCs conjugated with biotin were sorted by flow cytometry. Immunofluorescence images show biotin (labeled with red) at the N-terminus of hGPA on mature RBCs (labeled with Ter119 antibody, purple). (F) HEK293T cells were transfected with 3A-myc-hGPA, hKell-LPETG (SEQ ID NO:44)-HA, or both. Cells were incubated with S. pyogenes sortase and a biotin probe followed by S. aureus sortase and TAMRA-containing probe incubation. Specific conjugation of biotin to GPA and of TAMRA to Kell is demonstrated by immunoblotting and fluorescence imaging.

Extension of the N-terminus of GPA (GPA) with glycine residues was the minimal modification needed to render GPA a suitable sortase substrate. In the modified version, the N-terminal signal sequence was retained, followed by glycine residues and a myc epitope tag. Cleavage of the signal peptide would yield (Gly)n-myc tag-GPA. Incubation of cells carrying the modified GPA with sortase A from *Staphylococcus aureus* and an LPETG (SEQ ID NO: 44)-based probe leads to conjugation of this probe to the N-terminus of GPA (FIG. 16A).

Figure 17:
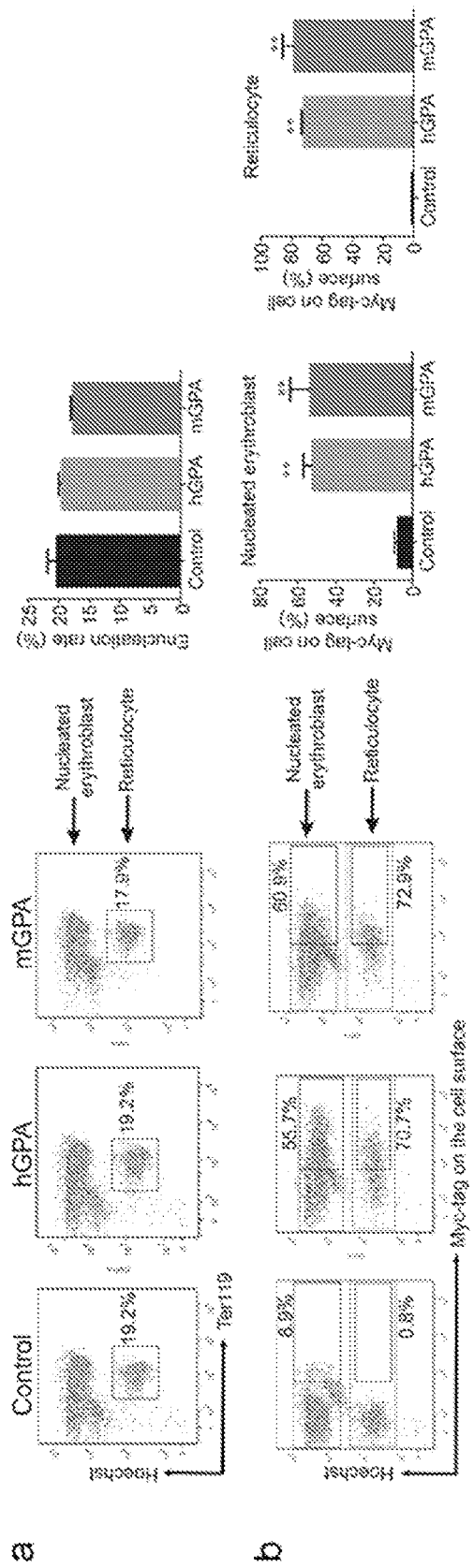
FIG. 17 is a diagram showing the overexpression of modified human GPA and mouse GPA containing myctag at N-termini do not affect in vitro differentiation of mouse erythroid progenitor. (A) Flow cytometry analysis of the differentiation capacity of in vitro differentiated murine fetal-liver derived progenitor cells infected with retroviral constructs containing modified human (h) or mouse (m) GPA constructs extended at their N-terminus with myc-tag: myc-hGPA and myc-mGPA. Differentiation capacity in these cells is assessed based on the expressions of Ter119 and enucleation, i.e. nuclei expulsion, resulting in Ter119$^+$ reticulocytes. The percentages of reticulocytes produced by erythroid progenitor cells infected with myc-hGPA or myc-mGPA (~20%) are comparable to cells infected with empty (control) vector, indicating that these constructs do not disturb erythroid terminal differentiation. Quantification of enucleation rate represents 3 independent experiments and graphed as mean values+/−standard deviation. (B) Evaluation of murine terminally differentiated erythroblasts, i.e. nucleated erythroblasts and reticulocytes, for the surface expression of myc-hGPA or myc-mGPA. More than 60% of these terminally differentiated cells expressed the desired modified GPA proteins as measured by flow cytometry using α-myc tag antibodies. Percentage of erythroblasts and reticulocytes with myc-tag on cell surface was determined from 3 independent experiments, graphed as mean value+/−standard deviation; ** indicates p<0.01. (C) Immunofluorescence images further confirm the surface expression of myc-tag (labelled with red) and enucleation capacity (blue nucleus staining) of the in vitro terminally differentiated erythroblasts.
Figure 17:
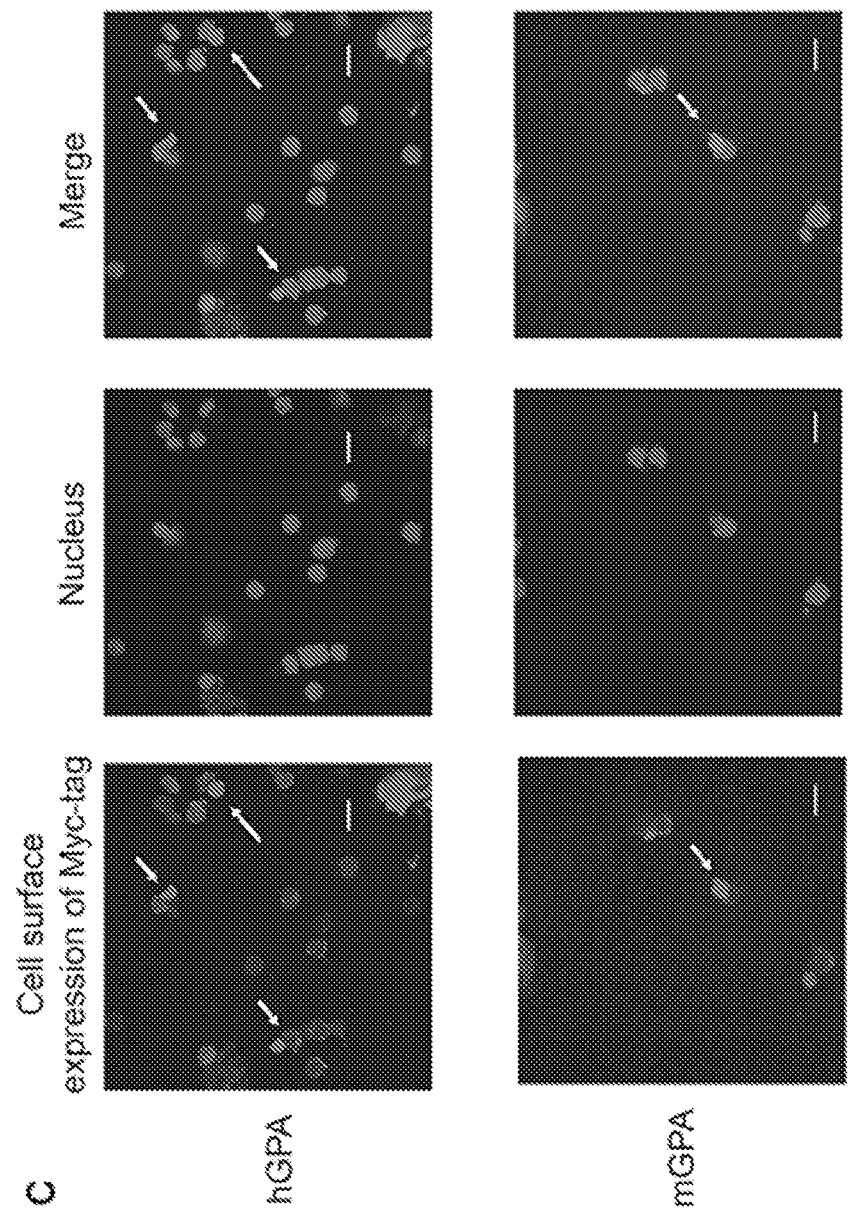
Figure 18:
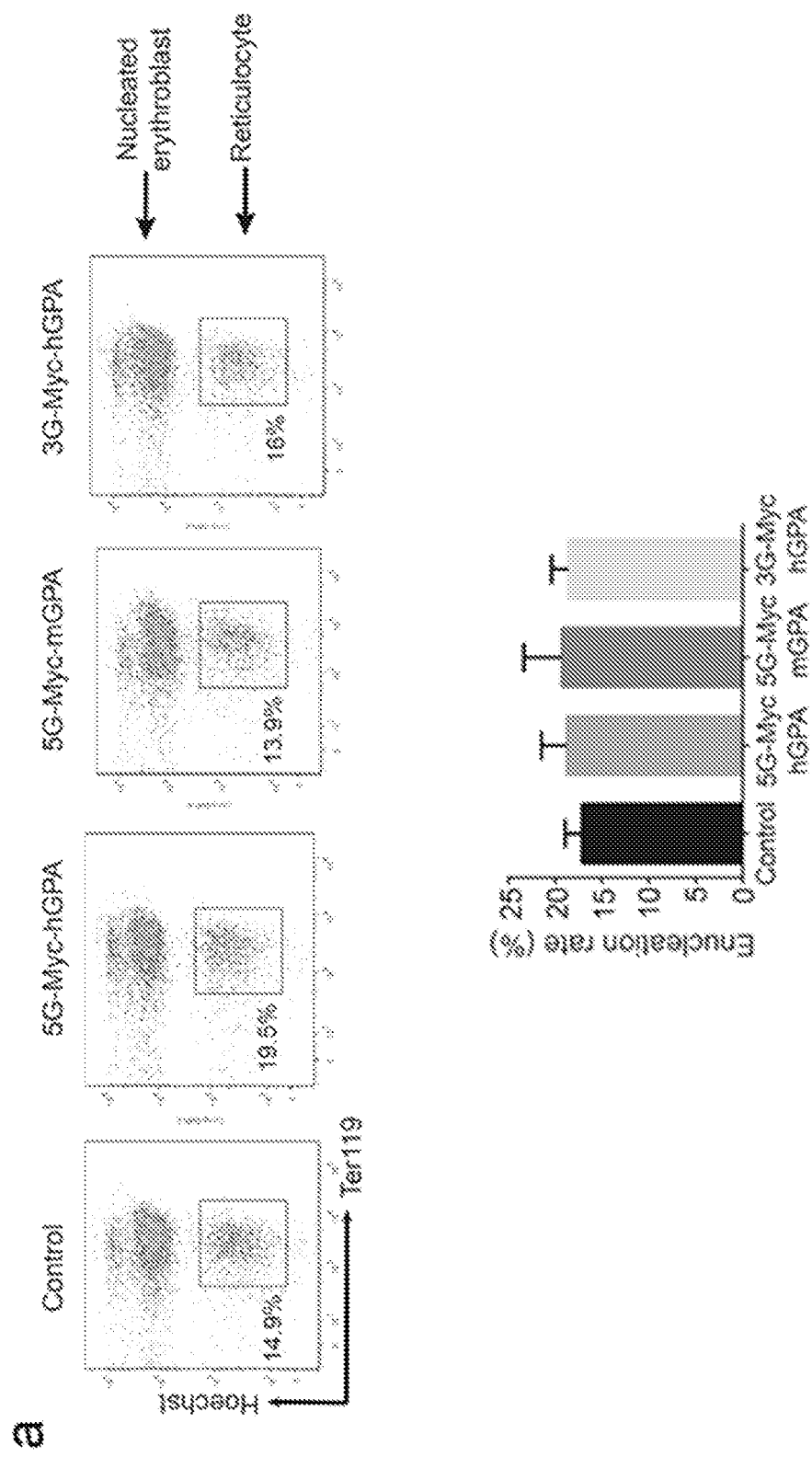
FIG. 18 is a diagram showing the overexpression of engineered human GPA and mouse GPA containing myc-tag with multiple (3 or 5) glycines (SEQ ID NO:3) at their N-termini do not affect in vitro differentiation of mouse erythroid progenitors. Only cells expressing engineered human GPA with myc-tag and 3 glycines at the N-terminus can be efficiently biotin-labeled by sortagging. (A) Flow cytometry analysis on the differentiation capacity of in vitro differentiated murine fetal-liver derived progenitor cells infected with retroviral constructs containing modified human (h) or mouse (m) GPA constructs extended at their N-terminus with myc-tag and multiple (3 or 5) glycines (SEQ ID NO:3) (G): 5G (SEQ ID NO:3)-myc-hGPA, 5G (SEQ ID NO:3)-mycmGPA, and 3G-myc-hGPA. Differentiation capacity in these cells is assessed based on the expressions of Ter119 and enucleation, i.e. nuclei expulsion, resulting in Ter119$^+$ reticulocytes. See upper panel. The percentages of reticulocytes produced by erythroid progenitor cells infected with 5G (SEQ ID NO:3)-myc-hGPA, 5G-myc-mGPA, and 3G-myc-hGPA (~17.5%) are comparable to cells infected with empty (control) vector, indicating that these constructs do not disturb erythroid terminal differentiation. Quantification of enucleation rate represents 3 independent experiments and graphed as mean values+/−standard deviation. See lower panel. (B) Evaluation of murine terminally differentiated erythroblasts, i.e., nucleated erythroblasts and reticulocytes, for the surface expression of 5G (SEQ ID NO:3)-myc-hGPA, 5G (SEQ ID NO:3)-myc-mGPA, and 3G-myc-hGPA. More than 50% of these terminally differentiated cells expressed the desired modified GPA proteins as measured by flow cytometry using α-myc tag antibodies. See upper panel. Percentage of erythroblasts and reticulocytes with myc-tag on cell surface was determined from 3 independent experiments, graphed as mean value+/−standard deviation; ** indicates p<0.01. See lower panel. (C) HEK 293T cells were transfected to express 5G (SEQ ID NO:3)-myc-hGPA, 5G (SEQ ID NO:3)-myc-mGPA, 3G-myc-mGPA, and 3G-myc-hGPA. These cells were then incubated with a biotin probe with or without sortase, and total cell protein was immunoblotted for the myc-tag and biotin. Immunoblot stained for biotin shows successful biotin conjugation only to human GPA constructs 3G-myc-hGPA (strong band) and 5G (SEQ ID NO:3)-myc-hGPA (weak band) with a much higher efficiency for 3Gmyc (strong band) and 5G (SEQ ID NO:3)-myc-hGPA (weak band) with a much higher efficiency for 3Gmyc-hGPA. α-myc-tag immunoblotting further confirms biotin probe conjugation as indicated by a shift in hGPA molecular weight upon biotin conjugation.
Figure 18:
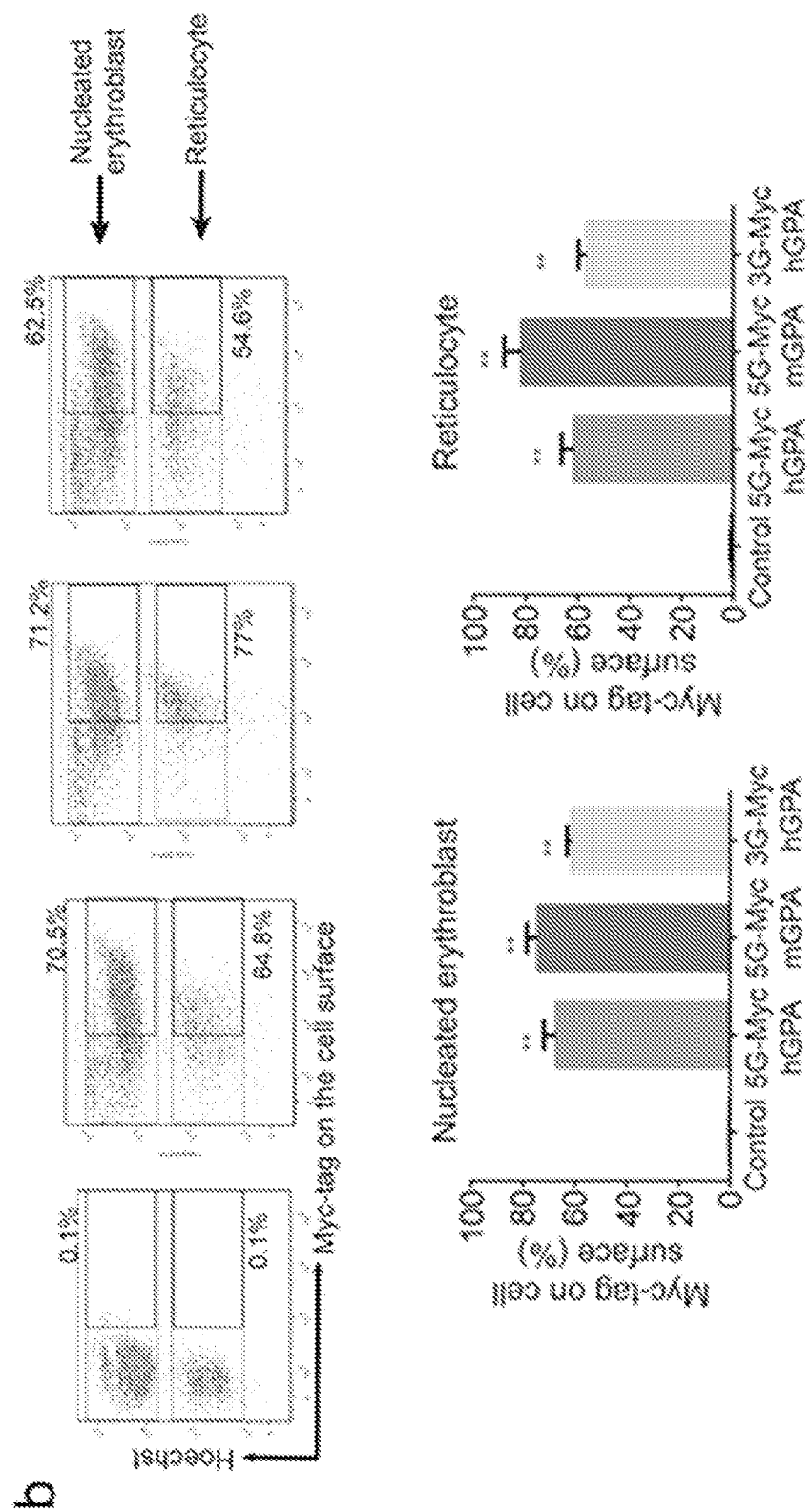
Figure 18:
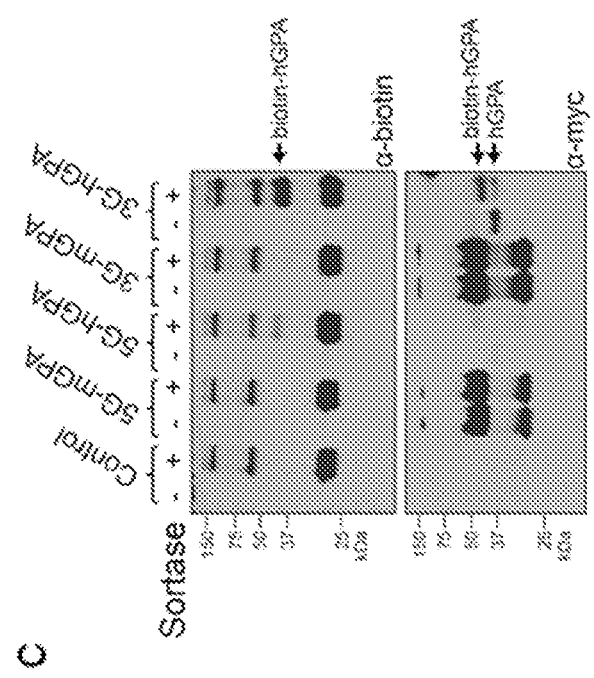

Four retroviral constructs were prepared for GPA, encoding products extended at their N-terminus with either 3 or 5 N-terminal glycine residues (SEQ ID NO: 3), using either mouse or human GPA and in vitro erythroid differentiation system (Zhang et al., 203, *Blood* 102(12):3938-3946) as with Kell below, to test GPA expression and modification by sortase. Upon retroviral transduction of progenitors none of the four GPA constructs affected the differentiation process, as in each case we obtained normal numbers of enucleated, Ter119 positive erythroblasts that expressed the modified GPA on their surface (FIG. 17 and FIG. 18, A,B).

Figure 19:
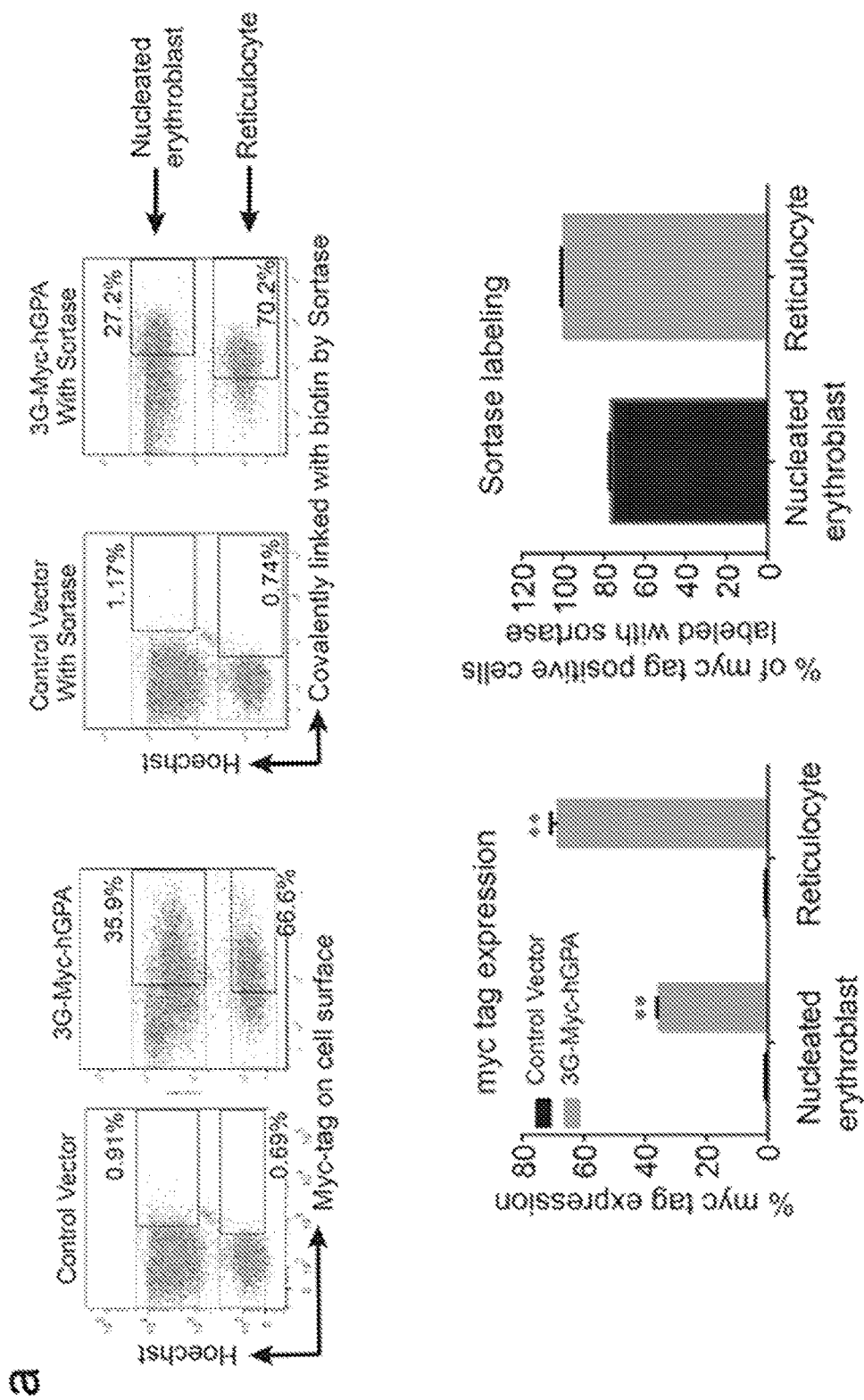
FIG. 19 is a diagram showing the expression and sortase-mediated N-terminal labeling of glycophorin A on the surface of in vitro differentiated erythroblasts. (A) Flow cytometry analysis of in vitro differentiated erythroblasts for the presence of 3G-myc-hGPA and for sortase-labelled biotin-3G-myc-hGPA on the cell surface by staining with α-myc and α-biotin tag antibodies. See upper panel. Percentage of erythroblasts and reticulocytes with myc-tag on cell surface and percentage of myc-tag positive cells sortagged with a biotin probe was determined from 3 independent experiments, graphed as mean value+/−standard deviation; ** indicates p<0.01. See lower panel. (B) Evaluation of in vitro differentiated erythroblasts for sortase-labeling by incubating control or 3G-myc-hGPA erythroblasts with sortase and the biotin containing probe by means of immunoblotting with α-myc tag and α-biotin antibodies. The shift in molecular weight of hGPA upon biotin conjugation in the α-myc blot indicates complete modification of hGPA. Biotin-conjugated GPA is denoted by an arrow in the α-biotin immunoblot. (C) Immunofluorescence shows biotin (labelled with red) at the N-terminus of hGPA on the surface of differentiated erythroblasts. Nucleus was stained by Hoechst (blue). The arrow indicates reticulocytes, while the arrowheads indicate enucleating erythroblasts. The scale bar is 10 μm.
Figure 19:
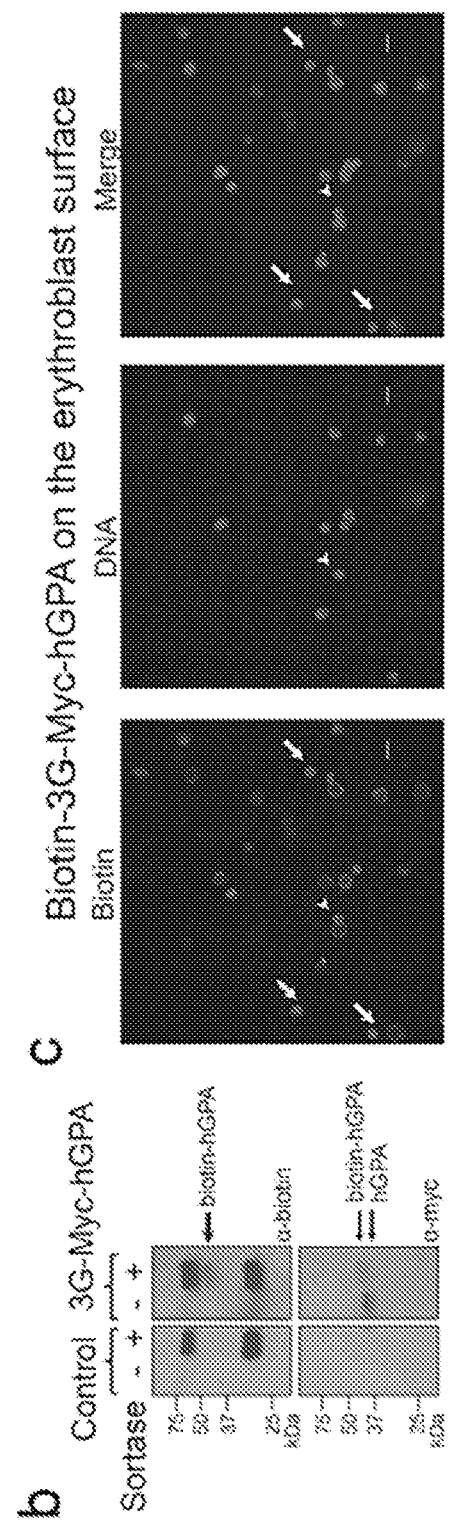

These GPA constructs were confirmed as sortase-modifiable by expressing them in HEK293T cells, followed by sortagging with a biotin-containing probe (FIG. 18C). While high levels of expression of the mouse constructs were observed, no biotinylation of the encoded products was detected. In contrast, human 3G-myc-GPA (3G-myc-hGPA) was readily sortagged and was used for subsequent experiments. Expression of 3Gmyc-hGPA in erythroid progenitors yielded ~36% of nucleated erythroblasts and ~67% of enucleated reticulocytes that bear the modified GPA on the surface upon in vitro differentiation. Almost all of the modified GPA on both nucleated and enucleated cells were sortagged with a biotin-containing probe, as monitored by flow cytometry, immunoblotting, and immunofluorescence (FIG. 19).

Figure 20:
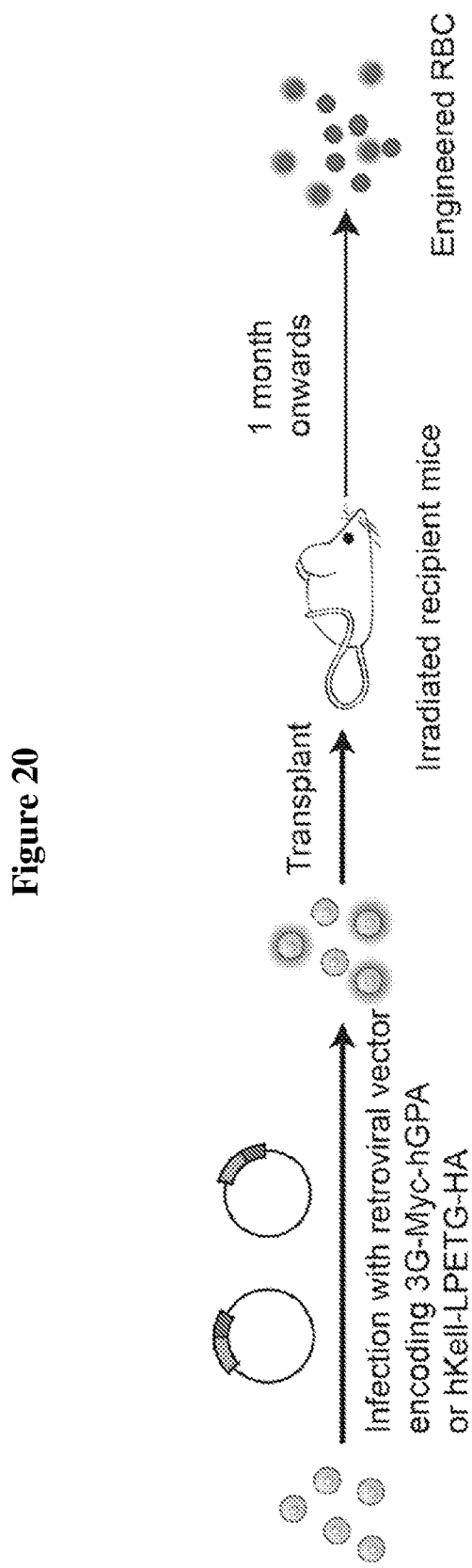
FIG. 20 is a schematic illustration of engineered RBC production by mouse bone marrow/fetal liver cell transplantation. Isolated murine bone marrow cells or fetal liver cells were transduced with a retrovirus carrying hKell-LPETG (SEQ ID NO:44)-HA or 3G-myc-hGPA. Lethally irradiated mice were reconstituted with transduced bone marrow or fetal liver cells. After 1 month and onward, a significant percentage of mature RBCs are derived from transduced donor progenitors.

As with Kell (see descriptions below), murine fetal liver lineage-negative cells were infected with retroviral vector expressing 3G-myc-hGPA and transplanted them into lethally irradiated mice (FIG. 20). After 4 weeks, these transplanted mice contained 20-50% of Ter119 positive, discoidshaped mature RBCs expressing the modified GPA (FIG. 16B; n=10), which can sortagged with a biotin-containing probe with the efficiency of 85%+/−5% as determined by flow cytometry (FIG. 16C). The observed reduction in gel mobility of 3Gmyc-hGPA upon sortagging with biotin can be used as a readout for reaction efficiency and indicates that most of GPA is modified by sortase (FIG. 16D). Immunofluorescence microscopy (FIG. 16E) confirmed that all of these modified red cells indeed have biotin conjugated to their surface. These results show that sortaggable GPA was retained on the surface of mature RBCs and was labeled efficiently in a sortase-catalyzed reaction.

(d) the Type-II Membrane Protein Kell was Expressed and Sortase-labeled on RBC Surface HEK293T cells were transfected with expression vectors for producing surface fusion proteins hsCD71-LPETG (SEQ ID NO: 44)-HA and hsKell-LPETG (SEQ ID NO: 44)-HA via routine recombinant technology. Stable cell lines expressing the fusion proteins were established. The cells were incubated with 200 μM sortase and 0.5 mM or 1 mM GGG-biotin and subjected to Western blotting analysis. The results indicate that biotin was successfully conjugated to the fusion proteins.

Figure 21:
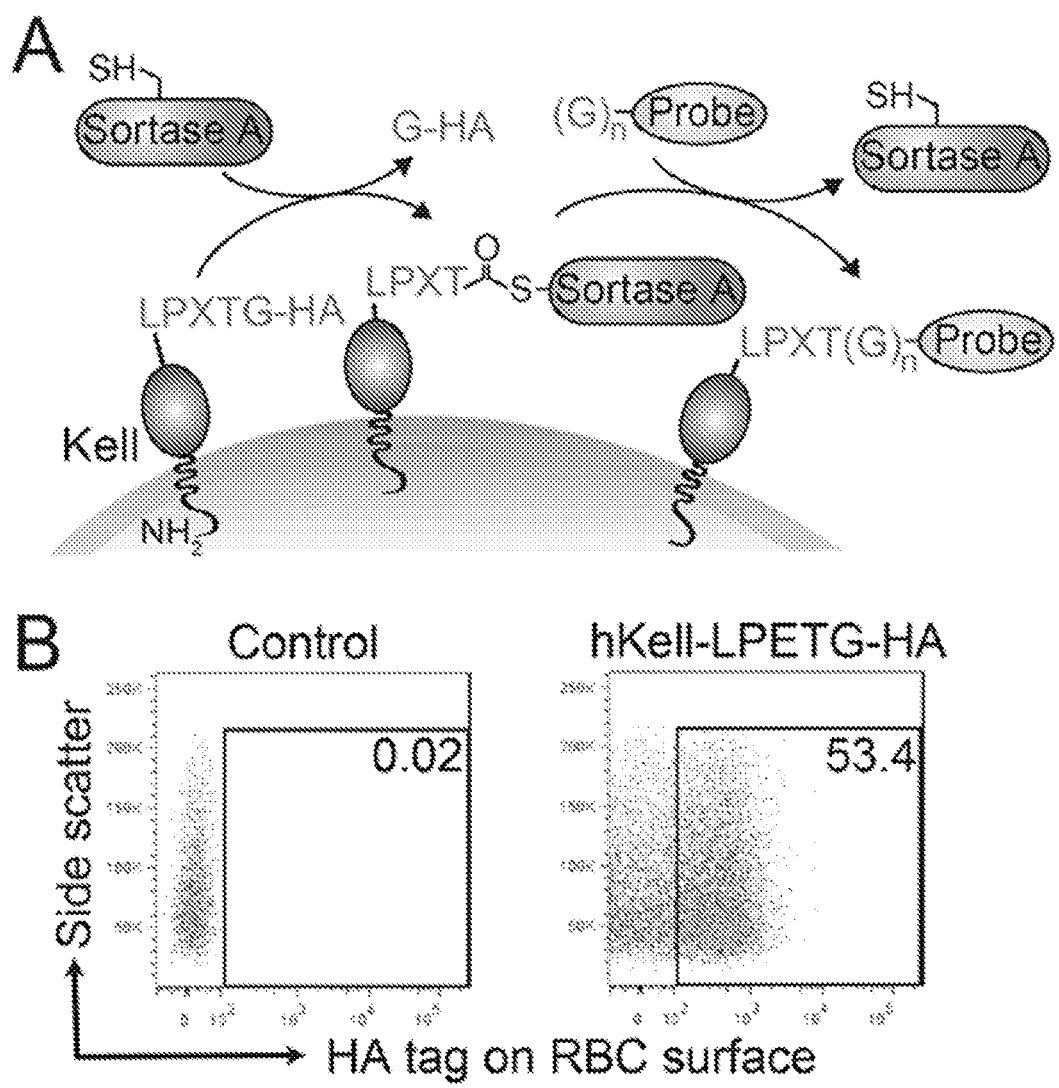
FIG. 21 is a diagram showing expression and sortase-mediated C-terminal labeling of Kell on the surface of mature mouse red blood cells. (A) Schematic for Kell C-terminal sortase labeling. Kell was extended at the C-terminus to include the sortase recognition motif LPETG (SEQ ID NO: 44) followed by an HA epitope tag. Incubation of sortase with cells containing Kell-LPETG (SEQ ID NO:44)-HA on the surface leads to peptide cleavage between T and G in the recognition motif and the formation of an acyl-enzyme intermediate between Cys on sortase and the sortase motif on Kell. Addition of a nucleophilic probe with N-terminal glycine residues (GGG-K(biotin); SEQ ID NO: 47; for biotin conjugation) resolves the intermediate, thus ligating the probe to the C-terminus of Kell. The probe can be a peptide, protein, lipid, carbohydrate, small molecule, etc; LPXTG (SEQ ID NO:1). (B) Evaluation of mature RBCs for the presence of Kell-LPETG (SEQ ID NO:44)-HA on the cell surface by staining either control blood or blood from mice that have undergone bone marrow transplantation to express Kell-LPETG (SEQ ID NO:44)-HA with α-HA tag antibody and analyzing via flow cytometry (gated on mature RBCs). (C) Evaluation of mature RBCs for sortase-labeling by incubating control blood or Kell-LPETG (SEQ ID NO:44)-HA blood with sortase and the biotin containing probe, staining with α-biotin antibody, and analyzing via flow cytometry (gated on mature RBCs). (D) Evaluation of RBCs for sortase-labeling by immune-blotting. Control or Kell-LPETG (SEQ ID NO:44)-HA blood was incubated with biotin probe with or without sortase. Total cell protein was resolved by SDS-PAGE and immunoblotted for α-HA tag and α-biotin. Loss of HA tag upon sortase labeling indicates complete modification. (E) Immunofluorescence images show biotin conjugated to the C-terminus of hKell on mature RBCs (labeled with Ter119 antibody).

Extension of Kell C-terminus with the sortase recognition motif LPXTG (SEQ ID NO: 1) was the minimal modification required to render it sortase-modifiable. A retroviral construct encoding human Kell, C-terminally modified by extension with LPETG (SEQ ID NO: 44), was constructed as described herein, followed by a hemagglutinin (HA) epitope tag. A sortase reaction performed on thus modified Kell as described herein using a glycine-based probe leads to conjugation of the probe onto the Cterminus of Kell, with concomitant loss of the HA tag (FIG. 21A).

Figure 22:
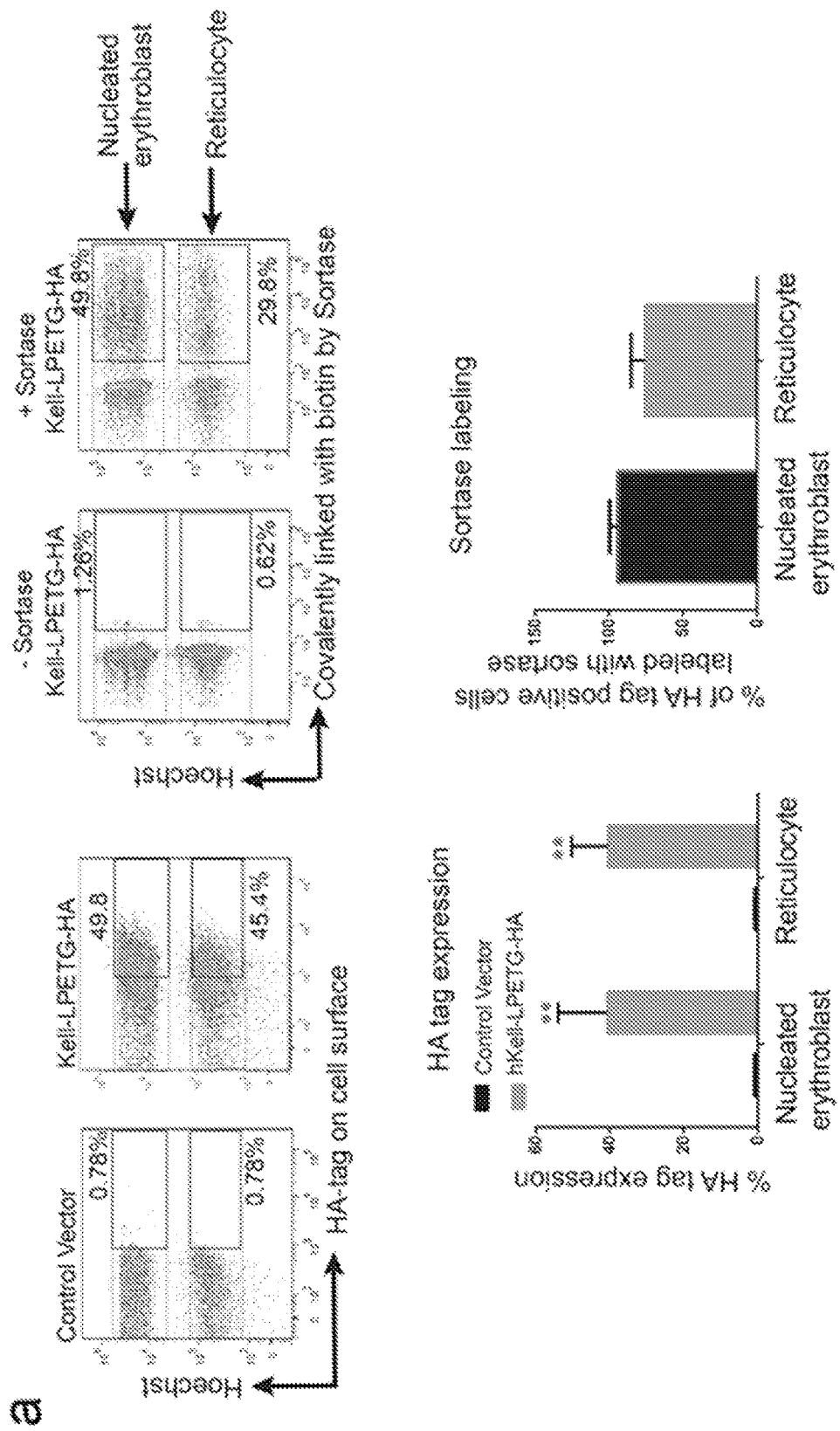
FIG. 22 is a diagram showing expression and sortase-mediated C-terminal labeling of Kell on the surface of in vitro differentiated erythroblasts. (A) Flow cytometry of in vitro differentiated erythroblasts for the presence of hKell-LPETG (SEQ ID NO: 44)-HA and for sortase-labelled hKell-LPETG (SEQ ID NO: 44)-biotin on the cell surface by staining with α-HA and α-biotin tag antibodies. See upper panel. Percentage of erythroblasts and reticulocytes with HA-tag on cell surface and percentage of HA-tag positive cells sortagged with a biotin probe was determined from 3 independent experiments, graphed as mean value +/−standard deviation; ** indicates p<0.01. See lower panel. (B) Evaluation of in vitro differentiated erythroblasts for sortase-labeling by incubating control or hKell-LPETG (SEQ ID NO: 44)-HA erythroblasts with sortase and the biotin containing probe followed by immunoblotting for biotin and Kell. (C) Immunofluorescence shows biotin (labelled with red) at the C-terminus of hKell on the surface of differentiated erythroblasts. Nucleus was stained by Hoechst (blue). The arrow indicates reticulocytes, while the arrowhead indicates enucleating erythroblasts. The scale bar is 10 μm.
Figure 22:
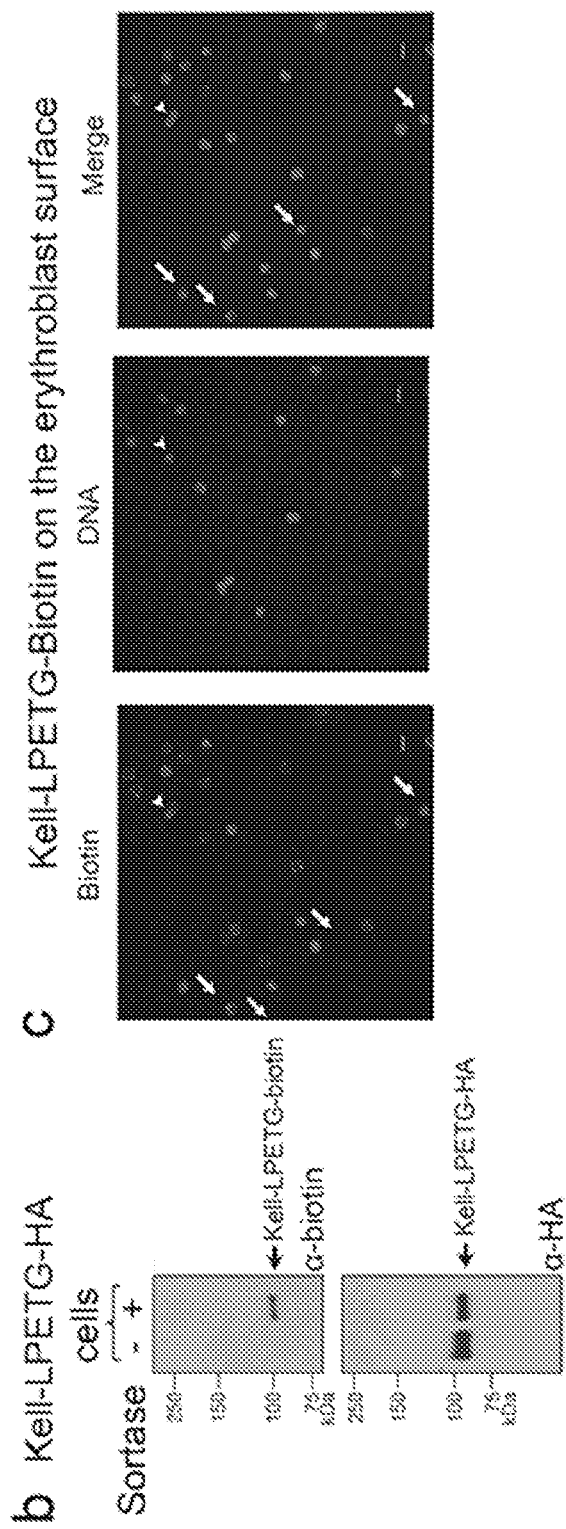

To test expression and modification of Kell by sortase, an in vitro erythroid differentiation system described previously was employed. Zhang et al., 2003. Culture of murine fetal liver-derived progenitors in vitro for ~48 hours allows ~4 terminal cell divisions and formation of hemoglobin-containing erythroblasts, about 30-50% of which undergo enucleation to yield reticulocytes. Expression of hKell-LPETG (SEQ ID NO: 44)-HA did not inhibit the in vitro differentiation process. Almost half of both nucleated erythroblasts and enucleated reticulocytes displayed modified Kell at the cell surface, and a large fraction of these could be sortagged with a biotin-containing probe as shown by flow cytometry, immunoblotting, and immunofluorescence (FIG. 22).

Reticulocytes obtained by in vitro differentiation must undergo not only expulsion of remaining organelles, they must also execute the membrane reorganizations that lead to the biconcave disk shape of mature RBCs. To ensure that this maturation step does not lead to loss of modified Kell, murine fetal liver lineage-negative cells were infected with retroviral vectors expressing engineered hKell-LPETG (SEQ ID NO: 44)-HA and transplanted into lethally irradiated mice (FIG. 20). Mature red blood cells were harvested from transplanted mice after 4 weeks and analyzed for the presence of sortase-modifiable Kell on their surface. It was routinely found that ~20-50% of mature RBCs in these chimeric mice contained sortaggable human Kell on their surface (FIG. 21B) and that these cells could be covalently modified with biotin using sortase (FIG. 21C) with efficiency of 81%+/−28% as determined by flow cytometry. A high level of conjugation of the biotin probe onto the C-terminus of Kell upon sortagging was observed, as evidenced by complete loss of the HA tag on the immunoblot (FIG. 21D). Immunofluorescence microscopy (FIG. 21E) confirms the presence of biotin conjugated to the surface of red blood cells. These data demonstrates that Kell, extended at its C-terminus with the sortase recognition motif, does not inhibit erythroid differentiation, is retained on the plasma membrane of mature red cells, and can be labeled in a sortagging reaction.

(e) Dual-labeling of RBCs

Using sortases with distinct substrate specificity, it is possible to combine N-terminal and C-terminal labeling strategies (Antos et al., 2009, J. Ameri. Chem. Soc., 131 (31):10800-10801) to generate multi-labeled RBCs. Unlike Sortase A from *Staphylococcus aureus*, Sortase A derived from *Streptococcus pyogenes* recognizes LPXTA (SEQ ID NO: 2) motifs and accepts oligo-alanine probes as nucleophiles. Therefore, the sortase reactions of both enzymes can be performed as orthogonal reactions.

Figure 23:
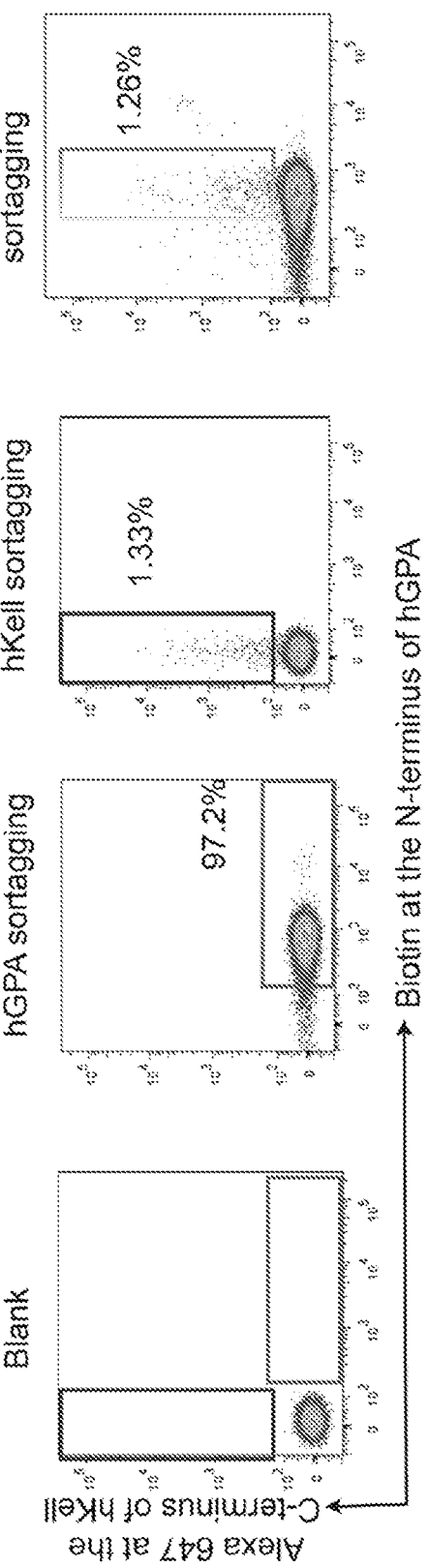
FIG. 23 is a diagram showing sortase-mediated dual labeling at the N-terminus of hGPA and C-terminus of hKell on the surface of mature RBCs. Mature RBCs expressing hKell-LPETG (SEQ ID NO: 44)-HA and 3A-myc-hGPA were incubated with sortase A from *S. pyogenes* and K(biotin)LPETAA (SEQ ID NO: 45) probe for N-terminal GPA labeling (second panel), or with sortase A from *S. aureus* and GGGC (Alexa-647; SEQ ID NO: 48) probe for C-terminal Kell labeling (third panel), or both sequential label with both sortase enzymes and their corresponding probes (fourth panel). Flow cytometry analysis of mature RBCs for the presence of both hKell-LPET (SEQ ID NO: 49)-Alexa-647 and biotin-myc-hGPA indicate successful dual labeling.

HEK293T cells were infected with 2 constructs: AAA-myc-hGPA and hKell-LPETG (SEQ ID NO: 44)-HA. The cells were sequentially incubated with 2 different types of Sortase A in the presence of either biotin-LPETA (SEQ ID NO: 119; for GPA sortagging via *S. pyogenes* sortase) or GGG-TAMRA (for Kell sortagging via *S. aureus* sortase), giving rise to HEK293T cells containing both the biotinylated GPA and TAMRA-modified Kell (FIG. 16F). Moreover, mature RBCs with cell surface expression of both 3A-myc-hGPA and hKell-LPETG (SEQ ID NO: 44)-HA were generated. Despite the fact that expression levels of hKell and hGPA on individual RBCs were somewhat variable, hGPA was successfully sortagged with biotin, and hKell with Alexa-647 on the RBC surface (FIG. 23). Dual labeling can thus be used to attach two different functional moieties onto the surface of RBCs.

(f) Survival of Engineered RBCs in Circulation

To assess whether the process of sortagging RBCs, including incubation with sortase, centrifugation, and washing, affects their in vivo survival, wild-type RBCs and wild-type RBCs that had undergone a mock C-terminal sortagging reaction—with or without sortase (no conjugation of a probe) were labeled with CFSE, a fluorescent dye that stably stains cytosol of live cells. The RBCs were then transfused into normal recipient mice; cell survival in circulation was assessed periodically using CFSE fluorescence. No difference was observed in in vivo survival of RBCs between the experimental groups (FIG. 24A), indicating that the sortagging procedure does not cause significant damage to the cells, which would lead to their premature removal.

Example 3

Conjugation of an Antibody to Engineered Red Blood Cells for Cell Type-Specific Targeting One potential application of modified RBCs is to provide them with a targeting moiety that would enable their delivery (and attached or incorporated payload) to particular tissues or cell types. Such targeting may be accomplished by installation of proteins or other entities, such as ligands for specific receptors that can participate in specific recognition of the intended target.

Figure 25:
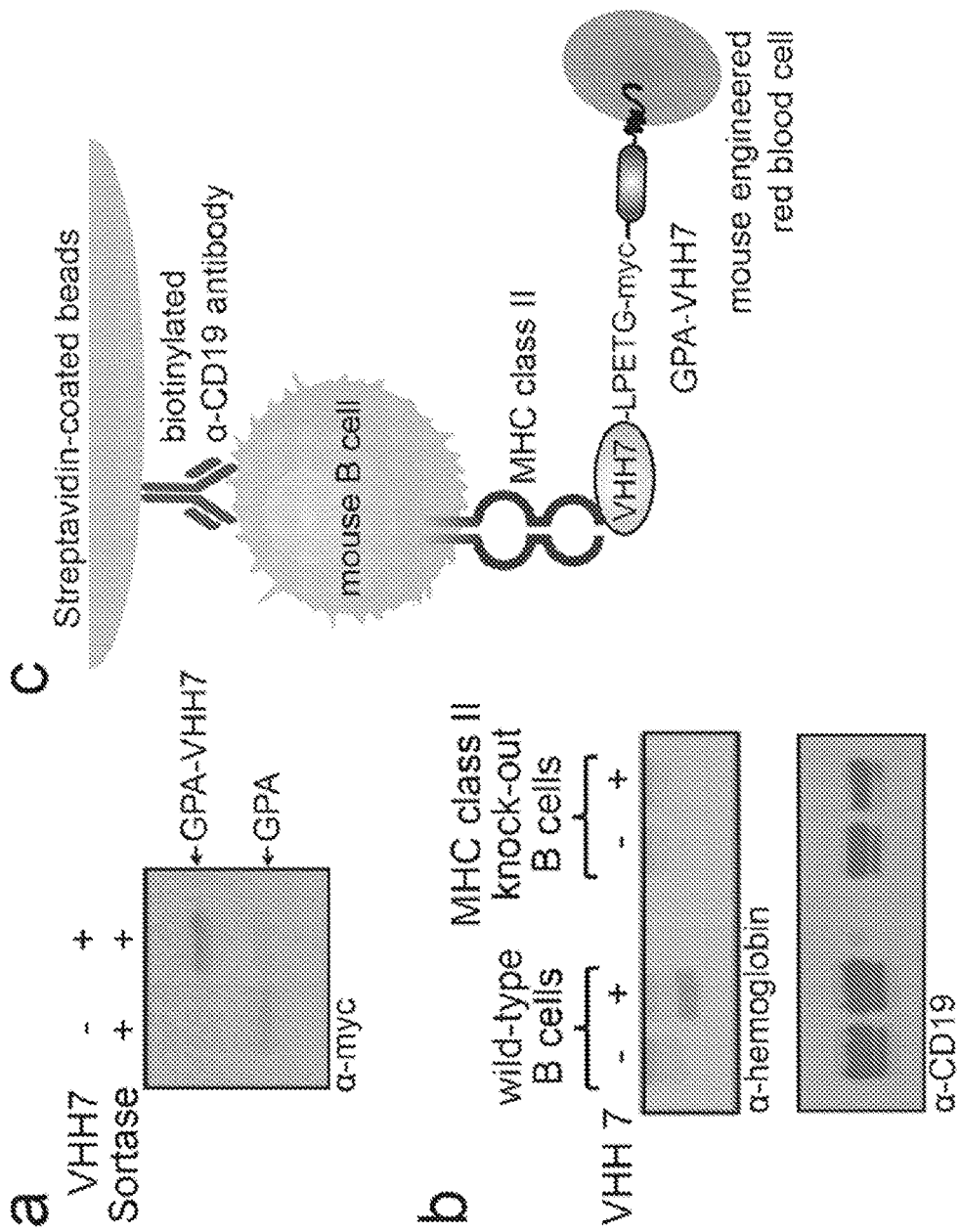
FIG. 25 is a diagram showing conjugation of single domain antibody to engineered red blood cells and cell type-specific targeting. (A) Mouse mature red blood engineered to contain 3G-myc-GPA on the cell surface were incubated with Sortase with or without VHH7-LPETG (SEQ ID NO: 44), a single domain antibody with binding specificity for mouse MHC class II molecules and sortase motif complementary to 3G. An immunoblot against myc epitope tag on glycophorin A reveals fusion of VHH7 to GPA, as an increase in GPA molecular weight. (B) Either wild type mouse B cells (expressing MHC class II) or B cells derived from MHC class II knock-out mice were immobilized on magnetic streptavidin beads via biotinylated α-CD19 antibody, incubated with 3G-myc-GPA red blood cells or red cells that contained sortase-labeled VHH7-LPETG (SEQ ID NO: 44)-myc GPA on their surface, and washed. Immobilization of B cells in all experimental set-ups was tested by presence of CD19 in α-CD19 immunoblot and binding between B cells and red blood cells was evaluated by the presence of hemoglobin in the α-hemoglobin immunoblot. (C) Schematic for experiment shown in (B); LPETG: (SEQ ID NO: 44).

To test conjugation of a functional protein onto the surface of RBCs, a sortaggable alpaca-derived single domain antibody was used. This antibody is specific for murine Class II MHC molecules, VHH7-LPETG (SEQ ID NO: 44), and was covalently attached it to red cells with 3G-myc-hGPA on their surface. As shown by the shift in gel mobility of the 3G-myc-hGPA, the sortagging reaction is stoichiometric (FIG. 25A).

A B cell-red blood cell binding assay was performed as follows. B cells were isolated from either wild-type C57BL/6 mice or mice knock-out for MHC class II using Dynabeads Mouse CD43 (Untouched B cells) (Life Technologies) according to manufacturer's recommendations. Cells from 1-1.5 spleen were incubated with 5 μg of biotin-labeled anti-murine CD19 antibody (BD Pharmigen) for 30 minutes on ice and washed once with 500 μl of ice-cold PBS. Cells were re-suspended in 500 μl of PBS along with 70 μl of pre-washed magnetic Dynabeads Myone streptavidin T1 (Life Technologies), incubated on a rotating platform for 1 hour at 4° C., and washed with 500 μl of ice-cold PBS. Resuspended cells (500 μl of PBS) were further incubated with ~2×10⁷ red blood cells expressing 3G-myc-hGPA and sortase-labeled with VHH7 for 1 hour at 4° C., washed 4 times with 1 ml of ice-cold PBS, and finally incubated with SDS sample buffer and boiled for subsequent SDS-PAGE analysis.

Incubation of these modified RBCs with Class II MHC-positive B cells immobilized on beads results in binding of the RBCs to B cells. Specific binding was inferred from the presence of hemoglobin, which co-purifies with B cells after washing. Neither incubation of wild-type B cells with unmodified red cells nor incubation of modified red cells with B cells derived from Class II MHC knock-out animals led to binding of the two cell types (FIG. 25B, C).

Example 4

Sortagging and Cytosolic Modification of Terminally Differentiated Human Red Blood Cells To extend the utility of the method described here, whether erythroid progenitor modification, as well as subsequent sortase-mediated cell surface labeling is feasible also for human cells, was investigated.

Terminally differentiated human red blood cells were genetically engineered as follows. Plasmids used to engineer in vitro-differentiated human RBCs were created by cloning the GGGcontaining human GPA into HIV/MSCV lentiviral vector with the addition of enhanced GFP at its C-terminus to make 3G-myc-hGPA-EGFP. Lentivirus was produced by cotransfection of 293T cells with pVSV-G envelope plasmids and pDelta 8.9 packaging vectors. G-CSF (granulocyte—colony stimulating factor)-mobilized CD34+ peripheral blood stem cells were differentiated in vitro in 18 days into hemoglobin-containing reticulocytes using the method as described previously (Zaitsev et al., 2010, *Blood* 115(25): 5241-5248). On day 3 of culture, differentiating cells were infected with by incubating 5×10$^5$ cells in 2 mL of lentivirus containing media in the presence of polybrene, and spun at 2500 RPM for 1.5 hours at room temperature, followed by further incubation in a CO2 incubator overnight. The day after, the infected cells were washed twice and put into fresh differentiation media. At day 18, the enucleated reticulocytes were collected and subjected to sortase-labeling with a biotin-containing probe as described above. Analyses of the resulting engineered human reticulocytes were carried out by means of flow cytometry using the following antibodies: PE-conjugated anti-biotin (1:1000, eBioscience, 12-9895-82), Hoechst (Sigma), and APC-conjugated (1:100, eBioscience, 17-0087-42).

Figure 26:
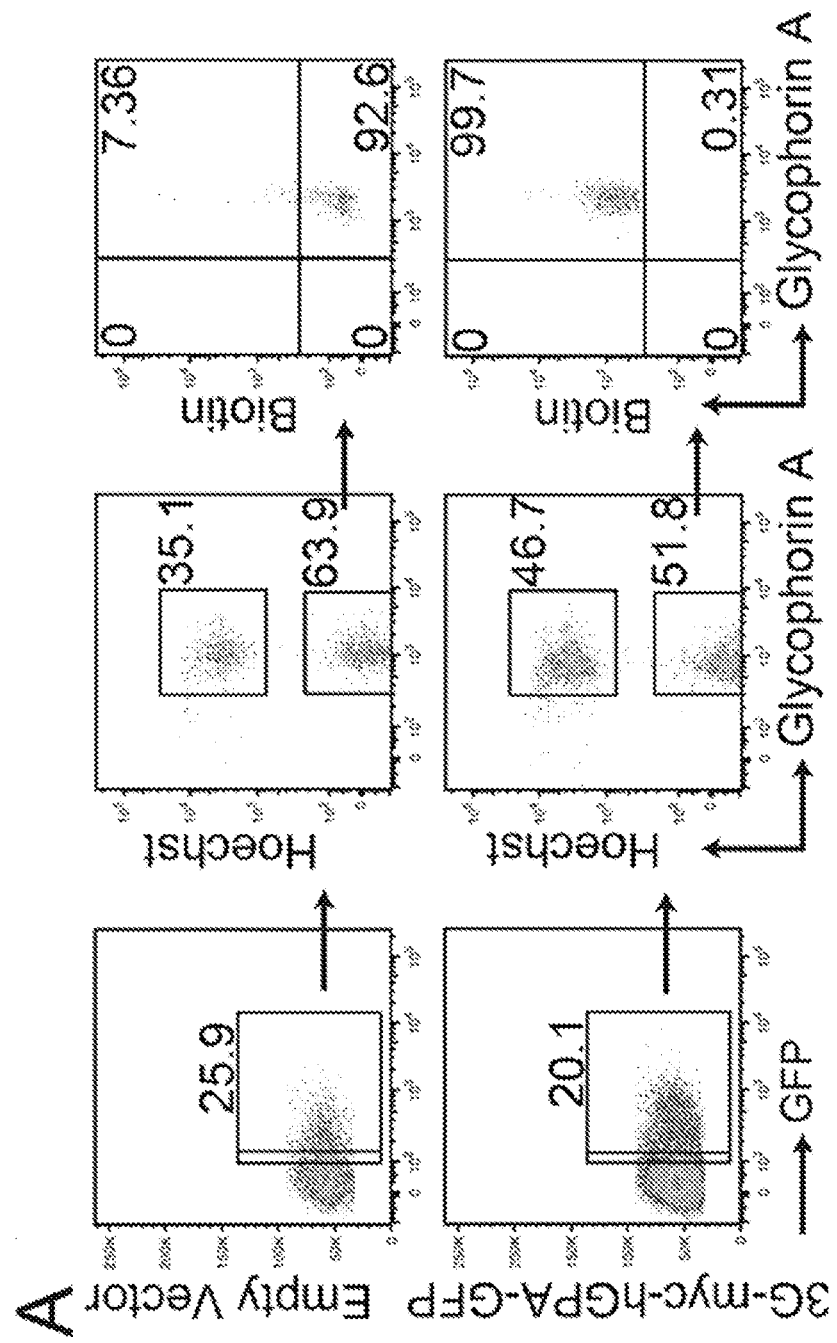
FIG. 26 is a diagram showing expression and sortase-mediated labeling of glycophorin A on the surface of human in vitro differentiated reticulocytes. (A) Human granulocyte—colony stimulating factor-mobilized peripheral blood CD34+ stem cells were virus transduced either with empty vector or a vector containing 3G-myc-GPA-GFP and differentiated for 18 days. Flow cytometry analysis of reticulocytes reveals the percentage of transduced cells (GFP+) and percentage of enucleated cells (lower panel with Hoechst staining). Reticulocytes, either control or 3G-myc-GPA-GFP (3G-myc-hGPA-GFP-IRES-GFP) transduced, were incubated with sortase and a biotin-containing probe, stained for biotin with α-biotin-PE antibody, analyzed via flow cytometry, and gated on enucleated cells. (B) 3G-myc-GPA- GFP transduced and in vitro differentiated reticulocytes were incubated with a biotin probe with or without sortase, and total cell protein immunoblotted for the myc tag and biotin. Both monomers as well as dimers (higher molecular weight) of 3G-myc-GPA-GFP are visible in both immunoblots. A shift in GPA-GFP molecular weight upon biotin conjugation in α-myc tag immunoblot indicates complete modification.
Figure 26:
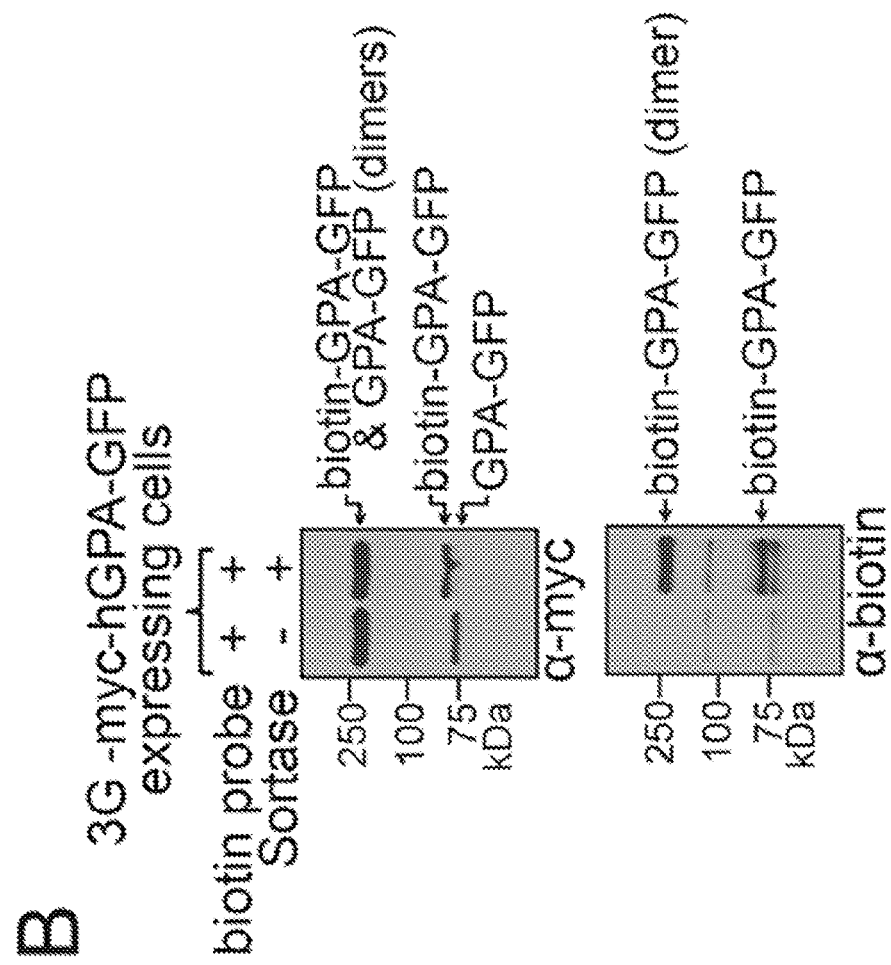

For the experiments described in this example, an in vitro human erythroid differentiation system as described previously. See, e.g., Hu et al., 2013. G-CSF (granulocyte—colony stimulating factor)-mobilized CD34+ peripheral blood stem cells were differentiated in vitro in 18 days into hemoglobin-containing reticulocytes, with an enucleation efficiency of ~50%. A lentiviral vector that encodes a version of 3G-myc-hGPA fused to enhanced GFP at its C-terminus (3G-myc-GPA-GFP) was constructed. This provides an example of a cytoplasmically expressed protein domain designed to be retained in mature RBC via its genetic fusion to GPA. Both the empty (control) vector and the 3G-myc-hGPA-GFP vector encoded a GFP moiety 3' of the IRES sequence (3G-myc-hGPA-GFP-IRES-GFP). When cells are successfully transduced with 3G-myc-hGPA-GFP, which contains an additional enhanced GFP attached to the cytoplasmic domain of GPA, these cells will express a significantly higher level (~2×) of GFP signal, as indicated by flow cytometry (FIG. 26A, first panel). Since the molecular weights of GFP and hGPA are 32.7 kDa and 37 kDa respectively, the mobility of the 3G-myc-hGPA-GFP on SDS-PAGE also indicates that the modified GPA proteins are expressed in monomeric and dimeric forms (FIG. 26B). Viral transduction of human CD34+ cells with 3G-myc-hGPA-GFP did not affect their differentiation, as similar numbers of enucleated reticulocytes (50-60%) were formed as in cultures infected with an empty (control) vector (FIG. 26A, middle panel).

All of the enucleated reticulocytes that contain the modified GPA at the surface could be sortaselabeled with a biotin-containing probe, as monitored by flow cytometry (FIG. 26A). Furthermore, all of the 3G-myc-hGPA-GFP present on the reticulocyte surface was modified by biotin sortagging, as evidenced by the shift in gel mobility of the 3G-mychGPA-GFP (FIG. 26B). This experiment therefore establishes the ability to equip mature human RBCs with a cytoplasmically disposed protein of interest, while retaining the ability to selectively target the RBC to an intended target by sortagging of the modified GPA with a targeting moiety of interest.

Example 5

Creation of mKell-LPETG (SEQ ID NO: 44) Mice Using CRISPR/Cas9 Technology

An sgRNA sequence for CRTSPR/Cas9-dependent double strand break to stimulate Homologous direct repair (HDR) was designed on the last exon of mKel locus as in Table 5, and the oligo DNA as a template to introduce LPETG (SEQ ID NO: 44) into mKel C-terminus was designed as in Table 6.

TABLE 5

| sgRNA | 5' to 3' sgRNA template sequence with PAM motif |
|---|---|
| mKel CT-targeting sgRNA | CTCTGCCCGCTGCAAGCTC<u>TGG</u> (SEQ ID NO: 120) |

*Underlined: PAM motif

TABLE 6

| Template Oligo DNA for HDR | 5' to 3' Oligo DNA sequence |
|---|---|
| mKel-LPETG (SEQ ID NO: 44) template Oligo DNA | TGAGCAATACTCCAGATTTTGCCAAACATTTTCAT TGTCCACGTGGGACCCTTCTGAATCCCTCTGCCCG CTGCAAGCTCGGAGGATCAGGAGGATCATTACCAG AGACAGGAGGATGGTAAAACTTGGCTACCAAAGAG ACTGATGTAAATGCATGGGCTGCTTGTGAGTCCAT CCTTGAAGTCAAAATAAATCT (SEQ ID NO: 121) |

Boldfaced/Underlined: LPETG (SEQ ID NO: 44)-encoding sequence

Potential off-target effects of the target sequence were explored using the NCBI *Mus musculus* Nucleotide BLAST. Cas9 mRNA was prepared as described in Wang et al., 2013. T7 promoter and the mKel-CT-targeting sgRNA coding sequence without PAM motif were added just in front of sgRNA generic tail (the part from hairpin region to terminal motif) by PCR amplification using pX330 vector as a template and the primers, mKel T7-sgRNA Fw and sgRNA generic Rv, as shown in Table 7 below.

TABLE 7

| Primers | 5' to 3' primer sequence |
|---|---|
| mKel T7-sgRNA Fw | *TAATACGACTCACTATA*<u>GCTCTGCCCGCTGCAAGCTC</u>gt tttagagctagaaatagcaag (SEQ ID NO: 122) |
| sgRNA generic Rv | TAAGTTATGTAACGGGTAC (SEQ ID NO: 123) |
| mKel sequencing Fw | ATCTAACCCATCCCTATCACCCTATGG (SEQ ID NO: 124) |
| mKel sequencing Rv | ATGGAGATGTAGCTGATGAGCAGC (SEQ ID NO: 125) |

Italic: T7 promoter
Underlined: sgRNA target template
Lower case: 5'-generic sequence of sgRNA tail The T7-sgRNA template PCR product for in vitro transcription (IVT) was gel purified by column (Promega), and the purified PCR product was used as a template for IVT using MEGAshortscript T7 kit (Life Technologies). Both the Cas9 mRNA and the sgRNA were purified using MEGAclear kit (Life Technologies) and eluted in RNase-free water. Fertilized zygotes were collected from oviducts of superovulated females, and Cas9 mRNAs, sgRNA and template oligo DNA were injected into the cytoplasm at the pronuclear stage. The injected zygotes were transferred at the 2-cell stage into the oviduct of pseudopregnant females. To genotype the mice: mouse-tails were lysed at 55° C. for 12 hours using tail lysis buffer and genomic DNA was purified from the lysates by isopropanol precipitation. Genomic DNA in the vicinity of the sgRNA target was amplified by PCR using primers mKel-sequencing Fw and mKel-sequencing Rv, as in table 3 [KOD Xtreme (VWR), Condition: 95° C. for 2 min; 35×(98° C. for 10 s, 50° C. for 30 s, 68° C. for 30 s); 68° C. for 2 min; hold at 4° C.], and then gel purified. The purified PCR products were sequenced using the same Fw primer.

The transgenic mice constructed using CRISPR/Cas-9 genome editing technology (Jinek et al., 2012, *Science* 337(6096):816-821; and Wang et al., 2013, *Cell* 153(4):910-918) were used to investigate RBC survival in vivo. Such a transgenic mouse contains LPETG (SEQ ID NO: 44) inserted at the C-terminus of the murine endogenous Kell gene (mKell-LPETG; SEQ ID NO: 44). These mice appear normal and reproduce normally. The mKell-LPETG (SEQ ID NO: 44) RBCs from these mice can be labeled with a probe in a sortase-mediated reaction as efficiently as hKell-LPETG (SEQ ID NO: 44)-HA RBCs.

Figure 24:
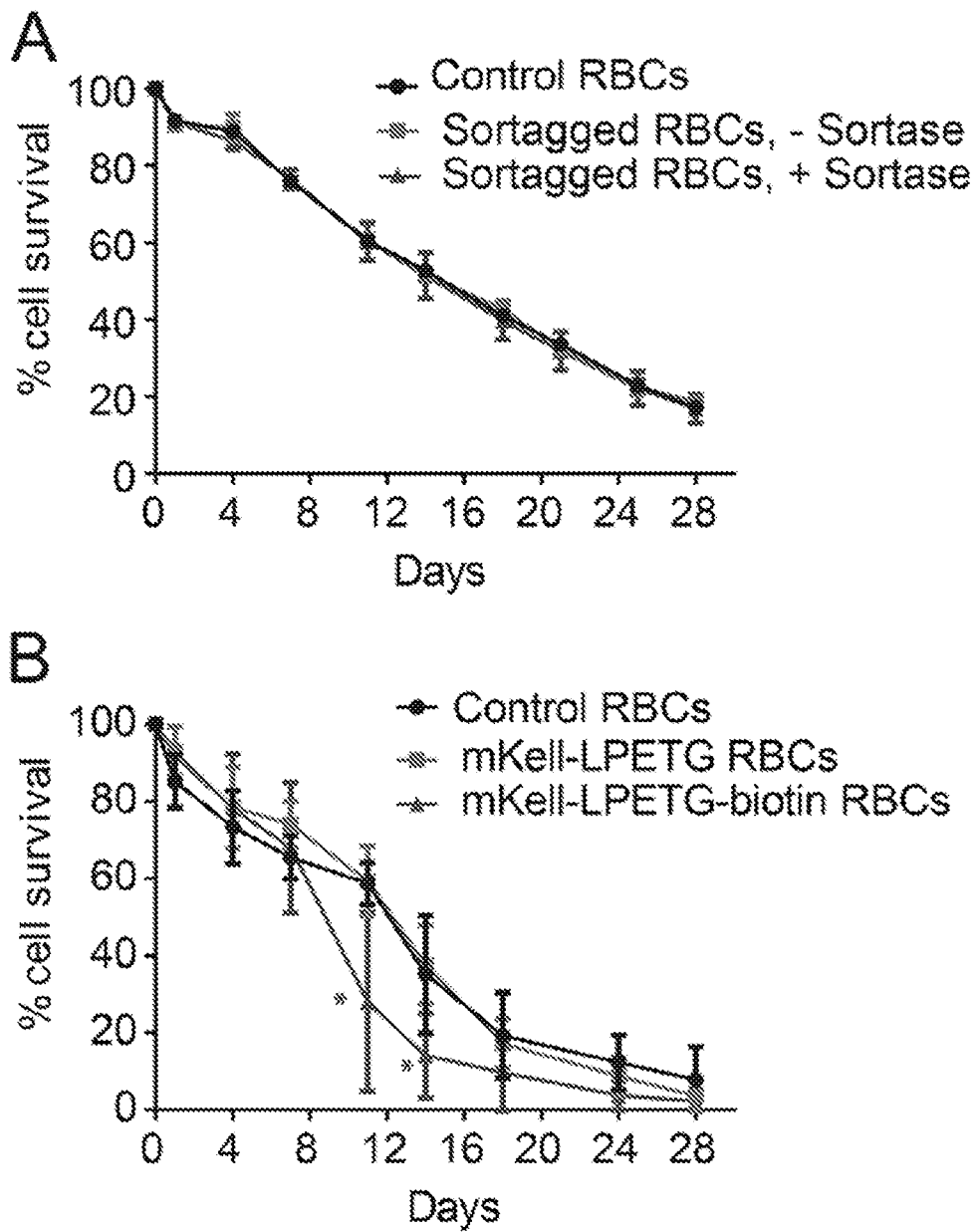
FIG. 24 is a number of charts showing survival of engineered red blood cells in vivo. (A) Wild-type RBCs subjected to mock C-terminal sortagging reacting with or without sortase (n=3, each group) or left untreated (n=3) were reacted with CFSE and transfused into recipient mice via intravenous injection. Their in vivo survival was tracked via CFSE fluorescence and flow cytometry. (B) mKell-LPETG (SEQ ID NO: 44) RBCs were obtained from mice genetically engineered to have endogenous Kell extended at is C-terminus with an LPETG (SEQ ID NO: 44) sequence. Wild-type RBCs (n=6), mKell-LPETG (SEQ ID NO: 44) RBCs (n=6), and mKell-LPETG (SEQ ID NO: 44)—RBCs sortagged with biotin (n=6) were stained with CFSE, transfused into recipients, and their survival monitored via CFSE fluorescence or anti-biotin staining using flow cytometry. (C) CFSE-stained wild-type RBCs (n=6) and hKell-LPETG (SEQ ID NO: 44) RBCs isolated from transplanted mice (See Example 5) and sortase-labeled with biotin (n=2) were transfused into recipient mice and their survival in circulation was tracked via CFSE fluorescence (wild-type RBCs) or anti-biotin staining (hKell-LPETG (SEQ ID NO: 44)-biotin RBCs) using flow-cytometry. (D) Wild-type RBCs (n=6) and sortase-labeled biotin-3G-myc-hGPA RBCs (n=6) were CFSE stained, transfused into mice and tracked via CFSE fluorescence or anti-biotin staining using flow-cytometry. Internal control RBCs are cells that originate from 3G-myc-hGPA transplanted mice, were subjected to the sortagging reaction and CFSE-staining, but are wild-type. Error bars represent standard deviation; * denotes p<0.01.
Figure 24:
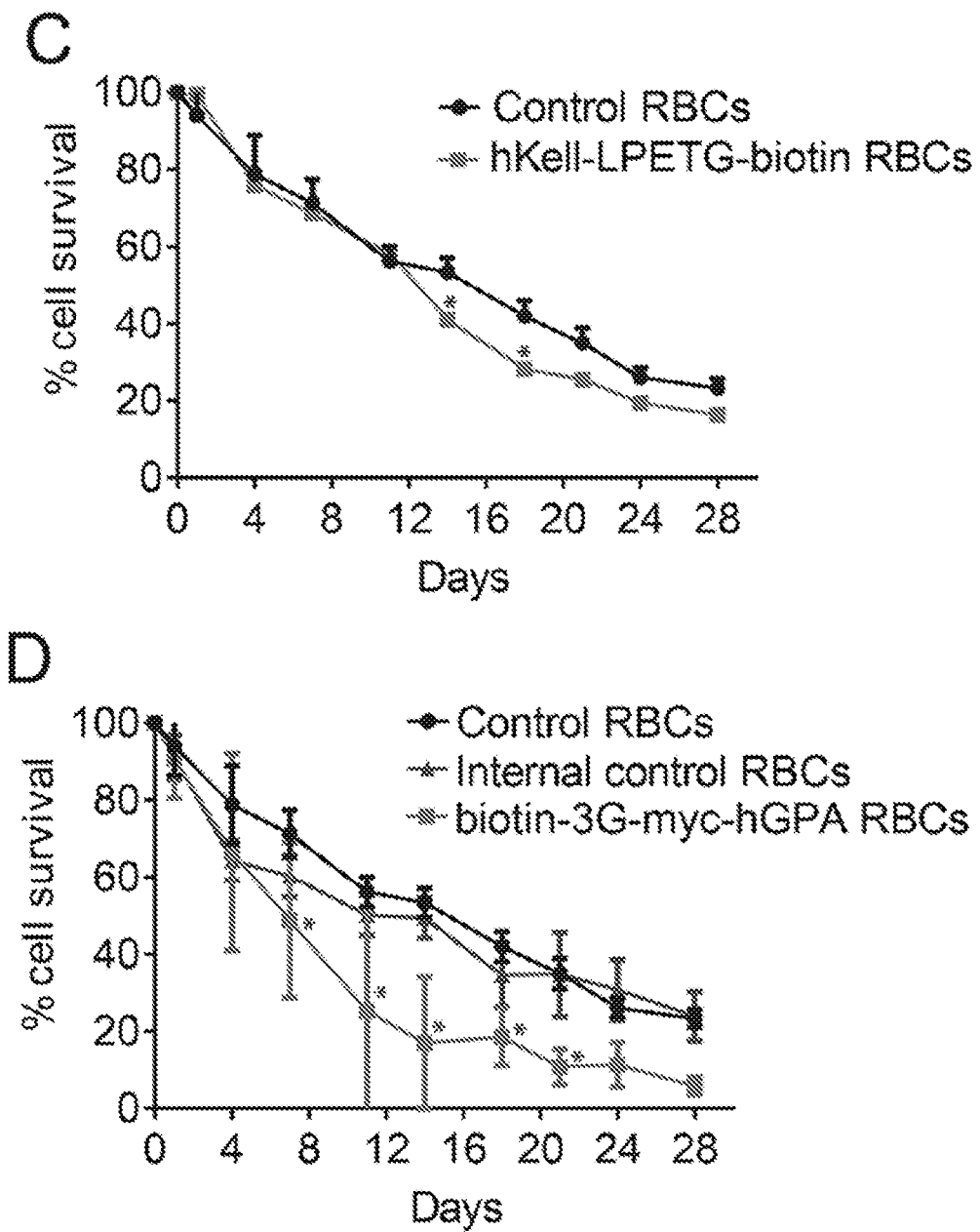

CFSE staining was performed on control RBCs, mKell-LPETG (SEQ ID NO: 44) RBCs, and mKell-LPETG (SEQ ID NO: 44) RBCs sortagged with biotin, transfused them into wild-type recipient mice, and their survival in circulation was monitored. The modification of mKell with LPETG (SEQ ID NO: 44) at its C-terminus did not affect the survival of the modified RBCs in vivo (FIG. 24B). A slight, but significant difference was observed in survival of mKell-LPETG (SEQ ID NO: 44) RBCs sortagged with a biotin probe. hKell-LPETG (SEQ ID NO: 44) RBCs were also harvested from transplanted mice, sortagged with biotin, and transfused into recipients. Similarly, engineered biotin-labeled Kell-LPETG (SEQ ID NO: 44) RBCs last in circulation more than 28 days albeit with a slight lower survival compared to wild-type RBCs (FIG. 24C). These results show similar experiments comparing the in vivo survival of normal RBCs to sortase-labeled biotin-3G-myc-hGPA RBCs. The results (FIG. 24D) echoed the trend seen with Kell-LPETG (SEQ ID NO: 44) RBCs; there was a slightly but significantly lower survival rate for sortagged RBCs (FIG. 24D). Importantly, the half-life of the engineered RBCs in normal mice, including the ones conjugated with biotin, nevertheless is at least 28 days and thus drastically longer than other RBC-based carriers designed thus far.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for conjugating a first polypeptide of interest to the surface of a red blood cell, the method comprising:

providing the red blood cell comprising a first sortaggable surface fusion protein, wherein the first sortaggable surface fusion protein comprises a first type I or type II red blood cell transmembrane protein and a first peptide;

contacting the red blood cell with the first polypeptide of interest in the presence of a first sortase, wherein the first sortase is a sortase A;

wherein when the N-terminus of the first sortaggable surface fusion protein is exposed to the extracellular space, the first peptide is either N-terminal oligoglycine or N-terminal oligoalanine fused to the first type I red blood cell transmembrane protein, and the first polypeptide of interest comprises a first sortase recognition motif;

wherein when the C-terminus of the first sortaggable surface fusion protein is exposed to the extracellular space, the first peptide is the first sortase recognition motif which is fused to the C-terminus of the first type II red blood cell transmembrane protein and is exposed to the extracellular space, and the first polypeptide of interest comprises either N-terminal oligoglycine or N-terminal oligoalanine;

wherein the first sortase recognition motif is the amino acid sequence LPXTG (SEQ ID NO: 1), LPXT, or LPTXA, in which X is any amino acid residue; and wherein the first sortase conjugates the first polypeptide of interest to the first sortaggable surface fusion protein, thereby conjugating the first polypeptide of interest to the surface of the red blood cell.

2. The method of claim 1, wherein the first sortase recognition motif is the amino acid sequence LPXTG (SEQ ID NO: 1), in which X is any amino acid residue.

3. The method of claim 1, wherein the first type I red blood cell transmembrane protein is glycophorin A (GPA).

4. The method of claim 1, wherein the N-terminus of the first sortaggable surface fusion protein is exposed to the extracellular space, and wherein the first peptide is N-terminal oligoglycine.

5. The method of claim 1, wherein the oligoglycine consists of 1-5 glycine residues.

6. The method of claim 1, wherein the first type II red blood cell transmembrane protein is Kell or CD71.

7. The method of claim 1, wherein the first polypeptide of interest is selected from the group consisting of protein drugs, vaccine antigens, fluorescent proteins, streptavidin, biotin, enzymes, and peptides capable of targeting a cell.

8. The method of claim 1, wherein the first polypeptide of interest is an antibody or a fragment thereof.

9. The method of claim 8, wherein the antibody is a single domain antibody.

10. The method of claim 1, wherein the red blood cell further comprises a second sortaggable surface fusion protein, wherein the second sortaggable surface fusion protein comprises a second type I or type II red blood cell transmembrane protein and a second peptide, and wherein the method further comprises:
    contacting the red blood cell with a second polypeptide of interest in the presence of a second sortase, wherein the second sortase is a sortase A;
    wherein when the N-terminus of the second sortaggable surface fusion protein is exposed to the extracellular space, the second peptide is either N-terminal oligoglycine or N-terminal oligoalanine fused to the second type I red blood cell transmembrane protein, and the second polypeptide of interest comprises a second sortase recognition motif;
    wherein when the C-terminus of the second sortaggable surface fusion protein is exposed to the extracellular space, the second peptide is the second sortase recognition motif which is fused to the C-terminus of the second type II red blood cell transmembrane protein and is exposed to the extracellular space, and the second polypeptide of interest comprises either N-terminal oligoglycine or N-terminal oligoalanine;
    wherein the second sortase recognition motif is the amino acid sequence LPXTG of SEQ ID NO: 1, LPXT, or LPTXA, in which X is any amino acid residue;
    wherein the first sortase recognition motif differs from the second sortase recognition motif; and
    wherein the second sortase conjugates the second polypeptide of interest to the second sortaggable surface fusion protein.

11. The method of claim 10, wherein the first peptide is different from the second peptide.

12. The method of claim 11, wherein the first sortase is a sortase A from *Staphylococcus aureus*, and wherein (a) when the C-terminus of the first sortaggable surface fusion protein is exposed to the extracellular space, the first sortase recognition motif is the amino acid sequence LPXTG which is fused to the C-terminus of the first type II red blood cell transmembrane protein, in which X is any amino acid residue (SEQ ID NO: 1), and the first polypeptide of interest comprises N-terminal oligoglycine; and (b) when the N-terminus of the first sortaggable surface fusion protein is exposed to the extracellular space, the first peptide is N-terminal oligoglycine which is fused to the first type I red blood cell transmembrane protein, and the first sortase recognition motif is the amino acid sequence LPXTG, in which X is any amino acid residue (SEQ ID NO: 1).

13. The method of claim 12, wherein the C-terminus of the first sortaggable surface fusion protein is exposed to the extracellular space, and wherein the first type II red blood cell transmembrane protein is Kell.

14. The method of claim 12, wherein the second sortase is a sortase A from *Streptococcus pyogenes*, and wherein (a) when the C-terminus of the second sortaggable surface fusion protein is exposed to the extracellular space, the second sortase recognition motif is the amino acid sequence LPXTA which is fused to the C-terminus of the second type II red blood cell transmembrane protein, in which X is any amino acid residue (SEQ ID NO: 2), and the second polypeptide of interest comprises N-terminal oligoalanine; and (b) when the N-terminus of the second sortaggable surface fusion protein is exposed to the extracellular space, the second peptide is N-terminal oligoalanine fused to the second type I red blood cell transmembrane protein, and the second sortase recognition motif is the amino acid sequence LPXTA, in which X is any amino acid (SEQ ID NO: 2).

15. The method of claim 14, wherein the N-terminus of the second sortaggable surface fusion protein is exposed to the extracellular space, and wherein the first type I red blood cell transmembrane protein is GPA.

16. The method of claim 10, wherein the first and second polypeptides of interest comprise or are each conjugated to a functional moiety, and the functional moieties are different.

17. The method of claim 1, wherein the first polypeptide of interest comprises a cytokine.

18. The method of claim 17, wherein the cytokine is an interferon, an interleukin, a colony stimulating factor, a leukemia inhibitory factor, or oncostatin M.

19. The method of claim 18, wherein the cytokine is an interleukin, and the interleukin is selected from the group consisting of IL-2, IL-3, IL-4, IL-5, IL-6, IL-7, IL-9, IL-10, IL-11, IL-12, IL-13, and IL-15.

20. The method of claim 18, wherein the cytokine is a colony stimulating factor, and the colony stimulating factor is selected from the group consisting of G-CSF, GM-CSF, and M-CSF.

21. The method of claim 1, wherein the first polypeptide of interest is an enzyme.

* * * * *